US009357722B2

(12) United States Patent
Regina et al.

(10) Patent No.: US 9,357,722 B2
(45) Date of Patent: Jun. 7, 2016

(54) HIGH AMYLOSE WHEAT-II

(71) Applicant: Arista Cereal Technologies Pty Limited, Black Mountain (AU)

(72) Inventors: Ahmed Regina, Palmerston (AU); Pierre Georges Louis Berbezy, Chanat la Mouteyre (FR); Elisabeth Marie-Anne Ida Chanliaud, Chateaugay (FR); Bernard Duperrier, Vic le comte (FR); Matthew Kennedy Morell, Aranda (AU)

(73) Assignee: ARISTA CEREAL TECHNOLOGIES PTY LIMITED, Black Mountain (AU)

( * ) Notice: Subject to any disclaimer, the term of this patent is extended or adjusted under 35 U.S.C. 154(b) by 478 days.

(21) Appl. No.: 13/668,177

(22) Filed: Nov. 2, 2012

(65) Prior Publication Data

US 2013/0115362 A1    May 9, 2013

Related U.S. Application Data

(60) Provisional application No. 61/556,051, filed on Nov. 4, 2011, provisional application No. 61/645,530, filed on May 10, 2012.

(51) Int. Cl.
*A23L 1/10* (2006.01)
*C08B 30/20* (2006.01)
*A01H 5/10* (2006.01)
*C08B 30/04* (2006.01)
*C12N 15/82* (2006.01)

(52) U.S. Cl.
CPC ............... *A01H 5/10* (2013.01); *A23L 1/1025* (2013.01); *C08B 30/046* (2013.01); *C12N 15/8218* (2013.01); *C12N 15/8245* (2013.01)

(58) Field of Classification Search
None
See application file for complete search history.

(56) References Cited

U.S. PATENT DOCUMENTS

| | | | |
|---|---|---|---|
| 3,690,896 A | 9/1972 | Maxwell et al. | |
| 4,770,710 A | 9/1988 | Friedman et al. | |
| 5,051,271 A | 9/1991 | Iyengar et al. | |
| 6,013,861 A | 1/2000 | Bird et al. | |
| 6,303,174 B1 | 10/2001 | McNaught et al. | |
| 6,307,125 B1 | 10/2001 | Block et al. | |
| 6,376,749 B1 | 4/2002 | Broglie et al. | |
| 6,483,009 B1 | 11/2002 | Poulsen et al. | |
| 6,730,825 B1 | 5/2004 | Goldsbrough et al. | |
| 6,734,339 B2 | 5/2004 | Block et al. | |
| 6,897,354 B1 | 5/2005 | Yamamori et al. | |
| 6,903,255 B2 | 6/2005 | Yamamori et al. | |
| 6,916,976 B1 | 7/2005 | Li et al. | |
| 7,001,771 B1 | 2/2006 | Morell et al. | |
| 7,009,092 B1 | 3/2006 | Jane et al. | |
| 7,041,484 B1 | 5/2006 | Baga et al. | |
| 7,521,593 B2 | 4/2009 | Regina et al. | |
| 7,667,114 B2 | 2/2010 | Morell et al. | |
| 7,700,139 B2 | 4/2010 | Morell et al. | |
| 7,700,826 B2 | 4/2010 | Morell et al. | |
| 7,790,955 B2 | 9/2010 | Li et al. | |
| 7,812,221 B2 | 10/2010 | Regina et al. | |
| 7,888,499 B2 | 2/2011 | Morell et al. | |
| 7,919,132 B2 | 4/2011 | Regina et al. | |
| 7,993,686 B2 | 8/2011 | Bird et al. | |
| 8,115,087 B2 | 2/2012 | Regina et al. | |
| 8,178,759 B2 | 5/2012 | Morell et al. | |
| 8,188,336 B2 | 5/2012 | Li et al. | |
| 2003/0035857 A1 | 2/2003 | Sroka | |
| 2004/0060083 A1 | 3/2004 | Regina et al. | |
| 2004/0199942 A1 | 10/2004 | Morell et al. | |
| 2004/0204579 A1 | 10/2004 | Block et al. | |
| 2005/0071896 A1* | 3/2005 | Regina et al. | ................. 800/284 |
| 2005/0164178 A1 | 7/2005 | Morell et al. | |
| 2006/0010517 A1 | 1/2006 | Li et al. | |
| 2006/0035379 A1 | 2/2006 | Morell et al. | |
| 2006/0204597 A1 | 9/2006 | Bird et al. | |
| 2006/0286186 A1 | 12/2006 | Bird et al. | |
| 2007/0300319 A1 | 12/2007 | Li et al. | |
| 2009/0226592 A1 | 9/2009 | Regina et al. | |
| 2010/0330253 A1 | 12/2010 | Morell et al. | |
| 2011/0010807 A1 | 1/2011 | Morell et al. | |
| 2011/0045127 A1 | 2/2011 | Ral et al. | |
| 2011/0059225 A1 | 3/2011 | Li et al. | |

(Continued)

FOREIGN PATENT DOCUMENTS

GB    2 360 521    9/2001
WO    WO 97/22703    6/1997

(Continued)

OTHER PUBLICATIONS

Uauy et al, 2009, BMC Plant Bio., 9:1-14.*

(Continued)

*Primary Examiner* — Jason Deveau Rosen
(74) *Attorney, Agent, or Firm* — John P. White; Cooper & Dunham LLP

(57) ABSTRACT

Wheat grain (*Triticum aestivum*) comprising an embryo and starch, wherein the embryo comprises two identical alleles of an SBEIIa-A gene, two identical alleles of an SBEIIa-B gene and two identical alleles of an SBEIIa-D gene, wherein each of the SBEIIa genes gives rise to an amount of protein (w/w) or a protein having SBEIIa activity which is lower than the corresponding wild-type gene, and at least one of said genes comprises a point mutation, wherein the starch comprises amylose such that the grain has an amylose content of at least 50% (w/w) as a proportion of the extractable starch of the grain.

3 Claims, 28 Drawing Sheets
(9 of 28 Drawing Sheet(s) Filed in Color)

(56) References Cited

U.S. PATENT DOCUMENTS

| | | | |
|---|---|---|---|
| 2011/0070352 A1 | 3/2011 | Regina et al. | |
| 2011/0212916 A1 | 9/2011 | Bird et al. | |
| 2012/0074247 A1 | 3/2012 | Regina et al. | |
| 2012/0114770 A1* | 5/2012 | Regina et al. | 424/750 |
| 2012/0266267 A1 | 10/2012 | Li et al. | |
| 2014/0044826 A1 | 2/2014 | Regina et al. | |

FOREIGN PATENT DOCUMENTS

| | | |
|---|---|---|
| WO | WO 99/14314 | 3/1999 |
| WO | WO 00/15810 | 3/2000 |
| WO | WO 00/66745 | 9/2000 |
| WO | WO 01/32886 | 5/2001 |
| WO | WO 01/62934 | 8/2001 |
| WO | WO 02/37955 | 5/2002 |
| WO | WO 02/101059 | 12/2002 |
| WO | WO 03/023024 | 3/2003 |
| WO | WO 03/094600 | 11/2003 |
| WO | WO 2005/001098 | 1/2005 |
| WO | WO 2005/040381 | 6/2005 |
| WO | WO 2013/052499 | 4/2013 |

OTHER PUBLICATIONS

Nakamura Y., "Towards a Better Understanding of the Metabolic System for Amylopectin Biosynthesis in Plants: Rice Endosperm as s Model Tissue," Plant Cell Physiology 43(7):718-725 (2002).

Nishi et al., "Biochemical and Genetic Analysis of the Effects of Amylose-Extender Mutation in Rice Endosperm," Plant Physiology 127:459-472 (2001).

Okagaki R. J., "Nucleotide Sequence of a Long cDNA from the Rice Waxy Gene," Plant Molecular Biology 19:513-516 (1992).

Puchta, "Gene Replacement by Homologous Recombination in Plants," Plant Mol. Biol. 48:173-182 (2002).

Rahman et al., GenBank Accession #AF076680, Aegilops tauschii starch branching enzyme-I (SBE-1) gene, complete cds. (May 1999).

Rahman, S. et al., "The Major Proteins of Wheat Endosperm Starch Granules," Aust. J. Plant Physiol. 22:793-803 (1995).

Rahman, S. et al., "A Complex Arrangement of Genes at a Starch Branching Enzyme I Locus in the D-genome Donor of wheat," Genome 40:465-474 (1997).

Rahman, S. et al., "Characterisation of a Gene Encoding Wheat Endosperm Starch Branching Enzyme-I," Theor. Appl. Genet. 98:156-163 (1999).

Rahman, S. et al., "Comparison of Starch-Branching Enzyme Genes Reveals Evolutionary Relationships Among Isoforms. Characterization of a Gene for StarchBranching Enzyme IIa from the Wheat D Genome Donor Aegilops tauschii II," Plant Physiology, vol. 125, pp. 1314-1324 (2001).

Safford et al., "Consequences of Antisense RNA Inhibition of Starch Branching Enzyme Activity on Properties of Potato Starch," Carbohydrate Polymers 35:155-168 (1998).

Sathish et al., "Cloning and Anti-Sense RNA Constructs of a Starch Branching Enzyme Gene From Barley Endosperm," Photosynthesis: from Light to Biosphere vol. V. P. Mathis (ed.) pp. 313-316 (1995).

Schondelmaier et al., "Genetical Studies in the Mode of Inheritance and Localization of the amol (High Amylose) Gene in Barley," Plant Breeding 109:274-280 (1992).

Schwall, et al., "Production of Very-High-Amylose Potato Starch by Inhibition of SBE A and B," Nature Biotechnology 18:551-554 (2000).

Shannon and Garwood, "In Starch: Chemistry and Technology," Whistler et al., eds, Academic Press, Orlando, FL, 25-86 (1984).

Sidebottom et al., "Characterization of the Difference of Starch Branching Enzyme Activities in Normal and Low-Amylopectin Maize during Kernel Development," Journal of Cereal Science 27:279-287 (1998).

Sun et al., "Identification of Four Starch-Branching Enzymes in Barley Endosperm: Partial Purification of forms I, IIa and IIb," New Phytol. 137:215-222 (1997).

Sun et al., "The Two Genes Encoding Starch-Branching Enzymes IIa and IIb Are Differentially Expressed in Barley," Plant Physiology 118:37-49 (1998).

Sundberg et al., "Glycaemic Responses and Hypocholesterolaemic Effects of High-Amylose Barley Diets on Broiler Chicks," J. Sci. Food Agric. 76:457-463 (1998).

Takaoka, M. et al., "Structural characterization of high molecular weight starch granule-bound proteins in wheat (*Triticum aestivum* L.)," J. Agric. Food Chern. 45:2929-2934 (1997).

Thomas, et al., "Size Constraints for Targeting Post-Transcriptional Gene Silencing and for RNA-directed Methylation in Nicotiana benthamiana Using a Potato Virus X Vector," Plant J. 25:417-425 (2001).

Topping et al., "Resistant Starch and Health—Himalaya 292, a Novel Barley Cultivar to Deliver Benefits to Consumers" Starch/Starke 55: 539-545, 2003.

USDA, ARS, National Genetic Resources Program. Germplasm Resources Information Network (GRIN) [Online Database] National Germplasm Resources Laboratory, Beltsville, Maryland (http://www.ars-grin.gov/npgs/), GRIN System [Accession No. GSHO 2476, Jun. 23, 1997].

Van der Leij et al., "Sequence of the Structural Gene for Granule-Bound Starch Synthase of Potato (*Solanum tuberosum* L.) and Evidence for a Single Point Deletion in the amf allele," Mol. Gen. Genet. 228:240-248 (1991).

Vrinten and Nakamura, "Wheat Granule-Bound Starch Synthase I and II Are Encoded by Separate Genes That Are Expressed in Different Tissues," Plant Physiology 122:255-263 (2000).

Walker and Merritt, "Genetic Control of Abnormal Starch Granules and High Amylose Content in a Mutant of Glacier Barley," Nature 221:482-484 (1969).

Walter et al., GenBank Accession #AAB17085, Starch Synthase (Oct. 1996).

Walter et al., GenBank Accession #U66377, Triticum aestivum soluble starch synthase mRNA, partial cds. (Oct. 1996).

Wasserman et al., "Microstructure, Thermal properties and susceptibility of the high amylose wheat starch to enzymatic hydrolysis: A new material for resistant starch (SRIII) production," Polish Journal of Food and Nutrition Sciences vol. 13-54, No. 2, pp. 151-156 (2004).

Wei et al., "C-Type Starch from High-Amylose Rice Resistant Starch Granules Modified by Antisense RNA Inhibition of Starch Branching Enzyme," Journal of Agricultural and Food Chemistry, 58:7383-7388 (2010).

Yamamori and Endo, "Variation of Starch Granule Proteins and Chromosome Mapping of Their Coding Genes in Common Wheat," Theor. Appl. Genet. 93:275-181 (1996).

Yamamori et al., "Genetic Elimination of a Starch Granule Protein, SGP-1, of Wheat Generates an Altered Starch with Apparent High Amylose," Theor. AJ2,eI. Genet. 101:21-29 (2000).

Yamamori, "Selection of a Wheat Lacking a Putative Enzyme for Starch Synthesis, SGP-1," Proc. 9th in Wheat Gen. Symp. 4:300-302 (1998).

Zobel et al., Starch Gelatinization: An X-ray Diffraction Study. Cereal Chem, 1988, 65(6):443-446.

Zobel, H.F., Starch Crystal Transformations and Their Industrial Importance. Starch, 1988, 40(1): 1-7.

Zwar and Chandler, α-Amylose production and leave protein synthesis in a gibberellin-responsive dwarf mutant of 'Himalaya' barley (*Hordeum vulgare* L.). Planta, 1995, 197:39-48.

English Language Abstract of PCT International Application Publication No. WO 2003/023024, published Mar. 20, 2003.

International Search Report, issued May 14, 2012 in connection with PCT International Patent Application No. PCT/AU2012/000098.

Abel et al., GenBank Accession #Y10416, S. Tuberosum mRNA for Soluble Starch Synthase (Jan. 1997).

Abel, G.J.W. et al., "Cloning and functional analysis of a cDNA encoding a novel 139 kDa Starch Synthase from Potato (*Solanum tuberosum* L.)," Plant J. 10(6) : 981-991 (1996).

Ainsworth, C. et al., "Expression, organization and structure of the genes encoding the waxy protein (granule-bound starch synthase) in wheat," Plant Mol. Biol. 22:67-82 (1993).

(56) References Cited

OTHER PUBLICATIONS

Baba, T. et al., "Identification, cDNA cloning and gene expression of soluble starch synthase in rice (*Oryza stativa* L.) Immature Seeds," Plant Physiol. 103:565-573 (1993).
Banks et al., "Studies on Starches of High Amylose Content," Starch 26:289-300 (1974).
Batey and Curtin, "Measurement of Amylose/Amylopectin Ratio by High-Performance Liquid Chromatography," Starch 48:338-344 (1996).
Bhullar et al., GenBank Accession #CAB40374, Starch synthase isoform SS III [Vigna unguiculata] (Apr. 1999).
Blauth et al., "Identification of Mutator Insertional Mutants of Starch-Branching Enzyme 2a in Corn," Plant Physiology 125:1396-1405 (2001).
Block et al., GenBank Accession #U48227, Triticum aestivum soluble starch synthase mRNA, partial cds. (Jun. 1996).
Boyer and Preiss, "Evidence for Independent Genetic Control of the Multiple Forms of Maize Endosperm Branching Enzymes and Starch Synthases," Plant Physiology 67:1141-1145 (1981).
Buleon et al., "Starch Granules: Structure and Biosynthesis," International Journal of Biological Macromolecules 23:85-112 (1998).
Craig et al., "Mutations in the Gene Encoding Starch Synthase II Profoundly Alter Amylopectin Structure in Pea Embryos," The Plant Cell 10:413-426 (1998).
Denyer, K. et al., "Identification of Multiple Isoforms of Soluble and Granule Bound Starch Synthase in Developing Wheat Endosperm," Planta 196:256-265 (1995).
D'Hulst et al., GenBank Accession #AAC17969, Granule-bound starch synthase I precursor [Chlamydomonas reinhardtii] (Nov. 2001).
Dry, I. et al., "Characterization of cDNAs encoding two isoforms of granule-bound synthase which show differential expression in developing storage organs of pea and potato," Plant J. 2(2):193-202 (1992).
Edwards et al., "Biochemical and Molecular Characterization of a Novel Starch Synthase from Potato Tubers," Plant J. 8(2):283-294 (1995).
Flipse et al., "Introduction of Sense and Antisense cDNA for Branching Enzyme in the Amylose-Free Potato Mutant Leads to Physico-Chemical Changes in the Starch," Plant a 198:340-347 (1996).
Fujita et al., "Grain and Starch Characteristics of the Double Recessive Lines for Amylose-free and High Amylose Gene in Barley," Breeding Science 49:217-219 (1999).
Fujita et al., "Antisense Inhibition of Isoamylase Alters the Structure of Amylopectin and the Physiochemical Properties of Starch in Rice Endosperm," Plant Cell Physiol. 44(6):607-618 (2003).
Gao and Chibbar, "Isolation, Characterization, and Expression Analysis of Starch Synthase IIa cDNA from wheat (*Triticum aestivum* L.)," Genome 43:768-775 (2000).
Gao et al., GenBank Accession #AAC14014, Starch synthase DULL 1 [Zea mays] (Apr. 1998).
Gao et al., GenBank Accession #AAC14015, Starch synthase DULL 1 [Zea mays] (Apr. 1998).
Gao et al., "Characterization of dull I, a Maize Gene Coding for a Novel Starch Synthase," Plant Cell 10:399-412 (1998).
Gao et al., Triticum aestivum mRNA for Starch Synthase IIa-2 (wSs2a-2), EMBL Abstract Accession No. AJ269503 (Jul. 6, 2000).
Gao et al., GenBank Accession #AJ26502, Triticum aestivum mRNA for starch synthase Iia-1 (wSs2a-1 gene) (Apr. 2002).
Gao et al., GenBank Accession #CAB86618, Starch synthase Iia-1 [Triticum aestivum] (Apr. 2002).
Goering and DeHass, "A Comparison of the Properties of Large- and Small-Granule Starch Isolated from Several Isogenic Lines of Barley," Cereal Chemistry 51:573-578 (1974).
Harn et al., "Isolation and Characterization of the zSSIIA and zSSIIb Starch Synthase cDNA Clones from Maize Endosperm," Plant Mol. Biol. 37:639-649 (1998).
Jansson et al., "Cloning, Characterization and Modification of Genes Encoding Starch Branching Enzymes in Barley," Starch: Structure and Functionality, Royal Society of Chemistry, London, pp. 196-203 (1997).

Jarvi and Eslick, "Shrunken Endosperm Mutants in Barley," Crop Science 15:363-366 (1975).
Klosgen et al., "Molecular Analysis of the Waxy Locus of Zea mays," Mol. Gen. Genet. 203:237-244 (1986).
Knight et al., "Molecular Cloning of Starch Synthase I from Maize (w64) Endosperm and Expression in *Escherichia coli*," Plant J. 14(5):613-622 (1998).
Kull et al., "Genetic Engineering of Potato Starch Composition: Inhibition of Amylose Biosynthesis in Tubers from Transgentic Potato Lines by the Expression of Antisense Sequences of the Gene for Granule-bound Starch Synthase," J. Genet. Breed. 49:69-76 (1995).
Li et al., "The structural organisation of the gene encoding class II starch synthase of wheat and barley and the evolution of the genes encoding starch synthases in plants" Funct Integr Genomics 3:76-85 (2003).
Li et al., "Cloning and Characterization of a Gene Encoding Wheat Starch Synthase I," Theor. AEEI. Genet. 98:1208-1216 (1999).
Li et al., "The Localization and Expression of the Class II Starch Synthases of Wheat," Plant Physiology 120:1147-1155 (1999).
Li et al., Triticum aestivum Starch Synthase IIa mRNA, complete cds., EMBL Abstract Accession No. AF155217 (Sep. 7, 1999).
Liu et al., "Stable Inheritance of the Antisense Waxy Gene in Transgenic Rice with Reduced Amylose Level and Improved Quality," Transgenic Research, 12:71-82, (2003).
Mazzolini et al., "Assaying synthetic ribozymes in plants: high-level expression of a functional hammerhead structure fails to inhibit target gene activity in transiently transformed protoplasts," Plant Mol. Biol. 20:715-731 (1992).
Miao, Hongmei et al., "Evaluation and Characterization of an Endosperm-Specific sbella Promoter in Wheat II," Chinese Science Bulletin, vol. 49, No. 6, pp. 579-585 (2004).
Mizuno et al., "Alteration of the Structural Properties of Starch Components by the Lack of an Isoform of Starch Branching Enzyme in Rice Seeds," J. Biol. Chem. 268(25):19084-19091 (1993).
Morell et al., "Barley sex6 Mutants Lack Starch Synthase iia Activity and Contain a Starch with Novel Properties," The Plant Journal 34:173-185 (2003).
Morell et al., "The Biochemistry and Molecular Biology of Starch Synthesis in Cereals," Aust. J. Plant. Physiol. 22:647-660 (1995).
Myers et al., "Recent Progress toward Understanding Biosynthesis of the Amylopection Crystal," Plant Physiology 122:989-997 (2000).
Jul. 29, 2013 Office Action, issued in connection with U.S. Appl. No. 13/289,884.
Nov. 27, 2013 Response, filed in connection with U.S. Appl. No. 13/289,884.
Feb. 14, 2014 Final Office Action, issued in connection with U.S. Appl. No. 13/289,884.
May 14, 2014 Response, filed in connection with U.S. Appl. No. 13/289,884.
Jun. 17, 2014 Advisory Action and Interview Summary, issued in connection with U.S. Appl. No. 13/289,884.
Jul. 24, 2014 Response, filed in connection with U.S. Appl. No. 13/289,884.
Apr. 8, 2015 Office Action, issued in connection with U.S. Appl. No. 13/883,456.
Apr. 14, 2014 Extended European Search Report, issued in connection with European Patent Application No. 11837339.8.
Notification concerning Transmittal of International Preliminary Report on Patentability (IPRP), including IPRP, issued May 15, 2014 in connection with PCT International Patent Application No. PCT/AU2012/01349.
Notification concerning Transmittal of International Preliminary Report on Patentability (IPRP), including IPRP, issued May 7, 2013 in connection with PCT International Patent Application No. PCT/AU2011/001426.
Arnold CN., "Molecular pathogenesis of colorectal cancer," 2005, Cancer, vol. 104, pp. 2035-2047.
Gillespie, K., "Type 1 diabetes: pathogenesis and prevention," 2006, CMAJ, vol. 175, pp. 165-170.
Holmes et al., Henderson's Dictionary of Biological Terms, 9th Ed., Van Nostrand Reinhold Co., New York, 1979, p. 218.

(56) References Cited

OTHER PUBLICATIONS

Regina A., (2006) "High-amylose wheat generated by RNA interference improves indices of large-bowel health in rats," PNAS, vol. 103, pp. 3546-3551.

Siddiqui et al. (2008) "Germination Behavior of Wheat (*Triticum aestivum*) Varieties to Artificial Ageing Under Varying Temperature and Humidity" 40(3): 1121-1127, Pak. J. Bot.

Slade et al., (2012) "Development of High Amylose Wheat Through Tilling," BMC Plant Biology, 12:69-100.

Slade et al., (2005) "A reverse genetic, nontransgenic approach to wheat crop improvement by Tilling," Nature Biotechnology 23(1):75-81.

Terada at al., "Efficient Gene Targeting by Homologous Recombination in Rice," Nature Biotech. 20: 1030-1034, 2002.

Tetlow IJ et al., (2004) "Recent developments in understanding the regulation of starch metabolism in higher plants," Journal of Experimental Botany 55(406):2131-2145.

Topping et al., (2001) "Short-Chain Fatty Acids and Human Colonic Function: Roles of Resistant Starch and Nonstarch Polysaccharides," Physiological Review, vol. 81(3), pp. 1031-1064.

Wesley SV et al., (2001) "Construct design for efficient, effective and high-throughput gene silencing in plants," Plant J. 27(6):581-90.

Wang et al., (2009) "Simultaneous selection of major and minor genes: use of QTL to increase selection efficiency of coleoptile length of wheat (*Triticum aestivum* L.)," Theor Appl Genet, 119:65-74.

Wolters AM, Visser RG., (2000) "Gene silencing in potato: allelic differences and effect of ploidy," Plant Mol Biol. 43 (2-3):377-86.

\* cited by examiner

```
                      10        20        30        40        50        60        70        80        90       100
                      ....|....|....|....|....|....|....|....|....|....|....|....|....|....|....|....|....|....|....|....|
SBE IIa sr tauschii AAK26821.1    MATFAVSGATIGVAR---AGVGVA-RAGSERRGGADLPSLLLRKKDSSRAVLSRAASPGKVLVPDGESDDL-ASPAQPEELQIPEDIEEQTAEVNMTGGT
SBE IIa Italy CAR95900.1 aesti    ..............PAS.G.LL-.S......V...........................A.T.....................................
SBE IIa Baga aestivum CAA72154    ..............PAG.G.LLP.S......V........................................-............................

110       120       130       140       150       160       170       180       190       200
                      ....|....|....|....|....|....|....|....|....|....|....|....|....|....|....|....|....|....|....|....|
SBE IIa sr tauschii AAK26821.1    AEKLQSSEPTQGIVETITDGVTKGVKELVVGEKPRVVPKPGDGQKIYEIDPTLKDFRSHLDYRYSEYKRIRAAIDQHEGGLEAFSRGYEKLGFTRSAEGI
SBE IIa Italy CAR95900.1 aesti    ....Y................................................................................................
SBE IIa Baga aestivum CAA72154    ....E....................................................R.........................................

210       220       230       240       250       260       270       280       290       300
                      ....|....|....|....|....|....|....|....|....|....|....|....|....|....|....|....|....|....|....|....|
SBE IIa sr tauschii AAK26821.1    TYREWAPGAHSAALVGDFNNWNPNADTMTRDDYIGWEIFLPNNADGSSAIPHGSRVKIRMDTPSGVKDSISAWIKFSVQAPGEIPFNGIYDPPEEEKYV
SBE IIa Italy CAR95900.1 aesti    ...............................P....................................................................
SBE IIa Baga aestivum CAA72154    ...............................P....................................................................

310       320       330       340       350       360       370       380       390       400
                      ....|....|....|....|....|....|....|....|....|....|....|....|....|....|....|....|....|....|....|....|
SBE IIa sr tauschii AAK26821.1    FQHPQRKRPESLRIYESHIGMSSPEPKINSYANFRDEVLPRIKRLGYNAVQIMAIQEHSYYASFGYHVTNFFAPSSRFGTPEDLKSLIDRAHELGLLVLM
SBE IIa Italy CAR95900.1 aesti    ....P..................................G............................................................
SBE IIa Baga aestivum CAA72154    ....P.................................................................................................
```

FIGURE 1

```
                            410        420        430        440        450        460        470        480        490        500
                            ....|....|....|....|....|....|....|....|....|....|....|....|....|....|....|....|....|....|....|....|
SBE IIa sr tauschii AAK26821.1    DIVHSHSSNNTLDGLNGFDGTDTHYFHGGPERGHHWMWDSRLFNYGSWEVLRFLLSNARWWLEEYKFDGFRFDGVTSMMYTHHGLQMTFTGNYGEYFGFAT
SBE IIa Italy CAR95900.1 aesti    ....................................................................................................
SBE IIa Baga aestivum CAA72154    ....................................................................................................

510        520        530        540        550        560        570        580        590        600
                            ....|....|....|....|....|....|....|....|....|....|....|....|....|....|....|....|....|....|....|....|
SBE IIa sr tauschii AAK26821.1    DVDAVVYLMLIVNDLIHGLYPDAVSIGEDVSGMPTFCIPVPDGGVGFDYRLHMAVADKWIELLKQSDESWKMGDIVHTLTNRRWLEKCVTYAESHDQALVG
SBE IIa Italy CAR95900.1 aesti    ....................................................................................................
SBE IIa Baga aestivum CAA72154    ..........H.....................................L..................................................

610        620        630        640        650        660        670        680        690        700
                            ....|....|....|....|....|....|....|....|....|....|....|....|....|....|....|....|....|....|....|....|
SBE IIa sr tauschii AAK26821.1    DKTIAFWLMDKDMYDFMALDRPSTLRIDRGIALHKMIRLVTMGLGGEGYLNFMGNEFGHPEWIDFPRGPQTLPTGKVLPGNNNSYDKCRRRFDLGDADFL
SBE IIa Italy CAR95900.1 aesti    .................P..................................................................................
SBE IIa Baga aestivum CAA72154    .................P..................................................................................

710        720        730        740        750        760        770        780        790        800
                            ....|....|....|....|....|....|....|....|....|....|....|....|....|....|....|....|....|....|....|....|
SBE IIa sr tauschii AAK26821.1    RYRGMQEFDQAMQHLLEEKYGFMTSEHQYVSRKHEEDKVIILKRGDLVFVFNFHWSNSFFDYRVGCSKPGKYKVALDSDDALFGGFSRLDHDVDYFTTEHP
SBE IIa Italy CAR95900.1 aesti    ...............................................FE..................................................
SBE IIa Baga aestivum CAA72154    .H.............................................FE...................R..............................

810        820
                            ....|....|....|....|....
SBE IIa sr tauschii AAK26821.1    HDNRPRSFSVYTPSRTAVVYALTE
SBE IIa Italy CAR95900.1 aesti    ........L...............
SBE IIa Baga aestivum CAA72154    ........................
```

FIGURE 1 (CONTINUED)

```
                        10        20        30        40        50        60        70        80        90       100
                         |    .    |    .    |    .    |    .    |    .    |    .    |    .    |    .    |    .    |
SbeIIb_B_prot Exon 2 to 3 ...........................................................AVSVGGSWRVVMRAGGPSGEVMIPDGGSGGTSPSIDGPVQFDSDDLKVP
SbeIIb_D_prot Exon 1 to 3 MAAPAFAVSAAGLARPSAPRSGGAERRGRGVELQSPSLLFGRNKGTRSPR..G.............................P.........................
SbeIIb A prot Exon 1 to3  MAAPAFAVSAAGLARPSAPRSGGPERRGRGVELQSPSLLFGRNKGTRSPR..G.............................P...H.....................

110       120       130       140       150
                         |    .    |    .    |    .    |    .    |
SbeIIb_B_prot Exon 2 to 3 FIDDEPSLQDEGEDSIWSSETNQVTEEIDVEGMKIMDKESSTGEKLRIV------
SbeIIb_D_prot Exon 1 to 3 ....T....G..............S....A.DTSR......R....LPPP-----
SbeIIb A prot Exon 1 to3  ....T....G..T...........A..TSR................LPPPGNGQQ
```

FIGURE 2

```
                                     10        20        30        40        50        60        70        80        90       100
                                     ....|....|....|....|....|....|....|....|....|....|....|....|....|....|....|....|....|....|....|....|
Chara IIa B genome F1-13 0686        CATTCGTCAAATAATACCCTGACGGTTGAAATGGTTTGATGGCACTGATACACATTACTTCCACGGTGGTCCACGTGGCCATCATTGGATGTGGGATT
Chara IIa A genome_F1-15 0687        ................................C..........C..A...............................................
Chara IIa D genome F1-1 0678         ................................C..........C..T...............................................

110       120       130       140       150       160       170       180       190       200
                                     ....|....|....|....|....|....|....|....|....|....|....|....|....|....|....|....|....|....|....|....|
Chara IIa B genome F1-13 0686        CTCGTCTGTTCCACTATGGGAGTTGGGAAGTATGGCGACTTCTGTCACCATATATTGGCTAACTGTTCCTGTC-AATCTGTTCTTCTTACACGTGTCAA
Chara IIa A genome_F1-15 0687        A...A.......................................CT.........................TA.............A....G.
Chara IIa D genome F1-1 0678         A...A.......................................CT.........................TA.............A....G.

210       220       230       240       250       260       270       280       290       300
                                     ....|....|....|....|....|....|....|....|....|....|....|....|....|....|....|....|....|....|....|....|
Chara IIa B genome F1-13 0686        TATTCTATTCTTATACAGGTATTAAGATTCTTACTGTCAAACGCGAGATGGTGGCTTGATGAATATAAGTTTGATGGATTTCGATTTGATGGGGTGACCT
Chara IIa A genome_F1-15 0687        .........GT..................................A..................................................
Chara IIa D genome F1-1 0678         ......C..GT..................................A..................................................

310       320       330       340       350       360       370       380       390       400
                                     ....|....|....|....|....|....|....|....|....|....|....|....|....|....|....|....|....|....|....|....|
Chara IIa B genome F1-13 0686        CCATGATGTATACTCACCATGGATTACAAGTCATCAACTGGTTTCAGTAACTTCTTCAGGGCACTCAAACAATTGCTATGCATCATATAACATGTATC
Chara IIa A genome_F1-15 0687        ..................................................T..T........T...............................
Chara IIa D genome F1-1 0678         ..................................................T..T........T...............................
```

FIGURE 7

```
                           410       420       430       440       450       460       470       480       490       500
                           ....|....|....|....|....|....|....|....|....|....|....|....|....|....|....|....|....|....|....|....|
Chara IIa B genome F1-13 0686  ATGATCAGTACTTATGCGCTATGGAGTCTCAGATAGTTCCCTAGTATGCTTGTACAATTTTACCTGACGAGATCATGGAAGATTGGAAGTGATTGTTATTAT
Chara IIa A genome_F1-15 0687  ........G....G...................T............C...................T.........................A....TA
Chara IIa D genome F1-1  0678  ........G....G...................T............................T..............C..C.........A....TA 510       520       530       540       550       560       570       580       590       600
                           ....|....|....|....|....|....|....|....|....|....|....|....|....|....|....|....|....|....|....|....|
Chara IIa B genome F1-13 0686  TTTTTCTTCTAAGTTGCTTCTTGTTCTAGATGACATTTACTGGGAACTATGGCGAGTATTTGGATTTGCCACTGATGTTGATGCGGTGTATACTTAA
Chara IIa A genome_F1-15 0687  .........T....................................T............T................C....A..T......G.
Chara IIa D genome F1-1  0678  ....CT...........................A.............T.............................A..T......G.

610       620       630       640       650
                           ....|....|....|....|....|....|....|....|....|....|
Chara IIa B genome F1-13 0686  TGCTGGTCAACGATCTAATTCATGGACTTTATCCTGATGCTGTATCCATTGGTGAAGAA
Chara IIa A genome_F1-15 0687  ...........................................................
Chara IIa D genome F1-1  0678  ...........................................................
```

FIGURE 7 (CONTINUED)

```
                         10        20        30        40        50        60        70        80        90       100
                          |         |         |         |         |         |         |         |         |         |
                  ....|....|....|....|....|....|....|....|....|....|....|....|....|....|....|....|....|....|....|....|
CS_exon_3a_D_genome  GATACCTGAAGATATCGAGGAGCAAACGGGCGAAGTGAACATGACAGGGGGGACTGCAGAGAACTTCAATCTTCAGAACCGACTCAGGGCATTGTGGAA
CS_exon_3b_B_genome  ............................................T.................................A....................
CS_exon_3d_A_genome  ............................................T...A.............A...A...............................

110       120       130       140       150       160       170       180       190       200
                          |         |         |         |         |         |         |         |         |         |
                  ....|....|....|....|....|....|....|....|....|....|....|....|....|....|....|....|....|....|....|....|
CS_exon_3a_D_genome  ACAATCACTGATGGTGTAACCAAAGGAGTTAAGGAACTAGTCGTGGGGGAGAAACCGCGAGTTGTCCCAAAACCAGGAGATGGGCAGAAAATATACGAGA
CS_exon_3b_B_genome  ....................................................................................................
CS_exon_3d_A_genome  ............................................................................A.......................

210       220       230       240
                          |         |         |         |
                  ....|....|....|....|....|....|....|....
CS_exon_3a_D_genome  TTGACCCAACACTGAAAGATTTTCGGAGCCATCTTGACTACCG
CS_exon_3b_B_genome  .........G................................
CS_exon_3d_A_genome  .........G................................
```

FIGURE 9

Relationship of amylose content and enzyme resistant starch in wheat starch samples (a)
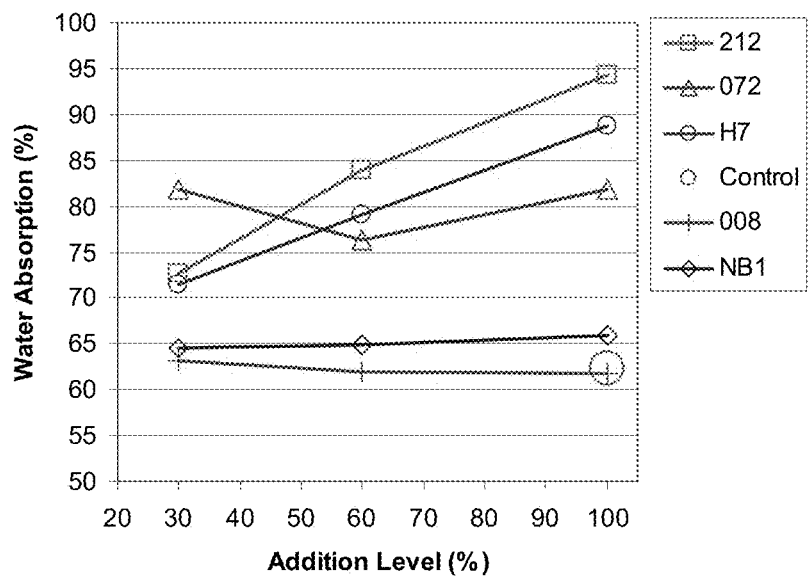
(b)
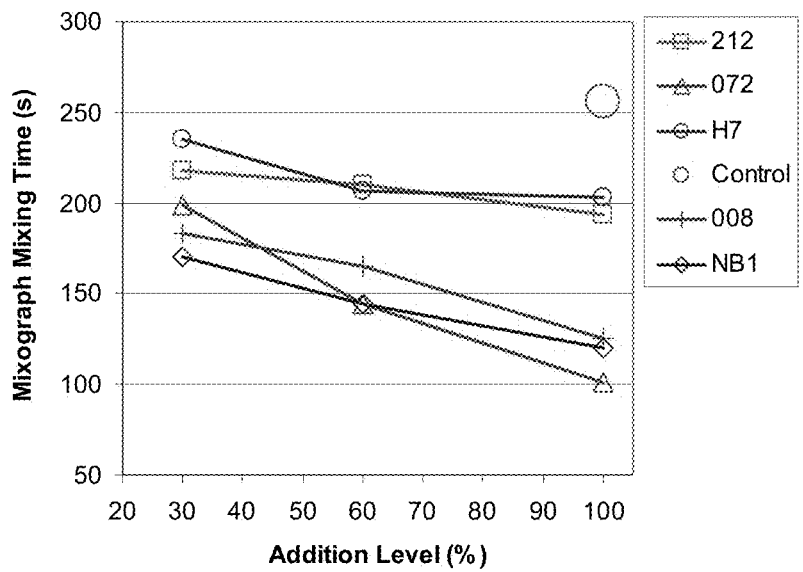
FIGURE 17

(a)
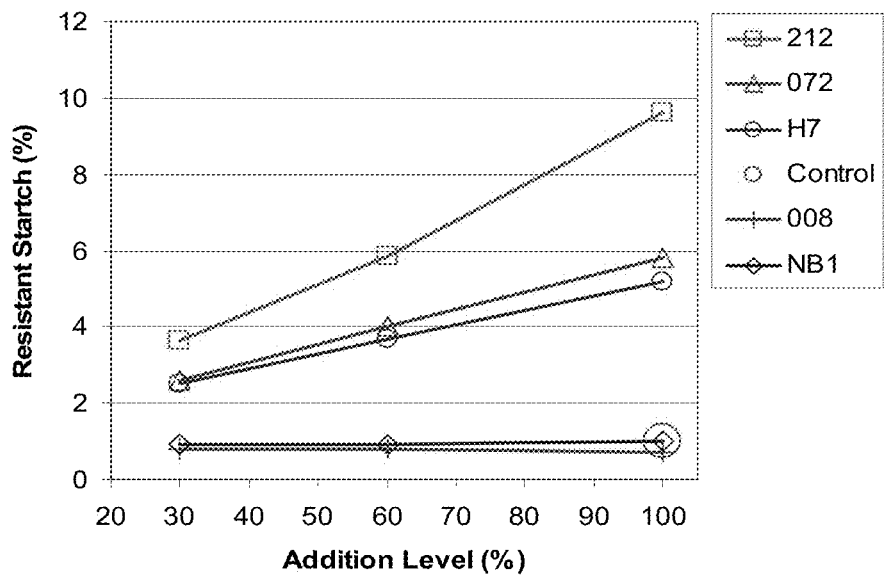
(b)
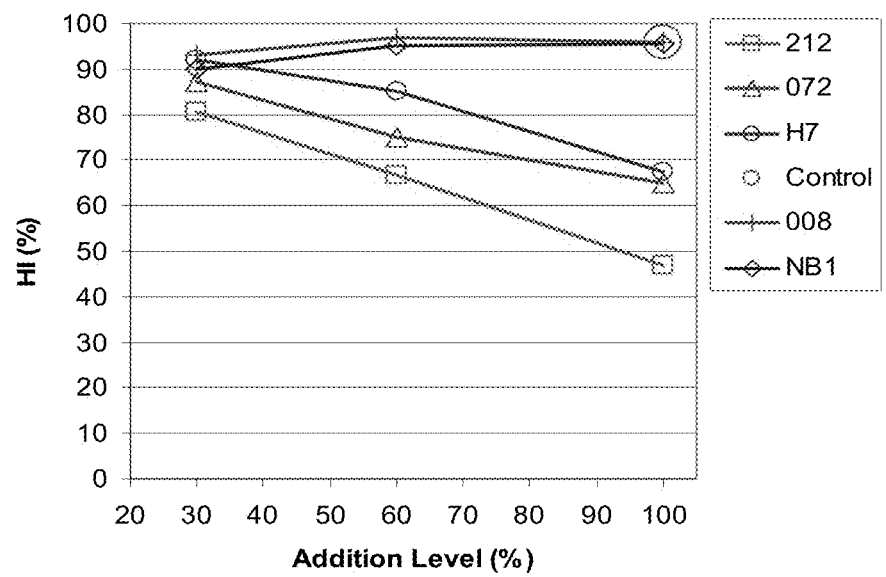
FIGURE 18

HIGH AMYLOSE WHEAT-II

CROSS-REFERENCE TO RELATED APPLICATIONS

This application claims the benefit of U.S. Provisional Applications Nos. 61/645,530, filed May 10, 2012 and 61/556,051, filed Nov. 4, 2011, the contents of each of which are hereby incorporated by reference in their entirety.

Throughout this application, various publications are referenced, including referenced in parenthesis. Full citations for publications referenced in parenthesis may be found listed in alphabetical order at the end of the specification immediately preceding the claims. The disclosures of all referenced publications in their entireties are hereby incorporated by reference into this application in order to more fully describe the state of the art to which this invention pertains.

REFERENCE TO SEQUENCE LISTING

This application incorporates-by-reference nucleotide and/or amino acid sequences which are present in the file named "130909_0687_83529_A_Substitue_Sequence_Listing_BI.txt," which is 132 kilobytes in size, and which was created Sep. 9, 2013 in the IBM-PC machine format, having an operating system compatibility with MS-Windows, which is contained in the text file filed Sep. 9, 2013 as part of this application.

FIELD

The specification describes methods of obtaining hexaploid wheat plants having high amylose starch and the use of such plants, and particularly grain or starch therefrom in a range of food and non-food products.

BACKGROUND

Reference to any prior art in this specification is not, and should not be taken as, an acknowledgment or any form of suggestion that this prior art forms part of the common general knowledge in any country.

In the last decade, much has been learnt about the molecular, genetic and cellular events underpinning plant life cycles and plant production. One particularly important plant product is wheat grain. Wheat grain is a staple food in many countries and it supplies at least 20% of the food kilojoules for the total world population. Starch is the major component of wheat grain and is used in a vast range of food and non-food products. Starch characteristics vary and they play a key role in determining the suitability of wheat starch for a particular end use. Despite this huge global consumption and despite an increased awareness of the importance of starch functionality on end product quality, research on genetic variation in wheat and its precise impact on starch characteristics lags behind that for other commercially important plant crops.

Bread wheat (*Triticum aestivum*) is a hexaploid having three pairs of homoeologous chromosomes defining genomes A, B and D. The endosperm of grain comprises 2 haploid complements from a maternal cell and 1 from a paternal cell. The embryo of wheat grain comprises one haploid complement from each of the maternal and paternal cells. Hexaploidy has been considered a significant obstacle in researching and developing useful variants of wheat. In fact, very little is known regarding how homoeologous genes of wheat interact, how their expression is regulated, and how the different proteins produced by homoeologous genes work separately or in concert.

Cereal starch is made up of two glucose polymers, amylose and amylopectin. The ratio of amylose to amylopectin appears to be a major determinant in (i) the health benefit of wheat grain and wheat starch and (ii) the end quality of products comprising wheat starch.

Amylose is an essentially linear polymer of $\alpha$-1,4 linked glucose units, while amylopectin is highly branched with $\alpha$-1,6 glucosidic unit bonds linking linear chains.

High amylose starches are of particular interest for their health benefits. Foods comprising high amylose have been found inter alia to be naturally higher in resistant starch (RS), a form of dietary fibre. RS is starch or starch digestive products that are not digested or absorbed in the small intestine. Resistant starch is increasingly seen to have an important role in promoting intestinal health and in protecting against diseases such as colorectal cancer, type II diabetes, obesity, heart disease and osteoporosis. High amylose starches have been developed in certain grains such as maize and barley for use in foods as a means of promoting bowel health. The beneficial effects of resistant starch result from the provision of a nutrient to the large bowel wherein the intestinal microflora are given an energy source which is fermented to form inter alia short chain fatty acids. These short chain fatty acids provide nutrients for the colonocytes, enhance the uptake of certain nutrients across the large bowel and promote physiological activity of the colon. Generally, if resistant starches or other dietary fibre are not provided to the colon it becomes metabolically relatively inactive. Thus high amylose products have the potential to facilitate increased consumption of fibre. Some of the potential health benefits of consuming high amylose wheat grains or their products such as starch include its role in regulating sugar and insulin and lipid levels, promoting intestinal heath, producing food of lower calorie value that promote satiety, improving laxation, water volume of faeces, promoting growth of probiotic bacteria, and enhancing faecal bile acid excretion.

Most processed starchy foods contain very little RS. The breads made using wild-type wheat flour and a conventional formulation and baking process contained <1% RS. In comparison, breads baked using the same process and storage conditions but containing the modified high amylose wheats had levels of RS as much as 10-fold higher (see International Publication No. WO 2006/069422). Legumes, which are one of the few rich sources of RS in the human diet, contain levels of RS that are normally <5%. Therefore, consumption of the high amylose wheat bread in amounts normally consumed by adults (e.g. 200 g/d) would readily supply at least 5-12 g of RS. Thus, incorporation of the high amylose wheat into food products has the potential to make a considerable contribution to dietary RS intakes of developed nations, where average daily intakes of RS are estimated to be only about 5 g.

Starch is widely used in the food, paper and chemical industries. The physical structure of starch can have an important impact on the nutritional and handling properties of starch for food or non-food or industrial products. Certain characteristics can be taken as an indication of starch structure including the distribution of amylopectin chain length, the degree and type of crystallinity, and properties such as gelatinisation temperature, viscosity and swelling volume. Changes in amylopectin chain length may be an indicator of altered crystallinity, gelatinisation or retrogradation of the amylopectin.

Whilst chemically or otherwise modified starches can be used in foods that provide functionality not normally afforded by unmodified sources, such processing has a tendency to either alter other components of value or carry the perception of being undesirable due to processes involved in modification. Therefore it is preferable to provide sources of constituents that can be used in unmodified form in foods.

Starch is initially synthesized in plants in chloroplasts of photosynthesizing tissues such as leaves, in the form of transitory starch. This is mobilized during subsequent dark periods to supply carbon for export to sink organs and energy metabolism, or for storage in organs such as seeds or tubers. Synthesis and long-term storage of starch occurs in the amyloplasts of the storage organs, such as the endosperm, where the starch is deposited as semicrystalline granules up to 100 µm in diameter. Granules contain both amylose and amylopectin, the former typically as amorphous material in the native starch granule while the latter is semicrystalline through stacking of the linear glucosidic chains. Granules also contain some of the proteins involved in starch biosynthesis.

The synthases of starch in the endosperm is carried out in four essential steps. ADP-glucose pyrophosphorylase (ADGP) catalyses the synthesis of ADP-glucose from glucose-1-phosphate and ATP. Starch synthases then promote the transfer of ADP-glucose to the end of an α-1,4 linked glucose unit. Thirdly, starch branching enzymes (SBE) form new α-1,6 linkages in α-polyglucans. Starch debranching enzymes (SDBE) then remove some the branch linkages through a mechanism that has not been fully resolved.

While it is clear that at least these four activities are required for normal starch granule synthesis in higher plants, multiple isoforms of enzymes taking part in one of the four activities are found in the endosperm of higher plants. Specific roles for some isozymes have been proposed on the basis of mutational analysis or through the modification of gene expression levels using transgenic approaches (Abel et al., 1996; Jobling et al., 1999; Schwall et al., 2000). However, the precise contributions of each isoform of each activity to starch biosynthesis are still not known, and these contributions appear to differ markedly between species.

In the cereal endosperm, two isoforms of ADP-glucose pyrophosphorylase (ADGP) are present, one form within the amyloplast, and one form in the cytoplasm. Each form is composed of two subunit types. The shrunken (sh2) and brittle (bt2) mutants in maize represent lesions in large and small subunits respectively.

Some efforts have focussed on starch synthase enzymes to investigate strategies to modulate the amylose/amylopectin ratio in wheat (see Sestili et al. 2010).

Four classes of starch synthase (SS) are found in the cereal endosperm, an isoform exclusively localised within the starch granule (granule-bound starch synthase (GBSS)) two forms that are partitioned between the granule and the soluble fraction (SSI and SSII) and a fourth form that is entirely located in the soluble fraction (SSIII). GBSS has been shown to be essential for amylose synthesis and mutations in SSII and SSIII have been shown to alter amylopectin structure.

A mutant wheat plant entirely lacking the SGP-1 (SSIIa) protein was produced by crossing lines which were lacking the A, B and D genome specific forms of SGP-1 (SSII) protein (Yamamori et al., 2000). Examination of the SSII null seeds showed that the mutation resulted in alterations in amylopectin structure, deformed starch granules, and an elevated relative amylose content to about 30-37% of the starch, which was an increase of about 8% over the wild-type level (Yamamori et al., 2000). Amylose was measured by colorimetric measurement, amperometric titration (both for iodine binding) and a concanavalin A method. Starch from the SSII null mutant exhibited a decreased gelatinisation temperature compared to starch from an equivalent, non-mutant plant. Starch content was reduced from 60% in the wild-type to below 50% in the SSII-null grain.

In maize, the dull1 mutation causes decreased starch content and increased amylose levels in endosperm, with the extent of the change depended on the genetic background, and increased degree of branching in the remaining amylopectin. The gene corresponding to the mutation was identified and isolated by a transposon-tagging strategy using the transposon mutator (Mu) and shown to encode the enzyme designated starch synthase II (SSII). The enzyme is now recognized as a member of the SSIII family in cereals. Mutant endosperm had reduced levels of SBEIIa activity associated with the dull1 mutation. It is not known if these findings are relevant to other cereals.

Lines of barley having an elevated proportion of amylose in grain starch have been identified. These include High Amylose Glacier (AC38) which has a relative amylose content of about 45%, and chemically induced mutations in the SSIIa gene of barley which raised levels of amylose in kernel starch to about 65-70% (WO 02/37955 A1; Morell et al., 2003). The starch showed reduced gelatinisation temperatures.

Two main classes of SBEs are known in plants, SBEI and SBEII. SBEII can be further categorized into two types in cereals, SBEIIa and SBEIIb. Additional forms of SBEs are also reported in some cereals, a putative 149 kDa SBEI from wheat and a 50/51 kDa SBE from barley.

Sequence alignment reveals a high degree of sequence similarity at both the nucleotide and amino acid levels and allows the grouping into the SBEI, SBEIIa and SBEIIb classes. SBEIIa and SBEIIb generally exhibit around 80% nucleotide sequence identity to each other, particularly in the central regions of the genes.

In maize and rice, high amylose phenotypes have been shown to result from lesions in the SBEIIb gene, also known as the amylose extender (ae) gene (Boyer and Preiss, 1981, Mizuno et al., 1993; Nishi et al., 2001). In these SBEIIb mutants, endosperm starch grains showed an abnormal morphology, amylose content was significantly elevated, the branch frequency of the residual amylopectin was reduced and the proportion of short chains (<DP17, especially DP8-12) was lower. Moreover, the gelatinisation temperature of the starch was increased. In addition, there was a significant pool of material that was defined as "intermediate" between amylose and amylopectin (Boyer et al., 1980, Takeda et al 1993b). In contrast, maize plants mutant in the SBEIIa gene due to a mutator (Mu) insertional element and consequently lacking SBEIIa protein expression were indistinguishable from wild-type plants in the branching of endosperm starch (Blauth et al., 2001), although they were altered in leaf starch. In both maize and rice, the SBEIIa and SBEIIb genes are not linked in the genome.

SBEIIa, SBEIIb and SBEI may also be distinguished by their expression patterns, both temporal and spatial, in endosperm and in other tissues. SBEI is expressed from mid-endosperm development onwards in wheat and maize (Morell et al., 1997). In contrast, SBEIIa and SBEIIb are expressed from an early stage of endosperm development. In maize, SBEIIb is the predominant form in the endosperm whereas SBEIIa is present at high expression levels in the leaf (Gao et al., 1997). In rice, SBEIIa and SBEIIb are found in the endosperm in approximately equal amounts. However, there are differences in timing and tissues of expression. SBEIIa is expressed at an earlier stage of seed development, being detected at 3 days after flowering, and was expressed in leaves, while SBEIIb was not detectable at 3 days after flowering and was most abundant in developing seeds at 7-10 days after flowering and was not expressed in leaves. In wheat endosperm, SBEI (Morell et al, 1997) is found exclusively in the soluble fraction, while SBEIIa and SBEIIb are found in both soluble and starch-granule associated fractions (Rahman et al., 1995).

Very high amylose varieties of maize have been known for some time. Low amylopectin starch maize which contains very high amylose content (>90%) was achieved by a considerable reduction in the SBEI activity together with an almost complete inactivation of SBEII activity (Sidebottom et al., 1998).

In potato, down regulation of the main SBE in tubers (SBE B, equivalent to SBEI) by antisense methods resulted in some novel starch characteristics but did not alter the amylose content (Safford et al., 1998). Antisense inhibition of the less abundant form of SBE (SBE A, analogous to SBEII in cereals) resulted in a moderate increase in amylose content to 38% (Jobling et al., 1999). However, the down regulation of both SBEII and SBEI gave much greater increases in the relative amylose content, to 60-89%, than the down-regulation of SBEII alone (Schwall et al., 2000).

International Publication No. WO 2005/001098 and International Publication No. WO 2006/069422 describe inter alia transgenic hexaploid wheat comprising exogenous duplex RNA constructs that reduce expression of SBEIIa and/or SBEIIb in the endosperm. Grain from transgenic lines carried either no SBEIIa and/or SBEIIb protein or reduced protein levels. A loss of SBEIIa protein from endosperm was associated with increased relative amylose levels of more than 50%. A loss of SBEIIb protein levels did not appear to substantially alter the proportion of amylose in grain starch. It was proposed but not established that a SBEIIa and/or SBEIIb triple null mutant substantially lacking expression of SBEIIa and SBEIIb proteins would result in further elevations of amylose levels. However, it was not known or predictable from the prior art how many mutant alleles of SBEIIa and/or SBEIIb would be required to provide high amylose levels of at least 50% as a proportion of the total starch. It was also unknown whether the grain of triple null genotypes would be viable or whether the wheat plants would be fertile.

There is a need in the art for improved high amylose wheat plants and for methods of producing same.

SUMMARY

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

As used herein the singular forms "a", "an" and "the" include plural aspects unless the context clearly dictates otherwise. Thus, for example, reference to "a mutation" includes a single mutation, as well as two or more mutations; reference to "a plant" includes one plant, as well as two or more plants; and so forth.

Each embodiment in this specification is to be applied mutatis mutandis to every other embodiment unless expressly stated otherwise.

Genes and other genetic material (e.g. mRNA, constructs etc) are represented in italics and their proteinaceous expression products are represented in non-italicised form. Thus, for example, SBEIIa is an expression product of SBEIIa.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A sequence listing is provided after the claims. A table describing the sequences in the sequence listing is provided after the Examples.

Unless defined otherwise, all technical and scientific terms used herein have the same meaning as commonly understood by those of ordinary skill in the art to which the invention pertains. Although any methods and materials similar or equivalent to those described herein can be used in the practice or testing of the present invention, preferred methods and materials are described.

The present invention provides a range of wheat plants having modified starch characteristics.

In one aspect, the present specification describes wheat grain (*Triticum aestivum*) comprising an embryo and starch. In some embodiments, the embryo comprises two identical alleles of an SBEIIa-A gene, two identical alleles of an SBEIIa-B gene and two identical alleles of an SBEIIa-D gene, wherein each of the SBEIIa genes gives rise to an amount of protein (w/w) or a protein having SBEIIa activity which is lower than the corresponding wild-type gene, preferably where one or two or three of the SBEIIa genes give rise to no protein having SBEIIa activity, and at least one of said genes comprises a point mutation, wherein the starch comprises amylose such that the grain has an amylose content of at least 50% (w/w) as a proportion of the extractable starch of the grain. In other words, the wheat grain is homozygous for mutant alleles at each of the three SBEIIa genes.

In some embodiments, the grain comprises at least one SBEIIa protein which has starch branching activity when expressed in developing endosperm, the protein being present in an amount or having starch branching enzyme activity of between 2% to 60%, or between 10% to 50%, or between 2% to 30%, or between 2% to 15%, or between 3% to 10%, or between 2% to 20% or between 2% to 25% of the amount or activity of the corresponding protein in a wild-type wheat grain. Preferably, the SBEIIa protein, which is a SBEIIa-A protein, a SBEIIa-B protein or a SBEIIa-D protein, has an amino acid substitution relative to the corresponding wild-type SBEIIa protein. It may additionally exhibit an altered affinity for binding to starch. The altered affinity may be an increase in affinity or, preferably, a decreased affinity for starch.

In a particular embodiment, the amount or activity of the SBEIIa protein in the grain is less than 2% of the amount or activity of SBEIIa protein in a wild-type wheat grain, and is preferably essentially absent, such as for example, is undetectable by a Western blot assay. Such wheat grain is referred to herein as being a "triple null SBEIIa mutant".

In an embodiment, the grain comprises an SBEIIa protein which is inactive due to an amino acid substitution in the protein relative to the corresponding wild-type protein, but which protein is present in the grain at a level of at least 50% relative to the wild-type. Alternatively, such a protein may be present at a level of less than 50% relative to the wild-type. In an embodiment, the protein is a truncated polypeptide relative to the wild-type. Such a polypeptide may be produced from a mutant SBEIIa gene comprising a premature translation termination (nonsense) codon. The grain may comprise 2 or even 3 such proteins. The grain may further comprise only one or only two SBEIIb proteins, or only one or only two active SBEIIb proteins.

In some embodiments, the embryo has only 1 null SBEIIa gene.

In other embodiments, the embryo has only 2 null SBEIIa genes

In other embodiments, the embryo has 3 null SBEIIa genes. In a preferred embodiment, the grain is essentially lacking SBEIIa protein. In these embodiments, it is preferred that each of the null SBEIIa genes consists of alleles which comprise, independently, a deletion in part or in whole of the SBEIIa gene or a point mutation such as a premature translation termination mutation, a splice site mutation, an insertion or an amino acid substitution mutation which inactivates the encoded SBEIIa polypeptide, so long as at least one of the SBEIIa genes comprises a point mutation. In preferred embodiments, one, two, or not more than one or not more than two SBEIIa genes in the embryo are deleted in whole. The deletions may also delete the linked SBEIIb gene on the same genome in part or in whole. In a more preferred embodiment, the embryo is homozygous not only for the 3 null SBEIIa genes but also for one (but not more than one) or two (but not more than two) null alleles of SBEIIb genes which may each be, independently, a deletion of an SBEIIb gene, in part or in whole, or a point mutation such as a premature translation termination mutation, a splice site mutation, an insertion or an amino acid substitution mutation which inactivates the encoded SBEIIb polypeptide. In other words, the embryo may comprise one (but not more than one), or two (but not more than two) Type I mutations as described hereinafter. Such grain comprises at least one SBEIIb protein.

In some embodiments, the grain has only one SBEIIa protein as determined by Western blot analysis, and the protein is encoded by one of the SBEIIa-A, SBEIIa-B and SBEIIa-D genes and has reduced starch branching enzyme activity, preferably no SBE activity, when produced in developing endosperm when compared to an SBEIIa protein encoded by the corresponding wild-type gene. In these embodiments, at least one and preferably both of the other two SBEIIa genes may be deleted in part or in whole. The second SBEIIa gene may be deleted in part and the third SBEIIa gene deleted in whole. If only one of the second or third SBEIIa genes is deleted in part or in whole, one of the second or third SBEIIa genes has a point mutation, which is preferably a null mutation such as a premature translation termination mutation, a splice site mutation, an insertion, or an amino acid substitution mutation which inactivates the encoded SBEIIa polypeptide. In preferred embodiments, one, two, or not more than one or not more than two SBEIIa genes in the embryo are deleted in whole. The deletions may also delete the linked SBEIIb gene on the same genome in part or in whole. In a more preferred embodiment, the embryo is homozygous not only for the alleles of the 3 SBEIIa genes, one of which encodes the one SBEIIa protein as determined by Western blot analysis, but also for one (but not more than one) or two (but not more than two) null alleles of SBEIIb genes which may each be, independently, a deletion of a SBEIIb gene, in part or in whole, or a point mutation such as a premature translation termination mutation, a splice site mutation, an insertion or an amino acid substitution mutation which inactivates the encoded SBEIIb polypeptide. In other words, the embryo may comprise one (but not more than one), or two (but not more than two) Type I mutations as described hereinafter. Such grain comprises at least one SBEIIb protein.

In some embodiments, the amount or activity of SBEIIa-A protein is less than 60%, less than 50%, less than 40%, less than 35% less than 30%, less than 20%, less than 10%, less than 5%, less than 2% of the amount or activity of the corresponding protein in a wild type wheat grain. In some embodiments, there is no detectable SBEIIa-A protein in the grain.

In some embodiments, the amount or activity of SBEIIa-B protein is less than 60%, less than 50%, less than 40%, less than 35% less than 30%, less than 20%, less than 10%, less than 5%, less than 2% of the amount or activity of the corresponding protein in a wild type wheat grain. In some embodiments, there is no detectable SBEIIa-B protein in the grain.

In some embodiments, the amount or activity of SBEIIa-D protein is less than 60%, less than 50%, less than 40%, less than 35% less than 30%, less than 20%, less than 10%, less than 5%, less than 2% of the amount or activity of the corresponding protein in a wild type wheat grain. In some embodiments, there is no detectable SBEIIa-D protein in the grain.

In an embodiment, the SBEIIa protein which is the SBEIIa-A protein, the SBEIIa-B protein, or the SBEIIa-D protein, has an altered mobility relative to its corresponding wild-type SBEIIa protein, as determined by affinity gel electrophoresis on gels containing starch. The altered mobility is an indication of an altered binding affinity to starch, which may be an increased affinity or preferably a decreased binding affinity to starch. In an embodiment, the binding affinity is decreased by at least 30% or at least 50%. The altered affinity is due to the presence of one or more amino acid substitutions, preferably only one substitution, in the polypeptide relative to the corresponding wild-type protein. The SBEIIa protein with altered mobility may have some SBEIIa activity, preferably a reduced activity relative to the corresponding wild-type SBEIIa protein, or it may be lacking SBEIIa activity.

In another embodiment, the grain lacks detectable SBEIIa protein, such as determined by Western blot analysis.

In another embodiment, at least one of the SBEIIa genes, namely the SBEIIa-A gene, the SBEIIa-B gene and/or the SBEIIa-D gene, of the grain has a point mutation. In some embodiments the gene(s) having the point mutation encode a polypeptide which has an amino acid substitution relative to the corresponding wild-type polypeptide. That is, the encoded protein has the same number of amino acids as the wild-type polypeptide. Preferably, the amino acid substitution is a non-conservative amino acid substitution. In this context, the wild-type amino acid sequences are as described herein, such as SEQ ID Nos: 1, 2 and 3. In some embodiments, the point mutation is a single nucleotide change which generates a premature translation termination codon (nonsense codon) in the protein coding region of the gene. The nucleotide change generating the nonsense codon may be in exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, exon 19, exon 20 or exon 21 of the gene. In other embodiments, the point mutation is a splice site mutation which reduces or prevents normal splicing of the transcript of the SBEIIa gene. The point mutation may be at the 5'- or 3'-splice site of intron 1, intron 2, intron 3, intron 4, intron 5, intron 6, intron 7, intron 8, intron 9, intron 10, intron 11, intron 12, intron 13, intron 14, intron 15, intron 16, intron 17, intron 18, intron 19, or intron 20 of the SBEIIa gene.

In another embodiments, one of the SBEIIa-A, SBEIIa-B or SBEIIa-D genes in the embryo comprises a point mutation such that the protein encoded by said gene lacks starch branching enzyme activity.

In another embodiment, the grain embryo comprises null alleles which are deletion mutations in the B and D genomes which delete at least part of the SBEIIa-B and SBEIIa-D genes, respectively and wherein the SBEIIa-A gene comprises the point mutation; or having null alleles which are deletion mutations in the A and D genomes which delete at least part of the SBEIIa-A and SBEIIa-D genes, respectively and wherein the SBEIIa-B gene comprises the point mutation; or having null alleles which are deletion mutations in the A and B genomes which delete at least part of the SBEIIa-A and SBEIIa-B genes, respectively and wherein the SBEIIa-D gene comprises the point mutation.

In another embodiment, the embryo comprises 6 SBEIIb alleles of which at least one has a loss of function mutation.

In yet further embodiments, the embryo of the grain has no null alleles of SBEIIb genes, or only 2, only 4 or 6 null alleles of SBEIIb genes. Preferably, the embryo is homozygous for each of the three SBEIIa genes and each of the three SBEIIb genes.

In some embodiments, the embryo comprises only one or only two SBEIIb proteins which have starch branching enzyme activity when produced in developing endosperm, or only one or only two SBEIIb proteins which are detectable by Western blot analysis. In an embodiment, the grain comprises an SBEIIb protein which is inactive due to an amino acid substitution in the protein relative to the corresponding wild-type protein, but which protein is present in the grain at a level of at least 50% relative to the wild-type. Alternatively, such a protein may be present at a level of less than 50% relative to the wild-type. In an embodiment, the protein is a truncated polypeptide relative to the wild-type. Such a polypeptide may be produced from a mutant SBEIIb gene comprising a premature translation termination (nonsense) codon. The grain may comprise 2 or even 3 such proteins.

In another embodiment, the grain embryo comprises a null mutation which is a deletion mutation in the B genome which deletes at least part of the SBEIIa-B gene and at least a part of the SBEIIb-B gene, preferably which deletes the whole of the SBEIIa-B gene and/or the SBEIIb-B gene; or comprising a null mutation which is a deletion mutation in the D genome which deletes at least part of the SBEIIa-D gene and at least a part of an SBEIIb-D gene, preferably which deletes the whole of the SBEIIa-D gene and/or the SBEIIb-D gene; or comprising a null mutation which is a deletion mutation in the B genome which deletes at least part of the SBEIIa-A gene and at least a part of the SBEIIb-A gene, preferably which deletes the whole of the SBEIIa-A gene and/or the SBEIIb-A gene. In an embodiment, the grain embryo comprises point mutations in both of the SBEIIa-B and SBEIIb-B genes, both of the SBEIIa-D and SBEIIb-D genes, or both of the SBEIIa-A and SBEIIb-A genes.

In a particular embodiment, the wheat grain (*Triticum aestivum*) comprises (i) starch whose amylose content is about 60% (w/w) to about 90% (w/w) of the starch of the grain as determined by an iodometric method, or preferably about 67% (w/w) to about 90% (w/w) amylose, or preferably about 70% (w/w) to about 90% (w/w) amylose, (ii) an embryo which is homozygous for one or two different SBEIIa alleles each of which comprises a deletion of part or all of the SBEIIa gene relative to the corresponding wild-type SBEIIa gene, is homozygous for one or two different SBEIIa genes which each comprise a point mutation, the point mutation preferably being a splice site mutation or a single nucleotide polymorphism which generates a nonsense codon or a non-conservative amino acid substitution, and is homozygous for one or two different SBEIIb alleles which each comprise a deletion of part or all of the SBEIIb gene relative to the corresponding wild-type SBEIIb gene, (iii) no SBEIIa proteins or only one SBEIIa protein or only two different SBEIIa proteins, and (iv) no SBEIIb proteins or only one SBEIIb protein or only two different SBEIIb proteins. The one or two SBEIIa proteins and the one or two SBEIIb proteins may each independently have no activity, be a truncated protein relative to the corresponding wild-type protein, or be a starch binding affinity variant relative to the corresponding wild-type protein. The embryo may comprise deletions of the SBEIIa-A and SBEIIa-B genes and a point mutation in the SBEIIa-D gene, or deletions of the SBEIIa-A and SBEIIa-D genes and a point mutation in the SBEIIa-B gene, or deletions of the SBEIIa-D and SBEIIa-B genes and a point mutation in the SBEIIa-A gene, in combination with a deletion in the SBEIIb-A gene, SBEIIb-B gene or the SBEIIb-D gene or two thereof.

The invention also provides for a wheat plant capable of producing the grain of the aforesaid embodiment, and methods of producing and using the grain, and products produced from the grain. It is understood that the wheat plant of the invention and the wheat grain embryo from which it is produced have the same genotype, and therefore of the wheat grain of the invention as described herein.

Usefully, in some embodiments, the amount or activity of total SBEII protein in the grain is less than 60%, or less than 2%, of the amount or activity of total SBEII protein in a wild-type wheat grain.

Importantly, the present specification provides grain which is viable, which germinates at essentially the same rate as wild-type grain, which germinates at a rate equal to at least 80% relative to the wild-type grain when measured in the time period of 7-14 days post-imbibition, and/or which produces phenotypically normal plants that are male and female fertile and grow at essentially the same rate as a corresponding wild-type plant and/or produces essentially the same grain yield as the corresponding wild-type plant.

Further, in some embodiments, the grain has a germination rate of about 70% to about 90%, or about 90% to about 100%, relative to the germination rate of a wild-type grain, preferably measured in the time period of 7-14 days post-imbibition.

In embodiments, at least one, more than one, or all of the mutations are i) introduced mutations, ii) were induced in a parental wheat plant or seed by mutagenesis with a mutagenic agent such as a chemical agent, biological agent or irradiation, or iii) were introduced in order to modify the plant genome. The irradiation is preferably heavy ion bombardment (HIB), and the chemical agent is preferably an azide. In an embodiment, the chemical agent is not EMS and/or the wheat variety that was mutagenised is not Cadenza.

As described herein, in some embodiments, the starch of the grain has an amylose content of at least about 60% (w/w) or at least about 67% (w/w), or at least about 70% (w/w), or at least about 75% (w/w), or at least about 79% (w/w), or at least about 82% (w/w), or at least about 85% (w/w), as a proportion of the extractable starch of the grain. The amylose content of the grain starch may be to a maximum of about 90% (w/w). Preferably, the amylose content of the grain starch is about 80% (w/w) or about 85% (w/w) or about 90% (w/w). In this context, the amylose content is defined as a percentage on a weight basis of the starch of the grain.

In an embodiment, the grain provided herein is non-transgenic or is free of any exogenous nucleic acid that encodes an RNA which reduces expression of an SBEIIa gene.

As described herein SBEIIa activity and/or SBEIIb activity may be determined by assaying the enzymatic activity in developing endosperm, or by assaying the amount of SBEIIa protein and/or SBEIIb protein in harvested grain by immunological or other means known to the skilled artisan.

In another embodiment, the starch of the grain is characterised by one or more of properties selected from the group consisting of:
(i) comprising at least 2% resistant starch, preferably at least about 3% RS, more preferably at least about 6% or about 8% RS, or about 6% or about 8% or about 10% RS;
(ii) comprising a low relative glycaemic index (GI);
(iii) comprising low relative amylopectin levels;
(iv) distorted starch granules, preferably at least 50% of the starch granules are distorted in shape and/or size;
(v) reduced granule birefringence, preferably such that less than 50% of the granules show birefringence;
(vi) reduced swelling volume, such as reduced by at least 10%;
(vii) modified chain length distribution and/or branching frequency;
(viii) delayed end of gelatinisation temperature and higher peak temperature;
(ix) reduced viscosity (peak viscosity, pasting temperature, etc.);
(x) increased molecular weight of amylopectin; and
(xi) modified % crystallinity or % A-type or B-type starch, relative to wild-type wheat starch granules or starch.

In some embodiments, the grain as described herein is comprised in a wheat plant. In some embodiments, the grain is developing grain. In other embodiments the grain is mature, harvested grain, preferably grain harvested from field-grown plants. In some embodiments, the quantity of grain is at least 1 kg weight or at least 1 tonne weight.

In many embodiments, the grain is processed so that it is no longer capable of germinating, such as being kibbled, cracked, par-boiled, rolled, pearled, milled or ground grain. The invention also provides a process for producing a milled product, comprising the steps of obtaining the grain of the invention and milling the grain.

The present invention includes a wheat plant (*Triticum aestivum*) which is capable of producing grain as described herein. In an embodiment, the grain comprises an embryo and starch wherein the embryo comprises two identical alleles of an SBEIIa-A gene, two identical alleles of an SBEIIa-B gene and two identical alleles of an SBEIIa-D gene, wherein each of the SBEIIa genes gives rise to an amount of protein (w/w) or a protein having SBEIIa activity which is lower than the corresponding wild-type gene, and at least one of said genes comprises a point mutation, wherein the starch comprises amylose such that the starch of the grain has an amylose content of at least 50% (w/w) as a proportion of the extractable starch of the grain. Preferably, the starch of the grain has an amylose content of at least about 67% (w/w), or at least about 75% (w/w), or at least about 79% (w/w), or at least about 82% (w/w), or at least about 85% (w/w), as a proportion of the extractable starch of the grain. The amylose content of the grain starch may be to a maximum of about 90% (w/w). Preferably, the amylose content of the grain starch is about 80% (w/w) or about 85% (w/w) or about 90% (w/w).

In some embodiments, the grain of the wheat plant comprises at least one SBEIIa protein which has starch branching activity when expressed in developing endosperm, the protein being present in an amount or having starch branching enzyme activity of between 2% to 60%, or between 10% to 50%, or between 2% to 30%, or between 2% to 15%, or between 3% to 10%, or between 2% to 20% or between 2% to 25% of the amount or activity of the corresponding protein in a wild-type wheat grain.

In some embodiments, the amount or activity of at least one SBEIIa protein is less than 60%, less than 50%, less than 40%, less than 35% less than 30%, less than 20%, less than 10%, less than 5%, less than 2% of the amount or activity of the corresponding protein in a wild type wheat grain. In some embodiments, there is no detectable SBEIIa protein activity in the grain.

In some embodiments, the amount or activity of SBEIIa-A protein is less than 60%, less than 50%, less than 40%, less than 35% less than 30%, less than 20%, less than 10%, less than 5%, less than 2% of the amount or activity of the corresponding protein in a wild type wheat grain. In some embodiments, there is no detectable SBEIIa-A protein activity in the grain.

In some embodiments, the amount or activity of SBEIIa-B protein is less than 60%, less than 50%, less than 40%, less than 35% less than 30%, less than 20%, less than 10%, less than 5%, less than 2% of the amount or activity of the corresponding protein in a wild type wheat grain. In some embodiments, there is no detectable SBEIIa-B protein activity in the grain.

In some embodiments, the amount or activity of SBEIIa-D protein is less than 60%, less than 50%, less than 40%, less than 35% less than 30%, less than 20%, less than 10%, less than 5%, less than 2% of the amount or activity of the corresponding protein in a wild type wheat grain. In some embodiments, there is no detectable SBEIIa-D protein activity in the grain.

In preferred embodiments, the wheat plant is male and female fertile, or preferably has a level of both male and female fertility that is essentially the same as a corresponding wild-type plant.

The present specification describes wholemeal or flour produced from the grain described herein, and the use of the grain to produce such wholemeal or flour. In an embodiment, the grain comprises an embryo and starch wherein the embryo comprises two identical alleles of an SBEIIa-A gene, two identical alleles of an SBEIIa-B gene and two identical alleles of an SBEIIa-D gene, wherein each of the SBEIIa genes gives rise to an amount of protein (w/w) or a protein having SBEIIa activity which is lower than the corresponding wild-type gene, and at least one of said genes comprises a point mutation, wherein the starch comprises amylose such that the grain has an amylose content of at least 50% (w/w) as a proportion of the extractable starch of the grain. Preferably, the starch of the grain has an amylose content of at least about 60% (w/w) or at least about 67% (w/w), or at least about 75% (w/w), or at least about 79% (w/w), or at least about 82% (w/w), or at least about 85% (w/w), as a proportion of the extractable starch of the grain. The amylose content of the grain starch may be to a maximum of about 90% (w/w). Preferably, the amylose content of the grain starch is about 80% (w/w) or about 85% (w/w) or about 90% (w/w). The amylose content of the starch of the flour or wholemeal is the same as the amylose content of the starch of the grain. In an embodiment, the wholemeal or flour comprises at least about 3, preferably at least about 6, more preferably at least about 8 g resistant starch per 100 g wholemeal or flour. The starch of the flour or wholemeal preferably has an increased gelatinisation temperature relative to the starch of wild-type flour or wholemeal. The wholemeal, flour or food ingredient produced therefrom may be refined by fractionation, bleaching, heat treatment to stabilise the ingredient, treated with enzymes or blended with other food ingredients such as wholemeal or flour from a wild-type wheat. The flour is preferably white flour, having specifications as known in the art of baking. In a preferred embodiment, the wholemeal, flour or other food is packaged ready for sale as a food ingredient, which package may include instructions of recipes for its use.

In another aspect, the specification describes wheat starch granules or wheat starch produced from the grain as described herein. In an embodiment, the grain comprises an embryo and starch wherein the embryo comprises two identical alleles of an SBEIIa-A gene, two identical alleles of an SBEIIa-B gene and two identical alleles of an SBEIIa-D gene, wherein each of the SBEIIa genes gives rise to an amount of protein (w/w) or a protein having SBEIIa activity which is lower than the corresponding wild-type gene, and at least one of said genes comprises a point mutation, wherein the starch comprises amylose such that the grain has an amylose content of at least 50% (w/w) as a proportion of the extractable starch of the grain.

In some embodiments, the starch granules or starch of comprise at least 50% (w/w), or at least 60% (w/w), or at least 67% (w/w), or at least 70% (w/w), or at least 75% (w/w), or at least 79% (w/w), or at least 82% (w/w), or at least 85% (w/w) amylose as a proportion of the starch. The amylose content may be to a maximum of about 90% (w/w). Preferably, the amylose content is about 80% (w/w) or about 85% (w/w) or about 90% (w/w). The amylose content of the starch is the same as the amylose content of the starch of the grain from which it is produced, and is preferably determined by an iodometric method. In an embodiment, the starch granules or starch is characterised by one or more of:
(i) in the case of starch granules, comprising less than 2%, or 2% to 30% of the amount of total SBEII or SBEIIa relative to wild-type wheat starch granules, preferably comprising an SBEIIa protein with an altered affinity for starch; or
(ii) at least 2% resistant starch, preferably at least about 3%, at least about 6% or at least about 8% resistant starch;
(iii) comprising a low relative glycaemic index (GI);
(iv) comprising low relative amylopectin levels;
(v) distorted starch granules preferably at least 50% of the starch granules are distorted in shape and/or size;
(vi) reduced granule birefringence preferably such that less than 50% of the granules show birefringence;
(vii) reduced swelling volume;
(viii) modified chain length distribution and/or branching frequency;
(ix) delayed end of gelatinisation temperature and higher peak temperature;
(x) reduced viscosity (peak viscosity, pasting temperature, etc.);
(xi) increased molecular weight of amylopectin; and/or
(xii) modified % crystallinity % A-type or B-type starch, relative to a wild-type wheat starch granules or starch.

The present specification provides a food ingredient that comprises the grain, the wholemeal or flour, or the starch granules or starch as described herein. In an embodiment, the grain comprises an embryo and starch wherein the embryo comprises two identical alleles of an SBEIIa-A gene, two identical alleles of an SBEIIa-B gene and two identical alleles of an SBEIIa-D gene, wherein each of the SBEIIa genes gives rise to an amount of protein (w/w) or a protein having SBEIIa activity which is lower than the corresponding wild-type gene, and at least one of said genes comprises a point mutation, wherein the starch comprises amylose such that the grain has an amylose content of at least 50% (w/w) as a proportion of the extractable starch of the grain. Preferably, the starch of the grain, wholemeal or flour has an amylose content of at least about 60% (w/w) or at least about 67% (w/w), or at least about 75% (w/w), or at least about 79% (w/w), or at least about 82% (w/w), or at least about 85% (w/w), as a proportion of the extractable starch of the grain. The amylose content of the grain starch may be to a maximum of about 90% (w/w). Preferably, the amylose content of the grain starch is about 80% (w/w) or about 85% (w/w) or about 90% (w/w).

In some embodiments, the grain is processed such as kibbled, cracked, par-boiled, rolled, pearled, milled or ground grain or any combination of these.

In another embodiment, the food or drink product comprises a food or drink ingredient at a level of at least 10% on a dry weight basis, wherein the ingredient is wheat grain, the wholemeal or flour, or the starch granules or starch as described herein. In an embodiment, the grain comprises an embryo and starch wherein the embryo comprises two identical alleles of an SBEIIa-A gene, two identical alleles of an SBEIIa-B gene and two identical alleles of an SBEIIa-D gene, wherein each of the SBEIIa genes gives rise to an amount of protein (w/w) or a protein having SBEIIa activity which is lower than the corresponding wild-type gene, and at least one of said genes comprises a point mutation, wherein the starch comprises amylose such that the grain has an amylose content of at least 50% (w/w) as a proportion of the extractable starch of the grain. Preferably, the starch of the ingredient has an amylose content of at least about 60% (w/w) or at least about 67% (w/w), or at least about 75% (w/w), or at least about 79% (w/w), or at least about 82% (w/w), or at least about 85% (w/w), as a proportion of the extractable starch of the grain. The amylose content of the starch may be to a maximum of about 90% (w/w). Preferably, the amylose content of the starch is about 80% (w/w) or about 85% (w/w) or about 90% (w/w).

The present specification further described compositions or blends comprising the grain, or the wholemeal or flour, or the wheat starch granules or wheat starch at a level of at least 10% by weight, and wheat grain having a level of amylose lower than about 50% (w/w) or flour, wholemeal, starch granules or starch obtained therefrom.

In another aspect, the present specification described a process of producing a wheat plant that produces grain comprising an amylose content of at least 50% (w/w), or at least 60% (w/w), or at least 67% (w/w) as a proportion of the total starch in the grain, or at least about 75% (w/w), or at least about 79% (w/w), or at least about 82% (w/w), or at least about 85% (w/w), as a proportion of the extractable starch of the grain. The amylose content of the grain starch may be to a maximum of about 90% (w/w). Preferably, the amylose content of the grain starch is about 80% (w/w) or about 85% (w/w) or about 90% (w/w). The process comprises the steps of (i) crossing two parental wheat plants each comprising a point mutation in each of one, two or three SBEIIa or SBEIIb genes selected from the group consisting of SBEIIa-A, SBEIIa-B, SBEIIa-D, SBEIIb-A, SBEIIb-B and SBEIIb-D, or of mutagenising a parental plant comprising said point mutations; and step (ii) screening plants or grain obtained from the cross or mutagenesis, or progeny plants or grain obtained therefrom, by analysing DNA, RNA, protein, starch granules or starch from the plants or grain, and step (iii) selecting a fertile plant that lacks SBEIIa or SBEIIa starch branching activity. A preferred method of mutagenesis is heavy ion bombardment or another irradiation method, or the use of zinc finger nucleases or TAL effectors, as known in the art.

In some embodiments of the process, the grain of the selected fertile wheat plant is characterised by one of the features as described herein above.

In some embodiments, the specification provides a method of screening a wheat plant or grain, the method comprising (i) determining the amount or activity of SBEIIa and/or SBEIIb relative to the amount or activity in a wild-type or control plant or grain and selecting a plant which produces grain, or selecting grain as described herein, wherein the grain comprises an embryo and starch and wherein the embryo comprises two identical alleles of an SBEIIa-A gene, two identical alleles of an SBEIIa-B gene and two identical alleles of an SBEIIa-D gene, wherein each of the SBEIIa genes gives rise to an amount of protein (w/w) or a protein having SBEIIa activity which is lower than the corresponding wild-type gene, and at least one of said genes comprises a point mutation, wherein the starch comprises amylose such that the grain has an amylose content of at least 50% (w/w) or at least 60% (w/w), or at least 67% (w/w), or between about 60% (w/w) and about 90% (w/w) as a proportion of the extractable starch of the grain. Preferably, the starch of the grain has an amylose content of at least about 75% (w/w), or at least about 79% (w/w), or at least about 82% (w/w), or at least about 85% (w/w), as a proportion of the extractable starch of the grain. The amylose content of the grain starch may be to a maximum of about 90% (w/w). Preferably, the amylose content of the grain starch is about 80% (w/w) or about 85% (w/w) or about 90% (w/w).

In some embodiments, the invention comprises a process of producing a food or a drink comprising the following steps: (i) obtaining grain as described herein, or an ingredient comprising flour, wholemeal, starch granules or starch obtained therefrom, (ii) optionally processing the grain to produce a food or drink ingredient, and (iii) adding a food or drink ingredient from (i) or (ii) to another food or drink ingredient, thereby producing the food or drink.

In another aspect, the present invention contemplates a method for improving one or more parameters of metabolic health, bowel health or cardiovascular health in a subject in need thereof, or of preventing or reducing the severity or incidence of a metabolic disease such as diabetes, bowel disease or cardiovascular disease, the method comprising providing to the subject the grain, or the food or drink product as described herein.

In another aspect, the present specification contemplates a grain, or food or drink product as described herein for use in improving one or more parameters of metabolic health, bowel health or cardiovascular health, or of preventing or reducing the severity or incidence of metabolic, bowel or cardiovascular disease in a subject.

The present invention further contemplates a process of producing grain, comprising the steps of i) obtaining a wheat plant as described herein, ii) harvesting wheat grain from the plant, and iii) optionally, processing the grain, such as by milling the grain, preferably so as to render the grain unable to germinate.

The invention includes a process of producing starch, comprising the steps of i) obtaining wheat grain according to the present description, and ii) extracting the starch from the grain, thereby producing the starch.

In some embodiments, the invention includes a method of trading wheat grain, comprising obtaining the wheat grain as described herein, and trading the obtained wheat grain for pecuniary gain. In some embodiments, the obtaining the wheat grain comprises cultivating or harvesting the wheat grain. In some embodiments, the step of obtaining the wheat grain further comprises storing the wheat grain. In further embodiments, the step of obtaining the wheat grain further comprises transporting the wheat grain to a different location.

In another aspect, the specification provides a process of producing bins of wheat grain comprising:
a) reaping wheat stalks comprising wheat grain as defined herein;
b) threshing and/or winnowing the stalks to separate the grain from the chaff; and
c) sifting and/or sorting the grain separated in step b), and loading the sifted and/or sorted grain into bins, thereby producing bins of wheat grain.

Methods are provided for obtaining or identifying or selecting or producing a wheat plant that produces grain comprising an amylose content of at least 50% (w/w), or at least 60% (w/w), or at least 67% (w/w) or about 80% (w/w), or between about 60% (w/w) and about 90% (w/w) as a proportion of the total starch in the grain. The wheat plant may be identified or selected from a population of multiple candidate plants, such as a mutagenised population or a population of plants resulting from a crossing process or a back-crossing/breeding process.

In some embodiments, the method comprises: (i) crossing two parental wheat plants each comprising a loss of function mutation in each of one, two or three SBEIIa or SBEIIb genes selected from the group consisting of SBEIIa-A, SBEIIa-B, SBEIIa-D, SBEIIb-A, SBEIIb-B and SBEIIb-D, or of mutagenising a parental plant comprising said loss of function mutations; and (ii) screening plants or grain obtained from the cross or mutagenesis, or progeny plants or grain obtained therefrom, by analysing DNA, RNA, protein, starch granules or starch from the plants or grain, and (iii) selecting a fertile plant that exhibits a level or activity of SBEIIa in its grain that is less than 2% relative to the level or activity of the respective protein in a wild-type grain. Alternatively, the method comprises steps (ii) and (iii) above, with step (i) being optional, such as when selecting or identifying a plant from a population of multiple candidate plants.

In some embodiments, the grain of the selected fertile wheat plant is characterised by one or more features as defined herein.

In another embodiment, the invention provides a method of screening a wheat plant or grain, the method comprising (i) determining the level or activity of SBEIIa relative to the level or activity in a wild type or control plant or grain and selecting plant or grain having less than 2% of the level or activity of total SBEIIa protein in a wild-type plant. The grain may be further characterized by other features of the grain of the invention.

The above summary is not and should not be seen in any way as an exhaustive recitation of all embodiments of the present invention.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1 is a representation showing an alignment of SBE IIa protein alignment (AAK26821.1 (SEQ ID NO:3) is from the D genome, CAR95900.1 (SEQ ID NO:2) from the B genome and CAA72154 (SEQ ID NO:1) from the A genome). Dots in the alignment indicate the identical amino acid is present as in the uppermost sequence.

FIG. 2 is a representation showing an alignment of SBEIIb amino acid sequences encoded by exons 1 to 3 from the A (SEQ ID NO:4), B (SEQ ID NO:5) and D genomes (amino acids 1-152 of SEQ ID NO:6) of wheat. Dashes indicate amino acids are present in the protein but the sequence not known, dots in the alignment indicate the identical amino acid is present as in the uppermost sequence.

FIG. 7 is a representation showing an alignment of DNA sequences of the exons 12 to 14 region of homoeologous SBEIIa genes obtained from the wheat variety Chara. The nucleotide sequence for the Chara B genome fragment (SEQ ID NO:161) is shown in its entirety, while the corresponding nucleotides for the homoeologous A and D genome fragments are shown only where there are polymorphisms. Dots indicate the corresponding nucleotides are identical to the Chara B genome fragment. Dashes indicate that the corresponding nucleotide is absent from the sequence.

FIG. 9 is a representation showing an alignment of DNA sequences of the exon 3 region of homoeologous SBEIIa genes obtained from the wheat variety Chinese Spring. The nucleotide sequence for the Chinese Spring D genome fragment (SEQ ID NO:163) is shown in its entirety, while the corresponding nucleotides for the homoeologous A and B genome fragments are shown only where there are polymorphisms. Dots indicate the corresponding nucleotides are identical to the Chinese Spring D genome fragment.

FIGS. 17 (a) and (b) are graphical representations of data showing the effect of adding increasing quantities of wheat lines on water absorption (a) and Mixograph mixing times (b).

FIGS. 18 (a) and (b) are graphical representations of data illustrating the effect of adding increasing quantities of high amylose wheat flour on Resistant Starch (a) and predicted GI (b) (HI %) of small scale bread loaves.

BRIEF DESCRIPTION OF THE TABLES

Figure 3:
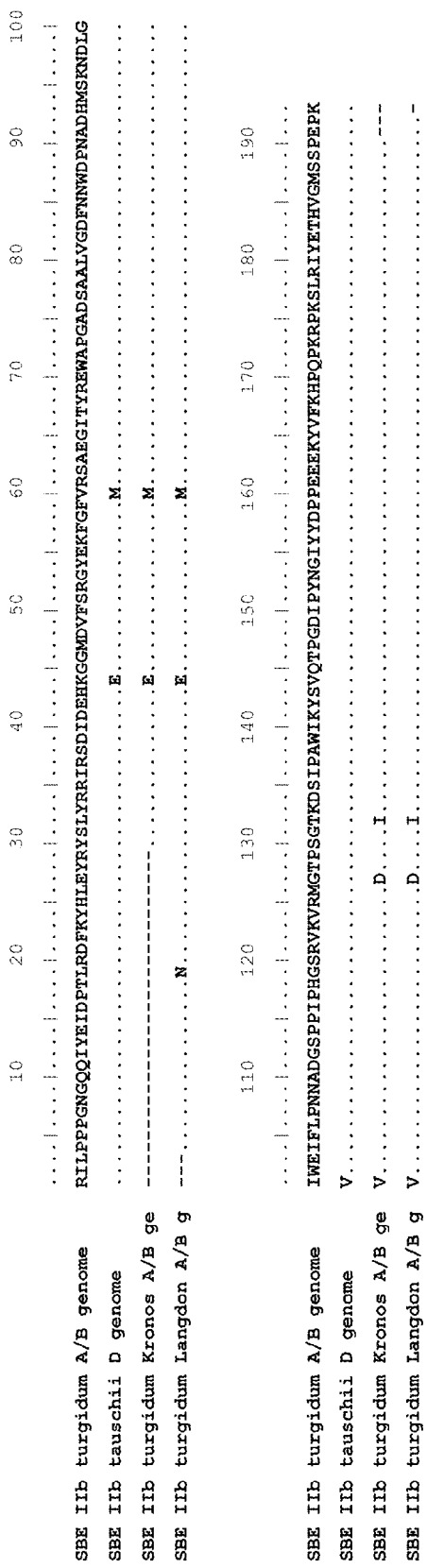
FIG. 3 is a representation of an alignment of SBEIIb amino acid sequences. SBE IIb *turgidum* A/B genome (SEQ ID NO:160).

Table A provides a description of the sequences in the sequence listing.

Table 1 provides starch branching enzyme genes characterized from cereals.

Table 2 provides an amino acid sub-classification.

Table 3 provides exemplary amino acid substitutions.

Table 4 provides genome specific primers for wheat SBEIIa gene.

Table 5 provides nucleotide sequences of genome specific primers for SBEIIa.

Table 6 provides primers designed to amplify parts of the SBEIIa gene specifically from the A genome of wheat.

Table 7 provides primers designed to amplify parts of the SBEIIa gene specifically from the B genome of wheat.

Table 8 provides primers designed to amplify parts of the SBEIIa gene specifically from the D genome of wheat.

Table 9 provides genome specific primers for wheat SBEIIb gene.

Table 10 provides nucleotide sequences of genome specific primers for SBEIIb.

Table 11 provides total SBEII and SBEIIa and SBEIIb expression and amylose content of RNAi lines of wheat as described in Example 4.

Table 12 provides a list of microsatellite markers tested in the mutants as described in Example 5.

Table 13 provides mutants identified from HIB population and microsatellite mapping data as described in Example 5.

Table 14 provides a description of double null mutants of SBEII identified as described in Example 5.

Table 15 provides a description of crosses performed between double and single null mutants as described in Example 5.

Table 16 provides tabulation of amylose content in grain starch of triple nulls mutants as described in Example 5.

Table 17 provides fertility observations on F2 progeny plants.

Table 18 provides SBEII allelic composition and amylose proportion data for double nulls identified.

Table 19 provides a summary of the SNP mutants identified from the azide-mutagenised population of wheat (cv. Sunstate)

Table 20 provides the amylose content of the SBEIIa triple null mutants as determined by an iodometric method Table 21 provides amylose content of SBEIIa triple null mutants.

Table 22 provides amylose content of SBEIIa triple null mutants.

Table 23 provides preliminary agronomic data on the triple null plants

Table 24 provides starch characterisation of grain starch from transgenic wheat lines.

Table 25 provides molecular weight distribution of starch fractions from wheat transgenic lines.

Table 26 provides RVA parameters of hp5'-SBEIIa transgenic wheat starch.

Table 27 provides DSC parameters of gelatinisation peak of hp5'-SBEIIa transgenic wheat starch compared to the control NB1.

Table 28 provides RS content in rolled and flaked grain products.

Table 29 provides resistant starch content in food products at varying level of incorporation of high amylose wheat (HAW).

Table 30 provides genome-specific primers referred to in Example 18.

Table 31 provides details of selected print mutants from Arche and Apache populations.

Table 32 provides details of selected print mutant plants for crosses with double null (HIB deletions) mutants.

Table 33 provides details of results of crosses (F1 seed population) from crosses between single SBEIIa point mutant and double null (deletion) mutants.

Table 34 provides provides results of NIRS screening of F2 seeds from crosses between single SBEIIa point mutants and double null (HIB deletions) mutants.

Table 35 provides amylose levels and thousand kernel weight (TKW) for HAW SBEIIa triple null grain compared to control grain and RNAi reference line 85.2c.

DETAILED DESCRIPTION

The present invention is based in part on the observations made in the experiments described herein that mutant plants and grain comprising at least one point mutation in an SBEIIa gene were favoured over plants and grain which had deletions in each of the SBEIIa genes for combining mutant SBEIIa genes, in particular to obtain phenotypically normal, male and female fertile plants and grain which germinated at rates similar to wild-type grain. One likely explanation of this observation was that deletions tend to remove important genetic elements adjacent to the SBEIIa genes.

It was also observed that to obtain an amylose content of at least 50% (w/w) in the grain starch, at which level the amount of resistant starch and associated health benefits were increased substantially, the total SBEII activity and particularly the SBEIIa activity in the grain needed to be reduced to below 30% of the wild-type level.

Figure 5:
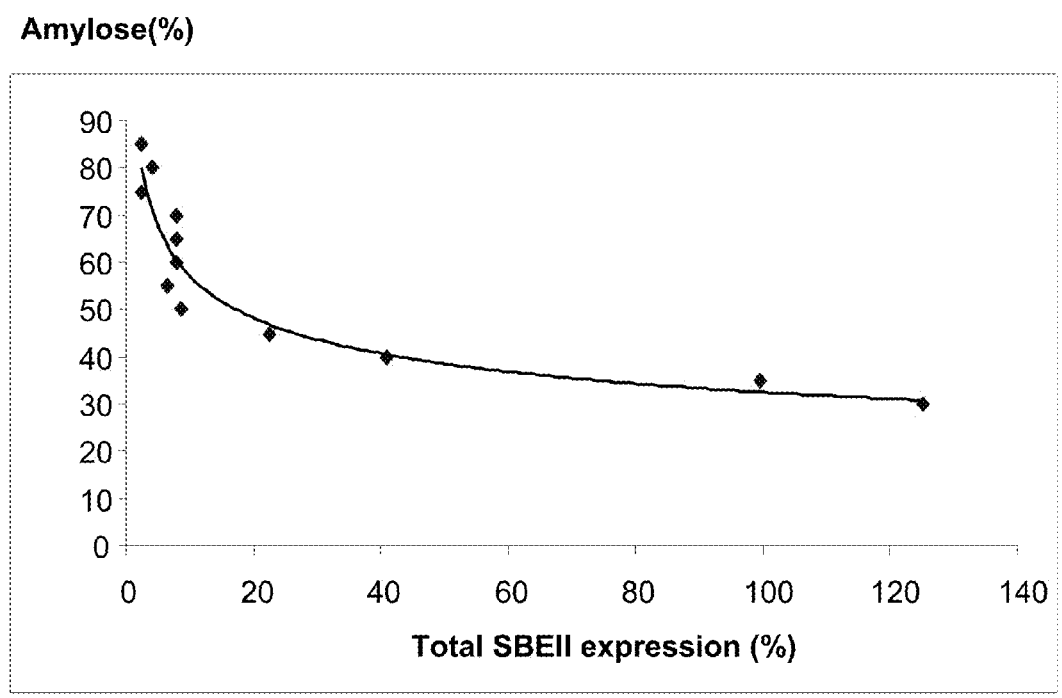
FIG. 5 is a graphical representation of data showing an amylose model derived from behaviour of SBEII transgenic lines.

As described herein, it was determined that, in hexaploid wheat, reducing the level and/or activity of starch branching enzyme II (SBEII) protein from each of three homoeologous SBEIIa genes or from at least two homoeologous SBEIIa genes and two or three homoeologous SBEIIb genes leads to a substantial non-linear increase in the proportion of amylose in starch of the wheat endosperm compared to plants having null mutation in two homoeologous SBEIIa genes. This non-linear relationship between amylose content and SBEII levels in grain of hexaploid wheat is illustrated graphically in FIGS. 5 and 6.

By studying partial and complete loss of function mutations in combinations of SBEIIa and/or SBEIIb alleles from the A, B and D genomes, the role of multiple SBEII genes in modulating starch characteristics has been established. Specifically, the number of mutant alleles and combinations of mutant alleles required to obtain fertile wheat plants having very high levels of amylose has been investigated and determined.

As shown herein, developing hexaploid wheat endosperm expresses SBEIIa and SBEIIb from each of the A, B and D genomes. Tetraploid wheat expresses SBEIIa and SBEIIb from each of the A and B genomes. As used herein, "SBEIIa expressed from the A genome" or "SBEIIa-A" means a starch branching enzyme whose amino acid sequence is set forth in SEQ ID NO: 1 or which is at least 99% identical to the amino acid sequence set forth in SEQ ID NO: 1 or comprising such a sequence. The amino acid sequence of SEQ ID NO: 1 (Genbank Accession No. CAA72154) corresponds to an SBEIIa expressed from the A genome of wheat, which is used herein as the reference sequence for wild-type SBEIIa-A. The protein of SEQ ID NO: 1 is 823 amino acids long. Active variants of this enzyme exist in wheat, for example in cultivar Cheyenne, see Accession No. AF286319 which is 99.88% (822/823) identical to SEQ ID NO. 1, or for Accession No. AK335707 (Chinese Spring). Such variants are included in "SBEIIa-A" provided they have essentially wild-type starch branching enzyme activity as for SEQ ID NO: 1.

As used herein, "SBEIIa expressed from the B genome" or "SBEIIa-B" means a starch branching enzyme whose amino acid sequence is set forth in SEQ ID NO: 2 or which is at least 99% identical to the amino acid sequence set forth in SEQ ID NO: 2 or comprising such a sequence. The amino acid sequence of SEQ ID NO: 2 (Genbank Accession No. CAR95900) corresponds to the SBEIIa expressed from the B genome of wheat variety Chinese Spring, which is used herein as the reference sequence for wild-type SBEIIa-B. The protein of SEQ ID NO: 2 is 823 amino acids long. Active variants of this enzyme may exist in wheat and are included in SBEIIa-B provided they have essentially wild-type starch branching enzyme activity as for SEQ ID NO: 2. SEQ ID NO: 2 is 98.42% (811/824) identical to SEQ ID NO: 1. The alignment of the amino acid sequences in FIG. 1 shows the amino acid differences which may be used to distinguish the proteins or to classify variants as SBEIIa-A or SBEIIa-B.

As used herein, "SBEIIa expressed from the D genome" or "SBEIIa-D" means a starch branching enzyme whose amino acid sequence is set forth in SEQ ID NO: 3 or which is at least 98% identical to the amino acid sequence set forth in SEQ ID NO: 3 or comprising such a sequence. The amino acid sequence of SEQ ID NO: 3 (Genbank Accession No. AAK26821) corresponds to the SBEIIa expressed from the D genome in *A. tauschii*, a likely progenitor of the D genome of hexaploid wheat, which is used herein as the reference sequence for wild-type SBEIIa-D. The protein of SEQ ID NO: 3 is 819 amino acids long. Active variants of this enzyme may exist in wheat and are included in SBEIIa-D provided they have essentially wild-type starch branching enzyme activity as for SEQ ID NO: 3. SEQ ID NO: 3 is 97.57% (803/823) identical to SEQ ID NO: 1 and 97.81% (805/823) identical to SEQ ID NO: 2. The alignment of the amino acid sequences in FIG. 1 shows amino acid differences which may be used to distinguish the proteins or to classify variants as SBEIIa-A, SBEIIa-B or SBEIIa-D.

When comparing amino acid sequences to determine the percentage identity in this context, for example by Blastp, the full length sequences should be compared, and gaps in a sequence counted as amino acid differences.

As used herein, an "SBEIIa protein" includes protein variants which have reduced or no starch branching enzyme activity, as well as the proteins having essentially wild-type enzyme activity. It is also understood that SBEIIa proteins may be present in grain, particularly dormant grain as commonly harvested commercially, but in an inactive state because of the physiological conditions in the grain. Such proteins are included in "SBEIIa proteins" as used herein. The SBEIIa proteins may be enzymatically active during only part of grain development, in particular in developing endosperm when storage starch is typically deposited, but in inactive state otherwise. Such SBEIIa protein may be detected and quantitated readily using immunological methods such as Western blot analysis. An "SBEIIb protein" as used herein has an analogous meaning.

As used herein, "SBEIIb expressed from the A genome" or "SBEIIb-A" means a starch branching enzyme comprising the amino acid sequence set forth in SEQ ID NO: 4 or which is at least 98% identical to the amino acid sequence set forth in SEQ ID NO: 4 or comprising such a sequence. The amino acid sequence of SEQ ID NO: 4 corresponds to the amino terminal sequence of SBEIIb expressed from the A genome of wheat, which is used herein as the reference sequence for wild-type SBEIIb-A.

As used herein, "SBEIIb expressed from the B genome" or "SBEIIb-B" means a starch branching enzyme comprising the amino acid sequence set forth in SEQ ID NO: 5 or which is at least 98% identical to the amino acid sequence set forth in SEQ ID NO: 5 or comprising such a sequence. The amino acid sequence SEQ ID NO: 5, which is used herein as the reference sequence for wild-type SBEIIb-B, is a partial amino acid sequence encoded by exons 2-3 of the SBEIIb-B gene in wheat. A variant SBEIIb-B sequence is the amino acid sequence encoded by the nucleotide sequence of Accession No. AK335378 isolated from cv. Chinese Spring.

As used herein, "SBEIIb expressed from the D genome" or "SBEIIb-D" means a starch branching enzyme whose amino acid sequence is set forth in SEQ ID NO: 6 or which is at least 98% identical to the amino acid sequence set forth in SEQ ID NO: 6 or comprising such a sequence. The amino acid sequence of SEQ ID NO: 6 (Genbank Accession No. AAW80631) corresponds to the SBEIIb expressed from the D genome of *A. tauschii*, a likely progenitor of the D genome of hexaploid wheat, and is used herein as the reference sequence for wild-type SBEIIb-D. Active variants of this enzyme exist in wheat and are included in SBEIIb-D provided they have essentially wild-type starch branching enzyme activity as for SEQ ID NO: 6. For example, SEQ ID NO: 4 of US patent application publication No. 20050074891, beginning at the first methionine, shows the amino acid sequence of a SBEIIb-D protein which is 99.5% identical to SEQ ID NO: 6 in this application. The alignment of the amino acid sequences in FIG. 2 shows amino acid differences which may be used to distinguish SBEIIb proteins or to classify variants as SBEIIb-A, SBEIIb-B or SBEIIb-D.

Thus, "wild-type" as used herein when referring to SBEIIa-A means a starch branching enzyme whose amino acid sequence is set forth in SEQ ID NO: 1; "wild-type" as used herein when referring to SBEIIa-B means a starch branching enzyme whose amino acid sequence is set forth in SEQ ID NO: 2; "wild-type" as used herein when referring to SBEIIa-D means a starch branching enzyme whose amino acid sequence is set forth in SEQ ID NO: 3; "wild-type" as used herein when referring to SBEIIb-A means a starch branching enzyme whose amino acid sequence comprises the sequence set forth in SEQ ID NO: 4; "wild-type" as used herein when referring to SBEIIb-B means a starch branching enzyme whose amino acid sequence comprises the sequence set forth in SEQ ID NO: 5; and, "wild-type" as used herein when referring to SBEIIb-D means a starch branching enzyme whose amino acid sequence is set forth in SEQ ID NO: 6.

As used herein, the terms "SBEIIa gene", "SBEIIa-B gene" "wheat SBEIIa gene" and "wheat SBEIIb gene" and the like refer to the genes that encode functional SBEIIa or SBEIIb enzymes, respectively, in wheat, including homologous genes present in other wheat varieties, and also mutant forms of the genes which encode enzymes with reduced activity or undetectable activity. These include, but are not limited to, the wheat SBEII genes which have been cloned, including the genomic and cDNA sequences listed in Table 1 or described in the Figures. The genes as used herein encompasses mutant forms which do not encode any proteins at all, in which case the mutant forms represent null alleles of the genes. Alleles of the genes include mutant alleles where at least part of the gene is deleted, including where the entire gene is deleted, which alleles also represent null alleles of the genes.

An "endogenous SBEII gene" refers to an SBEII gene which is in its native location in the wheat genome, including wild-type and mutant forms. In contrast, the terms "isolated SBEII gene" and "exogenous SBEII gene" refer to an SBEII gene which is not in its native location, for example having been cloned, synthesized, comprised in a vector or in the form of a transgene in a cell, preferably as transgene in a transgenic wheat plant. The SBEII gene in this context may be any of the specific forms as described as follows.

As used herein, "the SBEIIa gene on the A genome of wheat" or "SBEIIa-A gene" means any polynucleotide which encodes SBEIIa-A as defined herein or which is derived from a polynucleotide which encodes SBEIIa-A, including naturally occurring polynucleotides, sequence variants or synthetic polynucleotides, including "wild-type SBEIIa-A gene(s)" which encode an SBEIIa-A with essentially wild-type activity, and "mutant SBEIIa-A gene(s)" which do not encode an SBEIIa-A with essentially wild-type activity but are recognizably derived from a wild-type SBEIIa-A gene. Comparison of the nucleotide sequence of a mutant form of an SBEII gene with a suite of wild-type SBEII genes is used to determine which of the SBEII genes it is derived from and so to classify it. For example, a mutant SBEII gene is considered to be a mutant SBEIIa-A gene if its nucleotide sequence is more closely related, i.e. having a higher degree of sequence identity, to a wild-type SBEIIa-A gene than to any other SBEII gene. A mutant SBEIIa-A gene encodes a SBE with reduced starch branching enzyme activity (partial mutant), or a protein which lacks SBE activity or no protein at all (null mutant gene). An exemplary nucleotide sequence of a cDNA corresponding to a SBEIIa-A gene is given in Genbank Accession No. Y11282. Other exemplary nucleotide sequences are provided in Accession No. AF286319 (SBEIIa-A), AK335707 (SBEIIa-A), a partial cDNA sequence in Accession No. EU670724, a genomic SBEIIa-B sequence in Accession No. FM865435, and a cDNA corresponding to a splicing variant for an SBEIIa-A protein in Accession No. AF338432. Sequences of parts of SBEIIa-A genes are also given herein as referred to in FIGS. 7, 8, 9 and 10 and SEQ ID NOs 13, 14 and 15.

As used herein, the terms "SBEIIa expressed from the B genome" or "SBEIIa-B", "SBEIIa expressed from the D genome" or "SBEIIa-D", "SBEIIb expressed from the A genome" or "SBEIIb-A", "SBEIIb expressed from the B genome" or "SBEIIb-B" and "SBEIIb expressed from the D genome" or "SBEIIb-D" have corresponding meanings to that for SBEIIa-A in the previous paragraph.

Illustrative partial SBEIIb-A, SBEIIb-B and SBEIIb-D protein sequences are provided in FIG. 2. Illustrative SBEIIb-A amino acid sequences are set out in SEQ ID NO: 4 (amino terminal sequence encoded by exon 1-3). Illustrative SBEIIb-B amino acid sequences are set out in SEQ ID NO: 5. Illustrative SBEIIb-D amino acid sequences are set out in SEQ ID NO: 6, SEQ ID NO: 7 and SEQ ID No: 9.

The SBEII genes as defined above include any regulatory sequences that are 5' or 3' of the transcribed region, including the promoter region, that regulate the expression of the associated transcribed region, and introns within the transcribed regions.

Figure 20:
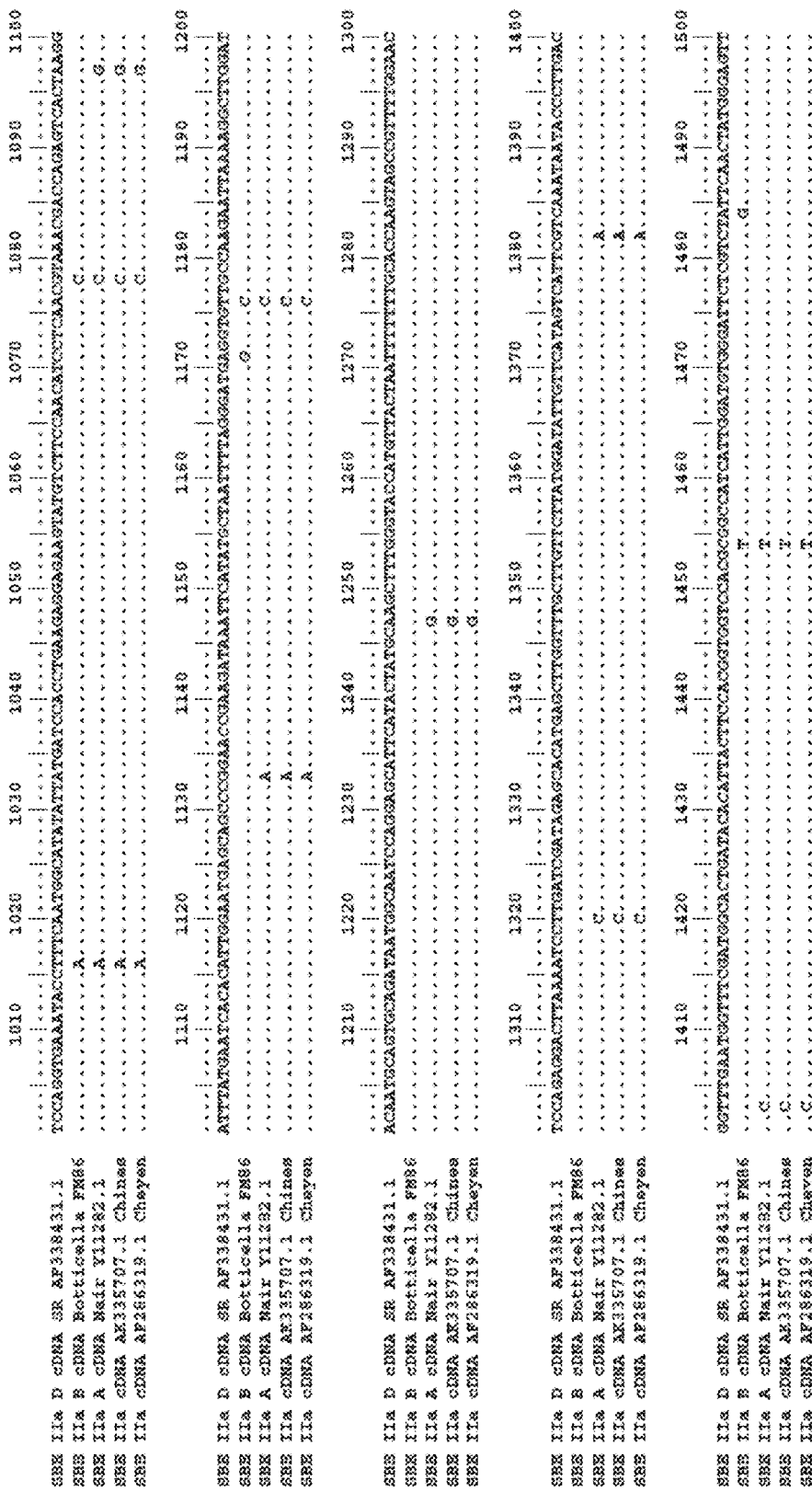
FIG. 20 is an alignment of nucleotide sequences of cDNAs from wild-type SBEIIa genes of wheat. The nucleotide sequence for the cDNA corresponding to SBEIIa-D (SEQ ID NO:165; Accession No. AF338431.1) from *A. tauschii* is shown in its entirety in the top line of each panel, while the corresponding nucleotides for the homoeologous cDNAs for SBEIIa-A (SEQ ID NO:150; Accession No. Y11282, Nair et al., 1997) and SBEIIa-B (SEQ ID NO:166; derived from the genomic sequence in Accession No. FM865435, Botticella et al., 2011) are shown only where there are polymorphisms. Dots indicate the corresponding nucleotides are identical to the AF338431 sequence. The AK335707.1 (SEQ ID NO:167) and AF286319.1 (SEQ ID NO:168) cDNA sequences are likely from SBEIIa-A, as they are closer to the A genome sequence than the B or D genomes, but from naturally occurring variants in cultivars Chinese Spring and Cheyenne, respectively.
Figure 20:
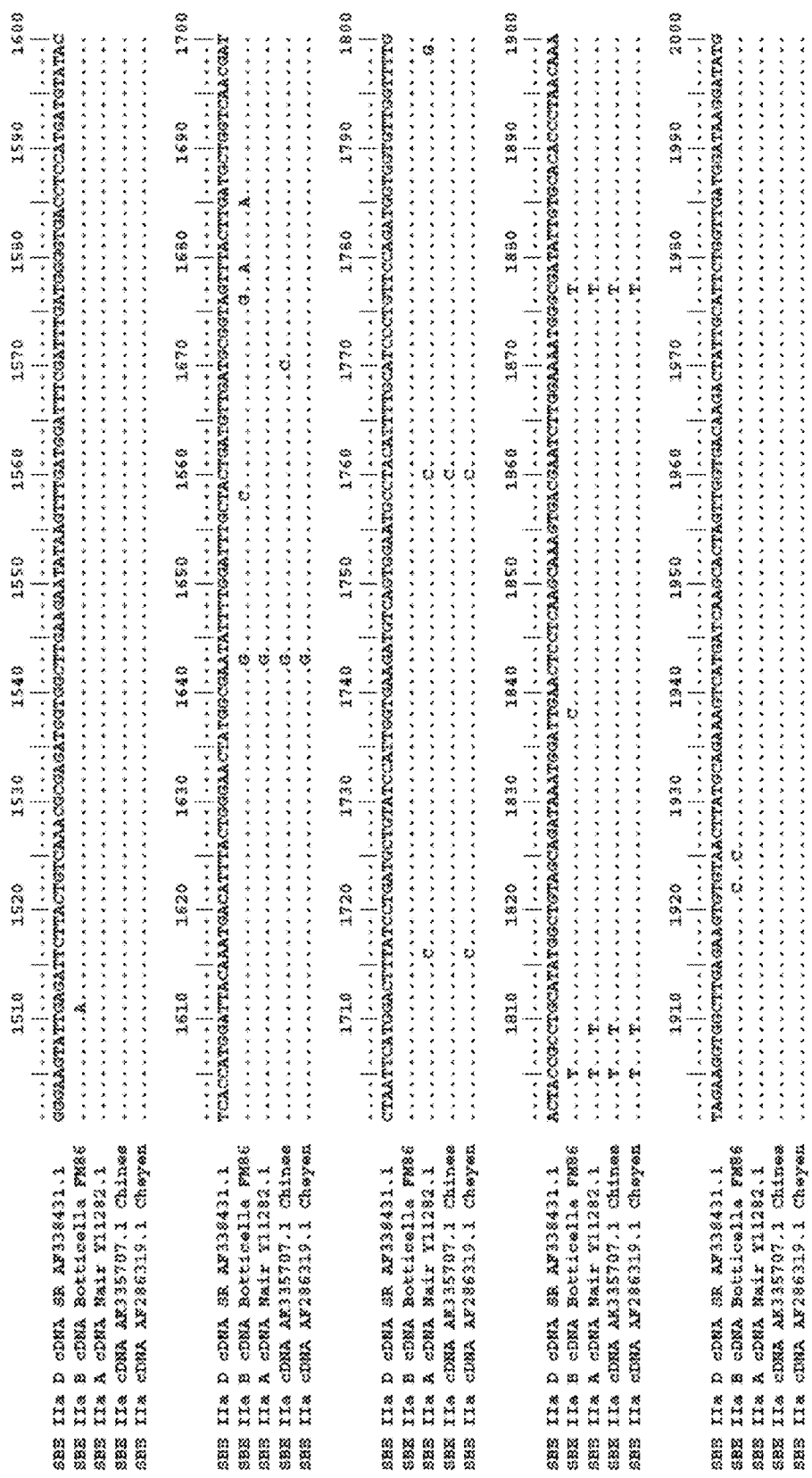
Figure 20:
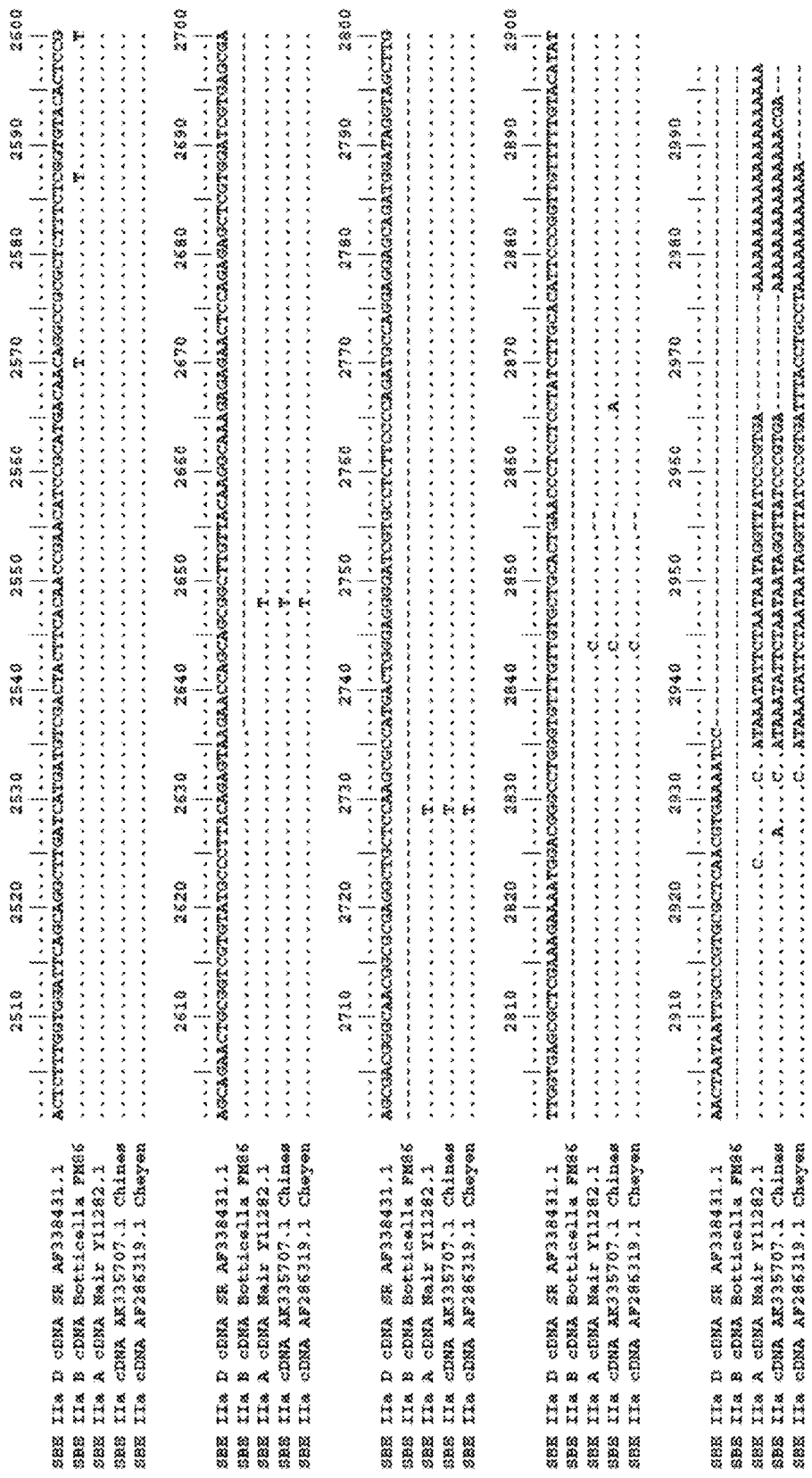

It would be understood that there is natural variation in the sequences of SBEIIa and SBEIIb genes from different wheat varieties. FIG. 20 provides an alignment of cDNA sequences for wild-type SBEIIa genes of wheat. The homologous genes are readily recognizable by the skilled artisan on the basis of sequence identity. The degree of sequence identity between homologous SBEIIa genes or the proteins is thought to be at least 90%, similarly for SBEIIb genes or proteins. Wheat SBEIIa genes are about 80% identical in sequence to wheat SBEIIb genes. The encoded proteins are also about 80% identical in sequence.

An allele is a variant of a gene at a single genetic locus. A diploid organism has two sets of chromosomes. Each chromosome has one copy of each gene (one allele). If both alleles are the same the organism is homozygous with respect to that gene, if the alleles are different, the organism is heterozygous with respect to that gene. The interaction between alleles at a locus is generally described as dominant or recessive.

Different alleles in the embryo may have the same or a different mutation and different alleles may be combined using methods known in the art.

Alleles that do not encode or are not capable of leading to the production of any active enzyme are null alleles.

Reference to a null mutation includes a null mutation independently selected from the group consisting of a deletion mutation, an insertion mutation, a splice-site mutation, a premature translation termination mutation, and a frameshift mutation. In an embodiment, one or more of the null mutations are non-conservative amino acid substitution mutations or a null mutation has a combination of two or more non-conservative amino acid substitutions. In this context, non-conservative amino acid substitutions are as defined herein.

A loss of function mutation, which includes a partial loss of function mutation in an allele as well as complete loss of function mutation, means a mutation in the allele leading to a reduced level or activity of SBEII, SBEIIa or SBEIIb enzyme in the grain. The mutation in the allele may mean, for example, that less protein having wild-type or reduced activity is translated or that wild-type or reduced levels of transcription are followed by translation of an enzyme with reduced enzyme activity. The mutation may mean, for example, that no or less RNA is transcribed from the gene comprising the mutation or that the protein produced has no or reduced activity.

A "point mutation" refers to a single nucleotide base change which includes a deletion, substitution or insertion. The mutation may further be a splice-site mutation, a premature translation termination mutation, a frame shift mutation or other loss of function mutation wherein the mutation results in no protein being produced or the protein is produced in lower amounts or the protein produced has lower SBE activity. In some embodiments, the point mutation results in a conservative or preferably a non-conservative amino acid substitution as described herein.

A "reduced" or "lower" amount or level of protein means reduced or lower relative to the amount or level produced by the corresponding wild-type allele. Typically, the reduction is by at least 40%, preferably at least 50% or at least 60%, more preferably at least 80% or 90% relative to the wild-type. In a most preferred embodiment, the protein is not detected, such as for example in a Western blot assay as described herein.

A "reduced" activity means reduced relative to the corresponding wild-type SBEII, SBEIIa or SBEIIb enzyme.

Protein "activity" refers to SBE activity which may be measured directly or indirectly by various means known in the art and as described herein. For example SBE activity may be measured directly by phosphorylation stimulation assay or by iodine stain assay. Binding to starch may be determined by measuring SBE affinity for starch by, for example, affinity gel electrophoresis as described herein. The affinity of binding to starch provides an indirect measure of SBE activity. As described herein, partial loss of function mutants include mutants expressing an SBEIIa protein having modified, including reduced or increased, affinity for starch. Such mutants expressing at least one SBEIIa protein exhibiting reduced (lower) affinity for starch by approximately (about) one third (30%) would be expected to exhibit a greater reduction or lowering of SBE protein activity when measured directly.

Different alleles in the embryo may have the same or a different mutation and different alleles may be combined using methods known in the art.

In some embodiments, the amount of SBEIIa protein or SBEIIb protein is reduced because there is less transcription or translation of the SBEIIa gene or SBEIIb gene, respectively.

In some embodiments, the amount by weight of SBEIIa protein or SBEIIb protein is reduced even though there is a wild-type number of SBEIIa protein molecules or SBEIIb protein molecules in the grain, because some of the proteins produced are shorter than wild-type SBEIIa protein or SBEIIb protein, e.g. the mutant SBEIIa protein or SBEIIb protein is truncated due to a premature translation termination signal.

As used herein, "two identical alleles of an SBEIIa-A gene", means that the two alleles of the SBEIIa-A gene are identical to each other; "two identical alleles of an SBEIIa-B gene", means that the two alleles of the SBEIIa-B gene are identical to each other; "two identical alleles of an SBEIIa-D gene", means that the two alleles of the SBEIIa-D gene are identical to each other; "two identical alleles of an SBEIIb-A gene", means that the two alleles of the SBEIIb-A gene are identical to each other; "two identical alleles of an SBEIIb-B gene", means that the two alleles of the SBEIIb-B gene are identical to each other; and, "two identical alleles of an SBEIIb-D gene", means that the two alleles of the SBEIIb-D gene are identical to each other.

The wheat plants of the invention can be produced and identified after mutagenesis. In some embodiments, the wheat plant is non-transgenic, which is desirable in some markets, or which is free of any exogenous nucleic acid molecule which reduces expression of an SBEIIa gene. In another embodiment, the wheat plant is transgenic, for example it comprises an exogenous nucleic acid molecule other than one which reduces expression of an SBEIIa gene, such as for example, an exogenous nucleic acid molecule which encodes a polypeptide that confers herbicide tolerance to the plant.

Mutant wheat plants having a mutation in a single SBEII gene which can be combined by crossing and selection with other SBEII mutations to generate the wheat plants of the invention can be either synthetic, for example, by performing site-directed mutagenesis on the nucleic acid, or induced by mutagenic treatment, or may be naturally occurring, i.e. isolated from a natural source. In some embodiments, a progenitor plant cell, tissue, seed or plant may be subjected to mutagenesis to produce single or multiple mutations, such as nucleotide substitutions, deletions, additions and/or codon modification.

Preferred wheat plants and grain of the invention comprise at least one introduced SBEII mutation, more preferably two or more introduced SBEII mutations, and may comprise no mutations from a natural source i.e. all of the mutant SBEIIa and SBEIIb alleles in the plant were obtained by synthetic means or by mutagenic treatment.

Mutagenesis can be achieved by chemical or radiation means, for example EMS or sodium azide (Zwar and Chandler, 1995) treatment of seed, or gamma irradiation, well know in the art. Chemical mutagenesis tends to favour nucleotide substitutions rather than deletions. Heavy ion beam (HIB) irradiation is known as an effective technique for mutation breeding to produce new plant cultivars, see for example Hayashi et al., 2007 and Kazama et al, 2008. Ion beam irradiation has two physical factors, the dose (gy) and LET (linear energy transfer, keV/um) for biological effects that determine the amount of DNA damage and the size of DNA deletion, and these can be adjusted according to the desired extent of mutagenesis. HIB generates a collection of mutants, many of them comprising deletions that may be screened for mutations in specific SBEII genes as shown in the Examples. Mutants which are identified may be backcrossed with non-mutated wheat plants as recurrent parents in order to remove and therefore reduce the effect of unlinked mutations in the mutagenised genome, see Example 9.

Biological agents useful in producing site-specific mutants include enzymes that include double stranded breaks in DNA that stimulate endogenous repair mechanisms. These include endonucleases, zinc finger nucleases, TAL effector proteins, transposases and site-specific recombinases. Zinc finger nucleases (ZFNs), for example, facilitate site-specific cleavage within a genome allowing endogenous or other end joining repair mechanisms to introduce deletions or insertions to repair the gap. Zinc finger nuclease technology is reviewed in Le Provost et al., 2009, See also Durai et al., 2005 and Liu et al., 2010.

Isolation of mutants may be achieved by screening mutagenised plants or seed. For example, a mutagenized population of wheat may be screened directly for the SBEIIa and/or SBEIIb genotype or indirectly by screening for a phenotype that results from mutations in the SBEII genes. Screening directly for the genotype preferably includes assaying for the presence of mutations in the SBEII genes, which may be observed in PCR assays by the absence of specific SBEIIa or SBEIIb markers as expected when some of the genes are deleted, or heteroduplex based assays as in Tilling. Screening for the phenotype may comprise screening for a loss or reduction in amount of one or more SBEIIa or SBEIIb proteins by ELISA or affinity chromatography, or increased amylose content in the grain starch. In hexaploid wheat, screening is preferably done in a genotype that already lacks one or two of the SBEII activities, for example in a wheat plant already mutant in the SBEIIa or SBEIIb genes on two of the three genomes, so that a mutant further lacking the functional activity is sought. In tetraploid wheat, screening is preferably done in a genotype that already lacks one SBEII activity, on either the A or B genome, and identifying a mutant which is reduced in the SBEII from the second genome. Affinity chromatography may be carried out as demonstrated in Example 11. Large populations of mutagenised seeds (thousands or tens of thousands of seeds) may be screened for high amylose phenotypes using near infra-red spectroscopy (NIR) as demonstrated in Example 10. Using NIR, a sub-population enriched for high amylose candidates was obtainable. By these means, high throughput screening is readily achievable and allows the isolation of mutants at a frequency of approximately one per several hundred seeds.

Plants and seeds of the invention can be produced using the process known as TILLING (Targeting Induced Local Lesions IN Genomes), in that one or more of the mutations in the wheat plants or grain may be produced by this method. In a first step, introduced mutations such as novel single base pair changes are induced in a population of plants by treating seeds or pollen with a chemical or radiation mutagen, and then advancing plants to a generation where mutations will be stably inherited, typically an M2 generation where homozygotes may be identified. DNA is extracted, and seeds are stored from all members of the population to create a resource that can be accessed repeatedly over time. For a TILLING assay, PCR primers are designed to specifically amplify a single gene target of interest. Next, dye-labeled primers can be used to amplify PCR products from pooled DNA of multiple individuals. These PCR products are denatured and reannealed to allow the formation of mismatched base pairs. Mismatches, or heteroduplexes, represent both naturally occurring single nucleotide polymorphisms (SNPs) (i.e., several plants from the population are likely to carry the same polymorphism) and induced SNPs (i.e., only rare individual plants are likely to display the mutation). After heteroduplex formation, the use of an endonuclease, such as Cel I, that recognizes and cleaves mismatched DNA, or the use of High Resolution Melting, is used to discovering novel SNPs within a TILLING population. For example, see Botticella et al., 2011.

Using this approach, many thousands of plants can be screened to identify any individual with a single base change as well as small insertions or deletions (1-30 bp) in any gene or specific region of the genome. Genomic fragments being assayed can range in size anywhere from 0.3 to 1.6 kb. At 8-fold pooling and amplifying 1.4 kb fragments with 96 lanes per assay, this combination allows up to a million base pairs of genomic DNA to be screened per single assay, making TILLING a high-throughput technique. TILLING is further described in Slade and Knauf, 2005, and Henikoff et al., 2004.

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms. This has been called Ecotilling (Comai et al., 2004). Plates containing arrayed ecotypic DNA can be screened rather than pools of DNA from mutagenized plants. Because detection is on gels with nearly base pair resolution and background patterns are uniform across lanes, bands that are of identical size can be matched, thus discovering and genotyping mutations in a single step. In this way, sequencing of the mutant gene is simple and efficient.

Identified mutations may then be introduced into desirable genetic backgrounds by crossing the mutant with a plant of the desired genetic background and performing a suitable number of backcrosses to cross out the originally undesired parent background.

In the context of this application, an "induced mutation" or "introduced mutation" is an artificially induced genetic variation which may be the result of chemical, radiation or biologically-based mutagenesis, for example transposon or T-DNA insertion.

In some embodiments, mutations are null mutations such as nonsense mutations, frameshift mutations, deletions, insertional mutations or splice-site variants which completely inactivate the gene. In other embodiments, mutations are partial mutations which retain some SBEII activity, but less than wild-type levels of the enzyme. Nucleotide insertional derivatives include 5' and 3' terminal fusions as well as intra-sequence insertions of single or multiple nucleotides.

Insertional nucleotide sequence variants are those in which one or more nucleotides are introduced into a site in the nucleotide sequence, either at a predetermined site as is possible with zinc finger nucleases (ZFN) or other homologous recombination methods, or by random insertion with suitable screening of the resulting product.

Deletional variants are characterised by the removal of one or more nucleotides from the sequence. Preferably, a mutant gene has only a single insertion or deletion of a sequence of nucleotides relative to the wild-type gene. The deletion may be extensive enough to include one or more exons or introns, both exons and introns, an intron-exon boundary, a part of the promoter, the translational start site, or even the entire gene. Deletions may extend far enough to include at least part of, or the whole of, both the SBEIIa and SBEIIb genes on the A, B or D genome, based on the close genetic linkage of the two genes. Insertions or deletions within the exons of the protein coding region of a gene which insert or delete a number of nucleotides which is not an exact multiple of three, thereby causing a change in the reading frame during translation, almost always abolish activity of the mutant gene comprising such insertion or deletion.

Substitutional nucleotide variants are those in which at least one nucleotide in the sequence has been removed and a different nucleotide inserted in its place. In some embodiments, the number of nucleotides affected by substitutions in a mutant gene relative to the wild-type gene is a maximum of ten nucleotides, more preferably a maximum of 9, 8, 7, 6, 5, 4, 3, or 2, or most preferably only one nucleotide. Substitutions may be "silent" in that the substitution does not change the amino acid defined by the codon. Nucleotide substitutions may reduce the translation efficiency and thereby reduce the SBEII expression level, for example by reducing the mRNA stability or, if near an exon-intron splice boundary, alter the splicing efficiency. Silent substitutions that do not alter the translation efficiency of a SBEIIa or SBEIIb gene are not expected to alter the activity of the genes and are therefore regarded herein as non-mutant, i.e. such genes are active variants and not encompassed in "mutant alleles". Alternatively, the nucleotide substitution(s) may change the encoded amino acid sequence and thereby alter the activity of the encoded enzyme, particularly if conserved amino acids are substituted for another amino acid which is quite different i.e. a non-conservative substitution. Typical conservative substitutions are those made in accordance with Table 3.

The term "mutation" as used herein does not include silent nucleotide substitutions which do not affect the activity of the gene, and therefore includes only alterations in the gene sequence which affect the gene activity. The term "polymorphism" refers to any change in the nucleotide sequence including such silent nucleotide substitutions. Screening methods may first involve screening for polymorphisms and secondly for mutations within a group of polymorphic variants.

As is understood in the art, hexaploid wheats such as bread wheat comprise three genomes which are commonly designated the A, B and D genomes, while tetraploid wheats such as *durum* wheat comprise two genomes commonly designated the A and B genomes. Each genome comprises 7 pairs of chromosomes which may be observed by cytological methods during meiosis and thus identified, as is well known in the art.

The terms "plant(s)" and "wheat plant(s)" as used herein as a noun generally refer to whole plants, but when "plant" or "wheat" is used as an adjective, the terms refer to any substance which is present in, obtained from, derived from, or related to a plant or a wheat plant, such as for example, plant organs (e.g. leaves, stems, roots, flowers), single cells (e.g. pollen), seeds, plant cells including for example tissue cultured cells, products produced from the plant such as "wheat flour", "wheat grain", "wheat starch", "wheat starch granules" and the like. Plantlets and germinated seeds from which roots and shoots have emerged are also included within the meaning of "plant". The term "plant parts" as used herein refers to one or more plant tissues or organs which are obtained from a whole plant, preferably a wheat plant. Plant parts include vegetative structures (for example, leaves, stems), roots, floral organs/structures, seed (including embryo, endosperm, and seed coat), plant tissue (for example, vascular tissue, ground tissue, and the like), cells and progeny of the same. The term "plant cell" as used herein refers to a cell obtained from a plant or in a plant, preferably a wheat plant, and includes protoplasts or other cells derived from plants, gamete-producing cells, and cells which regenerate into whole plants. Plant cells may be cells in culture. By "plant tissue" is meant differentiated tissue in a plant or obtained from a plant ("explant") or undifferentiated tissue derived from immature or mature embryos, seeds, roots, shoots, fruits, pollen, and various forms of aggregations of plant cells in culture, such as calli. Plant tissues in or from seeds such as wheat seeds are seed coat, endosperm, scutellum, aleurone layer and embryo.

Cereals as used herein means plants or grain of the monocotyledonous families Poaceae or Graminae which are cultivated for the edible components of their seeds, and includes wheat, barley, maize, oats, rye, rice, sorghum, triticale, millet, buckwheat. Preferably, the cereal plant or grain is wheat or barley plant or grain, more preferably wheat plant or grain. In a further preferred embodiment, the cereal plant is not rice or maize or both of these.

As used herein, the term "wheat" refers to any species of the Genus *Triticum*, including progenitors thereof, as well as progeny thereof produced by crosses with other species.

Wheat includes "hexaploid wheat" which has genome organization of AABBDD, comprised of 42 chromosomes, and "tetraploid wheat" which has genome organization of AABB, comprised of 28 chromosomes. Hexaploid wheat includes *T. aestivum, T. spelta, T. macha, T. compactum, T sphaerococcum, T. vavilovii*, and interspecies cross thereof. Tetraploid wheat includes *T. durum* (also referred to as *durum* wheat or *Triticum turgidum* ssp. *durum*), *T. dicoccoides, T. dicoccum, T. polonicum*, and interspecies cross thereof. In addition, the term "wheat" includes possible progenitors of hexaploid or tetraploid *Triticum* sp. such as *T. uartu, T. monococcum* or *T. boeoticum* for the A genome, *Aegilops speltoides* for the B genome, and *T. tauschii* (also known as *Aegilops squamosa* or *Aegilops tauschii*) for the D genome. A wheat cultivar for use in the present invention may belong to, but is not limited to, any of the above-listed species. Also encompassed are plants that are produced by conventional techniques using *Triticum* sp. as a parent in a sexual cross with a non-*Triticum* species, such as rye *Secale cereale*, including but not limited to Triticale. Preferably the wheat plant is suitable for commercial production of grain, such as commercial varieties of hexaploid wheat or *durum* wheat, having suitable agronomic characteristics which are known to those skilled in the art. More preferably the wheat is *Triticum aestivum* ssp. *aestivum* or *Triticum turgidum* ssp. *durum*, and most preferably the wheat is *Triticum aestivum* ssp. *aestivum*, herein also referred to as "breadwheat".

As used herein, the term "barley" refers to any species of the Genus *Hordeum*, including progenitors thereof, as well as progeny thereof produced by crosses with other species. It is preferred that the plant is of a *Hordeum* species which is commercially cultivated such as, for example, a strain or cultivar or variety of *Hordeum vulgare* or suitable for commercial production of grain.

Aspects of the invention provide methods of planting and harvesting wheat grain of the invention, and methods of producing bins of wheat grain of the invention. For instance, after the ground is prepared by plowing and/or certain other methods, the seeds (kernels) are planted either by sowing them broadcast (i.e., by distributing them on the surface of the ground) or by drilling furrows and planting the seeds in rows. To prevent scattering of the kernels, wheat is often harvested before it is fully ripe. There are several steps in harvesting: cutting, or reaping, the stalks; threshing and winnowing, to separate the kernels from the spikes, glumes, and other chaff; sifting and sorting the grain; loading the grain into trucks; and binding the straw. In some embodiments harvested wheat grain may be be stored in dry, well-ventilated buildings that keep out insect pests. In some embodiments, harvested wheat grain may be stored for a short time in bins or granaries. The wheat grain may then by hauled to country elevators, tall structures where the grain is dried and stored until it is sold or shipped to terminal elevators. Therefore, embodiments of the invention provide a process of producing bins of wheat grain comprising: a) reaping wheat stalks comprising wheat grain as defined herein; b) threshing and/or winnowing the stalks to separate the grain from the chaff; and c) sifting and/or sorting the grain separated in step b), and loading the sifted and/or sorted grain into bins, thereby producing bins of wheat grain.

The wheat plants of the invention may have many uses other than uses for food or animal feed, for example uses in research or breeding. In seed propagated crops such as wheat, the plants can be self-crossed to produce a plant which is homozygous for the desired genes, or haploid tissues such as developing germ cells can be induced to double the chromosome complement to produce a homozygous plant. The inbred wheat plant of the invention thereby produces seed containing the combination of mutant SBEII alleles which may be homozygous. These seeds can be grown to produce plants that would have the selected phenotype such as, for example, high amylose content in its starch.

The wheat plants of the invention may be crossed with plants containing a more desirable genetic background, and therefore the invention includes the transfer of the low SBEII trait to other genetic backgrounds. After the initial crossing, a suitable number of backcrosses may be carried out to remove a less desirable background. SBEII allele-specific PCR-based markers such as those described herein may be used to screen for or identify progeny plants or grain with the desired combination of alleles, thereby tracking the presence of the alleles in the breeding program. The desired genetic background may include a suitable combination of genes providing commercial yield and other characteristics such as agronomic performance or abiotic stress resistance. The genetic background might also include other altered starch biosynthesis or modification genes, for example genes from other wheat lines. The genetic background may comprise one or more transgenes such as, for example, a gene that confers tolerance to a herbicide such as glyphosate.

The desired genetic background of the wheat plant will include considerations of agronomic yield and other characteristics. Such characteristics might include whether it is desired to have a winter or spring types, agronomic performance, disease resistance and abiotic stress resistance. For Australian use, one might want to cross the altered starch trait of the wheat plant of the invention into wheat cultivars such as Baxter, Kennedy, Janz, Frame, Rosella, Cadoux, Diamondbird or other commonly grown varieties. Other varieties will be suited for other growing regions. It is preferred that the wheat plant of the invention provide a grain yield of at least 80% relative to the yield of the corresponding wild-type variety in at least some growing regions, more preferably at least 85% or at least 90%, and even more preferably at least 95% relative to a wild-type variety having about the same genetic background, grown under the same conditions. Most preferably, the grain yield of the wheat plant of the invention is at least as great as the yield of the wild-type wheat plant having about the same genetic background, grown under the same conditions. The yield can readily be measured in controlled field trials, or in simulated field trials in the greenhouse, preferably in the field.

Marker assisted selection is a well recognised method of selecting for heterozygous plants obtained when backcrossing with a recurrent parent in a classical breeding program. The population of plants in each backcross generation will be heterozygous for the gene(s) of interest normally present in a 1:1 ratio in a backcross population, and the molecular marker can be used to distinguish the two alleles of the gene. By extracting DNA from, for example, young shoots and testing with a specific marker for the introgressed desirable trait, early selection of plants for further backcrossing is made whilst energy and resources are concentrated on fewer plants.

Procedures such as crossing wheat plants, self-fertilising wheat plants or marker-assisted selection are standard procedures and well known in the art. Transferring alleles from tetraploid wheat such as *durum* wheat to a hexaploid, or other forms of hybridisation, is more difficult but is also known in the art.

To identify the desired phenotypic characteristic, wheat plants that contain a combination of mutant SBEIIa and SBEIIb alleles or other desired genes are typically compared to control plants. When evaluating a phenotypic characteristic associated with enzyme activity such as amylose content in the grain starch, the plants to be tested and control plants are grown under growth chamber, greenhouse, open top chamber and/or field conditions. Identification of a particular phenotypic trait and comparison to controls is based on routine statistical analysis and scoring. Statistical differences between plants lines can be assessed by comparing—enzyme activity between plant lines within each tissue type expressing the enzyme. Expression and activity are compared to growth, development and yield parameters which include plant part morphology, colour, number, size, dimensions, dry and wet weight, ripening, above- and below-ground biomass ratios, and timing, rates and duration of various stages of growth through senescence, including vegetative growth, fruiting, flowering, and soluble carbohydrate content including sucrose, glucose, fructose and starch levels as well as endogenous starch levels. In some embodiments, the wheat plants of the invention differ from wild-type plants in one or more of these parameters by less than 50%, more preferably less than 40%, less than 30%, less than 20%, less than 15%, less than 10%, less than 5%, less than 2% or less than 1% when grown under the same conditions.

As used herein, the term "linked" refers to a marker locus and a second locus being sufficiently close on a chromosome that they will be inherited together in more than 50% of meioses, e.g., not randomly. This definition includes the situation where the marker locus and second locus form part of the same gene. Furthermore, this definition includes the situation where the marker locus comprises a polymorphism that is responsible for the trait of interest (in other words the marker locus is directly "linked" to the phenotype). The term "genetically linked" as used herein is narrower, only used in relation to where a marker locus and a second locus being sufficiently close on a chromosome that they will be inherited together in more than 50% of meioses. Thus, the percent of recombination observed between the loci per generation (centimorgans (cM)), will be less than 50. In particular embodiments of the invention, genetically linked loci may be 45, 35, 25, 15, 10, 5, 4, 3, 2, or 1 or less cM apart on a chromosome. Preferably, the markers are less than 5 cM or 2 cM apart and most preferably about 0 cM apart. As described in Example 5 herein, the SBEIIa and SBEIIb genes are genetically linked on the long arm of chromosome 2 of each of the wheat genomes, being about 0.5 cM apart, which corresponds to about 100-200 kb in physical distance.

As used herein, the "other genetic markers" may be any molecules which are linked to a desired trait in the wheat plants of the invention. Such markers are well known to those skilled in the art and include molecular markers linked to genes determining traits such disease resistance, yield, plant morphology, grain quality, other dormancy traits such as grain colour, gibberellic acid content in the seed, plant height, flour colour and the like. Examples of such genes are stem-rust resistance genes Sr2 or Sr38, the stripe rust resistance genes Yr10 or Yr17, the nematode resistance genes such as Cre1 and Cre3, alleles at glutenin loci that determine dough strength such as Ax, Bx, Dx, Ay, By and Dy alleles, the Rht genes that determine a semi-dwarf growth habit and therefore lodging resistance (Eagles et al., 2001; Langridge et al., 2001; Sharp et al., 2001).

The wheat plants, wheat plant parts and products therefrom of the invention are preferably non-transgenic for genes that inhibit expression of SBEIIa i.e. they do not comprise a transgene encoding an RNA molecule that reduces expression of the endogenous SBEIIa genes, although in this embodiment they may comprise other transgenes, eg. herbicide tolerance genes. More preferably, the wheat plant, grain and products therefrom are non-transgenic, i.e. they do not contain any transgene, which is preferred in some markets. Such products are also described herein as "non-transformed" products. Such non-transgenic plants and grain comprise the multiple mutant SBEII alleles as described herein, such as those produced after mutagenesis.

The terms "transgenic plant" and "transgenic wheat plant" as used herein refer to a plant that contains a gene construct ("transgene") not found in a wild-type plant of the same species, variety or cultivar. That is, transgenic plants (transformed plants) contain genetic material that they did not contain prior to the transformation. A "transgene" as referred to herein has the normal meaning in the art of biotechnology and refers to a genetic sequence which has been produced or altered by recombinant DNA or RNA technology and which has been introduced into the plant cell. The transgene may include genetic sequences obtained from or derived from a plant cell, or another plant cell, or a non-plant source, or a synthetic sequence. Typically, the transgene has been introduced into the plant by human manipulation such as, for example, by transformation but any method can be used as one of skill in the art recognizes. The genetic material is typically stably integrated into the genome of the plant. The introduced genetic material may comprise sequences that naturally occur in the same species but in a rearranged order or in a different arrangement of elements, for example an antisense sequence. Plants containing such sequences are included herein in "transgenic plants". Transgenic plants as defined herein include all progeny of an initial transformed and regenerated plant (T0 plant) which has been genetically modified using recombinant techniques, where the progeny comprise the transgene. Such progeny may be obtained by self-fertilisation of the primary transgenic plant or by crossing such plants with another plant of the same species. In an embodiment, the transgenic plants are homozygous for each and every gene that has been introduced (transgene) so that their progeny do not segregate for the desired phenotype. Transgenic plant parts include all parts and cells of said plants which comprise the transgene such as, for example, seeds, cultured tissues, callus and protoplasts. A "non-transgenic plant", preferably a non-transgenic wheat plant, is one which has not been genetically modified by the introduction of genetic material by recombinant DNA techniques.

As used herein, the term "corresponding non-transgenic plant" refers to a plant which is the same or similar in most characteristics, preferably isogenic or near-isogenic relative to the transgenic plant, but without the transgene of interest. Preferably, the corresponding non-transgenic plant is of the same cultivar or variety as the progenitor of the transgenic plant of interest, or a sibling plant line which lacks the construct, often termed a "segregant", or a plant of the same cultivar or variety transformed with an "empty vector" construct, and may be a non-transgenic plant. "Wild-type", as used herein, refers to a cell, tissue or plant that has not been modified according to the invention. Wild-type cells, tissue or plants known in the art and may be used as controls to compare levels of expression of an exogenous nucleic acid or the extent and nature of trait modification with cells, tissue or plants modified as described herein. As used herein, "wild-type wheat grain" means a corresponding non-mutagenized, non-transgenic wheat grain. Specific wild-type wheat grains as used herein include but are not limited to Sunstate and Cadoux. The Sunstate wheat cultivar is described in: Ellison et al., (1994) *Triticum aestivum* spp. *vulgare* (bread wheat) cv. Sunstate, *Australian Journal of Experimental Agriculture*, 34(6):869-869, the entire contents of which are incorporated herein by reference.

Any of several methods may be employed to determine the presence of a transgene in a transformed plant. For example, polymerase chain reaction (PCR) may be used to amplify sequences that are unique to the transformed plant, with detection of the amplified products by gel electrophoresis or other methods. DNA may be extracted from the plants using conventional methods and the PCR reaction carried out using primers that will distinguish the transformed and non-transformed plants. An alternative method to confirm a positive transformant is by Southern blot hybridization, well known in the art. Wheat plants which are transformed may also be identified i.e. distinguished from non-transformed or wild-type wheat plants by their phenotype, for example conferred by the presence of a selectable marker gene, or by immunoassays that detect or quantify the expression of an enzyme encoded by the transgene, or any other phenotype conferred by the transgene.

The wheat plants of the present invention may be grown or harvested for grain, primarily for use as food for human consumption or as animal feed, or for fermentation or industrial feedstock production such as ethanol production, among other uses. Alternatively, the wheat plants may be used directly as feed. The plant of the present invention is preferably useful for food production and in particular for commercial food production. Such food production might include the making of flour, dough, semolina or other products from the grain that might be an ingredient in commercial food production.

As used herein, the term "grain" generally refers to mature, harvested seed of a plant but can also refer to grain after imbibition or germination, according to the context. Mature cereal grain such as wheat commonly has a moisture content of less than about 18-20%. As used herein, the term "seed" includes harvested seed but also includes seed which is developing in the plant post anthesis and mature seed comprised in the plant prior to harvest.

As used herein, "germination" refers to the emergence of the root tip from the seed coat after imbibition. "Germination rate" refers to the percentage of seeds in a population which have germinated over a period of time, for example 7 or 10 days, after imbibition. Germination rates can be calculated using techniques known in the art. For example, a population of seeds can be assessed daily over several days to determine the germination percentage over time. With regard to grain of the present invention, as used herein the term "germination rate which is substantially the same" means that the germination rate of the grain is at least 90%, that of corresponding wild-type grain.

Starch is readily isolated from wheat grain using standard methods, for example the method of Schulman and Kammiovirta, 1991. On an industrial scale, wet or dry milling can be used. Starch granule size is important in the starch processing industry where there is separation of the larger A granules from the smaller B granules.

Wild-type wheat grown commercially has a starch content in the grain which is usually in the range 55-65%, depending somewhat on the cultivar grown. In comparison, the seed or grain of the invention has a starch content of at least 90% relative to that of wild-type grain, and preferably at least 93%, at least 95%, or at least 98% relative to the starch content of wild-type grain when the plants are grown under the same conditions. In further embodiments, the starch content of the grain is at least about 25%, at least about 35%, at least about 45%, or at least about 55% to about 65% as a percentage of the grain weight (w/w). Other desirable characteristics include the capacity to mill the grain, in particular the grain hardness. Another aspect that might make a wheat plant of higher value is the degree of starch extraction from the grain, the higher extraction rates being more useful. Grain shape is also another feature that can impact on the commercial usefulness of a plant, thus grain shape can have an impact on the ease or otherwise with which the grain can be milled.

In another aspect, the invention provides starch granules or starch obtained from the grain of the plant as described above, having an increased proportion of amylose and a reduced proportion of amylopectin. Purified starch may be obtained from grain by a milling process, for example a wet milling process, which involves the separation of the starch from protein, oil and fibre. The initial product of the milling process is a mixture or composition of starch granules, and the invention therefore encompasses such granules. The starch granules from wheat comprise starch granule-bound proteins including GBSS, SBEIIa and SBEIIb amongst other proteins and therefore the presence of these proteins distinguish wheat starch granules from starch granules of other cereals. The starch from starch granules may be purified by removal of the proteins after disruption and dispersal of the starch granules by heat and/or chemical treatment. The starch granules from the wheat grain of the invention are typically distorted in shape and surface morphology, when observed under light microscopy, as exemplified herein, particularly for wheat grain having an amylose content of at least 50% as a percentage of the total starch of the grain. In an embodiment, at least 50%, preferably at least 60% or at least 70% of the starch granules obtained from the grain show distorted shape or surface morphology. The starch granules also show a loss of birefringence when observed under polarised light.

The starch of the grain, the starch of the starch granules, and the purified starch of the invention may be further characterized by one or more of the following properties:

i) at least 50% (w/w), or at least 60% (w/w), or at least 67% (w/w) amylose as a proportion of the total starch;
ii) modified swelling volume;
iii) modified chain length distribution and/or branching frequency;
iv) modified gelatinisation temperature;
v) modified viscosity (peak viscosity, pasting temperature, etc.);
vi) modified molecular mass of amylopectin and/or amylose;
vii) modified % crystallinity
viii) comprising at least 2% resistant starch; and/or
ix) comprising a low relative glycaemic index (GI).

The starch may also be characterized by its swelling volume in heated excess water compared to wild-type starch. Swelling volume is typically measured by mixing either a starch or flour with excess water and heating to elevated temperatures, typically greater than 90° C. The sample is then collected by centrifugation and the swelling volume is expressed as the mass of the sedimented material divided by the dry weight of the sample. A low swelling characteristic is useful where it is desired to increase the starch content of a food preparation, in particular a hydrated food preparation.

One measure of an altered amylopectin structure is the distribution of chain lengths, or the degree of polymerization, of the starch. The chain length distribution may be determined by using fluorophore-assisted carbohydrate electrophoresis (FACE) following isoamylose de-branching. The amylopectin of the starch of the invention may have a distribution of chain length in the range from 5 to 60 that is greater than the distribution of starch from wild-type plants upon debranching. Starch with longer chain lengths will also have a commensurate decrease in frequency of branching. Thus the starch may also have a distribution of longer amylopectin chain lengths in the amylopectin still present. The amylopectin of the grain may be characterised in comprising a reduced proportion of the 4-12 dp chain length fraction relative to the amylopectin of wild-type grain, as measured after isoamylase debranching of the amylopectin.

In another aspect of the invention, the wheat starch may have an altered gelatinisation temperature, which may be readily measured by differential scanning calorimetry (DSC). Gelatinisation is the heat-driven collapse (disruption) of molecular order within the starch granule in excess water, with concomitant and irreversible changes in properties such as granular swelling, crystallite melting, loss of birefringence, viscosity development and starch solubilisation. The gelatinisation temperature may be either increased or decreased compared to starch from wild-type plants, depending on the chain length of the remaining amylopectin. High amylose starch from amylose extender (ae) mutants of maize showed a higher gelatinisation temperature than normal maize (Fuwa et al., 1999; Krueger et al., 1987). On the other hand, starch from barley sex6 mutants that lack starch synthase IIa activity had lower gelatinisation temperatures and the enthalpy for the gelatinisation peak was reduced when compared to that from control plants (Morell et al., 2003).

The gelatinisation temperature, in particular the temperature of onset of the first peak or the temperature for the apex of the first peak, may be elevated by at least 3° C., preferably at least 5° C. or more preferably at least 7° C. as measured by DSC compared to starch extracted from a similar, but unaltered grain. The starch may comprise an elevated level of resistant starch, with an altered structure indicated by specific physical characteristics including one or more of the group consisting of physical inaccessibility to digestive enzymes which may be by reason of having altered starch granule morphology, the presence of appreciable starch associated lipid, altered crystallinity, and altered amylopectin chain length distribution. The high proportion of amylose also contributes to the level of resistant starch.

The starch structure of the wheat of the present invention may also differ in that the degree of crystallinity is reduced compared to normal starch isolated from wheat. The reduced crystallinity of a starch is also thought to be associated with enhance organoleptic properties and contributes to a smoother mouth feel. Thus, the starch may additionally exhibit reduced crystallinity resulting from reduced levels of activity of one or more amylopectin synthesis enzymes. Crystallinity is typically investigated by X-ray crystallography.

In some embodiments, the present starch provides modified digestive properties such as increased resistant starch including between 1% to 20%, 2% to 18%, 3% to 18% or 5% to 15% resistant starch and a decreased Glycaemic Index (GI).

The invention also provides flour, meal or other products produced from the grain. These may be unprocessed or processed, for example by fractionation or bleaching.

The invention also provides starch from grain of the exemplified wheat plants comprising increased amounts of dietary fibre, preferably in combination with an elevated level of resistant starch. This increase is also at least in part a result of the high relative level of amylose.

The term "dietary fibre" as used herein includes the carbohydrate and carbohydrate digestion products which are not absorbed in the small intestine of healthy humans but which enter the large bowel. This includes resistant starch and other soluble and insoluble carbohydrate polymers. It is intended to comprise that portion of carbohydrates that are fermentable, at least partially, in the large bowel by the resident microflora. The starch of the invention contains relatively high levels of dietary fibre, more particularly amylose. The dietary fibre content of the grain of the present invention results at least in part from the increased amylose content in the starch of the grain, and also, or in combination with an increased resistant starch content as a percentage of the total starch. "Resistant starch" is defined herein as the sum of starch and products of starch digestion not absorbed in the small intestine of healthy humans but entering into the large bowel. This is defined in terms of a percentage of the total starch of the grain, or a percentage of the total starch content in the food, according to the context. Thus, resistant starch excludes products digested and absorbed in the small intestine. Resistant starches include physically inaccessible starch (RS1 form), resistant native starch granules (RS2), retrograded starches (RS3), and chemically modified starches (RS4). The altered starch structure and in particular the high amylose levels of the starch of the invention give rise to an increase in resistant starch when consumed in food. The starch may be in an RS1 form, being somewhat inaccessible to digestion. Starch-lipid association as measured by V-complex crystallinity is also likely to contribute to the level of resistant starch.

Whilst the invention may be particularly useful in the treatment or prophylaxis of humans, it is to be understood that the invention is also applicable to non-human subjects including but not limited to agricultural animals such as cows, sheep, pigs and the like, domestic animals such as dogs or cats, laboratory animals such as rabbits or rodents such as mice, rats, hamsters, or animals that might be used for sport such as horses. The method may be particularly applicable to non-ruminant mammals or animals such as mono-gastric mammals. The invention may also be applicable to other agricultural animals for example poultry including, for example, chicken, geese, ducks, turkeys, or quails, or fish.

The method of treating the subject, particularly humans, may comprise the step of administering altered wheat grain, flour, starch or a food or drink product as defined herein to the subject, in one or more doses, in an amount and for a period of time whereby the level of the one or more of the bowel health or metabolic indicators improves. The indicator may change relative to consumption of non-altered wheat starch or wheat or product thereof, within a time period of hours, as in the case of some of the indicators such as pH, elevation of levels of SCFA, post-prandial glucose fluctuation, or it may take days such as in the case of increase in fecal bulk or improved laxation, or perhaps longer in the order of weeks or months such as in the case where the butyrate enhanced proliferation of normal colonocytes is measured. It may be desirable that administration of the altered starch or wheat or wheat product be lifelong. However, there are good prospects for compliance by the individual being treated given the relative ease with which the altered starch can be administered.

Dosages may vary depending on the condition being treated or prevented but are envisaged for humans as being at least 1 g of wheat grain or starch of the invention per day, more preferably at least 2 g per day, preferably at least 10 or at least 20 g per day. Administration of greater than about 100 grams per day may require considerable volumes of delivery and reduce compliance. Most preferably the dosage for a human is between 5 and 60 g of wheat grain or starch per day, or for adults between 5 and 100 g per day.

Glycaemic Index (GI) relates to the rate of digestion of foods comprising the starch, and is a comparison of the effect of a test food with the effect of white bread or glucose on excursions in blood glucose concentration. The Glycaemic Index is a measure of the likely effect of the food concerned on post prandial serum glucose concentration and demand for insulin for blood glucose homeostasis. One important characteristic provided by foods of the invention is a reduced glycaemic index. Serum glucose levels were lower 30 min after ingestion of high amylose wheat products by human volunteers compared to low amylose wheat (Goddard et al., 1984). Furthermore, the foods may have a low level of final digestion and consequently be relatively low-calorie. A low calorific product might be based on inclusion of flour produced from milled wheat grain. Such foods may have the effect of being filling, enhancing bowel health, reducing the post-prandial serum glucose and lipid concentration as well as providing for a low calorific food product.

The indicators of improved bowel health may comprise, but are not necessarily limited to:
 i) decreased pH of the bowel contents,
 ii) increased total SCFA concentration or total SCFA amount in the bowel contents,
 iii) increased concentration or amount of one or more SCFAs in the bowel contents,
 iv) increased fecal bulk,
 v) increase in total water volume of bowel or faeces, without diarrhea,
 vi) improved laxation,
 vii) increase in number or activity of one or more species of probiotic bacteria,
 viii) increase in fecal bile acid excretion,
 ix) reduced urinary levels of putrefactive products,
 x) reduced fecal levels of putrefactive products,
 xi) increased proliferation of normal colonocytes,
 xii) reduced inflammation in the bowel of individuals with inflamed bowel,
 xiii) reduced fecal or large bowel levels of any one of urea, creatinine and phosphate in uremic patients, and
 xiv) any combination of the above.

The indicators of improved metabolic health may comprise, but are not necessarily limited to:
 i) stabilisation of post-prandial glucose fluctuation,
 ii) improved (lowered) glycaemic response,
 iii) reduced pro-prandial plasma insulin concentration,
 iv) improved blood lipid profile,
 v) lowering of plasma LDL cholesterol,
 vi) reduced plasma levels of one or more of urea, creatinine and phosphate in uremic patients,
 vii) an improvement in a dysglucaemic response, or
 viii) any combination of the above.

It will be understood that one benefit of the present invention is that it provides for products such as bread that are of particular nutritional benefit, and moreover it does so without the need to post-harvest modify the starch or other constituents of the wheat grain. However, it may be desired to make modifications to the starch or other constituent of the grain, and the invention encompasses such a modified constituent. Methods of modification are well known and include the extraction of the starch or other constituent by conventional methods and modification of the starches to increase the resistant form. The starch may be modified by treatment with heat and/or moisture, physically (for example ball milling), enzymatically (using for example α- or β-amylase, pullalanase or the like), chemical hydrolysis (wet or dry using liquid or gaseous reagents), oxidation, cross bonding with difunctional reagents (for example sodium trimetaphosphate, phosphorus oxychloride), or carboxymethylation.

The wheat starch of the present invention will be a suitable substrate for fermentation for ethanol (biofuel) or ethanol-containing beverages and the wheat grain or wheat starch for other fermentation products such as foods, nutraceuticals (insoluble or soluble fibre), enzymes and industrial materials. The methods for fermentation using plant-derived starch are well known to those skilled in the art, with established processes for various fermentation products (see for example Vogel et al., 1996 and references cited therein). In one embodiment, the starch carbohydrates may be extracted by crushing the wheat plant parts of the invention such as grain, or by diffusion from the plant tissues into water or another suitable solvent. Wheat tissues or starch of the invention may be used directly as a substrate for fermentation or bioconversion in a batch, continuous, or immobilized-cell process.

The terms "polypeptide" and "protein" are generally used interchangeably herein. The terms "proteins" and "polypeptides" as used herein also include variants, mutants, modifications and/or derivatives of the polypeptides of the invention as described herein. As used herein, "substantially purified polypeptide" refers to a polypeptide that has been separated from the lipids, nucleic acids, other peptides and other molecules with which it is associated in its native state. Preferably, the substantially purified polypeptide is at least 60% free, more preferably at least 75% free, and more preferably at least 90% free from other components with which it is naturally associated. By "recombinant polypeptide" is meant a polypeptide made using recombinant techniques, i.e., through the expression of a recombinant polynucleotide in a cell, preferably a plant cell and more preferably a wheat cell. In an embodiment, the polypeptide has starch branching enzyme activity, particularly SBEII activity, and is at least 90% identical to a SBEII described herein.

As used herein a "biologically active" fragment is a portion of a polypeptide of the invention which maintains a defined activity of the full-length polypeptide. In a particularly preferred embodiment, the biologically active fragment has starch branching enzyme activity. Biologically active fragments can be any size as long as they maintain the defined activity, but are preferably at least 700 or 800 amino acid residues long.

The % identity of a polypeptide relative to another polypeptide can be determined by GAP (Needleman and Wunsch, 1970) analysis (GCG program) with a gap creation penalty=5, and a gap extension penalty=0.3. The query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Most preferably, two SBEII polypeptides are aligned over their full length amino acid sequences.

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence deletions or insertions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis for reduced activity of the polypeptide include sites identified as the active site(s). Other sites of interest are those in which particular residues obtained from various strains or species are identical i.e. conserved amino acids. These positions may be important for biological activity. These amino acids, especially those falling within a contiguous sequence of at least three other identically conserved amino acids, are preferably substituted in a relatively conservative manner in order to retain function such as SBEII activity, or in a non-conservative manner for reduced activity. Conservative substitutions are shown in Table 1 under the heading of "exemplary substitutions". "Non-conservative amino acid substitutions" are defined herein as substitutions other than those listed in Table 3 (Exemplary conservative substitutions). Non-conservative substitutions in an SBEII are expected to reduce the activity of the enzyme and many will correspond to an SBEII encoded by a "partial loss of function mutant SBEII gene".

Also included within the scope of the invention are polypeptides of the present invention which are differentially modified during or after synthesis, e.g., by phosphorylation, as has been shown for SBEI, SBEIIa and SBEIIb in amyloplasts of wheat (Tetlow et al., 2004). These modifications may serve to regulate the activity of the enzyme, for example by regulating the formation of protein complexes in amyloplasts during starch synthesis (Tetlow et al., 2008), or to increase the stability and/or bioactivity of the polypeptide of the invention, or serve as a ligand for binding of another molecule.

In some embodiments, the present invention involves modification of gene activity, particularly of SBEII gene activity, combinations of mutant genes, and the construction and use of chimeric genes. As used herein, the term "gene" includes any deoxyribonucleotide sequence which includes a protein coding region or which is transcribed in a cell but not translated, together with associated non-coding and regulatory regions. Such associated regions are typically located adjacent to the coding region on both the 5' and 3' ends for a distance of about 2 kb on either side. In this regard, the gene includes control signals such as promoters, enhancers, transcription termination and/or polyadenylation signals that are naturally associated with a given gene, or heterologous control signals in which case the gene is referred to as a "chimeric gene". The sequences which are located 5' of the protein coding region and which are present on the mRNA are referred to as 5' non-translated sequences. The sequences which are located 3' or downstream of the protein coding region and which are present on the mRNA are referred to as 3' non-translated sequences. The term "gene" encompasses both cDNA and genomic forms of a gene. The term "gene" includes synthetic or fusion molecules encoding the proteins of the invention described herein. Genes are ordinarily present in the wheat genome as double-stranded DNA. A chimeric gene may be introduced into an appropriate vector for extrachromosomal maintenance in a cell or for integration into the host genome. Genes or genotypes as referred to herein in italicised form (e.g. SBEIIa) while proteins, enzymes or phenotypes are referred to in non-italicised form (SBEIIa).

A genomic form or clone of a gene containing the coding region may be interrupted with non-coding sequences termed "introns" or "intervening regions" or "intervening sequences." An "intron" as used herein is a segment of a gene which is transcribed as part of a primary RNA transcript but is not present in the mature mRNA molecule. Introns are removed or "spliced out" from the nuclear or primary transcript; introns therefore are absent in the messenger RNA (mRNA). Introns may contain regulatory elements such as enhancers. "Exons" as used herein refer to the DNA regions corresponding to the RNA sequences which are present in the mature mRNA or the mature RNA molecule in cases where the RNA molecule is not translated. An mRNA functions during translation to specify the sequence or order of amino acids in a nascent polypeptide.

The present invention refers to various polynucleotides. As used herein, a "polynucleotide" or "nucleic acid" or "nucleic acid molecule" means a polymer of nucleotides, which may be DNA or RNA or a combination thereof, for example a heteroduplex of DNA and RNA, and includes for example mRNA, cRNA, cDNA, tRNA, siRNA, shRNA, hpRNA, and single or double-stranded DNA. It may be DNA or RNA of cellular, genomic or synthetic origin. Preferably the polynucleotide is solely DNA or solely RNA as occurs in a cell, and some bases may be methylated or otherwise modified as occurs in a wheat cell. The polymer may be single-stranded, essentially double-stranded or partly double-stranded. An example of a partly-double stranded RNA molecule is a hairpin RNA (hpRNA), short hairpin RNA (shRNA) or self-complementary RNA which include a double stranded stem formed by basepairing between a nucleotide sequence and its complement and a loop sequence which covalently joins the nucleotide sequence and its complement. Basepairing as used herein refers to standard basepairing between nucleotides, including G:U basepairs in an RNA molecule. "Complementary" means two polynucleotides are capable of basepairing along part of their lengths, or along the full length of one or both.

By "isolated" is meant material that is substantially or essentially free from components that normally accompany it in its native state. As used herein, an "isolated polynucleotide" or "isolated nucleic acid molecule" means a polynucleotide which is at least partially separated from, preferably substantially or essentially free of, the polynucleotide sequences of the same type with which it is associated or linked in its native state. For example, an "isolated polynucleotide" includes a polynucleotide which has been purified or separated from the sequences which flank it in a naturally occurring state, e.g., a DNA fragment which has been removed from the sequences which are normally adjacent to the fragment. Preferably, the isolated polynucleotide is also at least 90% free from other components such as proteins, carbohydrates, lipids etc. The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably connected to the nucleotide sequence to be transcribed in the cell.

The present invention refers to use of oligonucleotides which may be used as "probes" or "primers". As used herein, "oligonucleotides" are polynucleotides up to 50 nucleotides in length. They can be RNA, DNA, or combinations or derivatives of either. Oligonucleotides are typically relatively short single stranded molecules of 10 to 30 nucleotides, commonly 15-25 nucleotides in length, typically comprised of 10-30 or 15-25 nucleotides which are identical to, or complementary to, part of an SBEIIa or SBEIIb gene or cDNA corresponding to an SBEIIa or SBEIIb gene. When used as a probe or as a primer in an amplification reaction, the minimum size of such an oligonucleotide is the size required for the formation of a stable hybrid between the oligonucleotide and a complementary sequence on a target nucleic acid molecule. Preferably, the oligonucleotides are at least 15 nucleotides, more preferably at least 18 nucleotides, more preferably at least 19 nucleotides, more preferably at least 20 nucleotides, even more preferably at least 25 nucleotides in length. Polynucleotides used as a probe are typically conjugated with a detectable label such as a radioisotope, an enzyme, biotin, a fluorescent molecule or a chemiluminescent molecule. Oligonucleotides and probes of the invention are useful in methods of detecting an allele of a SBEIIa, SBEIIb or other gene associated with a trait of interest, for example modified starch. Such methods employ nucleic acid hybridization and in many instances include oligonucleotide primer extension by a suitable polymerase, for example as used in PCR for detection or identification of wild-type or mutant alleles. Preferred oligonucleotides and probes hybridise to a SBEIIa or SBEIIb gene sequence from wheat, including any of the sequences disclosed herein, for example SEQ ID NOs: 36 to 149. Preferred oligonucleotide pairs are those that span one or more introns, or a part of an intron and therefore may be used to amplify an intron sequence in a PCR reaction. Numerous examples are provided in the Examples herein.

The terms "polynucleotide variant" and "variant" and the like refer to polynucleotides displaying substantial sequence identity with a reference polynucleotide sequence and which are able to function in an analogous manner to, or with the same activity as, the reference sequence. These terms also encompass polynucleotides that are distinguished from a reference polynucleotide by the addition, deletion or substitution of at least one nucleotide, or that have, when compared to naturally occurring molecules, one or more mutations. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. Accordingly, these terms encompass polynucleotides that encode polypeptides that exhibit enzymatic or other regulatory activity, or polynucleotides capable of serving as selective probes or other hybridising agents. The terms "polynucleotide variant" and "variant" also include naturally occurring allelic variants. Mutants can be either naturally occurring (that is to say, isolated from a natural source) or synthetic (for example, by performing site-directed mutagenesis on the nucleic acid). Preferably, a polynucleotide variant of the invention which encodes a polypeptide with enzyme activity is greater than 400, more preferably greater than 500, more preferably greater than 600, more preferably greater than 700, more preferably greater than 800, more preferably greater than 900, and even more preferably greater than 1,000 nucleotides in length, up to the full length of the gene.

A variant of an oligonucleotide of the invention includes molecules of varying sizes which are capable of hybridising, for example, to the wheat genome at a position close to that of the specific oligonucleotide molecules defined herein. For example, variants may comprise additional nucleotides (such as 1, 2, 3, 4, or more), or less nucleotides as long as they still hybridise to the target region. Furthermore, a few nucleotides may be substituted without influencing the ability of the oligonucleotide to hybridise to the target region. In addition, variants may readily be designed which hybridise close (for example, but not limited to, within 50 nucleotides) to the region of the plant genome where the specific oligonucleotides defined herein hybridise.

By "corresponds to" or "corresponding to" in the context of polynucleotides or polypeptides is meant a polynucleotide (a) having a nucleotide sequence that is substantially identical or complementary to all or a portion of a reference polynucleotide sequence or (b) encoding an amino acid sequence identical to an amino acid sequence in a peptide or protein. This phrase also includes within its scope a peptide or polypeptide having an amino acid sequence that is substantially identical to a sequence of amino acids in a reference peptide or protein. Terms used to describe sequence relationships between two or more polynucleotides or polypeptides include "reference sequence", "comparison window", "sequence identity", "percentage of sequence identity", "substantial identity" and "identical", and are defined with respect to a defined minimum number of nucleotides or amino acid residues or preferably over the full length. The terms "sequence identity" and "identity" are used interchangeably herein to refer to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, U) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

The % identity of a polynucleotide can be determined by GAP (Needleman and Wunsch, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides, or at least 400, 500 or 600 nucleotides in each case. Reference also may be made to the BLAST family of programs as for example disclosed by Altschul et al., 1997. A detailed discussion of sequence analysis can be found in Unit 19.3 of Ausubel et al., 1994-1998, Chapter 15.

Nucleotide or amino acid sequences are indicated as "essentially similar" when such sequences have a sequence identity of at least about 95%, particularly at least about 98%, more particularly at least about 98.5%, quite particularly about 99%, especially about 99.5%, more especially about 100%, quite especially are identical. It is clear that when RNA sequences are described as essentially similar to, or have a certain degree of sequence identity with, DNA sequences, thymine (T) in the DNA sequence is considered equal to uracil (U) in the RNA sequence.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

In some embodiments, the present invention refers to the stringency of hybridization conditions to define the extent of complementarity of two polynucleotides. "Stringency" as used herein, refers to the temperature and ionic strength conditions, and presence or absence of certain organic solvents, during hybridization. The higher the stringency, the higher will be the degree of complementarity between a target nucleotide sequence and the labelled polynucleotide sequence. "Stringent conditions" refers to temperature and ionic conditions under which only nucleotide sequences having a high frequency of complementary bases will hybridize. As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6, herein incorporated by reference. Specific hybridization conditions referred to herein are as follows: 1) low stringency hybridization conditions in 6× sodium chloride/sodium citrate (SSC) at about 45° C., followed by two washes in 0.2×SSC, 0.1% SDS at 50-55° C.; 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and 4) very high stringency hybridization conditions are 0.5 M sodium phosphate, 7% SDS at 65° C., followed by one or more washes at 0.2×SSC, 1% SDS at 65° C.

As used herein, a "chimeric gene" or "genetic construct" refers to any gene that is not a native gene in its native location i.e. it has been artificially manipulated, including a chimeric gene or genetic construct which is integrated into the wheat genome. Typically a chimeric gene or genetic construct comprises regulatory and transcribed or protein coding sequences that are not found together in nature. Accordingly, a chimeric gene or genetic construct may comprise regulatory sequences and coding sequences that are derived from different sources, or regulatory sequences and coding sequences derived from the same source, but arranged in a manner different than that found in nature. The term "endogenous" is used herein to refer to a substance that is normally produced in an unmodified plant at the same developmental stage as the plant under investigation, preferably a wheat plant, such as starch or a SBEIIa or SBEIIb. An "endogenous gene" refers to a native gene in its natural location in the genome of an organism, preferably a SBEIIa or SBEIIb gene in a wheat plant. As used herein, "recombinant nucleic acid molecule" refers to a nucleic acid molecule which has been constructed or modified by recombinant DNA technology. The terms "foreign polynucleotide" or "exogenous polynucleotide" or "heterologous polynucleotide" and the like refer to any nucleic acid which is introduced into the genome of a cell by experimental manipulations, preferably the wheat genome, but which does not naturally occur in the cell. These include modified forms of gene sequences found in that cell so long as the introduced gene contains some modification, e.g. an introduced mutation or the presence of a selectable marker gene, relative to the naturally-occurring gene. Foreign or exogenous genes may be genes found in nature that are inserted into a non-native organism, native genes introduced into a new location within the native host, or chimeric genes or genetic constructs. A "transgene" is a gene that has been introduced into the genome by a transformation procedure. The term "genetically modified" includes introducing genes into cells, mutating genes in cells and altering or modulating the regulation of a gene in a cell or organisms to which these acts have been done or their progeny.

The present invention refers to elements which are operably connected or linked. "Operably connected" or "operably linked" and the like refer to a linkage of polynucleotide elements in a functional relationship. Typically, operably connected nucleic acid sequences are contiguously linked and, where necessary to join two protein coding regions, contiguous and in reading frame. A coding sequence is "operably connected to" another coding sequence when RNA polymerase will transcribe the two coding sequences into a single RNA, which if translated is then translated into a single polypeptide having amino acids derived from both coding sequences. The coding sequences need not be contiguous to one another so long as the expressed sequences are ultimately processed to produce the desired protein.

As used herein, the term "cis-acting sequence", "cis-acting element" or "cis-regulatory region" or "regulatory region" or similar term shall be taken to mean any sequence of nucleotides which regulates the expression of the genetic sequence. This may be a naturally occurring cis-acting sequence in its native context, for example regulating a wheat SBEIIa or SBEIIb gene, or a sequence in a genetic construct which when positioned appropriately relative to an expressible genetic sequence, regulates its expression. Such a cis-regulatory region may be capable of activating, silencing, enhancing, repressing or otherwise altering the level of expression and/or cell-type-specificity and/or developmental specificity of a gene sequence at the transcriptional or post-transcriptional level. In preferred embodiments of the present invention, the cis-acting sequence is an activator sequence that enhances or stimulates the expression of an expressible genetic sequence, such as a promoter. The presence of an intron in the 5'-leader (UTR) of genes has been shown to enhance expression of genes in monocotyledonous plants such as wheat (Tanaka et al., 1990). Another type of cis-acting sequence is a matrix attachment region (MAR) which may influence gene expression by anchoring active chromatin domains to the nuclear matrix.

By "vector" is meant a nucleic acid molecule, preferably a DNA molecule derived, for example, from a plasmid, bacteriophage or plant virus, into which a nucleic acid sequence may be inserted. The vector may also include a selection marker such as an antibiotic resistance gene that can be used for selection of suitable transformants, or sequences that enhance transformation of prokaryotic or eukaryotic (especially wheat) cells such as T-DNA or P-DNA sequences. Examples of such resistance genes and sequences are well known to those of skill in the art.

By "marker gene" is meant a gene that imparts a distinct phenotype to cells expressing the marker gene and thus allows such transformed cells to be distinguished from cells that do not have the marker, and are well known in the art. A "selectable marker gene" confers a trait for which one can 'select' based on resistance to a selective agent (e.g., a herbicide, antibiotic, radiation, heat, or other treatment damaging to untransformed cells) or based on a growth advantage in the presence of a metabolizable substrate. Exemplary selectable markers for selection of plant transformants include, but are not limited to, a hyg gene which confers hygromycin B resistance; a neomycin phosphotransferase (npt) gene conferring resistance to kanamycin, paromomycin, G418 and the like as, for example, described by Potrykus et al., 1985; a glutathione-S-transferase gene from rat liver conferring resistance to glutathione derived herbicides as, for example, described in EP-A-256223; a glutamine synthetase gene conferring, upon overexpression, resistance to glutamine synthetase inhibitors such as phosphinothricin as, for example, described WO87/05327, an acetyl transferase gene from *Streptomyces viridochromogenes* conferring resistance to the selective agent phosphinothricin as, for example, described in EP-A-275957, a gene encoding a 5-enolshikimate-3-phosphate synthase (EPSPS) conferring tolerance to N-phosphonomethylglycine as, for example, described by Hinchee et al., 1988, a bar gene conferring resistance against bialaphos as, for example, described in WO91/02071; a nitrilase gene such as bxn from *Klebsiella ozaenae* which confers resistance to bromoxynil (Stalker et al., 1988); a dihydrofolate reductase (DHFR) gene conferring resistance to methotrexate (Thillet et al., 1988); a mutant acetolactate synthase gene (ALS), which confers resistance to imidazolinone, sulfonylurea or other ALS-inhibiting chemicals (EP-A-154204); a mutated anthranilate synthase gene that confers resistance to 5-methyl tryptophan; or a dalapon dehalogenase gene that confers resistance to the herbicide.

Preferred screenable markers include, but are not limited to, a uidA gene encoding a β-glucuronidase (GUS) enzyme for which various chromogenic substrates are known, a β-galactosidase gene encoding an enzyme for which chromogenic substrates are known, an aequorin gene (Prasher et al., 1985), which may be employed in calcium-sensitive bioluminescence detection; a green fluorescent protein gene (GFP, Niedz et al., 1995) or one of its variants; a luciferase (luc) gene (Ow et al., 1986), which allows for bioluminescence detection, and others known in the art.

In some embodiments, the level of endogenous starch branching activity or other enzyme activity is modulated by decreasing the level of expression of genes encoding proteins involved in these activities in the wheat plant, or increasing the level of expression of a nucleotide sequence that codes for the enzyme in a wheat plant. Increasing expression can be achieved at the level of transcription by using promoters of different strengths or inducible promoters, which are capable of controlling the level of transcript expressed from the coding sequence. Heterologous sequences may be introduced which encode transcription factors that modulate or enhance expression of genes whose products down regulate starch branching. The level of expression of the gene may be modulated by altering the copy number per cell of a construct comprising the coding sequence and a transcriptional control element that is operably connected thereto and that is functional in the cell. Alternatively, a plurality of transformants may be selected, and screened for those with a favourable level and/or specificity of transgene expression arising from influences of endogenous sequences in the vicinity of the transgene integration site. A favourable level and pattern of transgene expression is one which results in a substantial increase in starch synthesis or amylose content in the wheat plant. This may be detected by simple testing of transformants.

Reducing gene expression may be achieved through introduction and transcription of a "gene-silencing chimeric gene" introduced into the wheat plant. The gene-silencing chimeric gene is preferably introduced stably into the wheat genome, preferably the wheat nuclear genome. As used herein "gene-silencing effect" refers to the reduction of expression of a target nucleic acid in a wheat cell, preferably an endosperm cell, which can be achieved by introduction of a silencing RNA. In a preferred embodiment, a gene-silencing chimeric gene is introduced which encodes an RNA molecule which reduces expression of one or more endogenous genes, preferably the SBEIIa and/or SBEIIb genes. Target genes in wheat also include the genes listed in Table 1. Such reduction may be the result of reduction of transcription, including via methylation of chromatin remodeling, or post-transcriptional modification of the RNA molecules, including via RNA degradation, or both. Gene-silencing should not necessarily be interpreted as an abolishing of the expression of the target nucleic acid or gene. It is sufficient that the level expression of the target nucleic acid in the presence of the silencing RNA is lower that in the absence thereof. The level of expression of the targeted gene may be reduced by at least about 40% or at least about 45% or at least about 50% or at least about 55% or at least about 60% or at least about 65% or at least about 70% or at least about 75% or at least about 80% or at least about 85% or at least about 90% or at least about 95% or effectively abolished to an undetectable level.

Antisense techniques may be used to reduce gene expression in wheat cells. The term "antisense RNA" shall be taken to mean an RNA molecule that is complementary to at least a portion of a specific mRNA molecule and capable of reducing expression of the gene encoding the mRNA, preferably a SBEIIa and/or SBEIIb gene. Such reduction typically occurs in a sequence-dependent manner and is thought to occur by interfering with a post-transcriptional event such as mRNA transport from nucleus to cytoplasm, mRNA stability or inhibition of translation. The use of antisense methods is well known in the art (see for example, Hartmann and Endres, 1999). Antisense methods are now a well established technique for manipulating gene expression in plants.

As used herein, "artificially introduced dsRNA molecule" refers to the introduction of double-stranded RNA (dsRNA) molecule, which preferably is synthesised in the wheat cell by transcription from a chimeric gene encoding such dsRNA molecule. RNA interference (RNAi) is particularly useful for specifically reducing the expression of a gene or inhibiting the production of a particular protein, also in wheat (Regina et al., 2006). This technology relies on the presence of dsRNA molecules that contain a sequence that is essentially identical to the mRNA of the gene of interest or part thereof, and its complement, thereby forming a dsRNA. Conveniently, the dsRNA can be produced from a single promoter in the host cell, where the sense and anti-sense sequences are transcribed to produce a hairpin RNA in which the sense and anti-sense sequences hybridize to form the dsRNA region with a related (to a SBEII gene) or unrelated sequence forming a loop structure, so the hairpin RNA comprises a stem-loop structure. The design and production of suitable dsRNA molecules for the present invention is well within the capacity of a person skilled in the art, particularly considering Waterhouse et al., 1998; Smith et al., 2000; WO 99/32619; WO 99/53050; WO 99/49029; and WO 01/34815.

The DNA encoding the dsRNA typically comprises both sense and antisense sequences arranged as an inverted repeat. In a preferred embodiment, the sense and antisense sequences are separated by a spacer region which may comprise an intron which, when transcribed into RNA, is spliced out. This arrangement has been shown to result in a higher efficiency of gene silencing (Smith et al., 2000). The double-stranded region may comprise one or two RNA molecules, transcribed from either one DNA region or two. The dsRNA may be classified as long hpRNA, having long, sense and antisense regions which can be largely complementary, but need not be entirely complementary (typically larger than about 200 bp, ranging between 200-1000 bp). hpRNA can also be rather small with the double-stranded portion ranging in size from about 30 to about 42 bp, but not much longer than 94 bp (see WO04/073390). The presence of the double stranded RNA region is thought to trigger a response from an endogenous plant system that destroys both the double stranded RNA and also the homologous RNA transcript from the target plant gene, efficiently reducing or eliminating the activity of the target gene.

The length of the sense and antisense sequences that hybridise should each be at least 19 or at least 21 contiguous nucleotides, preferably at least 30 or 50 nucleotides, and more preferably at least 100, 200, 500 or 1000 nucleotides. The full-length sequence corresponding to the entire gene transcript may be used. The lengths are most preferably 100-2000 nucleotides. The degree of identity of the sense and antisense sequences to the targeted transcript should be at least 85%, preferably at least 90% and more preferably 95-100%. The longer the sequence, the less stringent the requirement for the overall sequence identity. The RNA molecule may of course comprise unrelated sequences which may function to stabilize the molecule. The promoter used to express the dsRNA-forming construct may be any type of promoter that is expressed in the cells which express the target gene. When the target gene is SBEIIa or SBEIIb or other gene expressed selectively in the endosperm, an endosperm promoter is preferred, so as to not affect expression of the target gene(s) in other tissues.

Examples of dsRNA molecules that may be used to down-regulate SBEII gene(s) are provided in Example 4.

As used herein, "silencing RNAs" are RNA molecules that have 21 to 24 contiguous nucleotides that are complementary to a region of the mRNA transcribed from the target gene, preferably SBEIIa or SBEIIb. The sequence of the 21 to 24 nucleotides is preferably fully complementary to a sequence of 21 to 24 contiguous nucleotides of the mRNA i.e. identical to the complement of the 21 to 24 nucleotides of the region of the mRNA. However, miRNA sequences which have up to five mismatches in region of the mRNA may also be used (Palatnik et al., 2003), and basepairing may involve one or two G-U basepairs. When not all of the 21 to 24 nucleotides of the silencing RNA are able to basepair with the mRNA, it is preferred that there are only one or two mismatches between the 21 to 24 nucleotides of the silencing RNA and the region of the mRNA. With respect to the miRNAs, it is preferred that any mismatches, up to the maximum of five, are found towards the 3' end of the miRNA. In a preferred embodiment, there are not more than one or two mismatches between the sequences of the silencing RNA and its target mRNA.

Silencing RNAs derive from longer RNA molecules that are encoded by the chimeric DNAs of the invention. The longer RNA molecules, also referred to herein as "precursor RNAs", are the initial products produced by transcription from the chimeric DNAs in the wheat cells and have partially double-stranded character formed by intra-molecular basepairing between complementary regions. The precursor RNAs are processed by a specialized class of RNAses, commonly called "Dicer(s)", into the silencing RNAs, typically of 21 to 24 nucleotides long. Silencing RNAs as used herein include short interfering RNAs (siRNAs) and microRNAs (miRNAs), which differ in their biosynthesis. SiRNAs derive from fully or partially double-stranded RNAs having at least 21 contiguous basepairs, including possible G-U basepairs, without mismatches or non-basepaired nucleotides bulging out from the double-stranded region. These double-stranded RNAs are formed from either a single, self-complementary transcript which forms by folding back on itself and forming a stem-loop structure, referred to herein as a "hairpin RNA", or from two separate RNAs which are at least partly complementary and that hybridize to form a double-stranded RNA region. miRNAs are produced by processing of longer, single-stranded transcripts that include complementary regions that are not fully complementary and so form an imperfectly basepaired structure, so having mismatched or non-basepaired nucleotides within the partly double-stranded structure. The basepaired structure may also include G-U basepairs. Processing of the precursor RNAs to form miRNAs leads to the preferential accumulation of one distinct, small RNA having a specific sequence, the miRNA. It is derived from one strand of the precursor RNA, typically the "antisense" strand of the precursor RNA, whereas processing of the long complementary precursor RNA to form siRNAs produces a population of siRNAs which are not uniform in sequence but correspond to many portions and from both strands of the precursor.

MiRNA precursor RNAs of the invention, also termed herein as "artificial miRNA precursors", are typically derived from naturally occurring miRNA precursors by altering the nucleotide sequence of the miRNA portion of the naturally-occurring precursor so that it is complementary, preferably fully complementary, to the 21 to 24 nucleotide region of the target mRNA, and altering the nucleotide sequence of the complementary region of the miRNA precursor that basepairs to the miRNA sequence to maintain basepairing. The remainder of the miRNA precursor RNA may be unaltered and so have the same sequence as the naturally occurring miRNA precursor, or it may also be altered in sequence by nucleotide substitutions, nucleotide insertions, or preferably nucleotide deletions, or any combination thereof. The remainder of the miRNA precursor RNA is thought to be involved in recognition of the structure by the Dicer enzyme called Dicer-like 1 (DCL1), and therefore it is preferred that few if any changes are made to the remainder of the structure. For example, basepaired nucleotides may be substituted for other basepaired nucleotides without major change to the overall structure. The naturally occurring miRNA precursor from which the artificial miRNA precursor of the invention is derived may be from wheat, another plant such as another cereal plant, or from non-plant sources. Examples of such precursor RNAs are the rice mi395 precursor, the *Arabidopsis* mi159b precursor, or the mi172 precursor.

Artificial miRNAs have been demonstrated in plants, for example Alvarez et al., 2006; Parizotto et al., 2004; Schwab et al., 2006.

Another molecular biological approach that may be used is co-suppression. The mechanism of co-suppression is not well understood but is thought to involve post-transcriptional gene silencing (PTGS) and in that regard may be very similar to many examples of antisense suppression. It involves introducing an extra copy of a gene or a fragment thereof into a plant in the "sense orientation" with respect to a promoter for its expression, which as used herein refers to the same orientation as transcription and translation (if it occurs) of the sequence relative to the sequence in the target gene. The size of the sense fragment, its correspondence to target gene regions, and its degree of homology to the target gene are as for the antisense sequences described above. In some instances the additional copy of the gene sequence interferes with the expression of the target plant gene. Reference is made to patent specification WO 97/20936 and European patent specification 0465572 for methods of implementing co-suppression approaches. The antisense, co-suppression or double stranded RNA molecules may also comprise a largely double-stranded RNA region, preferably comprising a nuclear localization signal, as described in WO 03/076619.

Any of these technologies for reducing gene expression can be used to coordinately reduce the activity of multiple genes. For example, one RNA molecule can be targeted against a family of related genes by targeting a region of the genes which is in common. Alternatively, unrelated genes may be targeted by including multiple regions in one RNA molecule, each region targeting a different gene. This can readily be done by fusing the multiple regions under the control of a single promoter.

A number of techniques are available for the introduction of nucleic acid molecules into a wheat cell, well known to workers in the art. The term "transformation" as used herein means alteration of the genotype of a cell, for example a bacterium or a plant, particularly a wheat plant, by the introduction of a foreign or exogenous nucleic acid. By "transformant" is meant an organism so altered. Introduction of DNA into a wheat plant by crossing parental plants or by mutagenesis per se is not included in transformation. By "transgene" is meant a foreign or exogenous gene or sequence that is introduced into a plant. The nucleic acid molecule may be replicated as an extrachromosomal element or is preferably stably integrated into the genome of the plant. By "genome" is meant the total inherited genetic complement of the cell, plant or plant part, and includes chromosomal DNA, plastid DNA, mitochondrial DNA and extrachromosomal DNA molecules. In an embodiment, a transgene is integrated in the wheat nuclear genome which in hexaploid wheat includes the A, B and D subgenomes, herein referred to as the A, B and D "genomes".

The most commonly used methods to produce fertile, transgenic wheat plants comprise two steps: the delivery of DNA into regenerable wheat cells and plant regeneration through in vitro tissue culture. Two methods are commonly used to deliver the DNA: T-DNA transfer using *Agrobacterium tumefaciens* or related bacteria and direct introduction of DNA via particle bombardment, although other methods have been used to integrate DNA sequences into wheat or other cereals. It will be apparent to the skilled person that the particular choice of a transformation system to introduce a nucleic acid construct into plant cells is not essential to or a limitation of the invention, provided it achieves an acceptable level of nucleic acid transfer. Such techniques for wheat are well known in the art.

Transformed wheat plants can be produced by introducing a nucleic acid construct according to the invention into a recipient cell and growing a new plant that comprises and expresses a polynucleotide according to the invention. The process of growing a new plant from a transformed cell which is in cell culture is referred to herein as "regeneration". Regenerable wheat cells include cells of mature embryos, meristematic tissue such as the mesophyll cells of the leaf base, or preferably from the scutella of immature embryos, obtained 12-20 days post-anthesis, or callus derived from any of these. The most commonly used route to recover regenerated wheat plants is somatic embryogenesis using media such as MS-agar supplemented with an auxin such as 2,4-D and a low level of cytokinin, see Sparks and Jones, 2004).

*Agrobacterium*-mediated transformation of wheat may be performed by the methods of Cheng et al., 1997; Weir et al., 2001; Kanna and Daggard, 2003 or Wu et al., 2003. Any *Agrobacterium* strain with sufficient virulence may be used, preferably strains having additional virulence gene functions such as LBA4404, AGL0 or AGL1 (Lazo et al., 1991) or versions of C58. Bacteria related to *Agrobacterium* may also be used. The DNA that is transferred (T-DNA) from the *Agrobacterium* to the recipient wheat cells is comprised in a genetic construct (chimeric plasmid) that contains one or two border regions of a T-DNA region of a wild-type Ti plasmid flanking the nucleic acid to be transferred. The genetic construct may contain two or more T-DNAs, for example where one T-DNA contains the gene of interest and a second T-DNA contains a selectable marker gene, providing for independent insertion of the two T-DNAs and possible segregation of the selectable marker gene away from the transgene of interest.

Any wheat type that is regenerable may be used; varieties Bob White, Fielder, Veery-5, Cadenza and Florida have been reported with success. Transformation events in one of these more readily regenerable varieties may be transferred to any other wheat cultivars including elite varieties by standard backcrossing. An alternative method using *Agrobacterium* makes use of an in vivo inoculation method followed by regeneration and selection of transformed plants using tissue culture and has proven to be efficient, see WO00/63398. Other methods involving the use of *Agrobacterium* include: co-cultivation of *Agrobacterium* with cultured isolated protoplasts; transformation of seeds, apices or meristems with *Agrobacterium*, or inoculation in planta such as the floral-dip method for *Arabidopsis* as described by Bechtold et al., 1993. This latter approach is based on the vacuum infiltration of a suspension of *Agrobacterium* cells. Alternatively, the chimeric construct may be introduced using root-inducing (Ri) plasmids of *Agrobacterium* as vectors.

Another method commonly used for introducing the nucleic acid construct into a plant cell is high velocity ballistic penetration by small particles (also known as particle bombardment or microprojectile bombardment) with the nucleic acid to be introduced contained either within the matrix of small beads or particles, or on the surface thereof as, for example described by Klein et al., 1987.

Preferred selectable marker genes for use in the transformation of wheat include the *Streptomyces hygroscopicus* bar gene or pat gene in conjunction with selection using the herbicide glufosinate ammonium, the hpt gene in conjunction with the antibiotic hygromycin, or the nptII gene with kanamycin or G418. Alternatively, positively selectable markers such as the manA gene encoding phosphomannose isomerase (PMI) with the sugar mannose-6-phosphate as sole C source may be used.

The synthesis of starch in the endosperm of higher plants including wheat is carried out by a suite of enzymes that catalyse four key steps. Firstly, ADP-glucose pyrophosphorylase (EC 2.7.7.27) activates the monomer precursor of starch through the synthesis of ADP-glucose from G-1-P and ATP. Secondly, the activated glucosyl donor, ADP-glucose, is transferred to the non-reducing end of a pre-existing 1-4) linkage by starch synthases (EC 2.4.1.24). Thirdly, starch branching enzymes introduce branch points through the cleavage of a region of (1-4) linked glucan followed by transfer of the cleaved chain to an acceptor chain, forming a new (1-6) linkage. Starch branching enzymes are the only enzymes that can introduce the $\alpha(1-6)$ linkages into $\alpha$-polyglucans and therefore play an essential role in the formation of amylopectin. Fourthly, starch debranching enzymes (EC 2.4.4.18) remove some of the branch linkages.

Starch is the major storage carbohydrate in plants such as cereals, including wheat. Starch is synthesized in the amyloplasts and formed and stored in granules in the developing storage organ such as grain; it is referred to herein as "storage starch" or "grain starch". In cereal grains, the vast majority of the storage starch is deposited in the endosperm. "Starch" is defined herein as polysaccharide composed of glucopyranose units polymerized through a combination of both $\alpha(1-4)$ and α(1-6) linkages. The polydisperse molecules of starch are classified as belonging to two component fractions, known as amylose and amylopectin, on the basis of their degree of polymerization (DP) and the ratio of α(1-6) to α(1-4) linkages. Grain starch from wild-type cereal plants, including from wheat, comprises about 20%-30% of amylose and about 70%-80% of amylopectin.

"Amylose" is defined herein as including essentially linear molecules of α(1,4) linked glucosidic (glucopyranose) units, sometimes referred to as "true amylose", and amylose-like long-chain starch which is sometimes referred to as "intermediate material" or "amylose-like amylopectin" which appears as iodine-binding material in an iodometric assay along with true amylose (Takeda et al., 1993b; Fergason, 1994). Typically, the linear molecules in true amylose have a DP of between 500 and 5000 and contain less than 1% α(1-6) linkages. Recent studies have shown that about 0.1% of α(1-6)-glycosidic branching sites may occur in amylose, therefore it is described as "essentially linear". In contrast, amylopectin is a much larger molecule with a DP ranging from 5000 to 50,000 and contains 4-5% α(1-6) linkages. Amylopectin molecules are therefore more highly branched. Amylose has a helical conformation with a molecular weight of about $10^4$ to about $10^6$ Daltons while amylopectin has a molecular weight of about $10^7$ to about $10^8$ Daltons. These two types of starch can readily be distinguished or separated by methods well known in the art.

The proportion of amylose in the starch as defined herein is on a weight/weight (w/w) basis, i.e. the weight of amylose as a percentage of the weight of total starch extractable from the grain, with respect to the starch prior to any fractionation into amylose and amylopectin fractions. The terms "proportion of amylose in the starch" and "amylose content" when used herein in the context of the grain, flour or other product of the invention are essentially interchangeable terms. Amylose content may be determined by any of the methods known in the art including size exclusion high-performance liquid chromatography (HPLC), for example in 90% (w/v) DMSO, concanavalin A methods (Megazyme Int, Ireland), or preferably by an iodometric method, for example as described in Example 1. The HPLC method may involve debranching of the starch (Batey and Curtin, 1996) or not involve debranching. It will be appreciated that methods such as the HPLC method of Batey and Curtin, 1996 which assay only the "true amylose" may underestimate the amylose content as defined herein. Methods such as HPLC or gel permeation chromatography depend on fractionation of the starch into the amylose and amylopectin fractions, while iodometric methods depend on differential iodine binding and therefore do not require fractionation.

From the grain weight and amylose content, the amount of amylose deposited per grain can be calculated and compared for test and control lines.

Examples of genes encoding starch branching enzymes (SBE) from cereals including wheat are given in Table 1. As used herein, "starch branching enzyme" means an enzyme that introduces α-1,6 glycosidic bonds between chains of glucose residues (EC 2.4.1.18). Three forms of starch branching enzyme are expressed in cereals such as rice, maize, barley and wheat, including in the developing cereal endosperm, namely starch branching enzyme I (SBEI), starch branching enzyme IIa (SBEIIa) and starch branching enzyme IIb (SBEIIb) (Hedman and Boyer, 1982; Boyer and Preiss, 1978; Mizuno et al., 1992, Sun et al., 1997). Genomic and cDNA sequences for genes encoding these enzymes have been characterized for rice, barley and wheat (Table 1). Sequence alignment reveals a high degree of sequence similarity at both the nucleotide and amino acid levels, but also the sequence differences and allows the grouping into the SBEI, SBEIIa and SBEIIb classes. SBEIIa and SBEIIb from any one species generally exhibit around 80% amino acid sequence identity to each other, particularly in the central regions of the genes. SBEIIa and SBEIIb may also be distinguished by their expression patterns, but this differs in different species. In maize, SBEIIb is most highly expressed in endosperm while SBEIIa is present in every tissue of the plant. In barley, both SBEIIa and SBEIIb are present in about equal amounts in the endosperm, while in wheat endoperm, SBEIIa is expressed about 3-4-fold more highly than SBEIIb. Therefore, the cereal species show significant differences in SBEIIa and SBEIIb expression, and conclusions drawn in one species cannot readily be applied to another species. In wheat, SBEIIa and SBEIIb proteins are different in size (see below) and this is a convenient way to distinguish them. Specific antibodies may also be used to distinguish them.

In developing wheat endosperm, SBEI (Morell et al., 1997) is found exclusively in the soluble fraction (amyloplast stroma), while SBEIIa and SBEIIb are found in both soluble and starch-granule associated fractions in endosperm (Rahman et al., 1995). In wheat, apparent gene duplication events have increased the number of SBEI genes in each genome (Rahman et al., 1999). The elimination of greater than 97% of the SBEI activity by combining mutations in the highest expressing forms of the SBEI genes from the A, B and D genomes had no measurable impact on starch structure or functionality (Regina et al., 2004). In contrast, reduction of SBEIIa expression by a gene silencing construct in wheat resulted in high amylose levels (>70%), while a corresponding construct that reduced SBEIIb expression but not SBEIIa had minimal effect (Regina et al., 2006). In barley, a gene silencing construct which reduced both SBEIIa and SBEIIb expression in endosperm was used to generate high amylose barley grain (Regina et al., 2010).

Starch branching enzyme (SBE) activity may be measured by enzyme assay, for example by the phosphorylase stimulation assay (Boyer and Preiss, 1978). This assay measures the stimulation by SBE of the incorporation of glucose 1-phosphate into methanol-insoluble polymer (α-D-glucan) by phosphorylase A. SBE activity can be measured by the iodine stain assay, which measures the decrease in the absorbency of a glucan-polyiodine complex resulting from branching of glucan polymers. SBE activity can also be assayed by the branch linkage assay which measures the generation of reducing ends from reduced amylose as substrate, following isoamylose digestion (Takeda et al., 1993a). Preferably, the activity is measured in the absence of SBEI activity. Isoforms of SBE show different substrate specificities, for example SBEI exhibits higher activity in branching amylose, while SBEIIa and SBEIIb show higher rates of branching with an amylopectin substrate. The isoforms may also be distinguished on the basis of the length of the glucan chain that is transferred. SBE protein may also be measured by using specific antibodies such as those described herein. The SBEII activity may be measured during grain development in the developing endosperm. Alternatively, SBEII levels are measured in the mature grain where the protein is still present and can be assayed by immunological methods.

In some embodiments, the level or activity of SBEII or SBEIIa may be assessed by assessing transcript levels such as by Northern or RT-PCR analysis. In a preferred method, the amount of SBEIIa protein in grain or developing endosperm is measured by separating the proteins in extracts of the grain/endosperm on gels by electrophoresis, then transferring the proteins to a membrane by Western blotting, followed by quantitative detection of the protein on the membrane using specific antibodies ("Western blot analysis"). This is exemplified in Example 11.

The present invention is further described by the following non-limiting Examples.

EXAMPLE 1

Methods and Materials

Carbohydrate Determination and Analysis.

Starch was isolated on small scale from both developing and mature wheat grain using the method of Regina et al., (2006). Large scale starch extraction was carried out following the method of Regina et al., (2004). Starch content was determined using the total starch analysis kit supplied by Megazyme (Bray, Co Wicklow, Republic of Ireland) and calculated on a weight basis as a percentage of the mature, unmilled grain weight. The starch content was then compared to control plants. Subtraction of the starch weight from the total grain weight to give a total non-starch content of the grain determined whether the reduction in total weight was due to a reduction in starch content.

The amylose content of starch samples was determined by the colorimetric (iodometric) method of Morrison and Laignelet (1983) with slight modifications as follows. Approximately 2 mg of starch was weighed accurately (accurate to 0.1 mg) into a 2 ml screw-capped tube fitted with a rubber washer in the lid. To remove lipid, 1 ml of 85% (v/v) methanol was mixed with the starch and the tube heated in a 65° C. water bath for 1 hour with occasional vortexing. After centrifugation at 13,000 g for 5 min, the supernatant was carefully removed and the extraction steps repeated. The starch was then dried at 65° C. for 1 hour and dissolved in urea-dimethyl sulphoxide solution (UDMSO; 9 volumes of dimethyl sulphoxide to 1 volume of 6 M urea), using 1 ml of UDMSO per 2 mg of starch (weighed as above). The mixture was immediately vortexed vigorously and incubated in a 95° C. water bath for 1 hour with intermittent vortexing for complete dissolution of the starch. An aliquot of the starch-UDMSO solution (50 µl) was treated with 20 µl of $I_2$-KI reagent that contained 2 mg iodine and 20 mg potassium iodide per ml of water. The mixture was made up to 1 ml with water. The absorbance of the mixture at 620 nm was measured by transferring 200 µl to microplate and reading the absorbance using an Emax Precision Microplate Reader (Molecular Devices, USA). Standard samples containing from 0 to 100% amylose and 100% to 0% amylopectin were made from potato amylose and corn (or potato) amylopectin (Sigma) and treated as for the test samples. The amylose content (percentage amylose) was determined from the absorbance values using a regression equation derived from the absorbances for the standard samples. Analysis of the amylose/amylopectin ratio of non-debranched starches may also be carried out according to Case et al., (1998) or by an HPLC method using 90% DMSO for separating debranched starches as described by Batey and Curtin, (1996).

Statistical analysis of the amylose data was carried out using the $8^{th}$ edition of Genstat for Windows (VSN International Ltd, Herts, UK).

The distribution of chain lengths in the starch was analysed by fluorophore assisted carbohydrate electrophoresis (FACE) using a capillary electrophoresis unit according to Morell et al., (1998) after debranching of the starch samples. The gelatinisation temperature profiles of starch samples were measured in a Pyris 1 differential scanning calorimeter (Perkin Elmer, Norwalk Conn., USA). The viscosity of starch solutions was measured on a Rapid-Visco-Analyser (RVA, Newport Scientific Pty Ltd, Warriewood, Sydney), for example using conditions as reported by Batey et al., (1997). The parameters measured included peak viscosity (the maximum hot paste viscosity), holding strength, final viscosity and pasting temperature. The swelling volume of flour or starch was determined according to the method of Konik-Rose et al., (2001). The uptake of water was measured by weighing the sample prior to and after mixing the flour or starch sample in water at defined temperatures and following collection of the gelatinized material.

Starch granule morphology was analysed by microscopy. Purified starch granule suspensions in water were examined under both normal and polarized light using a Leica-DMR compound microscope to determine the starch granule morphology. Scanning electron microscopy was carried out using a Joel JSM 35C instrument. Purified starches were sputter-coated with gold and scanned at 15 kV at room temperature.

β-Glucan levels were determined using the kit supplied by Megazyme (Bray, Co, Wicklow, Republic of Ireland).

Analysis of Protein Expression in Endosperm.

Specific expression of SBEI, SBEIIa and SBEIIb proteins in endosperm, in particular the level of expression or accumulation of these proteins, was analysed by Western blot procedures. Endosperm was dissected away from all maternal tissues and samples of approximately 0.2 mg were homogenized in 600 µl of 50 mM Kphosphate buffer (42 mM $K_2HPO_4$ and 8 mM $KH_2PO_4$), pH 7.5, containing 5 mM EDTA, 20% glycerol, 5 mM DTT and 1 mM Pefabloc. The ground samples were centrifuged for 10 min at 13,000 g and the supernatant aliquoted and frozen at −80° C. until use. For total protein estimation, a BSA standard curve was set up using 0, 20, 40, 60, 80 and 100 µl aliquots of 0.25 mg/ml BSA standard. The samples (3 µl) were made up to 100 µl with distilled water and 1 ml of Coomassie Plus Protein reagent was added to each. The absorbance was read after 5 min at 595 nm, using the zero BSA sample from the standard curve as the blank, and the protein levels in the samples determined. Samples containing 20 µg total protein from each endosperm were run on an 8% non denaturing polyacrylamide gel containing 0.34 M Tris-HCl (pH 8.8), acrylamide (8.0%), ammonium persulphate (0.06%) and TEMED (0.1%). Following electrophoresis, the proteins were transferred to a nitrocellulose membrane according to Morell et al., 1997 and immunoreacted with SBEIIa, SBEIIb or SBEI specific antibodies. Antiserum against wheat SBEIIa protein (anti-wBEIIa) was generated using a synthetic peptide having the amino acid sequence of the N-terminal sequence of mature wheat SBEIIa, AASPGKVLVPDGESDDL (SEQ ID NO: 16) (Rahman et al., 2001). Antiserum against wheat SBEIIb (anti-wBEIIb) was generated in an analogous manner using the N-terminal synthetic peptide, AGGPSGEVMI (SEQ ID NO: 17) (Regina et al., (2005). This peptide was thought to represent the N-terminal sequence of the mature SBEIIb peptide and furthermore was identical to the N-terminus of the barley SBEIIb protein (Sun et al., 1998). A polyclonal antibody against wheat SBEI was synthesised in an analogous manner using the N-terminal synthetic peptide VSAPRDYTMATAEDGV (SEQ ID NO: 18) (Morell et al., 1997). Such antisera were obtained from rabbits immunised with the synthetic peptides according to standard methods.

Enzyme Assay for SBE.

Enzyme activity assays of branching enzymes to detect the activity of all three isoforms, SBEI, SBEIIa and SBEIIb was based on the method of Nishi et al., 2001 with minor modification. After electrophoresis, the gel was washed twice in 50 mM HEPES, pH 7.0 containing 10% glycerol and incubated at room temperature in a reaction mixture consisting of 50 mM HEPES, pH 7.4, 50 mM glucose-1-phosphate, 2.5 mM AMP, 10% glycerol, 50 U phosphorylase a 1 mM DTT and 0.08% maltotriose for 16 h. The bands were visualised with a solution of 0.2% (W/V) $I_2$ and 2% KI. The SBEI, SBEIIa and SBEIIb isoform specific activities were separated under these conditions of electrophoresis. This was confirmed by immunoblotting using anti-SBEI, anti-SBEIIa and anti-SBEIIb antibodies. Densitometric analysis of immunoblots using TotalLab software package (Nonlinear Dynamics Ltd, Newcastle, UK) which measures the intensity of each band was conducted to determine the level of enzyme activity of each isoform.

Starch branching enzyme (SBE) activity may be measured by enzyme assay, for example by the phosphorylase stimulation assay (Boyer and Preiss, 1978). This assay measures the stimulation by SBE of the incorporation of glucose 1-phosphate into methanol-insoluble polymer (α-D-glucan) by phosphorylase A. Activity of specific isoforms of SBE can be measured by this assay following purification of individual isoforms as described in Regina et al., 2004. The total soluble protein extracts were applied to a 3 ml β-cyclodextrin (β-CD) affinity column pre-equilibrated with the extraction buffer described above. The column was prepared by coupling β-CD to Epoxy-activated sepharose 6B (Amersham Biosciences, Uppsala, Sweden) following the manufacturer's instructions. The bound proteins (containing SBEs) were eluted using 1% β-CD in Phosphate buffer and then dialysed against buffer A (20 mM phosphate buffer, pH 8.0, 1 mM EDTA and 1 mM DTT). The dialysed samples were subjected to anion exchange chromatography using a 1 ml MonoQ column (Amersham Pharmacia), pre-equilibrated with buffer A. After elution of the unbound proteins, a 30 min linear gradient was applied by introducing buffer B (500 mM Phosphate buffer, pH 8.0, 1 mM EDTA, 1 mM DTT) into buffer A to elute the bound proteins.

SBE activity can also be measured by the iodine stain assay, which measures the decrease in the absorbency of a glucan-polyiodine complex resulting from branching of glucan polymers. SBE activity can also be assayed by the branch linkage assay which measures the generation of reducing ends from reduced amylose as substrate, following isoamylase digestion (Takeda et al., 1993a). Preferably, the activity is measured in the absence of SBEI activity. Isoforms of SBE show different substrate specificities, for example SBEI exhibits higher activity in branching amylose, while SBEIIa and SBEIIb show higher rates of branching with an amylopectin substrate. The isoforms may also be distinguished on the basis of the length of the glucan chain that is transferred. SBE protein may also be measured by using specific antibodies such as those described herein. Preferably, the SBEII activity is measured during grain development in the developing endosperm. SBEII protein levels are preferably measured in the mature grain where the protein is still present by immunological methods such as Western blot analysis.

DNA Analysis of Wheat Plants.

PCR analysis of transformed wheat plants or of plants to be tested for the presence of transgenes was performed on genomic DNA extracted from 1-2 $cm^2$ of fresh leaf material using the mini-prep method described by Stacey and Isaac, (1994). PCR assays to determine the presence of the hairpin RNA constructs used the primers SBEIIa-For: 5'-CCCGCT-GCTTTCGCTCATTTTG-3' (SEQ ID NO: 19) and SBEIIa-Rev: 5'-GACTACCGGAGCTCCCACCTTC-3' (SEQ ID NO: 20) designed to amplify a fragment (462 bp) from the SBEIIa gene. Reaction conditions were as follows: "hot start" (94° C., 3 min) followed by 30 cycles of denaturation (95° C., 30 sec), annealing (55° C., 30 sec), extension (73° C., 2 min) followed by 1 cycle at 73° C. (5 min). Reaction products were analysed by agarose or polyacrylamide gel electrophoresis.

Southern blot hybridization analysis was performed on DNA from a larger scale (9 ml) extraction from lyophilized ground tissue (Stacey and Isaac, 1994). DNA samples were adjusted to 0.2 mg/ml and digested with restriction enzymes such as HindIII, EcoRI and KpnI. Restriction enzyme digestion, gel electrophoresis and vacuum blotting are carried out as described by Stacey and Isaac, (1994). Digoxygenin-labelled probes including the intron 3 region of the ds-SBEII constructs are produced by PCR according to the method of McCreery and Helentjaris, (1994). Hybridization of the probes to the Southern blot and detection by chemiluminescence are performed according to the method of McCreery and Helentjaris, (1994).

Transformation of Wheat by *Agrobacterium*.

Genetic constructs for transformation of wheat were introduced by electroporation into the disarmed *Agrobacterium tumefaciens* strain LBA4404 carrying the vir plasmid pAL4404 and pSB1, with subsequent selection on media with spectinomycin. Transformed *Agrobacterium* strains were incubated on solidified YEP media at 27° C. for 2 days. Bacteria were then collected and re-suspended in TSIM1 (MS media with 100 mg/l myo-inositol, 10 g/l glucose, 50 mg/l MES buffer pH5.5) containing 400 mM acetosyringone to an optical density of 2.4 at 650 nm for wheat inoculation.

Wheat plants (variety NB1, a Spring wheat variety obtained from Nickerson Seeds Ltd, Rothwell, Lincs.) were grown in a glasshouse at 22/15° C. day/night temperature with supplemented light to give a 16 hour day. Tillers were harvested approximately 14 days post-anthesis (embryos approximately 1 mm in length) to include 50 cm tiller stem. All leaves were then removed from the tillers except the flag leaf, which was cleaned to remove contaminating fungal spores. The glumes of each spikelet and the lemma from the first two florets were then carefully removed to expose the immature seed. Generally, only these two seed in each spikelet were uncovered. This procedure was carried out along the entire length of the inflorescence. The ears were then sprayed with 70% IMS as a brief surface sterilization.

*Agrobacterium* suspensions (1 µl) were inoculated using a 10 µl Hamilton syringe into the immature seed approximately at the position of the scutellum:endosperm interface so that all exposed seed were inoculated. The tillers were then placed in water, covered with a translucent plastic bag to prevent seed dehydration, and placed in a lit incubator for 3 days at 23° C., 16 hr day, 45 $\mu Em^{-2}s^{-1}$ PAR. After 3 days of co-cultivation, the inoculated immature seed were removed and surface sterilized with 70% ethanol (30 sec), then 20% bleach (Domestos, 20 min), followed by thorough washing in sterile distilled water. Immature embryos were aseptically isolated and placed on W3 media (MS supplemented with 20 g/l sucrose and 2 mg/l 2,4-D and solidified with 6 g/l Type I agarose, Sigma) with the addition of 150 mg/l Timentin (W3T medium) and with the scutellum uppermost (20 embryos per plate). Cultures were placed at 25° C. in the light (16 hour day, 80 $\mu Em^{-2}s^{-1}$ PAR). The development of the embryonic axis on the embryos was assessed about 5 days after isolation and the axis was removed where necessary to improve callus production. The embryos were maintained on W3T for 4 weeks, with a transfer to fresh media at 2 weeks post-isolation and assessed for embryogenic capacity.

After 4 weeks growth, callus derived from the inoculated embryos was very similar to control callus obtained from uninoculated embryos plated on W3T medium. Presence of the bacteria did not appear to have substantially reduced the embryogenic capacity of the callus derived from the inoculated embryos. Embryogenic calli were transferred to W3 media with 2 mg/l Asulam or geneticin at 25 mg/l and 150 mg/l Timentin (W32AT medium). Calli were maintained on this media for a further 2 weeks and then each callus was divided into 2 mm-sized pieces and re-plated onto W32AT. Control embryos derived from inoculations with the LBA4404 without binary vector constructs did not produce transformed callus on selection media.

After a further 2 weeks culture, all tissue was assessed for development of embryogenic callus: any callus showing signs of continued development after 4 weeks on selection was transferred to regeneration media (RMT—MS with 40 g/l maltose and 150 mg/l Timentin, pH 5.8, solidified with 6 g/l agarose, Sigma type 1). Shoots were regenerated within 4 weeks on this media and then transferred to MS30 with 150 mg/l Timentin for shoot elongation and rooting. Juvenile plants were then transferred to soil mixture and kept on a misting bench for two weeks and finally transferred to a glasshouse.

Alternative *Agrobacterium* strains such as strain AGL1 or selectable markers such as genes encoding hygromycin resistance can also be used in the method.

EXAMPLE 2

Inhibition of SBEIIa Genes in Wheat Using Four Hairpin RNA Constructs

Four hairpin RNA (dsRNA) constructs were made to reduce the expression of i) the SBEIIa, or ii) the SBEIIa, SBEIIb and SBEI genes of wheat. In each construct, the DNA encoding the hairpin RNA was linked to a high molecular weight glutenin (HMWG) promoter sequence obtained from a wheat Dx5 gene to provide endosperm-specific expression of the hairpin RNA, and a transcription terminator sequence from the nopaline synthase gene from *Agrobacterium* (nos3'). This promoter provided for endosperm-specific expression of the synthetic genes encoding the hairpin RNAs.

hp5'-SBEIIa.

The construction and use of the first of the constructs, designated as hp5'-SBEIIa, is described in Regina et al., (2006). The hp5'-SBEIIa construct contained 1536 bp of nucleotide sequence amplified by PCR from the wheat SBEIIa gene (GenBank Accession number AF338431). This included a 468 bp sequence that comprises the whole of exons 1 and 2 and part of exon 3 (nucleotide positions 1058 to 1336, 1664 to 1761 and 2038 to 2219 (that includes nucleotide positions 1 to 578 of *Aegilops tauschii* cDNA encoding SBEIIa, GenBank accession number AF338431.1) with EcoRI and KpnI restriction sites on either side (fragment 1), a 512 bp sequence consisting of part of exons 3 and 4 and the whole of intron 3 of SBEIIa (nucleotide positions 2220 to 2731) with KpnI and SacI sites on either side (fragment 2) and a 528 bp fragment consisting of the complete exons 1, 2 and 3 of SBEIIa (nucleotide positions 1058 to 1336, 1664 to 1761 and 2038 to 2279 in AF338431, that includes nucleotide positions 1 to 638 of *Aegilops tauschii* SBEIIa cDNA, GenBank accession number AF338431.1) with BamHI and SacI sites on either side (fragment 3). Fragments 1, 2 and 3 were then ligated so that the sequence of fragment 3 was ligated to fragment 2 in the antisense orientation relative to fragment 1. The hairpin RNA constructs were initially generated in the vector pDVO3000 which contains the HMWG promoter sequence and nos3' terminator.

hpc-SBEIIa.

The SBEIIa construct designated hpc-SBEIIa comprised a 293 basepair DNA fragment corresponding to nucleotides 1255 to 1547 of the SBEIIa cDNA (GenBank Accession No. AF338432.1), which corresponds to part of exon 12, exons 13 and 14 and part of exon 15 of the SBEIIa gene. This region of SBEIIa was chosen because it had only about 81% identity to the nucleotide sequence of the corresponding region of SBEIIb cDNA, thus increasing the chance of specificity of silencing of SBEIIa but not SBEIIb.

hp3'-SBEIIa.

The SBEIIa construct designated hp3'-SBEIIa comprised a 130 basepair DNA fragment corresponding to nucleotides 2305 to 2434 of the SBEIIa cDNA, corresponding to part of exon 21, exon 22 and part of the 3' untranslated region (3' UTR) of the SBEIIa gene.

hp-Combo.

The hairpin RNA construct designated hp-combo comprised regions of the wheat SBEI gene in addition to parts of the SBEIIa gene, and contained i) a 417 basepair sequence corresponding to nucleotides 1756 to 2172 from the SBEIIa cDNA, corresponding to part of exon 16, exons 17 to 19, and part of exon 20, and ii) a 357 basepair sequence corresponding to nucleotides 267 to 623 of an SBEI cDNA (GenBank Accession No. AF076679), corresponding to part of exon 3, exon 4, and part of exon 5 of the SBEI gene. The SBEIIa gene fragment had about 86% identity to the corresponding region of the SBEIIb gene, including several regions of 23 consecutive nucleotides with 100% identity to their corresponding regions of SBEIIb, and therefore the combination construct was designed with the expectation that it would reduce expression of the genes encoding SBEIIb as well as the genes encoding SBEIIa and SBEI in wheat.

Two copies of each of the fragments described above were inserted, one in sense and the other in antisense orientation, into a suitable vector, such that a rice tubulin gene intron was present between the two copies. The synthetic gene was inserted into a binary vector and used to transform wheat.

These constructs were used to transform wheat as described in Example 1. The numbers of independent wheat transgenic lines that were PCR positive for the respective constructs were as follows: hp5'-SBEIIa, 27; hpc-SBEIIa, 10; hp3'-SBEIIa, 10; and hp-combo, 63.

Analyses of Transgenic Plants: DNA Analysis.

PCR analysis was performed to detect one or more of the transgenes in the regenerated plants using genomic DNA extracted from 1-2 cm$^2$ of fresh leaf material using the miniprep method described by Stacey and Isaac, (1994). PCR reactions were performed for plants transformed with the hp5'-SBEIIa transgene, for example, using the primers SBEIIa-For: 5'-CCCGCTGCTTTCGCTCATTTTG-3' (SEQ ID NO: 19) and SBEIIa-Rev: 5'-GACTACCGGAGCTC-CCACCTTC-3' (SEQ ID NO: 20). These PCR reactions were designed to amplify a fragment of about 462 bp from the SBEIIa gene. Reaction conditions were as follows: "hot start" (94° C., 3 min) followed by 30 cycles of denaturation (95° C., 30 sec), annealing (55° C., 30 sec) and extension (73° C., 2 min), followed by 1 cycle at 73° C. (5 min).

Starch Granule Morphology.

The morphology of starch granules from mature T1 seed obtained from the T0 transformed wheat plants was observed by light microscopy. Ten individual grains from each of 25 T0 hp5'-SBEIIa plants were analysed. Each endosperm was gently crushed to release the starch granules which were dispersed in water and visualized under a light microscope. Of the 25 lines analysed, 12 had grains with distorted granules although the visual observation revealed varying levels of distortion in different seeds. Nine seeds from each of the plants transformed with the hpc-SBEIIa, hp3'-SBEIIa and hp-combo transgenes were similarly analysed for morphological alterations in the starch granules. In this case, half-seeds were analysed so that each remaining halfseed could be grown into a T1 plant, thus preserving each line. Fifty-five out of 63 hp-combo lines had seeds with altered granule morphology with varying levels of distortion. All of the ten hp5'-SBEIIa lines had seeds with altered starch granule morphology, again with varying levels of distortion. No significant starch granule morphology alteration was observed in any of the SBEIIa 3' lines. Distorted starch granules are an indicator of elevated amylose levels in the starch of the endosperm, typically above 50% amylose, or above 70% amylose for highly distorted starch granules. This indicated that a range in the extent of the phenotype was observed for each of the effective silencing constructs.

Protein Expression by Western Blotting in Developing Endosperm.

Four to seven T2 developing endosperms from T1 transgenic lines were analysed for the level of SBEIIa and SBEIIb proteins by Western blotting using anti-SBEIIa and anti-SBEIIb antibodies, respectively. In the case of hp-combo lines, SBEI expression was also analysed using anti-SBEI antibody. Total SBEII protein levels (SBEIIa and SBEIIb) from selected transgenic lines were calculated as a percentage of the level in the wild-type (variety NB1) and is shown in Table 11. Amylose levels in mature grain from the transgenic lines, calculated as a percentage of the total starch in the grain, was also determined (Table 11) using an iodometric method as described in Example 1. This is represented graphically in FIG. 5.

A range of expression levels of SBEIIa and SBEIIb were obtained in the grain of the transgenic plants of independent lines. Such a range is normally expected in transgenic lines obtained with any one construct, due to the variation in integration sites of the transgene in different transgenic events, commonly referred to as "position effect". The range of expression levels seen in these experiments was extended because it was observed that the four constructs were not equally efficient in reducing the expression of the SBEIIa and SBEIIb genes. In particular, the extent of reduction in the expression of SBEIIb caused by the hp-combo construct in some transformed lines did not correlate with the extent of reduction in expression of SBEIIa, for example lines 679.5.3 and 672.2.3. However, all of the constructs reduced expression of the corresponding genes in a majority of transformed lines.

When the percentage of amylose was plotted against the total SBEII protein level and a curve of best fit generated from the data points (see FIG. 5), it was observed that reducing the total SBEII by at least 75% relative to the wild-type yielded an amylose content of 50% (w/w) or greater in the endosperm starch. Reducing the total SBEII activity by at least 40% relative to the wild-type yielded an amylose content of at least 40% (w/w).

When the percentage of amylose was plotted against the remaining SBEIIa protein level, a very similar curve was obtained (see FIG. 6), leading to the conclusion that the level of SBEIIa in wheat endosperm was the primary determinant of the amylose level in the starch, and that the levels of SBEIIb and SBEI were secondary determinants.

Figure 6:
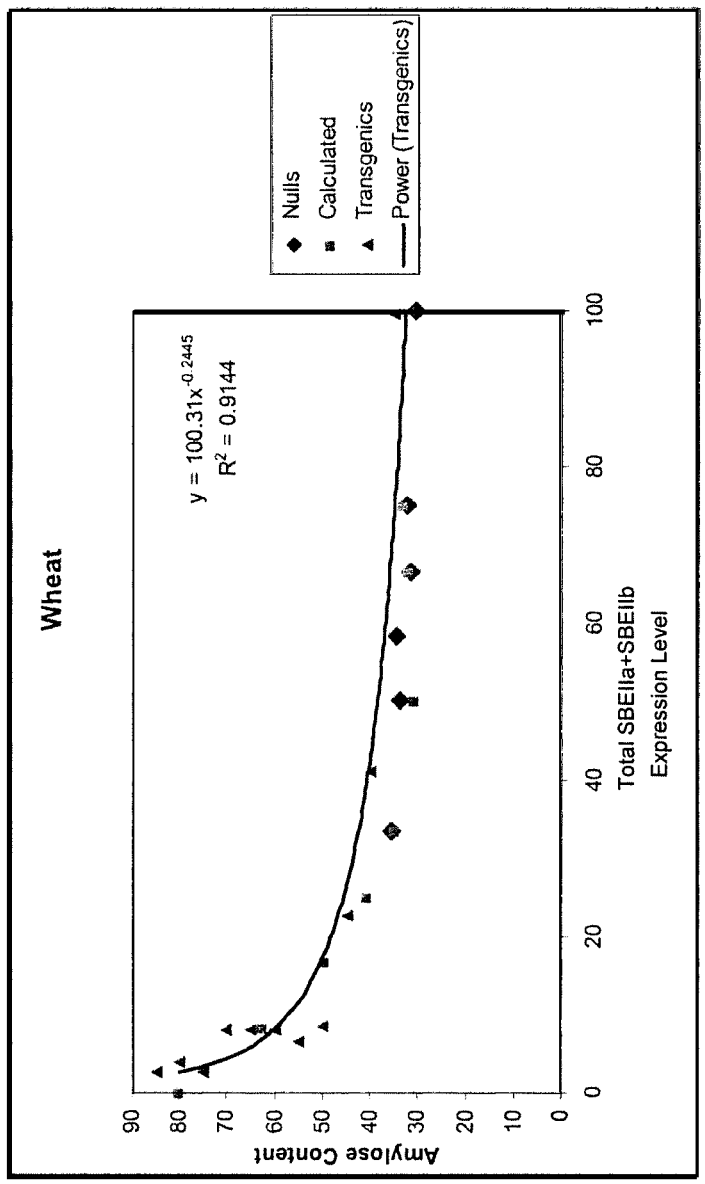
FIG. 6 is a graphical representation of data showing an amylose model derived from behaviour of SBEII transgenic line.

The amylose model was further developed based on three sets of inputs (FIG. 6):

theoretical data based on relative expression levels of SBEIIa and SBEIIb and amylose data from transgenics amylose data for single and double nulls and theoretical data based on relative expression levels of SBEIIa and SBEIIb measured amylose data and measured SBEIIa and SBEIIb levels from the "additional construct" transgenics In FIG. 6, a power curve has been fitted to this data. Bringing together these three data sets generated a model that was highly consistent between input types, reinforcing the model as a predictive tool. The model predicted the importance of generating multiple mutations in SBEII genes in order to generate high amylose in bread wheat or tetraploid wheat.

EXAMPLE 3

Cloning and Comparison of SBEII Gene Sequences from Wheat

Isolation of SBEII genes from an *Aegilops tauschii* genomic library and their characterisation by PCR are described in WO99/14314 and WO200162934-A. DNA sequences from the intron 5 region of SBEIIa gene of the A, B and D genomes are described in WO200162934-A. Further research has led to obtaining sequences from other regions of wheat SBEIIa genes from different wheat genotypes and further characterisation of the homoeologous genes, for example as follows. The exons 12 to 14 region of SBEIIa was amplified from the hexaploid wheat variety Chara using the primers AR2aE12F07 (5'-CATTCGTCAAATAATACCCT-TGACGG-3' (SEQ ID NO: 21)) and AR2aE14R07 (5'-CT-TCACCAATGGATACAGCATCAG-3' (SEQ ID NO: 22)). This yielded a PCR product of about 656 bp which was presumed to be a mixture of the amplified fragments from each of the three homoeologous genes. This product was sequenced following cloning in a TOPO vector. Three polymorphic sequences were obtained that covered the region between exon 12 to 14 (FIG. 7). Based on PCR analysis of Chinese Spring chromosome engineered lines using cleavage amplified polymorphic (CAP) markers, the sequence F1-1 was assigned to the D genome, the sequence F1-13 was assigned to the B genome and the sequence F1-15 was assigned to the A genome as detailed in Example 4.

Figure 8:
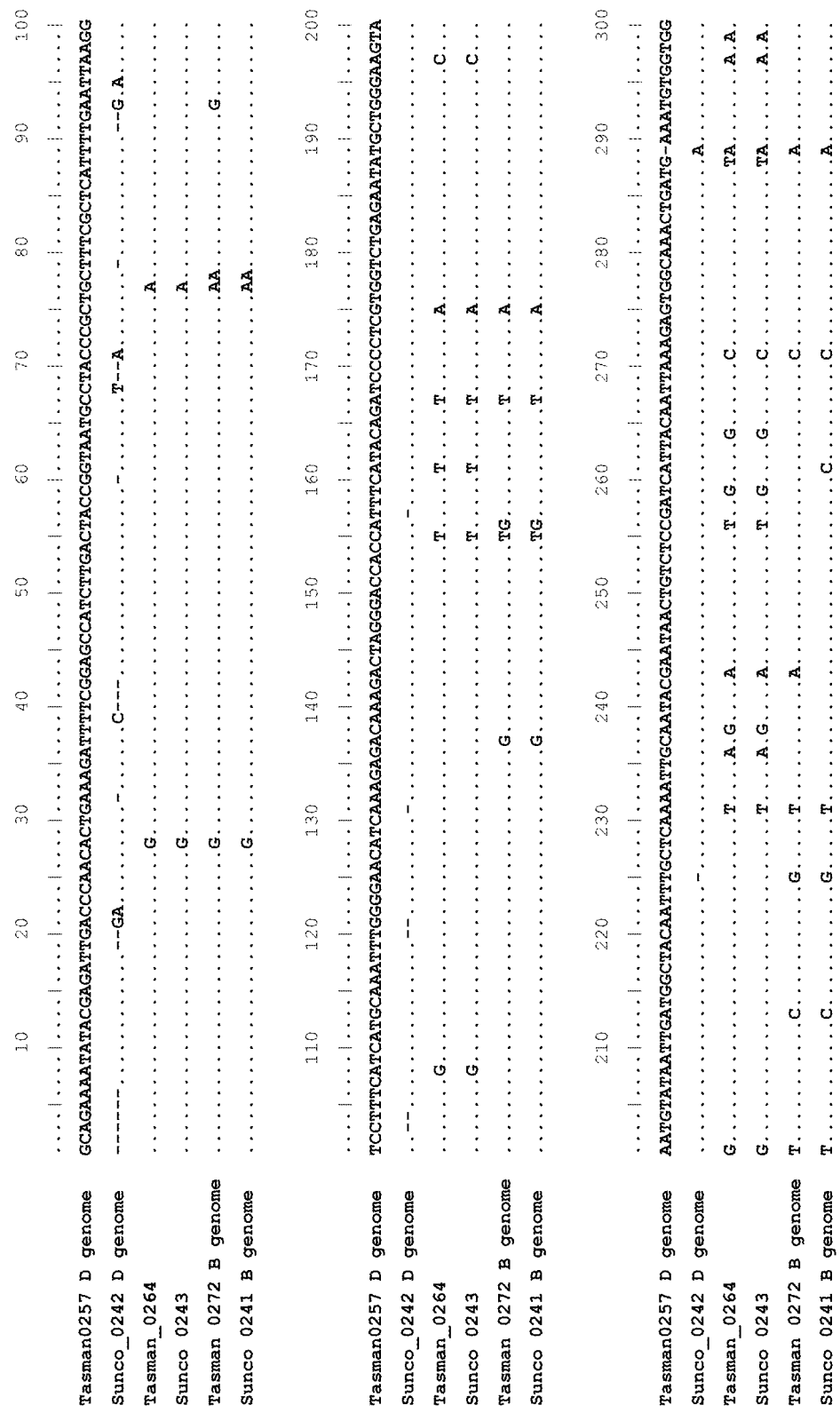
FIG. 8 is a representation showing an alignment of DNA sequences of the intron 3 region of SBEIIa genes obtained from the wheat varieties Sunco and Tasman. The nucleotide sequence for the Tasman D genome fragment (SEQ ID NO:162) is shown in its entirety, while the corresponding nucleotides for the homoeologous fragments are shown only where there are polymorphisms. Dots indicate the corresponding nucleotides are identical to the Tasman D genome fragment. Dashes indicate that the corresponding nucleotide is absent from the sequence.
Figure 8:
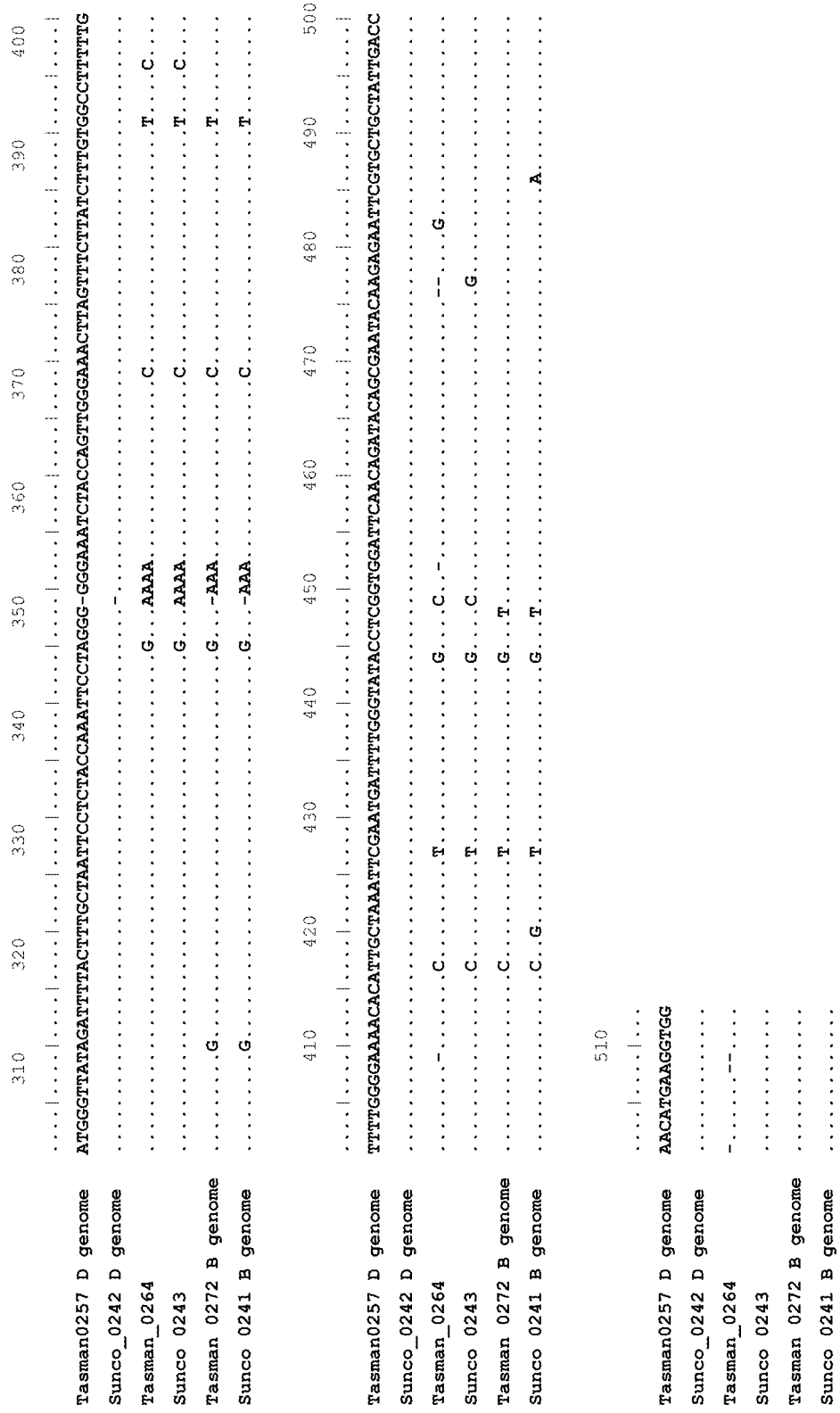

The intron 3 region of SBEIIa was amplified from two hexaploid wheat varieties, Sunco and Tasman, using the primer pair AR2akpnIF (5'-GGTACCGGCAAATATACGAG ATTGACCCG-3' (SEQ ID NO: 23)) and AR2aSacIR (5'-GAGCTCCCACCTTCATGTT GGTCAATAGC-3' (SEQ ID NO: 24)). Three polymorphic sequences were obtained from each of Sunco and Tasman (FIG. 8). By comparison with the wheat SBEIIa D genome sequence (GenBank Accession No. AF338431.1), the sequences Tasman 0257 and Sunco 0242 were assigned to the D genome. Tasman 0272 and Sunco 0241 sequences were assigned to the B genome based on mapping a polymorphic marker based on a single nucleotide polymorphism in a segregating population. The sequences Tasman 0264 and Sunco 0243 appeared to be different from the B and D genome sequences and it was concluded they must be from the A genome. Genotype specific polymorphisms were also observed for this region of SBEIIa between Sunco and Tasman in each of the three genomes.

The exon 3 region of SBEIIa from Chinese Spring (CS) was amplified using the primers AR2aexon3F (5'-GATAC-CTGAAGATATCGAGGAGC-3' (SEQ ID NO: 25)) and AR2aexon3R (5'-CGGTAGTCAAGATGGCTCCG-3' (SEQ ID NO: 26)). Three polymorphic sequences were obtained (FIG. 9). Comparison with the wheat SBEIIa gene (GenBank Accession No. AF338431.1) revealed that the sequence CS exon 3a was from the D genome. The sequence CS exon 3b was found to be from the B genome based on the 100% identity with the GenBank Accession No. FM865435 which was reported to be from a bread wheat 2B chromosome. The third sequence CS exon 3d showed 99% identity with the GenBank Accession No. Y11282.1, which in turn had a high degree of identity (99%) with a partial coding sequence reported from the A genome of Chinese Spring (GenBank Accession No. EU670724). This led to the prediction that the sequence CS exon 3d was from the A genome.

Figure 10:
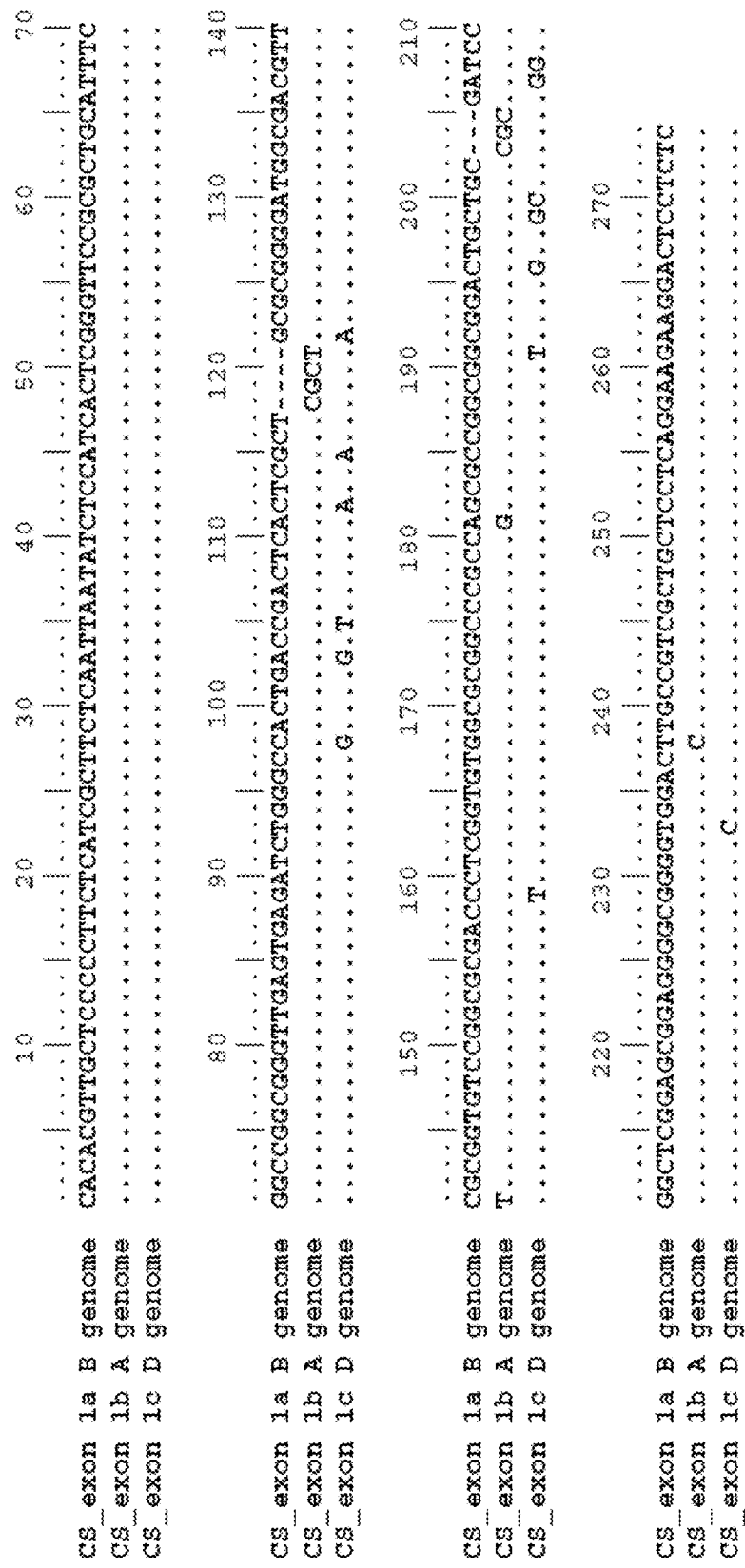
FIG. 10 is an alignment of exon 1 nucleotide sequences from cDNAs from SBEIIa genes of wheat variety Chinese Spring. The nucleotide sequence for the Chinese Spring B genome fragment (SEQ ID NO:164) is shown in its entirety, while the corresponding nucleotides for the homoeologous A and D genome fragments are shown only where there are polymorphisms. Dots indicate the corresponding nucleotides are identical to the Chinese Spring B genome fragment.

The exon 1 region of SBEIIa from CS was amplified using the primers AR2aexon1F (5'-CACACGTTGCTCCCCCT-TCTC-3' (SEQ ID NO: 29)) and AR2aexon1R (5'-GAGAG-GAGTCCTTCTTCCTGAGG-3' (SEQ ID NO: 28)). The sequences were obtained (FIG. 10). Alignment with SBEII GenBank accessions led to assigning the sequence CS exon 1a to the B genome (100% homology to FM865435), CS exon 1b to the A genome (99% homology to Y11282.1) and CS exon 1c to the D genome (100% homology to AF338431.1).

SBEIIa gene sequences were also obtained from the diploid progenitors or relatives of breadwheat, *Triticum urartu* which is thought to be the A genome progenitor of breadwheat, *Aegilops speltoides* (also known as *Triticum speltoides*) which is thought to be the B genome progenitor, and *Aegilops tauschii* which is thought to be related closely to the D genome progenitor. Gene fragments were obtained from these species as follows: Ten primers were designed based on the nucleotide sequence of the SBEIIa gene of the D genome (Accession No. AF338432) or its complement and covering the whole of that sequence. These primer sets were used to amplify fragments of the SBEIIa genes of diploid species by PCR. Using the 10 primers, 16 combinations were used in PCRs with DNA from the diploid species *T. urartu* (AA genome), *A. speltoides* (BB), *A. tauschii* (DD) and the tetraploid species *T. durum* (AABB genome). In total, 35 fragments were selected from these amplifications which were of sufficient quality for sequencing, to determine their nucleotide sequences. The sequences will be compared and edited using Contig Express and combined sequences determined for the progenitor SBEIIa genes from the diploids. Polymorphisms such as SNPs or insertions/deletions will be identified which can be used to distinguish the genes on the A, B and D genomes, and specific primers designed using Amplifier for identification of mutants.

The nucleotide sequence of the exon 11-22 region of the SBEIIa gene from *T. urartu* is shown in SEQ ID NO: 13, of the exons 3-8 as SEQ ID NO: 15 and of exons 1-3 as SEQ ID NO: 14. The nucleotide sequence of the entire SBEIIa gene of *A. tauschii* is provided in WO2005001098 (incorporated herein by reference).

Mapping of SBEIIa and SBEIIb—Genetic Linkage of SBEIIa and SBEIIb in Wheat.

The SBEIIa and SBEIIb genes were both located on the long arm of wheat chromosome 2 (Regina et al., 2005; Rahman et al., 2001) and based on these reports were thought to be linked, although it was not known exactly how close the linkage was. Genetic mapping of the SBEIIa and SBEIIb genes was carried out using a segregating population obtained from a 4-way cross involving the parental cultivars Baxter, Yitpi, Chara and Westonia. The analysis of the population for recombinants between the genes revealed only one recombinant out of approximately 900 progeny. From this data, it was calculated that the genetic distance between SBEIIa and SBEIIb was only 0.5 cM, which was a very tight linkage between the two genes.

To determine the physical distance between the two genes, a BAC library of *Aegilops tauschii* constructed by Moullet et al., (1999) was screened to identifying SBEII containing clones. Hybridisation probes labelled with $^{32}$P were prepared from the 5' and 3' regions from each of the SBEIIa and SBEIIb genes and used to screen the BAC library. When screened with a mixture of the four probes, nine clones were identified with positive hybridisation signals. The nine clones were then screened separately with each of the probes and three clones selected. One of them (BAC2) was fully sequenced and shown to contain a full length SBEIIb gene. Of the other clones, BAC1 was shown to contain a SBEIIa gene by partial direct sequencing and BAC3 appeared to contain portions of both of the SBEIIa and SBEIIb genes as shown by PCR. This indicated how closely the two genes are physically linked. BAC1 and BAC3 will be fully sequenced. This physical data confirmed the close genetic linkage.

It was therefore predicted that deletion mutations created by agents such as radiation which affected one of the genes were likely to extend into or across both genes i.e. be null for both genes. Furthermore, this suggested to us the possibility that such deletion mutants might be viable and have wild-type fitness. At least, the observed tight linkage raised the possibility of obtaining mutants with relatively small deletions which did not extend to other linked genes needed for viability or fitness. Such mutants were therefore sought as described below in Examples 5-7.

EXAMPLE 4

Distinguishing the SBEIIa and SBEIIb Homoeologous Genes in Wheat

Figure 11:
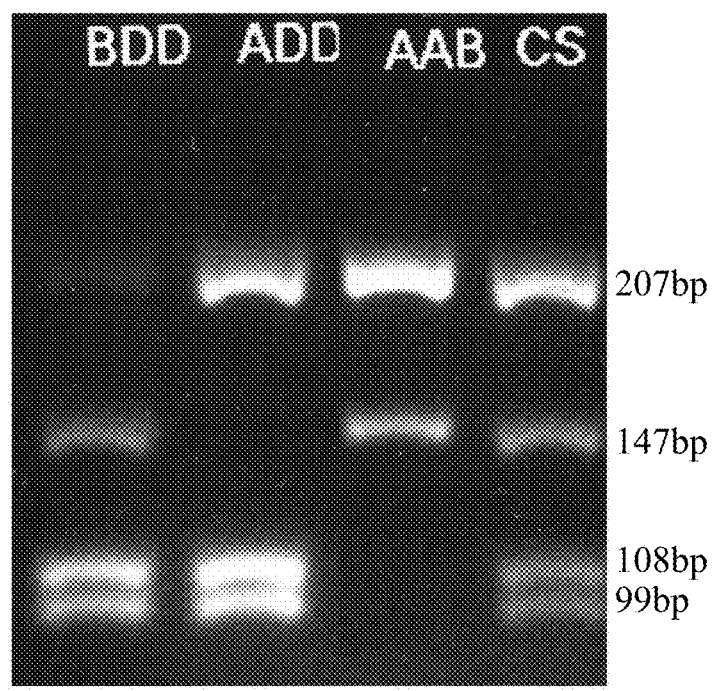
FIG. 11 is a representation showing a PCR amplification of the region spanning exons 12-14 of SBEIIa genes from CS nullisomic-tetrasomic lines. The line designated BDD is null for A genome, ADD is a null for B genome and AAB is a null for D genome.
Figure 12:
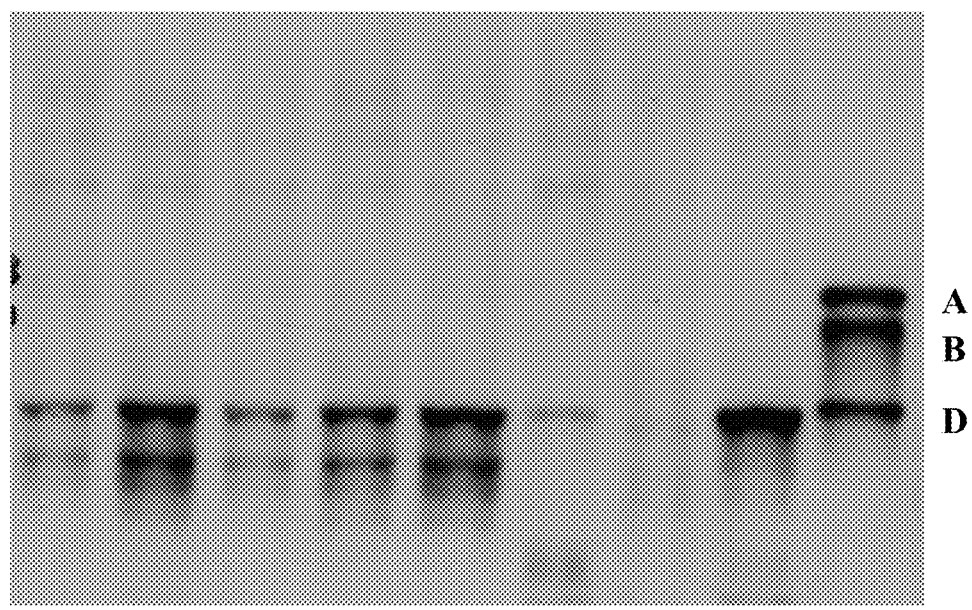
FIG. 12 is photographic representation of a Western blot showing SBEIIa protein expression in developing endosperms from the line S28. Protein extracts from endosperms were assayed by Western blot analysis as described in Example 1, using SBEIIa-specific antibodies. The last lane on the right-hand side shows the bands appearing from wild-type endosperm (variety NB1). The positions of SBEIIa proteins encoded by the A, B and D genomes are indicated.

Based on the sequence polymorphisms obtained in Example 2, PCR assays were designed and prepared to distinguish the homoeologous SBEIIa genes in breadwheat. A nested primer pair, AR2aI13genomeF2 (5'-GTACAATTT-TACCTGATGAGATC ATGG-3' (SEQ ID NO: 29)) and AR2aI13genomeR2 (5'-CTTCAGGAATGGATACAGCAT-CAG-3' (SEQ ID NO: 30)) was designed to amplify a 207 bp product from the region between the exons 12 to 14 of wheat SBEIIa. When digested with two restriction enzymes, Ssp1 and Mse1, the product amplified using these primers from Chinese Spring (CS) yielded four clear bands of sizes 207 bp, 147 bp, 99 bp and 108 bp. Use of this PCR marker assay on CS chromosome engineered lines revealed that the 207 bp product came from the A genome, the 147 bp product came from the B genome and the 99 bp and 108 bp products came from the D genome (FIG. 11).

Based on SBEIIa sequences from the diploid ancestors of wheat namely *Triticum urartu* for genome A, *Aegilops speltoides* for genome B and *Aegilops tauschii* for genome D, primer pairs were designed that could specifically amplify fragments from different regions of the SBEIIa genes from the different genomes and distinguish them (Tables 4 to 8). Tables 6 to 8 list some of the nucleotide polymorphisms (column labelled SNP) and the sizes of the amplified fragments obtained when the designated primer pairs are used. These same primer combinations can be used to distinguish the A and B genome homoeologous SBEIIa genes from *durum* wheat.

Development of some PCR primer sets distinguishing the homoeologous SBEIIb genes from the A, B and D genomes of breadwheat and the identification of SBEIIb in each of these genomes in hexaploid wheat are described in WO200162934-A. Based on SBEIIb sequences from the diploid ancestors of wheat namely *Triticum urartu* for genome A, *Aegilops speltoides for genome B and *Aegilops tauschii* for genome D, primer pairs that could amplify specifically each of the three genomes from different regions of SBEIIb were designed (Tables 9 to 10). These same primer combinations can be used to distinguish the A and B genome homoeologous SBEIIb genes from *durum* wheat.

EXAMPLE 5

Generation and Identification of SBEII Deletion Mutants

Mutagenesis of Wheat by Heavy Ion Bombardment.

A mutagenised wheat population was generated in the wheat variety Chara, a commonly used commercial variety, by heavy ion bombardment (HIB) of wheat seeds. Two sources of heavy ions were used, namely carbon and neon, for mutagenesis which was conducted at Riken Nishina Centre, Wako, Saitama, Japan. Mutagenised seeds were sown in the greenhouse to obtain the M1 plants. These were selfed to produce the M2 generation. DNA samples isolated from each of approximately 15,000 M2 plants were individually screened for mutations in each of the SBEIIa and SBEIIb genes using the genome specific PCR primers for SBEIIa (ARIIaF2/ARIIaR2) and SBEIIb (ARA19F/ARA23R) (diagnostic PCR). Each of the PCR reactions on wild-type DNA samples yielded 3 distinct amplification products which corresponded to the amplified regions of SBEIIa or SBEIIb genes on the A, B and D genomes, whereas the absence of one of the fragments in the PCRs from mutagenised M2 samples indicated the absence of the corresponding region in one of the genomes, i.e. the presence of a mutant allele in which at least part of the gene was deleted. Such mutant alleles would almost certainly be null alleles.

Screening of the M2 lines using the genome specific primer pairs identified a total of 34 mutants which were mutant for the SBEIIa and/or SBEIIb genes. The mutants in SBEIIa were then screened for the presence of the SBEIIb genes, and vice versa. The identified mutants were thereby classified into three groups: "Type 1" where both SBEIIa and SBEIIb genes were mutant i.e. lacking both wild-type genes in one genome, "Type 2", where only the SBEIIa gene was mutant while the SBEIIb gene was wild-type, and "Type 3", where only the SBEIIb gene was mutant and the SBEIIa gene was wild-type in the particular genome. Since the SBEIIa genes on the A, B and D genomes were distinguished by the diagnostic PCR reactions, and likewise the SBEIIb genes, the mutant alleles could be assigned to one of the genomes according to which amplification product was absent. As used herein, the designation "A1" refers to the genotype where both the SBEIIa and SBEIIb genes on the A genome were mutant, "A2" refers to the genotype where the SBEIIa gene was mutant and the SBEIIb gene on the A genome was wild-type, and "A3" refers to the genotype where the SBEIIa gene was wild-type and the SBEIIb gene on the A genome was mutant. The designations "B1", "B2", "B3", "D1", "D2" and "D3" have the analogous meanings for the B and D genomes. Mutants of each of these nine possible types were identified among the collection of 34 mutants.

The extent of the chromosome deletion in each of the 34 mutants was determined by microsatellite mapping. Microsatellite markers previously mapped to the long arm of chromosomes 2A, 2B and 2D (Table 12) were tested on these mutants to determine the presence or absence of each marker in each mutant. Mutant plants in which either all or most of the specific chromosome microsatellite markers were retained, based on the production of the appropriate amplification product in the reactions, were inferred to be relatively small deletion mutants. Such mutants were preferred, considering that it was less likely that other, important genes were affected by the mutations. The identified mutants and the results from the microsatellite mapping are summarized in Table 13.

Crossing of Mutants.

Mutant plants that were homozygous for smaller deletions as judged by the microsatellite marker analysis were selected for crossing to generate progeny plants and grain which had mutant SBEII alleles on multiple genomes. F1 progeny plants from the crosses were selfed, and F2 seed obtained and analysed for their SBEII genotype. Screening 12 such F2 populations led to the identification of 11 different combinations of mutant alleles ("double nulls") (Table 14). The double null combination of the B1D1 genotype was not obtained in the twelfth cross in spite of screening more than 1200 F2 progeny of that particular cross. One possible explanation for this might be the presence of a critical gene in the vicinity of the SBEII locus in the B and D genomes, but not in the A genome, and hence the combination of the B1 and D1 double null mutations might render the seed non viable. Twenty seven combinations of double-null mutants are theoretically possible, and more F2 populations will be screened to identify the other combinations.

EXAMPLE 6

Amylose Content of Single and Double Null SBEII Mutants of Wheat

Figure 4:
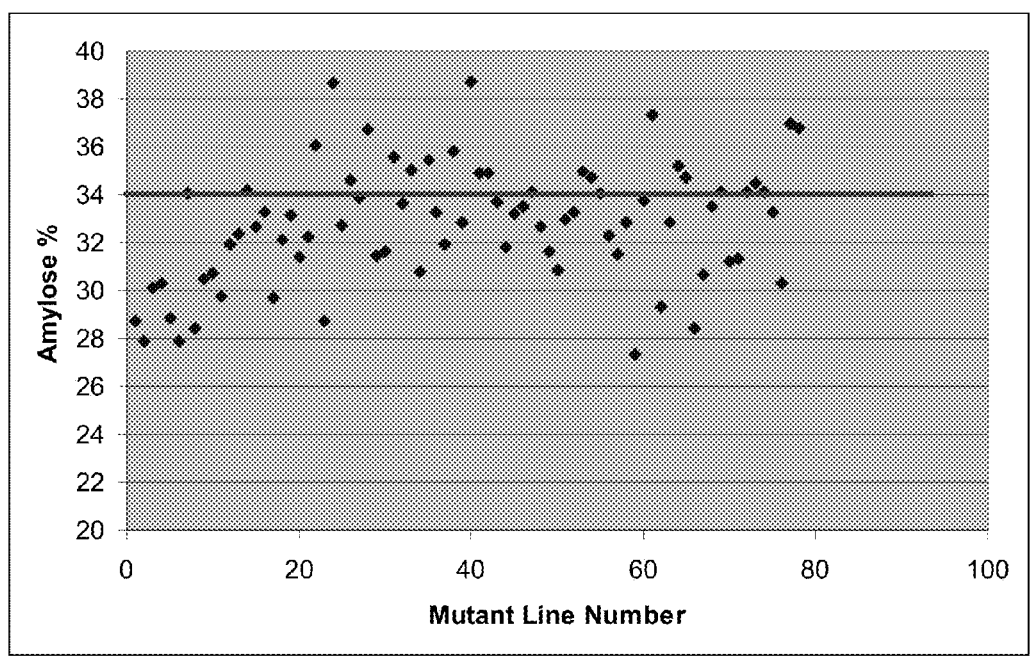
FIG. 4 is a graphical representation showing a scatter plot of amylose content of transgenic mutant lines (see Example 5).

The percentage of amylose in the grain starch of single and double null plants described in Example 5 was determined using the iodometric method as described in Example 1. A scatter diagram plotting amylose content (Y-axis) against the mutant line number (X-axis) is shown in FIG. 4. The amylose content in the mutant grains ranged from 27.3 to 38.7%. The amylose content of wild-type (unmutagenised) Chara samples ranged from 27.4% to 29.5%. Twenty six lines recorded an amylose content of above 34%. It was observed that of these 26 lines, 20 were double nulls, of which some were replicates from the same cross, of either Type 1 or Type 2 combinations. In other words, there was a trend in significantly increasing amylose content in Type 1 and Type 2 double null combinations compared to the amylose content in single null grains.

Importantly, and unexpectedly prior to this study, none of the double null mutant grains had starch with greater than 40% amylose. This included the A1B1, A1D1 and B1D1 genotypes which each contained four SBEIIa and four SBEIIb null alleles and retained two wild-type SBEIIa and two wild-type SBEIIb alleles. This observation was consistent, however, with the prediction made from the data in Example 2. It was therefore concluded that to obtain wheat grain with more than 40% amylose by combining mutations, the grain needed to have more than four mutant alleles of SBEIIa, or alternatively, if only four mutant alleles of SBEIIa were present, more than four mutant SBEIIb alleles in combination with the four SBEIIa alleles, preferably all six SBEIIb genes being mutant. It was also suggested from the data that the SBEIIa genes on each of the A, B and D genomes were expressed at similar levels relative to each other, i.e. SBEIIa expression in breadwheat was not predominantly from any one genome.

It was interesting to note that the "A3" and "A3D3" genotypes had low amylose contents consistent with the data in Example 2, confirming that SBEIIb had a lesser role in determining amylose content in wheat relative to SBEIIa.

EXAMPLE 7

Crosses in Attempts to Create Triple Null Deletion Mutants

In order to create mutant lines with more than four SBEIIa mutant alleles using the deletion mutants isolated in the previous examples, some of the single null and double null lines were crossed and the F2 progeny of these crosses analysed using the diagnostic PCR assays. The assays tested for the presence of the three SBEIIa and three SBEIIb genes and were therefore used in an attempt to identify plants which had null (deletion) mutations in the SBEIIa and/or SBEIIb genes in each of the A, B and D genomes (triple null lines for SBEIIa and/or SBEIIb). The crosses that were carried out in a first experiment and the genotypes of the parental lines and potential triple null F2 progeny are listed in Table 15.

Starch granule morphology was analysed by microscopy of selected normal looking and shriveled/shrunken F2 seeds from these crosses. Six shrivelled/shrunken seeds were selected, 5 from the 08/dd cross and 1 from the 08/bb cross, each of which were obtained from crosses between a D2 single null parent plant and an A1B2 double null parent plant. Each of the six seeds showed severe distortion of starch granules, showing abnormal, distorted shapes for most granules in the seeds which was similar to granules observed in transgenic seeds with elevated amylose levels (Example 2). Inspection of a number of shrivelled/shrunken seeds and selected odd looking seeds from the other crosses revealed no altered starch granule morphology, indicating that the phenotype observed in 08/dd and 08/bb seeds was genotype specific and not due to developmental problems during seed development.

Starch isolated from 6 of the seeds having distorted starch granules was pooled and tested for amylose content using the iodometric method as described in Example 1. The amylose content of the pooled sample was measured to be 67% (Table 16). Amylose levels in the wild-type seeds (control) of cultivars Cadoux and Chara were approximately 35%.

Genotypic Analysis of Seeds with Altered Starch Granule Morphology.

The seeds from the crosses 08/dd and 08/bb with altered starch granule morphology were sown and the resultant plants grown in the greenhouse. DNA extracted from the plants was analysed using the genome specific primers for SBEIIa and SBEIIb described in Example 3. Results from the PCR assays indicated that each of these seeds were homozygous double null mutants with an A1B2, B2D2 or A1D2 genotype while the third (wildtype) gene was present in either the homozygous or heterozygous state. DNA from these plants were further tested using quantitative PCR (Real-time PCR, Rotor-gene 6000) using genome specific individual primer pairs to assay the presence or absence and the homozygosity or heterozygosity of the 3 SBEIIa genes in the plants. The primer pairs used for SBEIIa were Snp6for/Arev5 (SEQ ID NO: 51/SEQ ID NO: 61) (A genome, 205 bp amplification product), BSnp4/Arev5 (SEQ ID NO: 55/SEQ ID NO: 61) (B genome, 494 bp amplification product) and DSnp7for/Drev1 (SEQ ID NO: 58/SEQ ID NO: 62) (D genome, 278 bp amplification product). In order to normalize the SBEIIa amplification reactions, a primer pair (SJ156/SJ242) which amplified a 190 bp product from the CslF6 gene, which is a cell-wall biosynthesis gene expected to be equally expressed in all of the plants and located on wheat Chromosome 7, was used in control amplifications. DNAs from a wild-type plant from the mutagenised population, designated 2B2, and from wild-type cv. Chinese Spring (CS) were used as control templates. The relative concentration values generated in the reactions with the SBEIIa primers were normalised with the value for Cslf6 primers for each template DNA preparation. The values for the potential triple null plants and CS were calculated relative to line 2B2.

Out of these three primer pairs, the D genome primers produced a clear single band for one plant designated as S14 which enabled quantitation. No bands were obtained for the SBEIIa genes on the A and B genomes of S14, indicating it was homozygous for the mutant alleles (deletions) on these genomes. The quantitation indicated that S14 had approximately 30-50% of the D allele complement compared to 2B2 whereas CS gave a value of approximately 95% of 2B2 for the D genome SBEIIa gene. This showed that S14 which gave seed with amylose levels of about 67% was homozygous for SBEIIa null mutations for two of the genomes (A and B) and heterozygous for the third genome (D), in addition to being homozygous for SBEIIb null mutation in the A genome. That is, S14 had an A1 (homozygous), B2 (homozygous), D2/+ (heterozygous) genotype. In a similar fashion, the quantitative PCR showed that plant designated as S24 had a B2 (homozygous), D2 (homozygous) and A1 (heterozygous) genotype. The PCR analysis showed that the remaining 5 plants had the following genotypes: 08dd9-B4 was homozygous for an A1B2 genotype i.e. homozygous mutant for SBEIIa and SBEIIb on the A genome, homozygous mutant SBEIIa and wild-type SBEIIb on the B genome and homozygous wildtype for both genes on the D genome, while 08bb11-D9 was homozygous for a B2D2 genotype and S28 and S22 were homozygous for an A1D2 genotype Analysis of F3 Seeds.

Seeds of the S28, S22, S14 and S24 lines were sown in the greenhouse, the resultant plants were selfed, and seeds (F3 generation) obtained from each plant. It was observed that the fertility of the plants was affected, in that the number of seeds per head and the percentage of spikes which were fertile were significantly reduced compared to wild type, single null and other double null mutants grown at the same time and under the same conditions, but not abolished (Table 17).

Starch granule morphology was determined by light microscopy on 100-200 seeds from each of the lines S28, S14 and S22. From the line S22, 102 F3 seeds were identified with distorted starch granules from among 200 seeds tested. The data revealed a distortion of the segregation ratios away from the expected 1:2:1 (homozygous mutant:heterozygote:wild-type) with a higher number of normal phenotypes than expected. In order to see whether a homozygous plant with a high amylose phenotype could be identified, 102 seeds with distorted granules were placed in conditions suitable for germination. Sixty one out of the 102 seeds germinated. DNA from these 61 plants were analysed by SBEIIa genome specific PCR and all 61 plants appeared to be double null of an A1D2 genotype, with no homozygous triple nulls identified. The wild-type SBEIIa gene on the B genome was shown to be heterozygous i.e. both wildtype and mutant alleles were present for the B genome.

The 41 seeds which had distorted starch granules but had not germinated were analysed for their SBEIIa genotype. Many of these were observed to be triple nulls, i.e. showing an absence of any amplification product for the SBEIIa genes and therefore having six null alleles for SBEIIa. This confirmed that the triple null (deletion of SBEIIa genes) seeds could be generated but these seeds had defects that affected germination. Embryos from some of these seeds were excised and cultured using tissue culture media under conditions to promote germination of the embryos. Some embryos germinated successfully, resulting in green plantlets. However, when these plantlets were transferred to soil, they grew poorly and did not produce fertile wheat plants.

From these data, it was concluded that a homozygous triple null mutant seed based on the HIB-generated deletion mutations, and plantlets derived from these seed and having six null SBEIIa alleles and entirely lacking SBEIIa, were recoverable from these crosses, but were affected in germination and growth, indicating either an essential role for some SBEIIa in these processes or the presence of a closely linked gene which was required for germination of seeds, normal growth and plant fertility, such that the gene was deleted in each of the HIB mutants used in the crosses. In contrast, the double null mutants for SBEIIa which were heterozygous for the third null allele and therefore having five null SBEIIa alleles were recovered, grew normally and were fertile, albeit with reduced fertility.

Protein Expression Analysis of Line S28.

SBEIIa protein expression in developing endosperms obtained from one whole spike from an S28 plant was analysed by Western blotting using a SBEIIa specific antibody. All 15 endosperms in the spike showed a pattern lacking both A and D genome isoforms of SBEIIa (AD double null) with only one SBEIIa band present, expressed from the B genome. Out of the 15 endosperms, 7 had a B genome SBEIIa expression level considerably lower than the others and that of the control line, NB1. Based on the band intensity, the SBEIIa expression in each endosperm was quantitated.

The remaining starch granules from the endosperms were purified using 90% Percoll. Following resuspension in 200 µl water, the granules were examined microscopically. It was observed that all endosperms having an expression level of SBEIIa which was less than about 36% of the wild-type had starch granules with distorted morphology typical of a high amylose phenotype. A range of SBEIIa protein expression levels were observed in the developing grains from one spike from an S24 plant, down to less than 5% of wild-type. Endosperms with the lower levels of SBEIIa also showed altered starch granule morphology; the phenotypes were therefore completely correlated in this experiment. SBEIIb expression levels in all these endosperms were also analysed using a SBEIIb specific antibody. The results clearly showed that there was a concomitant reduction in the SBEIIb expression corresponding to the reduction in SBEIIa expression.

Discussion.

The analysis of the seed from plants with the A1B2 mutant genotype (summarised in Table 18) having four mutant SBEIIa alleles indicated that the amylose content was elevated only slightly for that genotype, yielding an amylose level of less than 40%. In comparison, the data from the S14, S22, S24 and S28 seeds demonstrated that the addition of the fifth SBEIIa mutant (deletion) allele elevated the amylose level to about 67%. Accordingly, the increase in number from four SBEIIa null alleles to a minimum of five mutant SBEIIa alleles was critical to increasing the amylose level to greater than 50% (w/w), indeed greater than 60% (w/w). This conclusion fitted with the predictions made from the data in Example 2. The observed relationship of the allelic composition to the amylose content indicated that the total number of SBEIIa mutant alleles in the plant was important in determining the amylose content (Table 18). It was also concluded that the number of SBEIIb mutant alleles also played a role, although less important than the number of SBEIIa mutant alleles.

The double null mutants for SBEIIa which were heterozygous for the third null allele and therefore having five null SBEIIa alleles were recovered, grew normally and were fertile. In contrast, the homozygous triple null mutant seeds and plantlets having six null SBEIIa alleles and entirely lacking SBEIIa could be generated from the single null mutants containing the HIB-generated deletions that were used in the crosses, but these were affected in germination and growth, indicating either an essential role for some SBEIIa in these processes or the presence of a gene closely linked to SBEIIa which was deleted along with SBEIIa in the HIB-generated mutants and which was required for normal germination of seeds, growth and plant fertility. As shown from the data in Example 11, the second of these explanations appeared to be the correct explanation.

EXAMPLE 8

Further Attempts to Produce Triple-Null Deletion Mutants Entirely Lacking SBEIIa or SBEIIb The observed inability to generate a triple null mutant completely lacking SBEIIa from the HIB-induced deletion mutants in the Example above may have been dependent on the particular mutant plants used as parents in the crossing. To test this, a second set of crosses using additional parental deletion mutants, also obtained from the HIB-mutagenesis, was carried out. The F2 seeds from 38 crosses were harvested and DNA extracted. At least 96 DNA samples from each of 25 crosses, 12 of which were from crosses aimed at producing an A1B2D2 genotype (triple null mutant) but using different parental lines than described in Example 7, were screened by PCR to determine the trend of segregation. No viable triple nulls were identified from any of these crosses. Recovery of the double nulls also varied depending on the cross, but in most cases the expected genotypes were obtained. F2 seeds from six of the A1B2D2 crosses were also screened microscopically to identify seeds having a high amylose phenotype. Such seeds were identified at a moderate frequency.

Screening of Seeds from the A2B2D2 Cross, 08/mm-1.

Twelve of the crosses were between a parent with an A2 genotype and a parent with a B2D2 genotype, i.e. both parents were wild-type for all three SBEIIb genes, with the aim of generating triple null SBEIIa mutants having the A2B2D2 genotype. DNA preparations from approximately 672 F2 seeds obtained from the 08/mm-1 cross were screened by PCR. Segregation ratios were distorted from the expected Mendelian ratios, with significantly fewer double nulls identified than expected. Nevertheless, all possible combinations of double null mutations were identified in viable seed. No triple nulls of the A2B2D2 genotype were identified amongst the 672 seeds, even though by Mendelian segregation about 10 would have been expected.

In parallel, F2 seeds of the 08/mm-1 cross were screened by microscopy to identify any seeds with a high amylose/distorted starch granule (HA) phenotype. Of 576 F2 seeds that were screened, no seeds were identified with the HA phenotype. This population of seeds should have included a low frequency of seeds having 5 mutant SBEIIa alleles, being homozygous mutant in two genomes and heterozygous mutant/wild-type in the third genome for SBEIIa. The observed lack of seeds with a HA phenotype in the A2B2D2 cross indicated that 5 mutant SBEIIa alleles, in the absence of any SBEIIb mutant alleles, did not appear to be sufficient to provide a high amylose (>50% amylose) phenotype. That is, a reduction in SBEIIb levels relative to wild-type in addition to the greatly reduced SBEIIa level in the context of 5 mutant SBEIIa alleles and one wild-type SBEIIa allele, or an equivalent level of SBEIIa activity in an endosperm having partial loss of function mutations in one or more SBEIIa genes, would provide greater than 50% amylose.

Screening of F2 seeds from eleven additional crosses between single SBEIIa mutant parents (wild-type for SBEIIb) and double SBEIIa mutant parents on the other two genomes also did not identify any viable triple null mutant seed of the A2B2D2 genotype.

Crosses Involving Type 3 Mutations.

Crosses involving Type 3 mutations were carried out with the aim of finding homozygous mutants having two, four or six mutant SBEIIb alleles combined with four mutant SBEIIa alleles, and determining the phenotype of the resultant plants and its grain. Triple nulls for SBEIIb were identified from A3B3D3 and A3B2D2 crosses, having 6 null alleles of SBEIIb with either zero or four null alleles of SBEIIa, all of which showed wild type starch granule morphology.

EXAMPLE 9

Further Screening for High Amylose Mutants

In further attempts to produce triple null SBEIIa mutants from identified single deletion mutants, an altered strategy was adopted. This strategy added the step of some initial backcrosses of the single mutants after their identification, in order to remove unlinked and unrelated mutations from the M2 plants having the single SBEIIa mutations. This was included to reduce the effect of the mutated background, due to the high level of mutagenic treatment used, which would have produced additional mutations in the plants independent of the desired SBEIIa mutations that could have detrimental effects when the mutations were combined. These initial backcrosses were carried out by crossing the M2 mutants with plants of either winter wheat cultivar Apache or spring wheat cultivar Chara.

Initially, 13 crosses were performed to combine mutations on all three genomes, and molecular analysis was done on DNA from 21,400 F2 half seeds, with the second half of each seed retained to preserve the line. A preliminary screening to detect mutations used dominant SSR markers which were genome specific for SBEIIa or SBEIIb. From this, 21 seeds were identified as being putative triple null mutants and 793 seeds as putative double mutants by the absence of genome specific amplification products.

Q-PCR TaqMan-Based Assays of Wheat Seed Genotypes.

The first round of screening using dominant markers as described above could not distinguish between seeds that were heterozygous or homozygous wild-type for any one SBEIIa gene. A TaqMan-based PCR assay was therefore developed to distinguish heterozygotes and homozygotes for the SBEIIa gene on the third genome, and to confirm the genotypes from the initial screening. Because the TaqMan analysis was done on half seeds and because wheat endosperm is triploid (3n) for each genome, two types of profiles were possible for heterozygous endosperm for the wild-type SBEIIa allele on the third genome, either 2n, where the wild-type allele was provided by the maternal parent, or 1n, where the wild-type allele was provided by the paternal parent through the pollen. Q-PCR TaqMan-based Assays used the Applied Biosystems 7900HT Fast Real Time PCR System (ABI, Foster City, Calif.) to detect the copy number of the SBEIIa gene on the third genome of putative double mutant wheat seeds. The assays used genomic DNA extracted from half seeds by magnetic bead methods (Nucleomag, Cat Ref No. 744 400.24). DNA was loaded on 384-well plates and duplex Q-PCR reactions were performed in duplicate for each plate. The PCR reactions were designed to amplify a 65 bp fragment from exon 21 of the SBEIIa genes using the primers SBE2a QPCRABDF4 (forward primer): 5'-ACGAT-GCA CTCTTTGGTGGAT-3' (SEQ ID NO: 31) and SBE2a QPCRABDR4 (reverse primer): 5'-ACTTACGGTTGT-GAAGTAGTCGACAT (SEQ ID NO: 32). The probe used to deliver the fluorescent signal during Q-PCR reactions was SBE2a QPCRABDS4 (TagMan® probe MGB, FAM) 5'-CAGCAGGCTTGATCAT-3' (SEQ ID NO: 33). A sequence from an endogenous gene, GamyB, was used as an internal control to normalize the signal value of each sample, using the primers GamyB1F (primer forward): 5'-GATC-CGAATAGCTGGCTCAAGTAT-3' (SEQ ID NO: 34) and GamyB2R (primer reverse): 5'-GGAGACTGCAGGTAGG-GATCAAC-3' (SEQ ID NO: 35). Reaction conditions were as follows: "hot start" (95° C., 10 min) followed by 40 cycles of denaturation (95° C., 15 sec), annealing (58° C., 60 sec). Reaction products were analysed using Relative Quantification manager software integrated to the 7900HT Fast Real Time PCR System.

Using this TaqMan assay, all of the 21 putative triple null mutants were confirmed to be double nulls, not triple nulls. The incorrect identification in the initial screening was thought to be due to false negatives, perhaps caused by poor template DNA quality. When 14 of the seeds were examined for starch granule morphology by light microscopy, all 14 were observed to have a wild-type granule phenotype, which was consistent with the seeds being double null mutants, not triple null mutants. The assays also identified a few putative double mutant seeds that were 2n heterozygous on the third genome, from crosses M76, M77, M82, M83 and M86.

EXAMPLE 10

Screening for Mutant Wheat Seeds by NIR

A rapid, non-destructive and high throughput method was developed to screen single seeds for a phenotype that was associated with high amylose content. The PCR-based screening methods described in Examples 4-6, while successful in detecting mutants in a population of 15,000 seeds, required DNA preparation from each half seed after cutting each seed manually, and so was time-consuming and tedious. It was determined that Near Infrared Spectroscopy (NIRS) could be used to distinguish between the high amylose and normal amylose phenotypes. Near Infrared Red Spectroscopy (NIRS) is a non destructive technology that has been used to determine some wheat seed properties (McClure, 2003). Wheat single seed NIRS analysis for a waxy starch phenotype (low amylose) has been developed on *durum* wheat by Delwiche et al. (2006). Dowell et at (2009) developed an automated single seed NIR sorting system to separate waxy, partial waxy and normal *durum* and hexaploid wheat. To our knowledge, this method has not been used previously to distinguish high amylose seeds in hexaploid wheat.

Development and Validation of Scaled Down Biochemical Reference Method to Measure Apparent Amylose Content in Ground Seed Material.

In order to calibrate NIRS measurements according to apparent amylose content in individual seeds, a mathematical model had to be established to correlate NIRS spectrum data and a biochemical method measuring apparent amylose content on the same sample, in this case single seeds. Standard iodometric methods, for example, the method described in Example 1, routinely use a quantity of seeds which are combined before starch solubilisation, providing bulked (combined) starch which is normally defatted prior to colorimetric measurement of the amylose content based on iodine binding. To be suitable for use for NIRS calibration purposes, this method was modified, simplified and scaled down to allow measurement of apparent amylose content in single seeds, thereby to allow for variation in amylose content between seeds. The term "apparent amylose content" is used in this context because the modified method did not purify the starch from the ground grain, the lipids interacting with the amylose in the starch were not removed, and the results were expressed as percentage of fresh seed weight rather than as a percentage of the isolated starch from the seed. For these reasons, the values obtained for "apparent amylose content" were much lower than the values obtained using the standard method as described in Example 1.

As a first step, this method was developed by assessing the linearity between the colorimetric response and amylose content using ground wheat grain without starch purification. The high amylose material used for this was wheat grain transformed with the hp5'-SBEIIa construct and having reduced SBEIIa (WM, Line 85.2c, see Example 2) and wheat with the normal amylose level which was a wild-type wheat (WMC) grown at the same time and under the same conditions. Ground WM grain contained about 80% amylose as determined by the standard method of Example 1, while ground WMC grain had an amylose content of about 25%. Samples with different ratios of WM to WMC were prepared from ground seed material but not further purified. Approximately 17 mg samples were used for the assay. The WM and WMC mixtures were weighed accurately into 1.5 ml microcentrifuge tubes. To solubilise the starch in the samples, 1 ml of DMSO was added per 17 mg of sample and then the mixtures heated in a 95° C. water bath for 90 min with occasional vortexing. A 10 µl aliquot from each mixture was added to 1.98 ml of water and treated with 10 µl 0.3% $I_2$+3% KI in 0.01N NaOH solution. The absorbance of each mixture was measured at 605 nm and absorbance values were converted to percent amylose using a standard curve. The standard curve was made using maize amylopectin (Sigma catalogue No. A7780) and potato amylose (Sigma, A0512) in ratios from 0% to 100% amylose and treated the same way as the ground wheat samples.

The results showed a linear relationship between the level of WM incorporation and the apparent amylose content, showing that the simplified iodometric method could be used for NIRS calibration and that starch purification was not needed for this purpose.

Testing the Biochemical Reference Method to Measure Apparent Amylose Content in Half Seeds.

Seeds from the WM and WMC (control) lines obtained from field trial experiments conducted in Arizona and Washington were used for this testing. In total, 47 half seeds with embryos removed were individually placed in 1.5 ml microcentrifuge tubes and weighed accurately before addition of 0.6 ml of DMSO to each. The tubes were incubated in a waterbath at 95° C. for 20 min after which the samples were crushed in the tubes using a glass rod. The volume of each mixture was adjusted to precisely 1 ml of DMSO per 17 mg of sample after which the tubes were incubated at 95° C. in a waterbath for another 70 min with occasional vortexing. Apparent amylose was measured by taking 10 µl aliquots of each mixture and treating them with 10 µl 0.3% $I_2$+3% KI in 0.01N NaOH solution and diluted to 2 ml with $H_2O$, as before. Absorbance of each sample was measured at 605 nm and absorbance values were converted to percent "apparent amylose" using a standard curve as described above.

Using this method, the apparent amylose content of WM seeds ranged from 20% to 41% (average 27%) while the apparent amylose content of WMC seeds ranged from 7.5% to 17% (average 11.4%). The reasons why these values were much lower than the amylose content as determined by the method of Example 1 are described above. This simplified method therefore allowed seeds with high amylose to be distinguished from those with wild-type amylose content.

NIRS Calibration.

Single seed NIRS scans on WM and WMC seeds were obtained using a Multi Purpose Analyser (MPA) NIRS spectrometer (Bruker Optics, F-77420 Champs Sur Marnes, France). Each seed was placed at the bottom of a glass tube wrapped with aluminium foil and scanned twice. Spectra were recorded using a Bruker MPA Multi-Purpose-Analyser spectrometer (Bruker Optics) fitted with a fiber probe. Spectra were recorded using 32 scans reference and 16 sample scans over the range 4000-12,500 $cm^{-1}$ at a resolution of 16 $cm^{-1}$ resulting in 1100 data points. The fiber optic probe used was the IN 261 probe for solids.

To determine the correlation between apparent amylose levels and NIR readings, 226 individual WM or WMC seeds with apparent amylose contents ranging from 6 to 44% were analysed. First, duplicate NIRS spectra were acquired for each seed, after which the apparent amylose content was biochemically measured for each seed according to the method described above. Spectral outliers (6 samples) were identified as spectra that were abnormal compared to the spectra of the entire data set and eliminated, and the remaining spectra analysed with Normalisation Min-max pre-treatment. The Partial Least Square software with full (one out) cross validation was used to create the model. The spectral window used for the model development was 9827-7150 $cm^{-1}$ and 6271-4481 $cm^{-1}$. The number of PLS factors used to develop the calibration was 14. The accuracy of the calibration model was expressed by the standard error of cross validation (SECV) and the coefficient of determination ($R^2$). The efficiency of a calibration was shown by the RPD which is the ration of the standard error of prediction (RMSECV) to the standard deviation of the reference data of the set.

Figure 15:
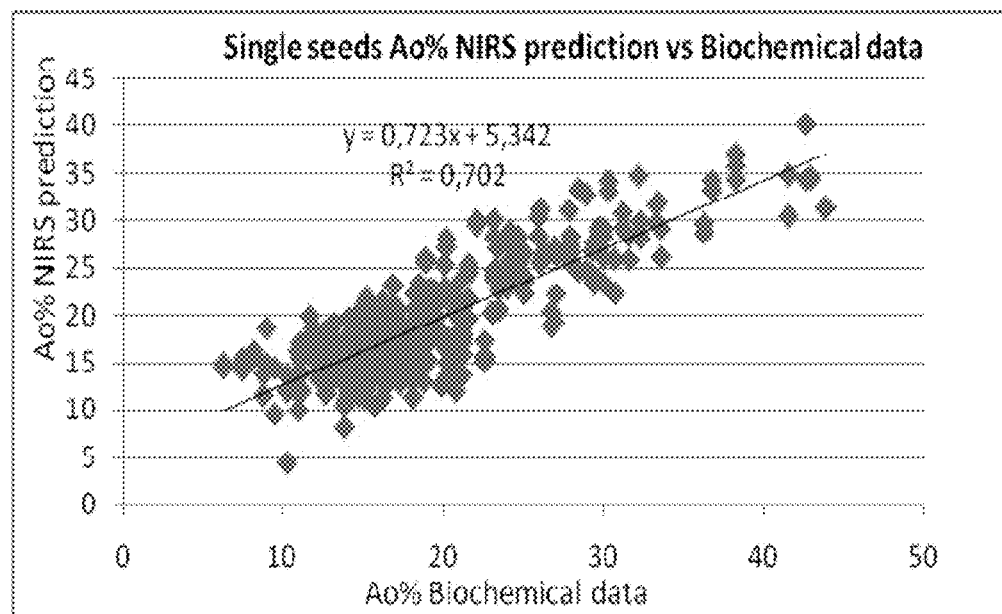
FIG. 15 provides scatter plot representations of NIRS-predicted and biochemical reference values for apparent amylose content in wheat single seeds.

A positive correlation ($R^2$=0.702) was obtained between the biochemical data and the NIR spectral data (FIG. 15). It was concluded that the model was robust enough to distinguish high amylose wheat seeds from normal amylose wheat seeds, but not yet accurate enough to precisely measure the amylose content in any one seed. The method was therefore capable of screening a very large population of seeds to enrich for grains with high amylose phenotype. This was validated as follows.

NIRS Validation.

Figure 16:
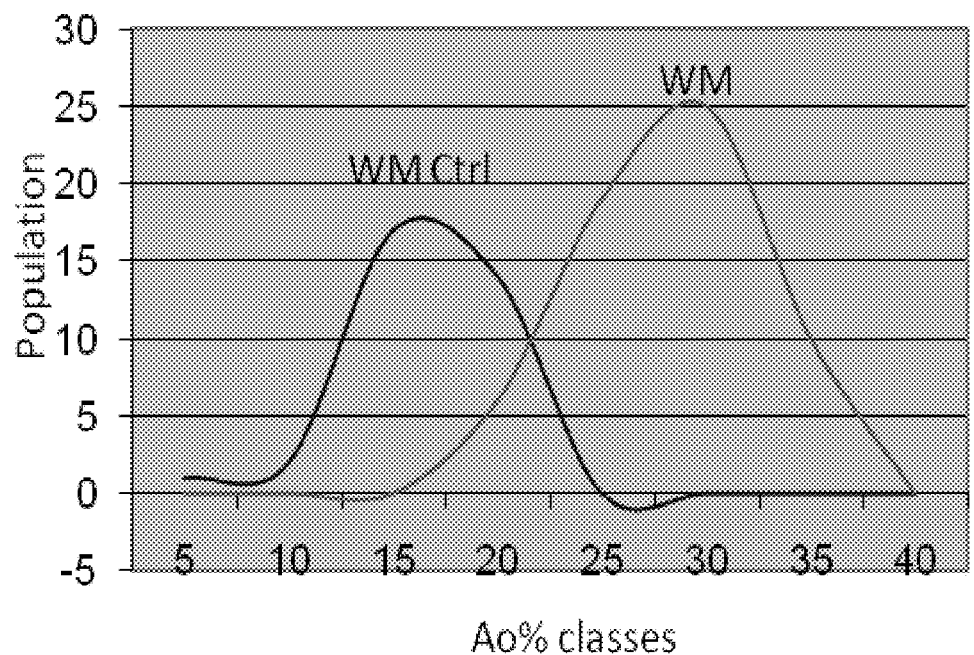
FIG. 16 is a graphical representation showing apparent amylose content distribution on WM and WMC populations as determined by NIRS.

To validate the NIR method in distinguishing high amylose grain and control grain, 60 more WM seeds and 34 WMC seeds were scanned twice by NIR and the predicted apparent amylose contents calculated. When the apparent amylose values so determined were plotted to obtain the distribution profile for the WM and WMC populations, it was seen that the two groups were mostly separated with a slight overlap (FIG. 16). According to these results, seeds having a predicted apparent amylose phenotype determined by NIRS equal to or above 30% could be considered as good candidates to be high amylose seed.

NIRS Screening of F2 Seeds from Wheat Crosses.

NIRS screening was carried out to detect mutant seeds having high amylose content. The screening used 2,700 F2 seeds from two different crosses: M80 and M85 which were, respectively: 21.142(B2)/Type I-20257(A1) [08/h-111]// Type I-19.832 (D1)/CHARA and 5.706 (D2)/21.668 (B2)//

20.257 (A1)/CHARA. The screening was therefore aimed at identifying seeds with an A1B2D1 or A1B2D2 genotype, respectively. Two NIRS spectra were recorded per seed as described above Seeds which gave a predicted apparent amylose value above 34% in at least one of the two duplicate screenings were first selected for further analysis. Out of the 2,700 seeds, 27 seeds were selected and were next assessed by light microscopy to determine the starch granule morphology. Each seed was carefully scraped to preserve the embryo, yet obtain enough endosperm material to be examined. Four seeds of the 27 were observed to have distorted starch granule morphology. These four seeds happened to have had the highest predicted apparent amylose content from the NIR screening and were the only ones where both predicted apparent amylose values were above 30%. The other 23 seeds showed normal (wild-type) granule morphology.

Molecular Data on Seeds Selected by NIRS Screening.

PCR analysis was carried out on the four seeds to determine the SBEIIa genotype of each. Initial assays used dominant PCR markers which showed the presence or absence of each SBEIIa gene on the three genomes. Three of the seeds were shown to be double null mutants while the fourth was a putative triple null mutant. However, when tested further with a co-dominant PCR marker (see below), all of the four seeds were shown to be double null mutants for SBEIIa (i.e. lacking SBEIIa in two genomes) and heterozygous for a mutant SBEIIa gene on the third genome. Therefore, these seeds contained 5 mutant SBEIIa alleles and at least two mutant SBEIIb alleles.

When the embryo from each seed was placed under conditions to germinate, none of them germinated successfully, perhaps because they were too damaged or the combination of mutations was too detrimental.

In order to try to identify more candidates, further NIRS screening was performed on more F2 progeny seeds from the M80 and M85 crosses, with less stringent selection of candidate seeds. The selection criterion for the second screen was that one of the predicted apparent amylose values had to be above 30% and the second one at least 23%. A new set of 22 seeds was selected for starch granule evaluation by light microscopy. Out of those 22 candidates, 1 seed, BD85;9F08 (P279-F08-834), showed a distorted starch granule phenotype. This mutant was further analysed by PCR and shown to be a double null SBEIIa mutant on the A and B genomes and heterozygous for the mutant SBEIIa gene on the D genome. It was successfully germinated for multiplication.

EXAMPLE 11

Detection of Alleles of Starch Branching Enzyme with Point Mutations

Populations of mutagenised wheat grains, produced by treatment with the chemical mutagens sodium azide or EMS were screened to identify mutants which had point mutations in SBEIIa genes. This screening was expected to detect mutants which lacked one of SBEIIa-A, -B, or -D, or SBEIIb-A, -B, or -D activity entirely, due to a mutation in the corresponding gene, as well as mutants with reduced, but not abolished, SBEIIa-A, -B or -D activity, or SBEIIb-A, -B or -D activity (partial mutants) relative to wild-type wheat. Screening for mutants was based on measuring the amount of the SBEIIa or SBEIIb proteins by using Western blotting with antibodies specific for SBEIIa or SBEIIb (see Example 2), or by affinity-based techniques, as follows.

Affinity (non-denaturing) gel electrophoresis of protein extracts from grain including starch branching enzymes through a polyacrylamide matrix containing glycogen, amylopectin, amylose or β-limit dextrin provided a method for identifying alleles of SBEIIa or SBEIIb which encode SBEIIa or SBEIIb with altered starch binding capacity or which lacked one of the isoforms of SBEIIa or SBEIIb. Given that the active site of starch branching enzymes contained a starch binding site, SBEII polypeptides with altered binding efficiency were likely to have alterations in catalytic rate and/or affinity. In particular, polypeptides with reduced binding efficiency were expected to have reduced SBEII activity or lack SBEII activity.

The following methods were used, based on Morell et al., (1997); and Kosar-Hashemi et al., (2006) with some modifications.

Preparation of Proteins.

Soluble proteins were extracted by homogenising the isolated endosperms from developing seeds (about 15 days post-anthesis) in 50 mM phosphate buffer, pH 7.5 containing 5 mM EDTA, 5 mM DTT, 0.4% protease inhibitor cocktail and 20% glycerol. After centrifugation at 14,000 g for 10 min the supernatant was used for the gel electrophoresis. Protein concentration in the extracts was estimated using a Coomassie Plus Protein Assay Reagent.

Affinity Electrophoresis.

In a two-dimensional (2D) affinity electrophoresis technique for separating SBEIIa protein isoforms, aliquots (40 or 100 µg) of the protein extracts were loaded onto the first dimension gel, a non-denaturing polyacrylamide gel cast in a Hoefer SE600 vertical 16 cm slab gel unit. The resolving component of the second dimension gel was a 6% non-denaturing gel (14×16 cm or 16×16 cm, 1.5 mm thickness) containing 10% glycerol with an appropriate amount of polysaccharide target (amylopectin, β-limit dextrin or glycogen) immobilised within the gel structure. A stacking gel (polysaccharide-free) was poured to 1 cm from the top of glass plates forming using a comb to form wells. Gels were run overnight at 4° C. at constant voltage (100V for glycogen and β-limit dextrin and 135V for amylopectin containing gels).

Alternatively, a one dimensional system was used to separate SBEIIa proteins in which protein extracts (20 µg) were loaded onto a non-denaturing polyacrylamide gel. The resolving component of the gel was a 6% non-denaturing gel containing 10% glycerol with 0.15% of β-limit dextrin immobilised within the gel structure, while the stacking gel was polysaccharide-free. Gels were run at 4° C. at constant current of 20 mA per gel and maximum voltage of 200V.

SBEIIb proteins are separated on a Bis-Tris 4-12% gradient gel (Invitrogen). The gel is run at 4° C. at constant current of 20 mA per gel and maximum voltage of 200V.

Immunological Detection.

For immunochemical detection of the SBEII proteins following electrophoresis, the proteins were transferred from the gels to nitrocellulose membranes using a TE 70 PWR semi-dry transfer unit (Amersham Biosciences). The transfer buffer contained 39 mM glycine, 48 mM Tris, 0.0375% SDS and 20% methanol. Transfer was carried out for 1-1.5 h with a constant current of 0.8 mA/cm$^2$. The membrane was blocked with 5% skim milk prior to Western blotting using primary rabbit polyclonal antibody specific for wheat SBEIIa.

The migration patterns of the SBEII isoforms encoded by the homeoalleles from the wheat A, B and D genomes showed differences between different wheat varieties when analysed by the one-dimensional affinity gel electrophoresis method. In some varieties, a clear separation of the A, B and D homeoforms was possible, allowing the simple scoring of polymorphisms in mutagenised populations from those varieties. For example, affinity gel electrophoresis of protein extracts from endosperms of the wild-type wheat varieties Sunstate and NB1 showed a clear separation of the SBEIIa-A, -B and -D isoforms. Branching enzyme polypeptides with a reduced affinity for starch migrated a greater distance through the polysaccharide-containing polyacrylamide gel than the respective native polypeptides encoded by the homeoalleles. Lines containing alleles with reduced expression or an absence of expression of a particular homeoallele were identified by presence/absence of a band in homozygous state and through densitometry to measure band intensity in heterozygous lines. To validate this method, SBEIIa- and SBEIIb-mutant plants which were identified by genotypic analysis (Example 6) were confirmed to be lacking specific SBEIIa or SBEIIb proteins by affinity gel electrophoresis, consistent with their genotypes. These experiments validated this protein analysis method for detection of mutants having a reduction in amount or activity of an SBEII isoform.

Figure 13:
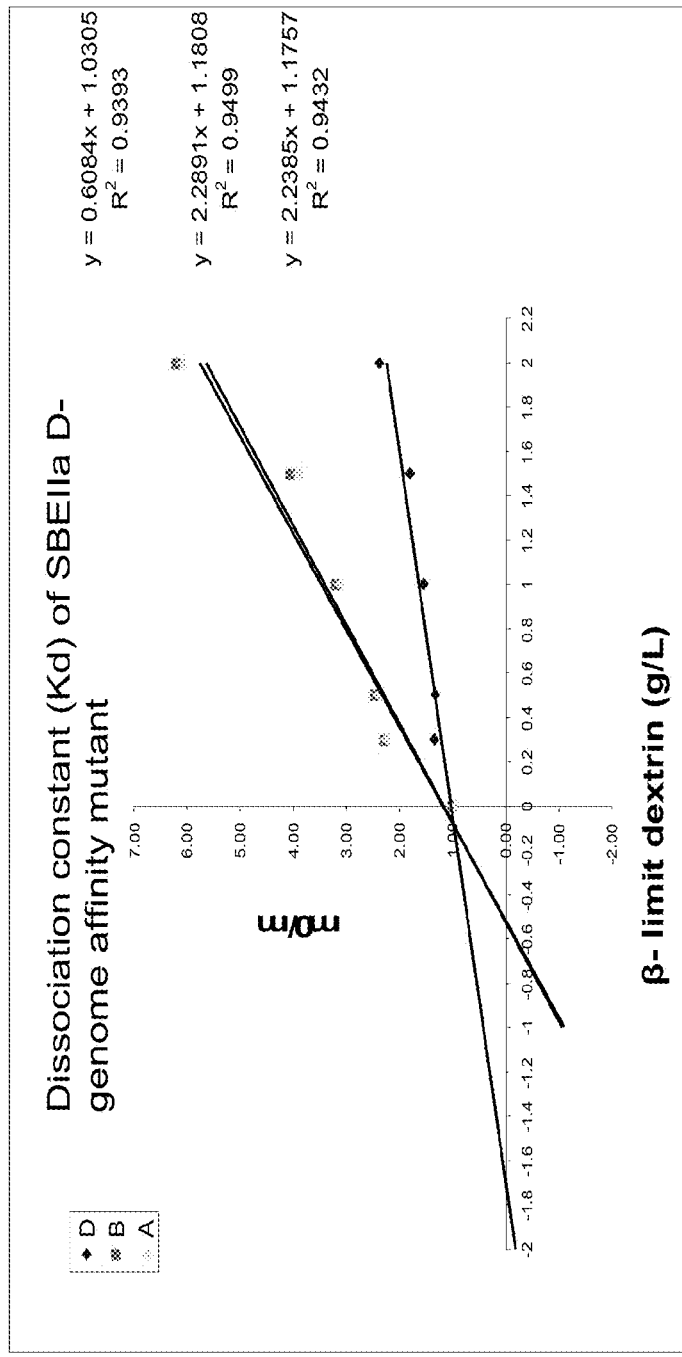
FIG. 13 is a plot of mobility ratio of interacting SBEIIa in the absence (m0) and presence (m) of β-limit dextrin in 1-D Native PAGE against the concentration of β-limit dextrin (S). The dissociation constant (Kd) is derived from the equation $m0/m = 1 + [S]/Kd$.
Figure 14:
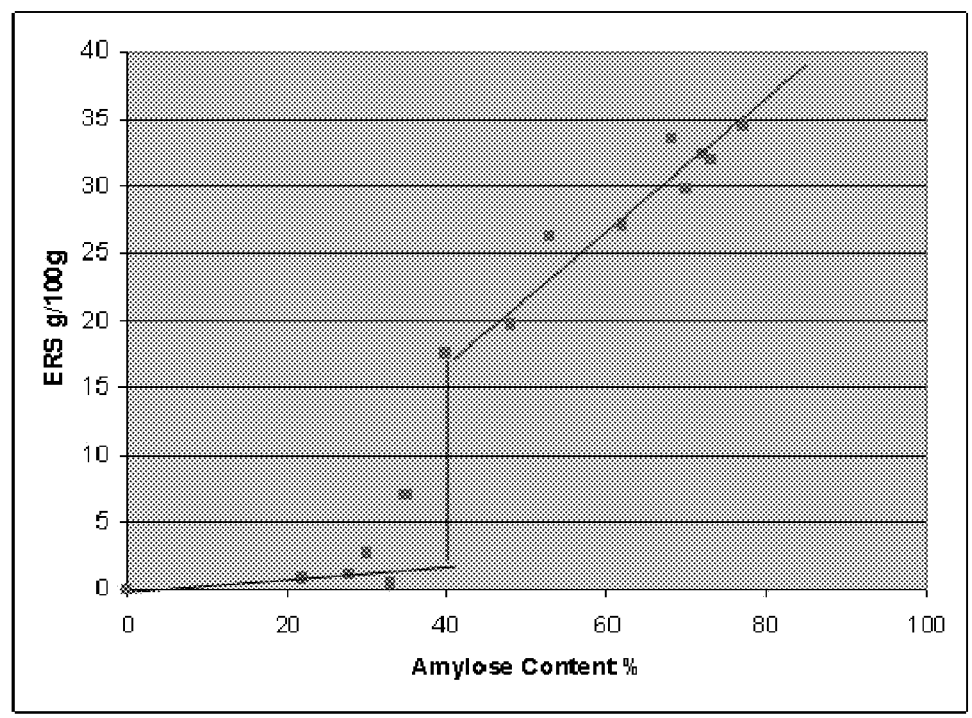
FIG. 14 shows the relationship of amylose content and enzyme resistant starch in pooled wheat starch samples derived from transgenic wheat lines described in Example 2.

Screening of a population of 2100 mutagenised wheat lines of the variety Sunstate, treated with sodium azide as described in Zwar and Chandler (1995), using β-limit dextrin affinity gel electrophoresis led to the identification of 18 mutants which had either an altered mobility of one of the SBEIIa proteins on the affinity gels (affinity mutants) or lacked one of the SBEIIa proteins and were therefore null mutants in one of the genes based on the lack of detectable protein encoded by that gene. The dissociation constant (Kd) of starch-enzyme interactions for each of the SBEIIa isoforms in some of the affinity mutants was calculated by measuring the change in enzyme mobility as a function of the β-limit dextrin concentration in a 1-D affinity gel as described in Kosar-Hashemi et al., 2006. The affinity mutant designated 7-25 had SBEIIa proteins with the following Kd values: 0.53 g/L, 0.52 g/L and 1.69 g/L for the SBEIIa-A, SBEIIa-B and SBEIIa-D isoforms respectively (FIG. 13). The higher observed Kd value for the D isoform compared to that of the A and B isoforms indicated a lower, reduced affinity of this isoform for binding to starch, indicating that this line was an affinity mutant for the SBEIIa-D gene. The D-genome isoform (SBEIIa-D) of this line is expected to have a lower enzyme activity, but not total loss of activity, compared to the other two isoforms. This expectation is confirmed by SBEII activity assays in the presence of null alleles of SBEIIa-A and SBEIIa-B.

Figure 19:
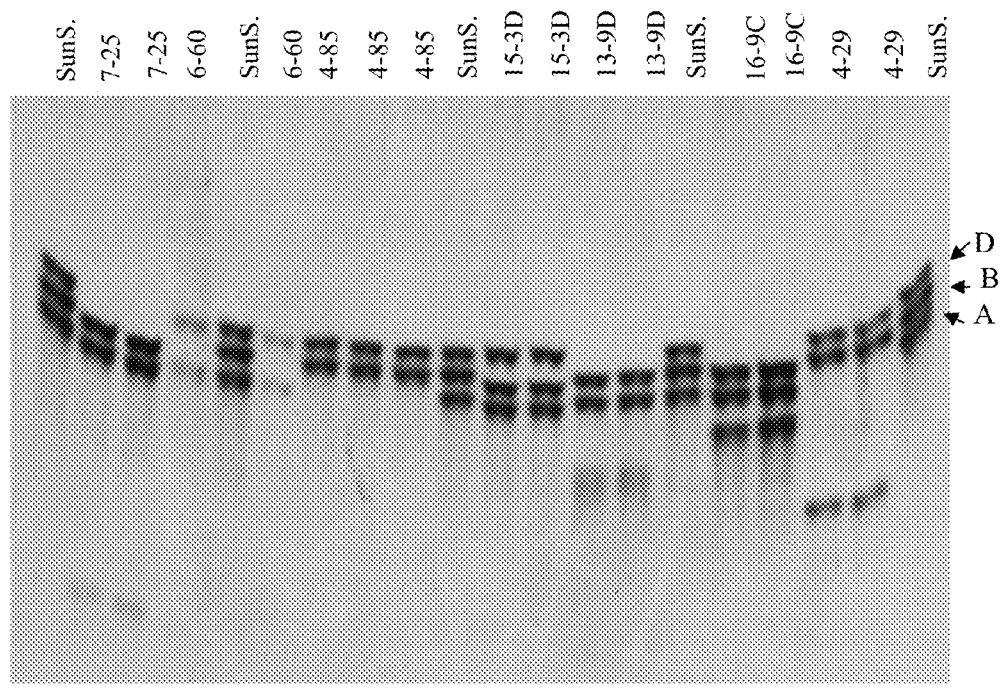
FIG. 19 is a photograph of a Western blot analysis of SBEIIa proteins isolated from wild-type wheat endosperms (variety Sunstate, lanes indicated as SunS) and mutant endosperms from the lines as indicated. The bands corresponding to the SBEIIa-A, -B, and -D proteins of Sunstate are arrowed.

The mutant plants were further confirmed by analysing several endosperms from developing seeds of the plants. These M3 endosperms were isolated from the M2 plants and examined for SBEIIa proteins by gel electrophoresis and Western blotting (FIG. 19). The nucleotide sequence of the mutant SBEIIa genes in the plants, and the deduced amino acid sequences, were determined by amplifying cDNA sequences using genome specific primers followed by sequencing of the coding regions. So far, the specific point mutations in 9 of the 18 mutants have been identified, out of which 2 were A genome mutants, 3 were B genome mutants and 4 were D genome mutants, as summarised in Table 19. The mutated gene in each of the remaining plants was deduced from the absence of a particular polypeptide band in the immunoblots. The assignment of the polypeptides was further confirmed in some of the lines by running a 2-dimensional gel with a non-denaturing affinity gel as the second dimension gel. The mutants were thereby classified into two groups (Table 19), namely a) null mutants, in which the endosperms exhibited only two SBEIIa bands in the immunoblots with the missing band representing the mutated genome A, B or D (designated 'n' for null in Table 19) and b) affinity mutants which exhibited three bands in the immunoblots, where one of the polypeptides migrating differently to the wild-type due to an altered affinity to starch (designated 'p' for partial).

Co-dominant PCR-based genetic markers were developed for four of the mutant lines designated 6-60, 7-25, 15-3D and 16-9C. The G to A point mutation at the exons 6/7 splice junction in the line 6-60 resulted in the absence of a Fok1 restriction site. This difference was exploited to generate a co-dominant cleavable amplified polymorphic sequence (CAPs) marker that involved PCR amplification of the exons 6-7 region using the primer pairs AR2aBI6F2 (5'-CATTTTTTGGTAGAACCTTTG-3'; SEQ ID NO: 152) and AR2aBI7R (5'-ATCCATCCGTATCTAGAAAAT-3'; SEQ ID NO: 153), followed by digestion of the products with the restriction enzyme Fok1. This yielded DNA fragments of about 245 bp from line 6-60 and about 138 bp from the wild-type (Sunstate) as observed by gel electrophoresis. A restriction enzyme map generated from the nucleotide sequence of the exon 21/22 region of SBEIIa-D from the wild-type and line 7-25 revealed changes in the restriction sites due to a C to T polymorphism in 7-25. This change was utilised to generate a CAPS marker for 7-25. PCR amplification of the exon 21/22 region was carried out using the primers AR2aDex21_22F (5'-CTGTTGTAGCCATAGGAAGG-3'; SEQ ID NO: 154) and AR2aex21_22R (5'-GAGCGCTCACCAACAAGCTACC-3'; SEQ ID NO: 155). The digestion of the PCR products with the restriction enzyme Mly1 resulted in a fragment of approximately 229 bp from the mutant line 7-25 and a 141 bp fragment from the wild-type. The restriction enzyme map generated from the nucleotide sequence of the exon 15 region of SBEIIa-D gene from the wild-type and line 15-3D revealed the deletion of the restriction site for Hpyl88III due to a G to A polymorphism in 15-3D. PCR amplification of the exon 15 region was carried out using the primers AR2aE15F07 (5'-GTCAGTGGAAT-GCCTACATTTTGC-3'; SEQ ID NO:156) and AR2aE15R07 (5'-GTCAGTGGAATGCCTACATTTTGC-3'; SEQ ID NO: 157). The digestion of the PCR products with the restriction enzyme Hpyl88III resulted in a fragment of approximately 105 bp from the mutant line 15-3D and a 63 bp fragment from the wild-type. The restriction enzyme map generated from the nucleotide sequence of the exons 17 to 20 region of SBEIIa-D from the wild-type and line 16-9C revealed the deletion of the restriction site for BseR1 due to a C to T polymorphism in 16-9C. PCR amplification of the exons 17 to 20 region was carried out using the primers AR2aDex17_20F. (5'-GGAGATATGCTTAGTAACAG-3'; SEQ ID NO: 158) and AR2aDex17_20R (5' GCTGTTAAGAACAACCTTCC-3'; SEQ ID NO: 159). The digestion of the PCR products with the restriction enzyme BseR1 resulted in a fragment of approximately 1529 bp from the mutant line 16-9C and two bands of sizes about 1159 bp and 370 bp from the wild-type.

The SBEIIa single mutants identified from the sodium azide mutagenised Sunstate population were then crossed with the previously identified HIB double null mutants (deletion mutants) in order to isolate triple mutants that lacked SBEIIa activity from two genomes with total or partial loss of activity from the third genome. Three groups of crosses were carried out. In a first group, four crosses to isolate mutants of the A1B2D2 genotype, two crosses each to isolate the A2B2D2 and A2B2D1 genotypes, and one cross to isolate the A1B2D1 genotype were performed. The second group included 2 crosses aimed at generating triple null mutants of the A2B2D2 genotype, and one cross each aimed at generating the A1B2D2, A1B1D2 and A2B1D2 genotypes. The third group included four crosses each aimed at producing the A2B1D2, A2B2D1 and A1B1D2 genotypes, 10 crosses aimed at the A2B2D2 genotype, 6 crosses aimed at the A1B2D2 genotype and 2 crosses aimed at the A1B2D1 genotype. The resultant F1 plants were selfed to produce F2 endosperms.

Starch granules from the F2 endosperms were examined by light microscopy for altered granule morphology. F2 seeds were identified which exhibited severely distorted starch granules similar to those found in grains having high amylose levels of at least 70% amylose. The results from the individual crosses in the first group were as follows.

Cross 7-25 (D2) X 08/h-92 (A1B2), Designated CS3.

Nineteen seeds with varying degrees of altered starch granule morphology were identified from a screening of 192 F2 seeds. These seeds were germinated and DNA extracted from leaf samples from the resultant plants. PCR was conducted on DNA from the 19 selected plants to detect 1) the CAPS codominant marker AR2aDex21_22F and AR2aex20_22R with digestion by Mly1 to detect the point mutation in the D genome coming from the parent 7-25 (above), and 2) AR2aI13genome F2 and AR2aI13genome R2 primers to detect SBEIIa deletions in the A and B genomes coming from 08/-H-92 parent line. Out of the 19 lines tested, four plants, designated C3, C10, A2 and F9, were homozygous for the point mutation in the SBEIIa-D gene coming from the 7-25 parent, and were clearly missing the SBEIIa-A and SBEIIa-B derived fragments and therefore homozygous for the deletion alleles, indicating the triple null genotype of these plants. SBEIIa protein expression from 4 developing seeds from each of the C3, C10, A2 and F9 plants was analysed through gel electrophoresis and Western blotting. The results confirmed that all of these plants are homozygous triple null mutants for the SBEIIa genes.

Cross 6-60 (B2) X 08/i-G3 (A1D2), Designated CS2.

Four triple null seeds, designated F11, D8, E6 and E11 were identified from this cross from a total of 288 F2 seeds that were screened. The triple null genotype of F11 and D8 was confirmed in plants produced from these seeds. The plants produced from the F11 and E6 seeds showed normal growth and development, plant E11 died at the seedling stage, and plant D8 had a late flowering phenotype. The lack of SBEIIa expression in each of 4 endosperms for plants F11 and E6 confirmed them to be homozygous triple null mutants of SBEIIa. Analysis of 10 F3 seeds from a heterozygous line from this cross, CS2-C6, also identified one triple null seed, CS2-C6.4, which was confirmed to be homozygous for lack of SBEIIa expression.

Cross 08/b-18 (A1D1) X 6-60 (B2), Designated CS1

Screening of 192 F2 seeds by microscopy and 288 seeds by PCR did not identify any homozygous triple nulls. However one confirmed heterozygous line, A1B2hetD1-G12 which was a homozygous double null for the SBEIIa-A and -B genes and heterozygous for the SBEIIa-D mutant allele was grown. Embryos were isolated from the F3 developing seeds and cultured to produce plants and the corresponding endosperms typed for SBEIIa polypeptides. Out of 29 seeds analysed, 5 were found to have the triple null genotype by gel electrophoresis and Western blotting. Out of these 5 CS1 triple null lines, only 4 survived to seed set. Out of these four, only one line, CS1-G12/15 appeared to be better in seed setting compared to other CS1 lines. It appeared that the A1D1B2 triple null homozygous plants generated from these parental mutant lines were reduced fertility, perhaps due to linkage drag from secondary mutations. Backcrossing to non-mutant lines.

Screening of 288 F2 seeds from a cross in the second group, 08/mm-M7-E11 (A2D2) X 6-60 (B2), designated CS10, identified one triple homozygous null seed of the A2B2D2 genotype, designated CS10-C12. That is, this genotype was null for the three SBEIIa genes and wild-type for the three SBEIIb genes. Analysis by light microscopy showed the presence of distorted starch granules in the CS10-C12 seeds, indicating a substantially elevated amylose level. This seed was sown to produce plants in the glasshouse. The triple null SBEIIa and wild-type SBEIIb genotype of this plant was confirmed from the plant DNA. Amylose content in starch of the F3 seeds is determined.

F2 seeds of the other crosses are examined in the same manner.

The amylose content in the grain starch of two of the triple null lines, CS3-A2 (08/h-92 (A1B2) X 7-25 (D2)) and CS2-F11 (08/i-G3 (A1D2) X 6-60 (B2)) were initially analysed using the iodometric method. The results are presented in Table 20 and compared to the SBEIIa silenced RNAi lines as a positive control, and Sunstate and NB1 as wild-types. The amylose content in the grain starch for the line CS3-A2 was 69.5% and for CS2-F11 was 85.3%. In comparison, the amylose level for the wild type grains was about 32.9% and that for the RNAi SBEIIa line 85.2c ranged from 72.2% to 75.1%. The amylose content was further analysed by iodometry to compare the performance of CS1, CS2 and CS3 and the data are given in Table 21. While both CS1 and CS2 lines showed an amylose content of >80%, in the range 80-86%, CS3 lines showed an amylose content ranged from about 67% to 70%. A third round of amylose analysis was carried out including the A2B2D2 triple null line CS10-C12 and the results are shown in Table 22. CS10-C12 showed an amylose content of 67.4%, falling within the range observed for the CS3 lines, while CS1 and CS2 triple null lines ranged from 74% to 84%. While the A1 single null line gave a value of 39.5%, A1B2 double lines ranged from 50.4% to 53.6% in this assay.

The growth and development of the plants produced from these seeds was observed. The preliminary agronomic characteristics of the triple null SBEIIa plants are summarised in Table 23. The average weight of individual seeds obtained from the triple null lines ranged from 34.2 to 46.5 mg. The total number of seeds per plant ranged from 15 to 254. The triple null lines of CS2 and C3 did not exhibit any significant loss of fertility compared to the control plants. Considerable sterility was observed in three out of four of CS1 triple null lines. Examination of the seed morphology from these plants revealed no obvious shrinking of seed. The seeds of the triple null plants from the CS3-A2 line had a chalky appearance compared to seeds from other triple null lines from CS3, CS2 and CS1 lines.

Chain length distribution of isoamylase debranched starch was carried out by capillary electrophoresis on starch isolated from grain of the CS2_F9 and CS3-A2 triple null lines. The difference plot, in which the values obtained for the wild type (Sunstate) were subtracted from that of the mutant, showed a profile for the triple null lines very similar to that of the RNAi SBEIIa line 85.2c, with a significant reduction in the proportion of chains having a length of DP 9 to 15 and an increase in the proportion of long chains of DP 17-19 and DP>26. In the line CS2-F11, the difference in the proportion of shorter chains of DP 9-15 was more pronounced than in CS3-A2 and 85.2c. Also in CS2-F11, there was a significant increase in the very short chains of DP 6-7.

Eight crosses were also performed between affinity single mutants to produce affinity double mutants of SBEIIa. This included crosses generated with the aim of isolating A2B2, A2D2 and B2D2 double affinity mutants. F2 progeny were analysed by the methods described above to identify the double homozygous affinity mutants.

EXAMPLE 12

Properties of Starch Granules and Starch from High Amylose Wheat Grain

Changes in Starch Granule Morphology and Birefringence.

Starch and starch granule properties were examined in the transgenic high amylose wheat described in Example 2. Scanning electron microscopy was used to identify gross changes in starch granule size and structure. Compared to the untransformed control, starch granules from endosperms having reduced SBEIIa expression displayed significant morphological alterations. They were highly irregular in shape and many of the A granules (>10 µm diameter) appeared to be sickle shaped. In contrast, both A and B (<10 µm diameter) starch granules from endosperms having reduced SBEIIb expression and unaltered SBEIIa expression were smooth surfaced, spherical or ellipsoid in shape and indistinguishable from wild-type wheat starch granules.

When observed microscopically under polarised light, wild-type starch granules typically show a strong birefringence pattern. However, the birefringence was greatly reduced for granules containing high amylose starch. Less than 10% of the starch granules from lines having reduced SBEIIa expression and 70%-80% amylose content were birefringent when visualized under polarized light. For lines having essentially no SBEIIb expression but with wild-type SBEIIa expression, no change in birefringence was observed compared to non-transformed controls. In both wild-type and SBEIIb-suppressed lines, approximately 94% of the starch granules exhibited full birefringence. The data is given in Table 24. Loss of birefringence therefore correlated closely with high amylose content.

Amylose Content of Transgenic Wheat Grain.

The amylose content of transgenic wheat grain was assayed by two independent methods, namely an iodometric method and a size exclusion chromatography (SEC) method. The iodometric determination of amylose content was based on measuring the colour change induced when iodine bound to linear regions of −1,4 glucan, with reference to a standard curve generated using known concentrations of purified potato amylose and amylopectin, as described in Example 1. The size exclusion chromatography method was based on the separation, by column chromatography, of amylose and amylopectin which had not been debranched, followed by measurement of the starch concentration in the fractions eluted from the column. Three genotypes of grain were analysed. Firstly, plants transformed with the hp-SBEIIa construct and having very low levels of SBEIIa expression; secondly, plants containing the hp-SBEIIb construct and having no detectable expression of SBEIIb but wild-type for SBEIIa; and thirdly, the non-transformed wild-type control (NB1). Grain from the plants lacking SBEIIb expression (008) had an amylose content of 27.3% determined by the iodometric method and 32% by the SEC method. This was not significantly different to the amylose content of grain from non-transformed control line NB1 (31.8% iodometric, 25.5% SEC). However, in grain having the reduced SBEIIa expression (line 087) the amylose content was significantly elevated (88.5% iodometric, 74.4% SEC). The difference in these two figures for line 087 was thought to be the presence of some "intermediate material" which binds iodine much like amylose and was measured in the iodometric assay as amylose but was separated in the column chromatography with the larger amylopectin.

Chain Length Distribution of Starch by FACE.

Chain length distribution of isoamylase de-branched starch was determined by fluorophore assisted carbohydrate electrophoresis (FACE). This technique provides a high resolution analysis of the distribution of chain lengths in the range from DP 1 to 50. From the molar difference plot in which the normalized chain length distribution of the non-transformed control was subtracted from the normalized distribution of the transgenic lines, it was observed that there was a marked decrease in the proportion of chain lengths of DP 6-12 and a corresponding increase in the chain lengths greater than DP12 in starch from grain having reduced SBEIIa expression. No statistically significant alteration in the chain length distribution of starch from hp-SBEIIb lines was observed when compared to wild-type.

Molecular Weight of Amylopectin and Amylose.

Molecular weight distribution of starch was determined by size exclusion-HPLC (SE-HPLC). The HPLC system comprised of a GBC pump (LC 1150, GBC Instruments, Vic, Australia) equipped with Auto Sampler (GBC, LC1610) and Evaporative Light Scattering Detector (ELSD) (ALLTech, Deerfield, USA). The Ultrahydrogel™ 1000 column, Ultrahydrogel™ 250 column and guard column (7.8 mm×300 mm, Waters, Japan) were used and maintained at 35° C. during HPLC operation. Ammonium acetate buffer (0.05 M; pH 5.2) was used as the mobile phase at a flow rate of 0.8 mL min$^{-1}$.

The molecular weight of amylopectin in the starch of the reduced SBEIIa grain appeared to be much lower than that of amylopectin in the starches of NB1 (wild-type, non-transgenic) and the reduced SBEIIb grain (peak position of 7166 kDa versus 45523, 43646 kDa). In contrast, the molecular weight of amylose from the reduced SBEIIb grain was not significantly different compared to that of wild-type grain from non-transformed variety NB1. The data is in Table 25.

Total Starch Content in Endosperm of Wheat with Reduced SBEIIa Expression.

Analysis of total starch content in grain as a percentage of grain weight revealed a slight reduction in the endosperm starch content of the hp-SBEIIa line (43.4%) compared to 52% in the control and 50.3% in hp-SBEIIb line (Table 24). This indicated that there was some reduction in total starch synthesis when SBEIIa expression was reduced by the inhibitory construct.

Starch Swelling Power (SSP).

Starch swelling power of gelatinized starch was determined following the small scale test of Konik-Rose et al., (2001) which measured the uptake of water during gelatinization of starch. The estimated value of SSP was significantly lower for starch from the reduced SBEIIa line with a figure of 3.51 compared to starch from the control (9.31) and reduced SBEIIb grain (10.74) (Table 24).

Starch Pasting Properties.

Starch paste viscosity parameters were determined using a Rapid Visco Analyzer (RVA) essentially as described in Regina et al., (2004). The temperature profile for the RVA comprised the following stages: hold at 60° C. for 2 min, heat to 95° C. over 6 min, hold at 95° C. for 4 min, cool to 50° C. over 4 min, and hold at 50° C. for 4 min. The results (Table 26) showed that the peak and final viscosities were significantly lower in starch from the reduced SBEIIa grain compared to the control wheat starch.

Starch Gelatinisation Properties.

Gelatinisation properties of starch were studied using differential scanning calorimetry (DSC) as described in Regina et al., (2004). DSC was carried out on a Perkin Elmer Pyris 1 differential scanning calorimeter. Starch and water were premixed at a ratio of 1:2 and approximately 50 mg weighed into a DSC pan which was sealed and left to equilibrate overnight. A heating rate of 10° C. per minute was used to heat the test and reference samples from 30 to 130° C. Data was analysed using the software available with the instrument. The results (Table 27) clearly showed a delayed end of gelatinisation temperature (72.6° C.) for starch from the reduced SBEIIa grain compared to the control (66.6° C.). The peak gelatinisation temperature was also higher in the reduced SBEIIa starch (63.51° C.) compared to the control starch (61.16° C.).

EXAMPLE 13

Analysis of High Amylose Wheat Flour During Processing

Pressure Processing Studies in Collaboration with CSIRO Food and Nutritional Sciences, Werribee.

Structural characterisation of high amylose wheat starches in comparison with native starch was carried out using Small Angle X-ray Scattering (SAXS). The study was designed to include a) characterising raw wheat flour and b) real-time analysis of the gelatinisation process while pressure cooking the flour or starch samples at temperatures of greater than 100° C. and c) Structural changes on cooling over a period of 0 to 10 days, and retrogradation. The study used wheat flour samples of varying amylose content ranging from about 25% (wild-type) to about 75%, increasing in increments of about 10%.

Three sets of flour samples were included in the experiments. Firstly, with pure lines without pooling from a high amylose wheat from the reduced SBEIIa lines, a medium level amylose wheat line AC45.1 which was transformed with the hp-combo construct having about 50% amylose (Example 2) and from the control wheat (NB1). Secondly, with pooled wheat material from transformed lines as described in Example 2, pooling samples in increments of 10% increasing amylose content. Thirdly, comparing flour from different species including wheat (high amylose, wild-type, and wheat lacking SSIIa), barley (wild-type, high amylose by reduced SBEIIa and SBEIIb, and high amylose by reduced SSII), and high amylose maize. The results from the resistant starch analysis on the pooled wheat material with a range of amylose content revealed a linear increase in resistant starch from an amylose content of >40%.

EXAMPLE 14

Production of Breads and Other Food Products

One of the most effective ways of delivering a grain such as high amylose wheat into the diet is through bread. To show that the high amylose wheat could readily be incorporated into breads and to examine the factors that allowed retention of bread making quality, samples of flour were produced, analysed and used in baking. The following methods were employed.

Methods.

Wheat grains were conditioned to 16.5% moisture content overnight and milled with either a Buhler laboratory scale mill at BRI Ltd, Australia, or using a Quadromat Junior mill followed by sieving, to achieve a final particle size of 150 μm. The protein and moisture content of the samples were determined by infrared reflectance (NIR) according to AACC Method 39-11 (1999), or by the Dumas method and air-oven according to AACC Method 44-15 A (AACC$_5$ 1999).

Micro Z-Arm Mixing.

Optimum water absorption values of wheat flours were determined with the Micro Z-arm Mixer, using 4 g of test flour per mix (Gras et al., (2001); Bekes et al., (2002). Constant angular velocity with shaft speeds for the fast and slow blades of 96 and 64 rpm, respectively, were used during all mixes. Mixing was carried out in triplicate, each for 20 minutes. Before adding water to the flour, the baseline was automatically recorded (30 sec) by mixing only the solid components. The water addition was carried out in one step using an automatic water pump. The following parameters were determined from the individual mixing experiments by taking the averages: WA %—Water Absorption was determined at 500 Brabender Unit (BU) dough consistency; Dough Development Time (DDT): time to peak resistance (sec).

Mixograms.

To determine optimal dough mixing parameters with the modified wheat flour, samples with variable water absorption corresponding to water absorption determined by the Micro Z-arm mixer, were mixed in a 10 g CSIRO prototype Mixograph keeping the total dough mass constant. For each of the flour samples, the following parameters were recorded: MT—mixing time (sec); PR—Mixograph peak resistance (Arbitrary Units, AU); BWPR—band width at peak resistance (Arbitrary Units, AU); RBD—resistance breakdown (%); BWBD—bandwidth breakdown (%); TMBW—time to maximum bandwidth (s); and MBW—maximum bandwidth (Arbitrary Units, A.U.).

Micro Extension Testing.

Dough extensibility parameters were measured as follows: Doughs were mixed to peak dough development in a 10 g prototype Mixograph. Extension tests at 1 cm/s were carried out on a TA.XT2i texture analyser with a modified geometry Kieffer dough and gluten extensibility rig (Mann et al., 2003). Dough samples for extension testing (~1.0 g/test) were moulded with a Kieffer moulder and rested at 30° C. and 90% RH for 45 min. before extension testing. The R_Max and Ext_R-max were determined from the data with the help of Exceed Expert software (Smewing, The measurement of dough and gluten extensibility using the SMS/Kieffer rig and the TA.TX2 texture analyzer handbook, SMS Ltd: Surrey, UK, 1995; Mann, (2002).

An illustrative recipe based on the 14 g flour as 100% was as follows: flour 100%, salt 2%, dry yeast 1.5%, vegetable oil 2%, and improver (ascorbic acid 100 ppm, fungal amylose 15 ppm, xylanase 40 ppm, soy flour 0.3%, obtained from Goodman Fielder Pty Ltd, Australia) 1.5%. The water addition level was based on the micro Z-arm water absorption values that were adjusted for the full formula. Flour (14 g) and the other ingredients were mixed to peak dough development time in a 35 g Mixograph. The moulding and panning was carried out in a two staged proofing steps at 40 C at 85% RH. Baking was carried out in a Rotel oven for 15 min at 190° C. Loaf volume (determined by the canola seed displacement method) and weight measurements were taken after cooling on a rack for 2 hours. Net water loss was measured by weighing the loaves over time.

The flour or wholemeal may be blended with flour or wholemeal from non-modified wheats or other cereals such as barley to provide desired dough and bread-making or nutritional qualities. For example, flour from cvs Chara or Glenlea has a high dough strength while that from cv Janz has a medium dough strength. In particular, the levels of high and low molecular weight glutenin subunits in the flour is positively correlated with dough strength, and further influenced by the nature of the alleles present.

Flour from transgenic wheat lines having reduced SBEIIa were used at 100%, 60% and 30% addition levels. e.g. either all the flour came from the various wheat lines or 60% or 30% were added to the Baking Control (B. extra) flour. Percentages are of total flour in the bread formulation. Four transgenic wheat lines were used as follows: 072 (reduced SBEIIa), 212 (a wheat line derived from the cross, reduced SBEIIa×SBEI triple null wheat), H7 (a wheat line derived from the cross, reduced SBE IIa×SSIIa triple null wheat) and 008 (reduced SBEIIb) were tested along with a non transformed control wheat (NB1). All wheats were milled in a Brabender Quadramat Junior mill. All blends had water absorptions determined on 4 g Z-arm mixer and optimal mixing times determined on 10 g Mixograph as described above. These conditions were used in preparing the 10 g test bake loaves.

Mixing Properties.

Apart from the control lines (Baking Control, NB1 and 008) all other wheat lines gave greatly elevated water absorption values (FIG. 17(a)). Lines 212 and 072 gave increasing water absorption values with increasing addition levels, including up to a high of 95% water absorption at 100% addition of 212 flour. Increased incorporation levels of flour from these lines also lead to a decrease in the optimal Mixograph mixing times (FIG. 17(b)). As with the water absorption data, the non-control lines showed a strong reduction in specific loaf volume (loaf volume/loaf weight) with increasing levels of addition. The effect was particularly strong for the 212 line.

These studies show that breads with commercial potential, including acceptable crumb structure, texture and appearance, could be obtained using the high amylose wheat flour blended with control flour samples. Furthermore, high amylose wheats are used in combination with preferred genetic background characteristics (e.g. preferred high and low molecular weight glutenins), the addition of improvers such as gluten, ascorbate or emulsifiers, or the use of differing bread-making styles (e.g. sponge and dough bread-making, sour dough, mixed grain, or wholemeal) to provide a range of products with particular utility and nutritional efficacy for improved bowel and metabolic health.

Other Food Products:

Yellow alkaline noodles (YAN) (100% flour, 32% water, 1% $Na_2CO_3$) were prepared in a Hobart mixer using the standard BRI Research Noodle Manufacturing Method (AFL 029). Noodle sheet was formed in the stainless steel rollers of an Otake noodle machine. After resting (30 min) the noodle sheet was reduced and cut into strands. The dimensions of the noodles were 1.5×1.5 mm.

Instant noodles (100% flour, 32% water, 1% NaCl and 0.2% Na2CO3) were prepared in a Hobart mixer using the standard BRI Research Noodle Manufacturing method (AFL 028). Noodle sheet was formed in the stainless steel rollers of an Otake noodle machine. After resting (5 min) the noodle sheet was reduced and cut into strands. The dimensions of the noodles were 1.0×1.5×25 mm. The noodle strands were steamed for 3.5 min and then fried in oil at 150 C for 45 sec.

Sponge and Dough (S&D) bread. The BRI Research sponge and dough baking involved a two-step process. In the first step, the sponge was made by mixing part of the total flour with water, yeast and yeast food. The sponge was allowed to ferment for 4 h. In the second step, the sponge was incorporated with the rest of the flour, water and other ingredients to make dough. The sponge stage of the process was made with 200 g of flour and was given 4 h fermentation. The dough was prepared by mixing the remaining 100 g of flour and other ingredients with the fermented sponge.

Pasta—Spaghetti. The method used for pasta production was as described in Sissons et al., (2007). Test sample flours from high amylose wheat (reduced SBEIIa) and control wheat (NB1) were mixed with Manildra semolina at various percentages (test sample: 0, 20, 40, 60, 80, 100%) to obtain flour mixes for small scale pasta preparation. The samples were corrected to 30% moisture. The desired amount of water was added to the samples and mixed briefly before being transferred into a 50 g farinograph bowl for a further 2 min mix. The resulting dough, which resembled coffee-bean-size crumbs, was transferred into a stainless steel chamber and rested under a pressure of 7000 kPa for 9 min at 50 C. The pasta was then extruded at a constant rate and cut into lengths of approximately 48 cm. Two batches of pasta were made for each sample. The pasta was dried using a Thermoline Temperature and Humidity Cabinet (TEC 2604) (Thermoline Scientific Equipment, Smithfield, Australia). The drying cycle consisted of a holding temperature of 25 C followed by an increase to 65 C for 45 min then a period of about 13 h at 50 C followed by cooling to 25 C. Humidity was controlled during the cycle. Dried pasta was cut into 7 cm strands for subsequent tests.

EXAMPLE 15

In Vitro Measurements of Glycaemic Index (GI) and Resistant Starch (RS) of Food Samples The Glycemic Index (GI) of food samples including the bread made as described herein was measured in vitro as follows: Food samples were homogenised with a domestic food processor. An amount of sample representing approximately 50 mg of carbohydrate was weighed into a 120 ml plastic sample container and 100 µl of carbonate buffer added without $\alpha$-amylase. Approximately 15-20 seconds after the addition of carbonate buffer, 5 ml of Pepsin solution (65 mg of pepsin (Sigma) dissolved in 65 ml of HCl 0.02M, pH 2.0, made up on the day of use) was added, and the mixture incubated at 37° C. for 30 minutes in a reciprocating water bath at 70 rpm. Following incubation, the sample was neutralised with 5 ml of NaOH (0.02M) and 25 ml of acetate buffer 0.2M, pH 6 added. 5 ml of enzyme mixture containing 2 mg/mL of pancreatin ($\alpha$-amylase, Sigma) and 28 U/mL of amyloglucosidase from *Aspergillus niger* (AMG, Sigma) dissolved in Na acetate buffer (sodium acetate buffer, 0.2 M, pH 6.0, containing 0.20 M calcium chloride and 0.49 mM magnesium chloride) was then added, and the mixture incubated for 2-5 minutes. 1 ml of solution was transferred from each flask into a 1.5 ml tube and centrifuged at 3000 rpm for 10 minutes. The supernatant was transferred to a new tube and stored in a freezer. The remainder of each sample was covered with aluminium foil and the containers incubated at 37° C. for 5 hours in a water bath. A further 1 ml of solution was then collected from each flask, centrifuged and the supernatant transferred as carried out previously. This was also stored in a freezer until the absorbances could be read.

All samples were thawed to room temperature and centrifuged at 3000 rpm for 10 minutes. Samples were diluted as necessary (1 in 10 dilution usually sufficient), 10 µl of supernatant transferred from each sample to 96-well microtitre plates in duplicate or triplicate. A standard curve for each microtitre plate was prepared using glucose (0 mg, 0.0625 mg, 0.125 mg, 0.25 mg, 0.5 mg and 1.0 mg). 200 ul of Glucose Trinder reagent (Microgenetics Diagnostics Pty Ltd, Lidcombe, NSW) was added to each well and the plates incubated at room temperature for approximately 20 minutes. The absorbance of each sample was measured at 505 nm using a plate reader and the amount of glucose calculated with reference to the standard curve.

The level of Resistant Starch (RS) in food samples including the bread made as described herein was measured in vitro as follows. This method describes the sample preparation and in vitro digestion of starch in foods, as normally eaten. The method has two sections: firstly, starch in the food was hydrolysed under simulated physiological conditions; secondly, by-products were removed through washing and the residual starch determined after homogenization and drying of the sample. Starch quantitated at the end of the digestion treatment represented the resistant starch content of the food.

On day 1, the food samples were processed in a manner simulating consumption, for example by homogenising with a domestic food processor to a consistency as would be achieved by chewing. After homogenising, an amount of food representing up to 500 mg of carbohydrate was weighed into a 125 mL Erlenmeyer flask. A carbonate buffer was prepared by dissolving 121 mg of $NaHCO_3$ and 157 mg of KCl in approximately 90 mL purified water, adding 159 μL of 1 M $CaCl_2.6H_2O$ solution and 41 μL of 0.49 M $MgCl_2.6H_2O$, adjusting the pH to 7 to 7.1 with 0.32 M HCl, and adjusting the volume to 100 mL. This buffer was stored at 4° C. for up to five days. An artificial saliva solution containing 250 units of α-amylase (Sigma A-3176 Type VI-B from porcine pancreas) per mL of the carbonate buffer was prepared. An amount of the artificial saliva solution, approximately equal to the weight of food, was added to the flask. About 15-20 sec after adding the saliva, 5 mL of pepsin solution in HCl (1 mg/mL pepsin (Sigma) in 0.02 M HCl, pH 2.0, made up on day of use) was added to each flask. The mixing of the amylase and then pepsin mimicked a human chewing the food before swallowing it. The mixture was incubated at 37° C. for 30 min with shaking at 85 rpm. The mixture was then neutralised with 5 mL of 0.02M NaOH. 25 mL of acetate buffer (0.2 M, pH 6) and 5 mL of pancreatin enzyme mixture containing 2 mg/mL pancreatin (Sigma, porcine pancreas at 4×USP activity) and 28 U of amyloglucosidase (AMG, Sigma) from *Aspergillus niger* in acetate buffer, pH6, were added per flask. Each flask was capped with aluminium foil and incubated at 37° C. for 16 hours in a reciprocating water bath set to 85 rpm.

On day 2, the contents of each flask were transferred quantitatively to a 50 mL polypropylene tube and centrifuged at 2000×g for 10 min at room temperature. The supernatants were discarded and each pellet washed three times with 20 mL of water, gently vortexing the tube with each wash to break up the pellet, followed by centrifugation. 50 μL of the last water wash was tested with Glucose Trinder reagent for the absence of free glucose. Each pellet was then resuspended in approximately 6 mL of purified water and homogenised three times for 10 seconds using an Ultra Turrax TP18/10 with an S25N-8G dispersing tool. The contents are quantitatively transferred to a 25 mL volumetric flask and made to volume. The contents were mixed thoroughly and returned to the polypropylene tube. A 5 mL sample of each suspension was transferred to a 25 mL culture tube and immediately shell frozen in liquid nitrogen and freeze dried.

On day 3, total starch in each sample was measured using reagents supplied in the Megazyme Total Starch Procedure kit. Starch standards (Regular Maize Starch, Sigma S-5296) and an assay reagent blank were prepared. Samples, controls and reagent blanks were wet with 0.4 mL of 80% ethanol to aid dispersion, followed by vortexing. Immediately, 2 mL of DMSO was added and solutions mixed by vortexing. The tubes were placed in a boiling water bath for 5 min, and 3 mL of thermostable α-amylase (100 U/ml) in MOPS buffer (pH 7, containing 5 mM $CaCl_2$ and 0.02% sodium azide) added immediately. Solutions were incubated in the boiling water bath for a further 12 min, with vortex mixing at 3 min intervals. Tubes were then placed in a 50° C. water bath and 4 mL of sodium acetate buffer (200 mM, pH 4.5, containing 0.02% sodium azide) and 0.1 mL of amyloglucosidase at 300 U/ml added. The mixtures were incubated at 50° C. for 30 min with gentle mixing at 10 min intervals. The volumes were made up to 25 mL in a volumetric flask and mixed well. Aliquots were centrifuged at 2000×g for 10 min. The amount of glucose in 50 μL of supernatant was determined with 1.0 mL of Glucose Trinder reagent and measuring the absorbance at 505 nm after incubation of the tubes at room temperature in the dark for a minimum of 18 min and a maximum of 45 min.

Bread loaves baked from flour from four transgenic wheat lines, namely 072 (reduced SBEIIa), 212 (a wheat line derived from the cross, reduced SBEIIa×SBEI triple null wheat), H7 (a wheat line derived from the cross, reduced SBEIIa×SSIIa triple null wheat) and 008 (reduced SBEIIb) were tested along with a non transformed control wheat (NB1) for RS and GI after incorporation levels of 100%, 60% and 30% flour, the remainder 40% or 70% flour being from wild-type grain. Increased incorporation of 212, 072, and H7 flour resulted in significant increases in RS (FIG. 18(*a*) and reductions in predicted GI (FIG. 18(*b*)). The magnitude of the changes was greatest when using flour from Line 212. For instance, bread made with 100% addition of this high amylose flour had an RS content of about 10% which represented a 150% increase above that for 30% level of inclusion and a 9-fold increase compared to the NB1 controls. Increasing the extent of incorporation of flour from the 008 lines had no effect on the RS and GI of the resultant loaves and the results were comparable to those of the baking control flour.

Flour produced from grain of lines F9 and F11 (Example 11) were tested for resistant starch content by the in vitro method. F9 flour showed an RS content of about 3 g/100 g flour (range 2.3-3.4 g/100 g flour), while F11 flour showed an RS content of about 6.5 g/100 g flour, compared to 0.2-0.4 g/100 g flour for control flour from thw wild-type varieties Sunstate and NB1. This represents an increase of about 8-fold or at least 10-fold relative to the RS level in wild-type flour.

EXAMPLE 16

Processing of High Amylose Wheat and Resultant RS Levels

A small scale study was conducted to determine the resistant starch (RS) content in processed grain from the high amylose wheat which had been rolled or flaked. The technique involved conditioning the grains to a moisture level of 25% for one hour, followed by steaming the grains. Following steaming, the grains were flaked using a small-scale roller. The flakes were then roasted in an oven at 120 C for 35 min. Two roller widths and three steaming timings were used on approximately 200 g of samples from high amylose wheat having reduced SBEIIa (HAW, line 85.2c) and wild-type, control wheat (cv. Hartog). The roller widths tested were 0.05 mm and 0.15 mm. The steaming timings tested were 60', 45' and 35'.

This study showed a clear and substantial increase in the amount of RS in processed high amylose wheat compared to the control (Table 28, FIG. 18). There also appeared to be some effect of the processing conditions on the RS level. For example with the high amylose grain, increased steaming times led to a slight reduction in the level of RS, most likely due to increased starch gelatinization during steaming (Table 28). The wider roller gap generated a higher RS level except at the longest steaming time. This could have been due to increased shear damage of the starch granules when the grains were rolled at narrower gaps, reducing RS levels slightly. Narrower roller gaps also led to higher RS levels in the Hartog control, albeit at much lower overall RS levels. In contrast to the high amylose results, increased steaming times led to higher RS levels, possibly due to increased starch gelatinization at longer steaming times contributing to more starch retrogradation during subsequent processing and cooling.

Consolidated Data on RS from Various Products.

RS data obtained from various products such as noodles, sponge and dough bread and spaghetti, prepared as described in Example 10, are presented in Table 29. Not all levels of incorporation were tested for all products, but incorporation levels of 20%, 40% and 60% were used in most of the products analysed. The results showed a linear relationship between RS content and the level of incorporation of high amylose flour.

EXAMPLE 17

Isolation of Further Plants Having Point Mutations in SBEIIa

A population of mutated plant lines was developed after EMS mutagenesis of seeds of the wheat cultivars Arche or Apache, using standard EMS treatment conditions. About 5000 Apache and 900 Arche individual M1 plants were grown from the mutagenised seed, self-fertilised, and seeds from each plant and subsequent progeny generations maintained as potentially mutant lines, each derived from an individual M1 plant. The lines were screened for mutations in the three homoeologous SBEIIa genes by next-generation Solexa sequencing (Illumina). To do this, 7 DNA pools were prepared, each by pooling DNA from about 130 M1 families from the Arche population and 96 from the Apache population. PCR was carried out on the pooled DNAs for 3 or 4 regions per homoeologous gene, targeting the exonic regions including splice sites of the genes. Genome-specific primers are set out in Table 30.

The 10 amplicons (amplification products) from the same DNA pools were merged after normalization of the PCR products, and sequencing was done with one flow cell per DNA pool. The sequence data were analysed to select from all of the polymorphisms the ones most likely due to mutations rather than to sequencing errors, based on the frequencies of the observed polymorphisms. 64 putative mutants from the Arche population and 48 from the Apache population were observed from the first sequence analysis covering the exonic regions and splice sites. SNP assays were designed for each polymorphism based on kaspar technology, and genotyping was performed on the 130 families in each pool that was positive for the particular polymorphism. Thereby, the individual mutant line containing each mutant gene was identified and the mutant SBEIIa sequences confirmed.

By this method, 31 mutant lines from the Apache population and 9 from the Arche population were identified each having an SBEIIa mutation, and M2 kernels of each retained. From each mutant line, depending on availability, around 10 M2 seeds, were cut in half, the half without the embryo was used for DNA extraction and analysis, the other half with the embryo was saved for sowing. A total of 5 mutants were confirmed on half seeds from Arche population and 28 from Apache population. The corresponding seeds were sown to produce progeny plants to confirm that the mutations were inherited in Mendelian fashion by repeating analysis on M2 plant leaf material, providing much better DNA quality. These analyses confirmed 19 homozygous mutants, 4 from the Arche population and 15 from the Apache population (Table 31) and allowed their ranking depending on their DNA and the deduced protein sequences encoded by the mutants.

The obtained mutants were categorised into three groups. The first group consisted of mutants which had mutated SBEIIa genes with stop codons in the protein coding regions of the SBEIIa genes on the B or D genomes, causing premature termination of translation of the SBEIIa proteins. The second group consisted of lines which comprised splice site mutations in the SBEIIa-B or -D genes. Such mutations were expected to be null mutations. The third group consisted of mutants which comprised point mutations in the SBEIIa-A, SBEIIa-B and SBEIIa-D genes which resulted in amino acid substitutions in the encoded polypeptides. The impact of the substitution mutations on the structure of the encoded proteins was predicted using Blosum 62 and Pam 250 matrices; in each case the impact was predicted to be strong. Using these homozygous plants as parents, crosses were performed between them or with the double null (deletion) SBEIIa mutants. Crosses were also carried out with *durum* wheat plants (cultivar Soldur) to introduce the mutations into the tetraploid wheat in order to achieve the production of high amylose *durum* wheat.

EXAMPLE 18

Production and Identification of SBEIIa Triple Null Wheat Combining Double Null Deletion Mutations and Single Point Mutations to Produce High Amylose Wheat Eight mutant lines which had been identified in the Apache and Arche mutagenised populations and two mutant lines from the Sunstate population were selected for use as parents in crosses to produce triple nulls. A total of 66 crosses were performed using plants that were homozygous for the point mutations as one parent (Table 32) and double-null SBEIIa mutants (HIB deletion mutants) as the second parent. The second parental plants included mutants of the A1D2, A2D2, A1B2 and B2D2 genotypes in order to produce triple nulls. F1 seeds from 34 crosses (Table 33) were retained and used to produce 50,000 F2 seeds by single seed descent. These were screened for the HAW phenotype using the single seed NIRS technique (Example 10). A total of 2,300 HAW seeds were identified. All of the crosses but one produced HAW seeds. Selected seeds were sown in a greenhouse and out of 415 F3 plants obtained, 91 were identified as triple nulls for the SBEIIa gene by molecular markers. Seeds were obtained from 85 plants among which 67 triple nulls plants were confirmed as high amylose wheat plants by NIRS measurement. Twenty-four plants produced seeds with amylose levels greater than for the GM 85.2c reference grain. Amylose content was measured by iodometry and showed that some of the SBEIIa triple null grain had amylose levels up to 158% higher than the control grain. In this same experiment, the HAW GM reference grain exhibited an amylose level 58% higher than the control line (Table 35). Measurement of the thousand kernel weight showed that the high amylose wheat grain were not significantly reduced in grain weight.

Seeds were sown for multiplication to allow further tests of the starch characteristics in the grain.

TABLE A

Sequence Listing

| SEQUENCE ID NO: | DESCRIPTION |
|---|---|
| 1 | Amino acid sequence of SBEIIa-A (Genbank Accession No. CAA72154) |
| 2 | Amino acid sequence of SBEIIa-B (Accession No. CAR95900) |
| 3 | Amino acid sequence of SBEIIa-D (Accession No. AAK26821) |
| 4 | partial amino acid sequence of SBEIIb-A, from amino terminus, encoded by exons 1-3 of *SBEIIb-A* |
| 5 | Partial amino acid sequence of SBEIIb-B, encoded by exons 2-3 of *SBEIIb-B* |
| 6 | Amino acid sequence of SBEIIb-D (Accession No. AAW80631) (nt sequence AY740401). 836 amino acids |
| 7 | SEQ ID NO: 6 from US Patent Publication 20050164178 (CSIRO) Organism: *Triticum* sp. encodes SBEIIb-D identical to AAW80631 |
| 8 | SEQ ID NO: 2 from US Patent Publication No. 20050074891. Organism: *Triticum aestivum*. 695 amino acids- partial SBEIIb sequence |
| 9 | SEQ ID NO 4 from US Patent Publication No. 20050074891, but without the amino terminus extension Organism: *Triticum aestivum*; 836 aas. This is SBEIIb-D, 832/836 identical to AAW80631 |
| 10 | SEQ ID NO: 5 from Patent US 20050074891 Organism: *Hordeum vulgare* SBEIIb from barley |
| 11 | SEQ ID NO: 1026 from US Patent Publication No. 20050177901 Organism: *Triticum aestivum*. Probably an SBEIIb |
| 12 | SEQ ID NO: 3480 from US Patent Publication No. 20040016025 Organism: *Triticum aestivum*. Probably an SBEIIb |
| 13 | Nucleotide sequence *SBE IIa* Urartu exons 11-22 |
| 14 | Nucleotide sequence *SbeIIa_A* Urartu exons 1-3 |
| 15 | Nucleotide sequence *SbeIIa_A* Urartu Exons 3-8 |
| 16 | Synthetic peptide sequence (Example 1) |
| 17 | Synthetic peptide sequence (Example 1) |
| 18 | Synthetic peptide sequence (Example 1) |
| 19 | Primer for SBEIIa (Example 1) |
| 20 | Primer for SBEIIa (Example 1) |
| 21 | Primer for exons 12 to 14 of *SBEIIa* (Example 3) |
| 22 | Primer for exons 12 to 14 of *SBEIIa* (Example 3) |
| 23 | Primer for intron 3 region of *SBEIIa* (Example 3) |
| 24 | Primer for intron 3 region of *SBEIIa* (Example 3) |
| 25 | Primer for exon 3 region of *SBEIIa* (Example 3) |
| 26 | Primer for exon 3 region of *SBEIIa* (Example 3) |
| 27 | Primer for exon 1 region of *SBEIIa* (Example 3) |
| 28 | Primer for exon 1 region of *SBEIIa* (Example 3) |
| 29 | Primer for distinguishing homeologous *SBEIIa* genes in breadwheat (Example 4) |
| 30 | Primer for distinguishing homeologous *SBEIIa* genes in breadwheat (Example 4) |
| 31 | SBEIIa gene PCR primer (Example 9) |
| 32 | SBEIIa gene PCR primer (Example 9) |
| 33 | SBEIIa gene PCR primer (Example 9) |
| 34 | SBEIIa gene PCR primer (Example 9) |
| 35 | SBEIIa gene PCR primer (Example 9) |
| 36-62 | Genome specific primers of SBEIIa (Table 5) |
| 63-88 | A-genome specific primers of SBEIIa (Table 6) |
| 89-118 | B-genome specific primers of SBEIIa (Table 7) |
| 119-134 | D-genome specific primers of SBEIIa (Table 8) |
| 135-149 | Genome specific primers of SBEIIb (Table 10) |
| 150 | Accession No. Y11282, 2970 nt (SBEIIa-A cDNA sequence, Nair et al, 1997), protein coding region is from the ATG at 151-153 to TAA at 2620-2620 |
| 151 | Nucleotide sequence of the cDNA predicted from the genomic sequence of Accession No. AF338432 (SBEIIa-D gene from *A. tauschii*), beginning at the translation start ATG, 2760 nt. Protein coding region is nucleotides 1-2457. |
| 152 | Primer for mutant line 6-60 (Example 11) |
| 153 | Primer for mutant line 6-60 (Example 11) |
| 154 | Primer for mutant line 7-25 (Example 11) |
| 155 | Primer for mutant line 7-25 (Example 11) |
| 156 | Primer for mutant line 15-3D (Example 11) |
| 157 | Primer for mutant line 15-3D (Example 11) |

TABLE A-continued

Sequence Listing

| SEQUENCE ID NO: | DESCRIPTION |
|---|---|
| 158 | Primer for mutant line 16-9C (Example 11) |
| 159 | Primer for mutant line 16-9C (Example 11) |

TABLE 1

Starch branching enzyme genes characterized from cereals

| Species | SBE isoform | Type of clone | Accession No. | Reference |
|---|---|---|---|---|
| Maize | SBEI | cDNA | U17897 | Fisher et al., 1995 |
|  |  | genomic | AF072724 | Kim et al., 1998 |
|  | SBEIIb | cDNA | L08065 | Fisher et al., 1993 |
|  |  | genomic | AF072725 | Kim et al., 1999 |
|  | SBEIIa | cDNA | U65948 | Gao et al., 1997 |
| Wheat | SBEII | cDNA | Y11282 | Nair et al., 1997 |
|  | SBEI | cDNA and genomic | AJ237897 (SBEI gene) AF002821 (SBEI pseudogene AF076680 (SBEI gene) AF076679 (SBEI cDNA) | Baga et al., 1999 Rahman et al., 1997, Rahman et al., 1999 |
|  | SBEI | cDNA | Y12320 | Repellin et al., 1997 |
|  | SBEIIa | cDNA and genomic | AF338432 (cDNA) AF338431 (gene) | Rahman et al., 2001 |
|  | SBEIIa | cDNA | AK335707, AF286319 |  |
|  | SBEIIb | cDNA and genomic |  | WO 01/62934 |
|  | SBEIIb | cDNA |  | WO 00/15810 |
|  | SBEIIb-D | cDNA |  | US2005074891 |
| Rice | SBEI | cDNA | D10752 | Nakamura, 2002 and Nakamura and Yamanouchi, 1992 |
|  | SBEI | genomic | D10838 | Kawasaki et al., 1993 |
|  | RBE3 | cDNA | D16201 | Mizuno et al., 1993 |
| Barley | SBEIIa and SBEIIb | cDNA and genomic | AF064563 (SBEIIb gene) AF064561 (SBEIIb cDNA) AF064562 (SBEIIa gene) AF064560 (SBEIIa cDNA) | Sun et al., 1998 |

TABLE 2

Amino acid sub-classification

| Sub-classes | Amino acids |
|---|---|
| Acidic | Aspartic acid, Glutamic acid |
| Basic | Noncyclic: Arginine, Lysine; Cyclic: Histidine |

TABLE 2-continued

Amino acid sub-classification

| Sub-classes | Amino acids |
|---|---|
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

TABLE 3

Exemplary and Preferred Conserved Amino Acid Substitutions

| Original Residue | Exemplary conservative substitutions | Preferred conservative substitutions |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe | Leu |
| Leu | Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala | Leu |

TABLE 4

Genome specific primers for wheat SBEIIa genes

| Genome | Primers | Region | Expected Size (bp) |
|---|---|---|---|
| A | SbeIIa_A_deb1F/SbeIIa_A_deb1R | Exons 1 to 8 | 615 |
| A | SbeIIa_A_deb2F/SbeIIa_A_deb1R | Exons 1 to 8 | 604 |
| A | SbeIIa_A_deb2F/SbeIIa_A_deb5R | Exons 1 to 8 | ~1039 |
| A | SbeIIa_A_deb3F/SbeIIa_A_deb1R | Exons 1 to 8 | 565 |
| A | SbeIIa_A_deb4F/AR2aE8R07 | Exons 1 to 8 | 735 |
| A | SbeIIa_A_deb5F/AR2aE8R07 | Exons 1 to 8 | 696 |
| B | SbeIIa_B_R4/BeIIaE1f | Exons 1 to 8 | ~600 on B, ~800 on A |
| D | SbeIIa_D_deb1F/SbeIIa_D_deb1R | Exons 1 to 8 | 573 |
| D | SbeIIa_D_deb1F/SbeIIa_D_deb2R | Exons 1 to 8 | 539 |
| D | SbeIIa_D_deb1F/SbeIIa_D_deb4R | Exons 1 to 8 | ~900 |
| D | SbeIIa_D_deb2F/SbeIIa_D_deb4R | Exons 1 to 8 | ~900 |
| D | SbeIIa_D_deb3F/SbeIIa_D_deb4R | Exons 1 to 8 | ~900 |
| D | SbeIIa_D_deb4F/AR2aE8R07 | Exons 1 to 8 | 736 |
| A | Snp1for/Arev5 | Exons 13-14 | 508 |
| A | Afor4/del4rev | Exons 12-14 | 863 |
| A | Snp6for/Arev5 | Exon 14 | 205 |
| A | Afor4/Snp6rev | Exons 12-13 | 637 |
| A | Afor4/del5rev | Exons 12-14 | 872 |
| B | Bsnp4/Arev5 | Exons 13-14 | 494 |
| B | Afor4/Bsnp17rev | Exons 12-14 | 905 |
| B | Afor4/Bsnp18rev | Exons 12-14 | 952 |
| D | Afor4/Dsnp7rev | Exons 12-14 | 901 |
| D | Dsnp7for/Drev1 | — | 278 |
| D | Afor4/Arev5 | Exons 12-14 | 802 |

TABLE 5

Nucleotide sequences of genome specific primers of SBEIIa

| Primer name | Nucleotide Sequence (5' to 3') | SEQ ID NO: |
|---|---|---|
| SbeIIa_A_deb1F | GTTCGATGCTGTTCCCCAG | 36 |
| SbeIIa_A_deb1R | AGCCGTTTGCTCCTCGATG | 37 |
| SbeIIa_A_deb2F | TTCCCCAGTTGATCTCCATC | 38 |
| SbeIIa_A_deb4F | CTTACTGAATACTGACCAGTTG | 39 |
| SbeIIa_A_deb5F | TTTATGATCTGGCTTTTGCATCCTA | 40 |
| SbeIIa_A_deb5R | GATGTTCCCCAAATTTGCATGAC | 41 |
| SbeIIa_B_deb4R | AATGCACAAGGCAGTGAAGTAG | 42 |
| SbeIIa_D_deb1F | CCCAATTGATCTCCATGAGT | 43 |
| SbeIIa_D_deb1R | AACCCCAAACGGTGCATTATG | 44 |
| SbeIIa_D_deb2F | CGGCTTTGATCATTCCTCG | 45 |
| SbeIIa_D_deb2R | GCTAGAATGCACATCCATCTGAT | 46 |
| SbeIIa_D_deb3F | GTAACTGCAAGTTGTGGCG | 47 |
| SbeIIa_D_deb4F | GCTTACTGAATACTGACCAGTTACTA | 48 |
| SbeIIa_D_deb4R | CCTTAATTCAAAATGAGCGAAAGC | 49 |
| snp1for | GGCTAACTGTTCCTGTTAAA | 50 |
| snp6for | GATGAGATCATGGACGATTC | 51 |
| snp6rev | AATAAATAATAATCACTTCG | 52 |
| Del4rev | GAGTAACAGCCTGATCCCAA | 53 |
| Del5rev | TAACAAAAGAGTAACAGCC | 54 |
| Bsnp4 | GTCAATCTGTTCTTACACG | 55 |
| Bsnp17 rev | CAAAAAGAGTAGTAACAGCT | 56 |
| Bsnp18 rev | CAAGGTATAAATTAGCATTC | 57 |
| D snp7 for | GTTTTATTTTGGGGATCAGT | 58 |
| D snp7 rev | CCCTAACAAAAAGTGTAACAGA | 59 |
| Afor4 | ATCAGACCTTGTCACCAAAT | 60 |
| Arev5 | GCACTTACATCTTCACCAATG | 61 |
| Drev 1 | GCCTTCTGAAGCAATTGACAAG | 62 |

TABLE 6

Primers designed to amplify parts of the SBEIIa gene specifically from the
A genome of wheat - detected polymorphisms and fragment sizes

| Primer code | Primer sequence | SNP details | Afor4 | Arev5 | Arev6 | SEQ ID NO |
|---|---|---|---|---|---|---|
| snp1for | GGCTAACTGTTCCTGTTAAA | extra A/B and D | | 508 | | 63 |
| SNP1REV | CGACATGTGTAAGAACAGAT | extra A/B and D | 334 | | | 64 |
| snp2for2a | GTCGATATTCTATTCTTATGT | t/D; a/B; a/B; c/B D | | 474 | | 65 |
| snp3for | CTTTTTTAGGGCACTGAAAT | c/B; c/B; c/B D | | 315 | | 66 |
| snp3reva | GTTATGATGCATAGCAATTA | c/B D | 528 | | | 67 |
| snp4for | TCTTAGATAGTTCCCTAGTAC | t/B D | | 245 | | 68 |
| snp4rev | CAGGTAAAATTGTACAAGCG | t/B D | 599 | | | 69 |
| snp5for | ACCTGATGAGATCATGGAC | a/B D | | 210 | | 70 |
| snp5for2 | TACCTGATGAGATCATGGAC | a/B D | | 211 | | 71 |
| snp6for | GATGAGATCATGGACGATTC | a/B D; g/B D | | 205 | | 72 |
| snp6rev | AATAAATAATAATCACTTCG | t/B; a/B; g/B; g/B D | 637 | | | 73 |
| snp7for | TCTTTTTGTTAGGGGTAAG | 3 first by extra/D; extra act in BD; a/B D | | | 390 | 74 |
| Afor3 | AGTTTGACCAAGTCTACTG | | | 1050 | | 75 |
| Afor4 | ATCAGACCTTGTCACCAAAT | t/D | | 802 | | 76 |
| Arev5 | GCACTTACATCTTCACCAATG | | 802 | | | 77 |
| Arev7 | GTAGTTATAAGCAATATG | | | | | 78 |
| del1for | CATCAAGTGGTTTCAGTAAC | 7 bp Difference/BD | | 334 | | 79 |
| del1rev | GTTACTGAAACCACTTGATG | | 490 | | | 80 |
| Del4for | TTGGGATCAGGCTGTTACTC | extra g in B D; t = a BD; extra act in BD | | | | 81 |
| Del4rev | GAGTAACAGCCTGATCCCAA | | 863 | | | 82 |
| Del5for | GGCTGTTACTCTTTTTGTTA | t/BD; extra t; act extra in BD; extra ct | | | | 83 |
| Del5rev | TAACAAAAAGAGTAACAGCC | | 872 | | | 84 |
| Del3for | TTAACCAGTTAAGTAGTT | extra cagt; extra a; extra ttaag in D and ttaatag in B | | | 432 | 85 |
| Del3rev1 | AACTACTTAACTGGTTAA | extra ttaag in D and ttaatag in B; extra a; extra actg | 836 | | | 86 |
| Del3rev2 | GATCCCAAAATAAAACTACTT | extra ttaag in D and ttaatag in B; extra a | 851 | | | 87 |
| Del3rev3 | CCCAAAATAAAACTACTT | extra ttaag in D and ttaatag in B; extra a | 848 | | | 88 |

TABLE 7

Primers designed to amplify parts of the SBEIIa gene specifically from the B
genome of wheat- detected polymorphisms and fragment sizes

| Primer code | Primer sequence | SNP details | Arev5 | Afor4 | Exons | SEQ ID NO: |
|---|---|---|---|---|---|---|
| Bsnp1for | GTGGGATTCTCGTCTG | a/A D | | | | 89 |
| Bsnp2 | TTGGGAAGTATGTAGCTGC | ct/A D | 546 | | 13_14 | 90 |

TABLE 7 -continued

Primers designed to amplify parts of the SBEIIa gene specifically from the B genome of wheat- detected polymorphisms and fragment sizes

| Primer code | Primer sequence | SNP details | Arev5 | Afor4 | Exons | SEQ ID NO: |
|---|---|---|---|---|---|---|
| Bsnp3 | TTGGCTAACTGTTCCTGTC | t/A D | 509 | | 13_14 | 91 |
| Bsnp4 | GTCAATCTGTTCTTACACG | t/A D; extra a in A; a/A D | 494 | | | 92 |
| Bsnp5 | ATCTGTTCTTACACGTGTCA | a/A D; t/D; g/A D | 494 | | | 93 |
| Bsnp6 | GTCAATATTCTATTCTTATA | t/D; g/A D; g/A D | 474 | | | 94 |
| Bsnp7 | CTATTCTTATACAGGTATTA | g/A D; g/A D | 465 | | | 95 |
| Bsnp8 | AACGCGAGATGGTGGCTTGAT | a/A D | 430 | | half 13_14 | 96 |
| Bsnp9 | CAAGTGGTTTCAGTAACTTC | t/A D | 331 | | 14 | 97 |
| Bsnp10 | TGGTTTCAGTAACTTCTTC | t/A D; t/A D | 327 | | | 98 |
| Bsnp11 | GGAAGATTGGAAGTGATTG | c/A; c/A; a/A D | 195 | | 14 | 99 |
| Bsnp13 | TGGAAGTGATTGTTATTAT | a/A D; ta/A D | 188 | | | 100 |
| Bsnp14 | TTGCTTCTTGTTCTAGATGG | t/D; a/A D | 155 | | | 101 |
| Bsnp1rev | TTCCCAACTCCCATAGTGAAC | a/A D | | 290 | half 12 | 102 |
| Bsnp2rev | CAAATATGGTGACAGAAGTCG | tc/A D | | 322 | | 103 |
| Bsnp3rev | CACGTGTAAGAACAGATTG | a/A D; extra a in A; t/A D | | 356 | | 104 |
| Bsnp4rev | AGAATAGAATATTGACAC | g/A D; t/D; g/A D | | 371 | | 105 |
| Bsnp6rev | GTAAGAATCTTAATACCTGT | g/A D; g/A D | | 396 | | 106 |
| B snprev7 | CGCGTTTGACAGTAAGAATCTT | g/A D | | 405 | | 107 |
| Bsnp8rev | CCATCAAACTTATATTCA | a/A D | | 437 | | 108 |
| Bsnp9rev | CAATTGTTTCAGTGCCCTGAAG | t/A; t/A D; t/A D | | 539 | 12_13 | 109 |
| Bsnp10rev | GCAATTGTTTCAGTGCCCTG | t/A; t/A D | | 540 | | 110 |
| Bsnp11rev | CTTAGAAGAAAAAATAATAAC | c/D; ta/A D; a/A D | | 673 | 12_13 | 111 |
| Bsnp13rev | GCAAACTTAGAAGAAAAAA | t/D; c/D; a/A D | | 678 | | 112 |
| Bsnp14rev | CCATAGTTCCCAGTAAATGC | a/A D | | 713 | 12_13 | 113 |
| Bextra1rev | CTACTATTAAATTAACTG | ct extra/A, at extra/AD, taa extra/A, g/AD, actg extra/D | | 868 | 12_14 | 114 |
| Bsnp16 rev | ATCCCCAAAATAAAACTACTAT | c extra/A, tat extra/AB | | 880 | 12_14 | 115 |
| Bsnp17 rev | CAAAAGAGTAGTAACAGCT | ag extra/D, agt extra/A, a extra/D, t/D, g/AD | | 905 | 12_14 | 116 |
| Bsnp18 rev | CAAGGTATAAATTAGCATTC | c/AD | | 952 | 12_14 | 117 |
| Bsnp19 rev | GCATTCTTATGAAAAGAC | c/AD, c/AD | | 938 | 12_14 | 118 |

TABLE 8

Primers designed to amplify parts of the SBEIIa gene specifically from the D genome of wheat-- detected polymorphisms and fragment sizes

| Primer code | Primer sequence | SNP details | Arev5 | Drev 1 | Afor4 | SEQ ID NO: |
|---|---|---|---|---|---|---|
| D snp1for | TCTGTTCTTACACATGTT | c/A B | 489 | 798 | | 119 |
| D snp1for/A | CTTTTTTAGGGCACTGAAAC | c/B; c/B; t/A | 315 | 624 | | 120 |
| Dsnp2 for | GATTATTATTTATTTTCCTTCTAAGTTTGTg/B; at/B; t/AB; cAB | | 184 | 490 | | 121 |
| Dsnp2bfor | ACCTGATGAGATCATGGAAGATTG | c/A; c/A | 210 | 519 | | 122 |
| D snp 3 for | GTGATTATTATTTATTTTC | g/B; at/B; t/AB; cAB | 183 | 492 | | 123 |
| D snp 4 for | TTATTTTCCTTCTAAGTTTGT | at/B; t/AB; c/AB | 172 | 481 | | 124 |
| D snp5for | GTGATTATTATTTATTTTC | g/B; at/B; t/AB | 137 | 446 | | 125 |
| D snp6for | TGATGCGGTAGTTTACTTGATGT | g/B; a/B; c/AB | 89 | 398 | | 126 |
| D del1for | GATTTTTAACTAGTTAAGTAGTT | t/B; cagt/AB; a/AB; t/B; at/B; del in A | | 298 | | 127 |
| D snp7 for | GTTTTATTTTGGGGATCAGT | del g in A; a/B; g/AB | | 278 | | 128 |
| D snp1 rev | CCTGCATAAGAATAGAATATCA | t/A; a/B; c/AB | | | 379 | 129 |
| D snp1a rev | CATGTTATGATGCATAGCAATTG | t/A | | | 556 | 130 |
| D snp2 rev | GTAAATGTCATCTAGAACAAGAAA | g/B; c/AB | | | 701 | 131 |
| D snp3 rev | CAAGAAACAAACTTAGAAGG | c/AB; t/AB | | | 684 | 132 |
| D snp4 rev | ACAAACTTAGAAGGAAAATAA | c/AB; t/AB; at/B | | | 678 | 133 |
| D snp5 rev | CATCAGTAGCAAATCCAAAATAT | g/AB | | | 739 | 134 |

TABLE 9

Genome specific primers for wheat SBEIIb genes

| Genome | Primers | Expected Size (bp) |
|---|---|---|
| A | SbeIIb_A_deb1F/2R | 741 |
| A | SbeIIb_A_deb1F/4R | 1007 |
| A | SbeIIb_A_deb4F/4R | 772 |
| B | SbeIIb_B_deb3F/2R | 615 |
| B | SbeIIb_B_deb2F/3R | 929 |
| B | SbeIIb_B_deb3F/4R | 772 |
| D | SbeIIb_D_deb1F/1R | 1126 |
| D | SbeIIb_D_deb3F/3R | 827 |
| D | SbeIIb_D_deb4F/4R | 669 |

TABLE 10

Nucleotide sequences of genome specific primers of SBEIIb

| Primer name | Nucleotide Sequence (5' to 3') | SEQ ID NO: |
|---|---|---|
| SbeIIb_A_deb1F | ACCCCGTAATTATTGGCGCT | 135 |
| SbeIIb_A_deb4F | ACTCTGATGATCTGAAGGTAG | 136 |
| SbeIIb_A_deb2R | TCATGCAGGCAGGTACTAG | 137 |
| SbeIIb_A_deb4R | GTGGCAGAATGCGTAATTTCTCT | 138 |
| SbeIIb_B_deb2F | CAGCGATCTTACGTTCCCTA | 139 |
| SbeIIb_B_deb3F | ATGTCTGTAGGTGCCGTCA | 140 |
| SbeIIb_B_deb2R | CAACAAATTAGAAAGAGGATATTCC | 141 |
| SbeIIb_B_deb3R | CCGTAGATGATTCTTTGTCCATTA | 142 |
| SbeIIb_B_deb4R | ATGGAACCTAACACAATGTGC | 143 |
| SbeIIb_D_deb1F | GCGCCACCTTTCTCACTCA | 144 |
| SbeIIb_D_deb3F | CGGTCCCGTTCAGTTCGAT | 145 |
| SbeIIb_D_deb4F | CCTGAGTAAATACTGCCACCA | 146 |
| SbeIIb_D_deb1R | AGAATGCGTAATTTCTCCCTCG | 147 |
| SbeIIb_D_deb3R | TGTCTTCAGCATCAATTTCTTCAC | 148 |
| SbeIIb_D_deb4R | CTGTAGGCTTGTTTCATCATCA | 149 |

TABLE 11

SBEII expression vs Amylose content of RNAi lines of wheat

| selected line | Construct | Amylose % | SBEIIa expression relative to a WT (%) | SBEIIb expression relative to a WT (%) | Total SBEII expression (% of WT) |
|---|---|---|---|---|---|
| 673.2.1 | hp-combo | 35 | 108 | 91 | 100 |
| 679.5.3 | hp-combo | 40 | 81 | 1 | 41 |
| 670.1.4 | hp-combo | 45 | 35 | 10 | 23 |
| 672.2.3 | hp-combo | 50 | 16 | 1 | 9 |
| 671.2.2 | hp-combo | 55 | 8 | 5 | 7 |
| 666.2.2 | hp-combo | 60 | 10 | 6 | 8 |
| 669.1.2 | hp-combo | 65 | 9 | 7 | 8 |
| 684.2.3 | hpc-SBEIIa | 70 | 6 | 10 | 8 |
| 677.1.2 | hp-combo | 75 | 4 | 1 | 3 |
| 684.2.1 | hpc-SBEIIa | 80 | 3 | 5 | 4 |
| 694.3.3 | hpc-SBEIIa | 85 | 2 | 3 | 3 |

TABLE 12

List of microsatellite markers tested in the mutants

| Chromosome 2A | Chromosome 2B | Chromosome 2D |
|---|---|---|
| gwm 304 | barc 128 | gwm 539 |
| gwm 328 | gwm 129 | cfd 270 |
| barc 309 | wmc 265 | cfd 168 |
| cfa 2043 | wmc 272 | cfd 233 |
| cfa 2058 | gwm 388 | wmc 175 |
| wmc 170 | wmc 441 | wmc 181 |
| gwm 312 | barc 101 | wmc 041 |
| gwm 294 | gwm 120 | cfd 239 |
| wmc 181 | gwm 130 | gwm 349 |
| gwm 356 | gwm 526 | barc 219 |
| gwm 265 | gwm 501 | gwm 382 |
| wmc 181 | wmc 332 | wmc 167 |
| gwm 311 | wmc 434 | gwm 320 |
| gwm 382 | wmc 361 | gwm 301 |
| cfa 2086 | gwm 382 | cfd 50 |
|  | wmc 317 | barc 159 |
|  | wmc 445 |  |

TABLE 13

Mutants identified from HIB population and microsatellite mapping data

| Mutant type | Genome | Mutant number | Microsatellite mapping (markers retained/markers tested) |
|---|---|---|---|
| Type 1 | A | 20-257 (H7) | 15/15 |
|  |  | 19-119 (G3) | 5/11 |
|  |  | 12-178 | 10/10 |
|  |  | 5-563 | 10/10 |
|  |  | 21C-880D | 4/10 |
|  | B | 12-679 | 7/15 |
|  |  | 5-173 | 15/15 |
|  |  | 13-963 (F10) | 4/11 |
|  |  | 18c-109 | 8/8 |
|  |  | 3-159 | 3/8 |
|  | D | 19-832 (A6) | 13/13 |
|  |  | 22-578 (B5) | 13/13 |
|  |  | 3-909 (D1) | 7/13 |
|  |  | 19b-918 (C11) | To be done |
| Type 2 | A | 20b-5B2-608 (H2) | 10/10 |
|  |  | 19c-342 | 9/10 |
|  |  | 19-744 | 12/12 |
|  | B | 21-142 (F6), | 15/15 |
|  |  | 21-668 (D2-2) | 15/15 |
|  |  | 20-365 | 15/15 |
|  |  | 19-220 | 14/15 |
|  |  | 21b-4B2-345 (A8) | 11/11 |
|  |  | 20-141 | 9/11 |
|  | D | 12-801 | 13/13 |
|  |  | 5-706 | 13/13 |
|  |  | 19c-905 | To be done |
|  |  | 18b-505 | To be done |
| Type 3 | A | 18-111/3 (D2-1) | 8/11 |
|  |  | 19-861 (F9) | 8/11 |
|  |  | 20-791 (G10) | 12/12 |
|  | B | 19b-55 (G7) | 11/11 |
|  | D | 18-96 (E12) | 18/18 |
|  |  | 18b-120 (E3) | To be done |
|  |  | 18b-190 (C12) | To be done |

TABLE 14

Double null mutants of SBEII identified

| Cross designation | Parental lines (genotype of parent) | Genotype of double null | Number of double nulls identified |
|---|---|---|---|
| 08/a | 20-257 (A1) × 5-173 (B1) | A1B1 | 6 |
| 08/b | 20-257(A1) × 19-832 (D1) | A1D1 | 2 |
| 08/c | 19-832 (D1) × 5-173 (B1) | B1D1 | 0 |
| 08/d | 21-142 (B2) × 12-801 (D2) | B2D2 | 4 |
| 08/e | 21-142 (B2) × 5-706 (D2) | B2D2 | 8 |
| 08/f | 20-365 (B2) × 12-801(D2) | B2D2 | 4 |
| 08/g | 21-668 (B2) × 5-706 (D2) | B2D2 | 6 |
| 08/h | 20-257 (A1) × 21-142 (B2) | A1B2 | 2 |
| 08/i | 20-257 (A1) × 12-801 (D2) | A1D2 | 5 |
| 08/j | 18-111/3 (A3) × 18-96 (D3) | A3D3 | 2 |
| 08/k | 18-111/3 (A3) × 5-173 (B1) | A3B1 | 3 |
| 08/l | 18-96 (D3) × 5-173 (B1) | B1D3 | 1 |

TABLE 15

Crosses performed between double and single null mutants

| Cross designation | Parent 1 Code | P1 genotype | Parent 2 Code | P2 genotype | Potential F2 genotype |
|---|---|---|---|---|---|
| 08/aa | 5-173 | B1 | 08/b-18 | A1D1 | A1B1D1 |
| 08/aa-2 | 5-173 | B1 | 08/b-33 | A1D1 | A1B1D1 |
| 08/bb | 5-706 | D2 | 08/h-92 | A1B2 | A1B2 D2 |
| 08/dd | 5-706 | D2 | 08/h-111 | A1B2 | A1B2 D2 |
| 08/ee | 5-173 | B1 | 08/b-12 | A1D1 | A1B1D1 |
| 08/ff | 21-142 | B2 | 08/b-12 | A1D1 | A1B2D1 |
| 08/gg | 20-365 | B2 | 08/b-12 | A1D1 | A1B2D1 |

TABLE 16

Amylose content in grain starch of progeny from crosses between double null mutants and single null mutants

| Lines | Genotype | Amylose % |
|---|---|---|
| HIB mutant | F2 of triple null cross | 67.38 |
| Cadoux | WT | 35.4 |
| 85.2c | hp-SBEIIa | 74.99 |
| 008 (IIb knock out) | hp-SBEIIb | 36.1 |
| Chara | WT | 36.09 |

TABLE 17

Fertility observations on F2 progeny plants

| Line ID | Genotype | % fertile spikes | Number of seed per head |
|---|---|---|---|
| 08/dd S28 | A1D2(hetB2) | 41.9 | 17.0 |
| 08/dd S14 | A1B2(hetD2) | 75.3 | 26.3 |
| 08/dd S22 | A1D2(hetB2) | 56.5 | 19.0 |
| 08/dd S24 | B2D2(hetA2) | 61.1 | 16.0 |
| 08/dd-2 D7 | A1B2 | 84.2 | 37.3 |
| 08/dd-2 F1 | B2 | 93.2 | 50.7 |
| 08/dd-2 G7 | A1D2 | 92.6 | 49.7 |
| 08/dd-2 A1 | B2D2 | 91.5 | 44.3 |
| 08/dd-2 F4 | D2 | 84.4 | 45.7 |
| 08/dd-2 D5 | wt | 95.3 | 49.0 |

TABLE 20

Amylose content of SBEIIa triple null mutants

| Line | Cross/genotype | Amylose % (mean of 3 replicates ± SD) |
|---|---|---|
| CS3-A2 | 08/h-92 (A1B2) × 7_25 (D2) | 69.5 ± 3.1 |
| CS2_F11 | 08/i-G3 (A1D2) × 6_60 (B2) | 85.3 ± 1.7 |
| Sunstate | WT | 32.9 ± 0.3 |
| 85.2c (2102) | RNAi SBEIIa | 75.1 ± 1.8 |
| NB1 | Control (wild-type) | 32.8 ± 0.8 |
| 85.2c (2007) | RNAi SBEIIa | 72.9 ± 0.2 |
| 85.2c (2006) | RNAi SBEIIa | 72.2 ± 2.9 |
| 008 | RNAi SBEIIb | 33.4 ± 0.8 |

TABLE 18

SBEII allelic composition of mutants with multiple SBEIIa and SBEIIb null alleles

| Plant Genotype | Number of wild-type SBEIIa alleles present on A, B and D genomes | | | | | | Total number of wild-type SBEIIa alleles present | Number of wild-type SBEIIb alleles present on A, B and D genomes | | | | | | Total number of wild-type SBEIIb alleles present | Total number of wild-type SBEIIa and SBEIIb alleles present | Amylose content % |
|---|---|---|---|---|---|---|---|---|---|---|---|---|---|---|---|---|
| | A | A | B | B | D | D | | A | A | B | B | D | D | | | |
| A1(+/−)B2D2 | 1 | — | — | — | — | — | 1/6 | 1 | — | 1 | 1 | 1 | 1 | 5/6 | 6/12 | 67% (pooled) |
| A1B2D2(+/−) | — | — | — | — | 1 | — | 1/6 | — | — | 1 | 1 | 1 | 1 | 4/6 | 5/12 | 67% (pooled) |
| A1B2(+/−)D2 | — | — | 1 | — | — | — | 1/6 | — | — | 1 | 1 | 1 | 1 | 4/6 | 5/12 | 67% (pooled) |
| B2D2 | 1 | 1 | — | — | — | — | 2/6 | 1 | 1 | 1 | 1 | 1 | 1 | 6/6 | 8/12 | 33.0-36.8 |
| A1B2 | — | — | — | — | 1 | 1 | 2/6 | — | — | 1 | 1 | 1 | 1 | 4/6 | 6/12 | 33.9-34.9 |
| A1D2 | — | — | 1 | 1 | — | — | 2/6 | — | — | 1 | 1 | 1 | 1 | 4/6 | 6/12 | 32.2-37.0 |
| A1B1 | — | — | — | — | 1 | 1 | 2/6 | — | — | — | — | 1 | 1 | 2/6 | 4/12 | 34.1-34.7 |
| A1D1 | — | — | 1 | 1 | — | — | 2/6 | — | — | 1 | 1 | — | — | 2/6 | 4/12 | 32.8-38.7 |
| A3D3 | 1 | 1 | 1 | 1 | 1 | 1 | 6/6 | — | — | 1 | 1 | — | — | 2/6 | 8/12 | 30.8-31.6 |
| A3B1 | 1 | 1 | — | — | 1 | 1 | 4/6 | — | — | — | — | 1 | 1 | 2/6 | 6/12 | 31.4 |
| B1D3 | 1 | 1 | — | — | 1 | 1 | 4/6 | 1 | 1 | — | — | — | — | 2/6 | 6/12 | 30.3 |

TABLE 19

Summary of the SNP mutants identified from the azide-mutagenised population of wheat (cv. Sunstate)

| Mutant designation | Western banding pattern | | | | Mutations characterised | | |
|---|---|---|---|---|---|---|---|
| | Band 1 (D) | Band 2 (B) | Band 3 (A) | New band | Nucleotide polymorphism (exon affected; amino acid substitution) | Genome | Mutant designation |
| 4-85 | 1 | 1 | 0 | none | tbd | A | A2n |
| 7-25 | 0 | 1 | 1 | none | Exon 21; S772F in SEQ ID NO: 3 | D | D2p |
| 6-60 | 1 | 0 | 1 | none | G to A, first nucleotide of intron 6 of SBEIIa-B (splice site mutation) | B | B2n |
| 3-3 | 1 | 1 | 0/weak | none | tbd | A? | A2p |
| 1-55 | 1 | 1 | 0 | high affinity A | Exon 20; E734K in SEQ ID NO: 1 | A | A2p |
| 2-120 | 1 | 0 | 1 | low affinity B | Exon 18; G674D in SEQ ID NO: 2 | B | B2p |
| 9-94 | 1 | 0 | 1 | low affinity B | tbd | B? | B2p |
| 4-29 | 1 | 1 | 0 | 1 (low affinity) | Exon 11; S374N in SEQ ID NO: 1 | A | A2p |
| 9-36 | 1/0 | 1 | 1/0 | none | tbd | A/D? | ? |
| 3-70 | 0 | 1 | 1 | altered affinity | tbd | D? | Dp? |
| 16-11A | 1 | 0 | 1 | none | tbd | B | B2n |
| 15-3D | 0 | 1 | 1 | high affinity D | Exon 15; D536N in SEQ ID NO: 3 | D | D2p |
| 16-3C | 1 | 1 | 0 | none | tbd | A | A2n |
| 16-9C | 0 | 1 | 1 | low affinity D | Exon 17; T619I in SEQ ID NO: 3 | D | D2p |
| 13-9D | 0 | 1 | 1 | low affinity D | Exon 17; G641D in SEQ ID NO: 3 | D | D2p |
| 20-5A | 1 | 1 | 0 | none | tbd | A? | A2n |
| 22-9G | 1 | 0 | 1 | low affinity B | Exon 10; D335N in SEQ ID NO: 2 | B | B2p |
| 21-1C | 0 | 1 | 1 | none | tbd | D? | D2n | tbd: to be determined

TABLE 21

Amylose content of SBEIIa triple null mutants

| ID No. | Lines | Amylose % (mean of 3 replicates ± SD) |
|---|---|---|
| Sunstate | WT 1 | 32.92 ± 1.1 |
| CS2-E6 | 6-60 × 08/i-G3-E6 | 84.37 ± 3.8 |
| CS2-C6/4 | 6-60 × 08/i-G3-C6-4 | 83.89 ± 3.7 |
| CS1-G12/15 | 6-60 × 08b-18- G12-15 | 81.78 ± 2.6 |
| CS3-F9 (New) | 7-25 × 08/h-92-F9 | 70.25 ± 1.3 |
| CS3-F9 (old) | 7-25 × 08/h-92-F9 | 67.68 ± 3.1 |
| CS3-C3 | 7-25 × 08/h-92-C3 | 66.87 ± 1.4 |
| CS3-C10 | 7-25 × 08/h-92-C10 | 68.62 ± 0.7 |
| 85.2c | RNAi SBEIIa | 76.78 ± 3.1 |
| CS2-F11 | 6-60 × 08/i-G3-E6-F11 | 86.05 ± 3.2 |
| NB1 | WT-2 | 32.98 ± 1.0 |

TABLE 22

Amylose content of SBEIIa triple null mutants

| Line ID | Genotype | Mean amylose content (±sd) |
|---|---|---|
| CS1-G12/3 | A1B2 Double null | 53.6 ± 2.2 |
| CS10-C12 | A2B2D2 | 67.4 ± 1.9 |
| CS1-G12/21 | A1B2D1 | 74.0 ± 2.8 |
| CS1-G12/6 | A1 single null | 39.5 ± 3.4 |
| CS1-G12/10 | A1B2D1 | 82.9 ± 2.4 |
| CS2-F11 | A1B2nD2 | 84.2 ± 3.5 |
| CS1-G12/19 | A1B2D1 | 80.1 ± 1.4 |
| CS1-G12/4 | A1B2 Double null | 50.4 ± 1.9 |
| Sunstate | WT | 27.2 ± 1.0 |
| CS3-A2 | A1B2D2p | 65.8 ± 2.4 |
| CS3-C10 | A1B2D2p | 66.4 ± 0.9 |
| 85.2c | RNAi SBEIIa | 72.4 ± 3.5 |

TABLE 23

Preliminary agronomic data on the triple null SBEIIa plants

| Line ID (F2 plant/F3 seed) | Cross | Plant height (cm) | No of Spikes | Seed set/no. of spikelets | Av seed weight (of 5 seed) (mg) | Total seed no per plant | Total seed weight per plant (g) |
|---|---|---|---|---|---|---|---|
| CS3-C3 | MC7-25 (D2) × 08/h-92 (A1B2) | 93 | 3 | 32/34, 29/32, 24/26 | 42.8 | 101 | 3.86 |
| CS3-C10 | MC7-25 (D2) × 08/h-92 (A1B2) | 75 | 3 | 33/33 | 41.7 | 72 | 2.84 |
| CS3-F8-control | MC7-25 (D2) × 08/h-92 (A1B2) | 89 | 3 | 17/19, 20/22, 12/14 | 42.1 | 61 | 2.65 |
| CS3-F9 | MC7-25 (D2) × 08/h-92 (A1B2) | 78 | 5 | 26/28, 20/26, 16/18 | 40.5 | 105 | 3.43 |
| CS3-A2 | MC7-25 (D2) × 08/h-92 (A1B2) | 79 | 3 | 26/28, 24/26, 29/30 | 40.7 | 116 | 4.69 |
| CS2-F11 | MC6-60 × 08/i-G3 | 85 | 4 | 26/28, 19/21, 20/22 | 39.4 | 85 | 2.56 |
| CS2-B12 control | MC6-60 × 08/i-G3 | 82 | 4 | 32/34, 34/36, 32/32 | 44.6 | 139 | 6.20 |
| CS1-G12/15 | 08/b-18 (A1D1) × MC6-60 (B2) | 81 | 6 | 18/30, 20/28, 10/22 | 43.7 | 81 | 3.54 |
| CS1-G12/21 | 08/b-18 (A1D1) × MC6-60 (B2) | 71 | 3 | 5/18, 6/20, 3/16 | 40.2 | 16 | 0.64 |
| CS1-G12/10 | 08/b-18 (A1D1) × MC6-60 (B2) | 81 | 10 | 4/16, 2/18, 7/18 | 45.1 | 22 | 9.92 |
| CS1-G12/19 | 08/b-18 (A1D1) × MC6-60 (B2) | 60 | 4 | High sterility | — | 15 | — |
| CS2-E6 | MC6-60(B2) × 08/i-G3 (A1D2) | 63 | 9 | 18/24, 15/24, 7/24 | 46.5 | 117 | 5.44 |
| CS2-C6/4 | MC6-60(B2) × 08/i-G3 (A1D2) | 83 | 9 | 35/38, 32/34, 21/24 | 34.2 | 254 | 8.64 |

TABLE 24

Starch characterisation of grain starch from transgenic wheat lines

| Line ID | Enzyme targeted | Birefringence nil (%) | Birefringence partial (%) | Birefringence Full (%) | Amylose content estimated iodometrically (%) | Amylose content determined by SEC % | Starch content (% w/w) | Starch swelling power |
|---|---|---|---|---|---|---|---|---|
| NB1 | Non-transformed | 1.6 | 3.5 | 94.9 | 31.8 | 25.5 | 52.0 | 9.31 |
| SBEIIa- | SBEIIa | 94.5 | 4.0 | 1.5 | 88.5 | 74.4 | 43.4 | 3.51 |
| SBEIIb- | SBEIIb | 0.6 | 5.21 | 94.1 | 27.3 | 32.8 | 50.3 | 10.74 |
| LSD (5%) | | 9.02 | 3.3 | 9.9 | 7.7 | nd | 4.9 | |

TABLE 25

Molecular weight distribution of starch fractions from wheat transgenic lines

| Line | Estimated Molecular Weight (kDa) Amylopectin | High MW amylose | Low MW amylose |
|---|---|---|---|
| Wild-type (control) | 45523.3 ± 2605.3 | 420.4 ± 23.2 | 8.56 ± 0.2 |
| Reduced for SBEIIb | 43646.4 ± 5259.6 | 409.6 ± 7.8 | 8.76 ± 0.1 |
| Reduced for SBEIIa and SBEIIb | 7166.1 ± 166.5 | 422.7 ± 26.8 | 9.70 ± 0.1 |

TABLE 26

RVA parameters of hp5'-SBEIIa transgenic wheat starch

| Line ID | Construct | Peak 1 | First Trough | Breakdown | Final Viscosity | Setback | Peak Time | Pasting Temp (° C.) |
|---|---|---|---|---|---|---|---|---|
| Control | none | 225.08 | 180.83 | 44.25 | 318 | 137.17 | 10 | 85.3 |
| SBEIIa | hp5'-BEIIa | 27.08 | 17.5 | 9.58 | 22.92 | 5.42 | 12.73 | * |

* Starch from the reduced SBEIIa grain (line 85.2c) did not paste at the temperature profile used in the RVA run.

TABLE 27

DSC parameters of gelatinisation peak of hp5'-SBEIIa transgenic wheat starch compared to the control NB1

| Line ID | Construct | Onset ° C. | Peak ° C. | End ° C. | Delta H |
|---|---|---|---|---|---|
| NB1 | Control | 57.93 | 61.16 | 66.61 | 5.036 |
| 85.2c | hp5'-SBEIIa | 57.38 | 63.51 | 72.61 | 2.385 |

TABLE 28

RS content in rolled and flaked grain products

| Treatment No | Line | Roller width | Steaming time (Minute) | % RS (g/100 g product) |
|---|---|---|---|---|
| HWFP03 | HAW | Wide | 60 | 13.3 |
| HWFP05 | HAW | Wide | 45 | 14.1 |
| HWFP08 | HAW | Narrow | 35 | 13.7 |
| HWFP09 | HAW | Wide | 35 | 16.1 |
| HWFP11 | HAW | Narrow | 60 | 13.1 |
| HWFP12 | HAW | Narrow | 45 | 11.4 |
| HWFP01 | Hartog | Narrow | 60 | 0.6 |
| HWFP02 | Hartog | Wide | 60 | 0.6 |
| HWFP04 | Hartog | Wide | 45 | 0.5 |
| HWFP06 | Hartog | Narrow | 45 | 0.4 |
| HWFP07 | Hartog | Narrow | 35 | 0.1 |
| HWFP10 | Hartog | Wide | 35 | 0.2 |

TABLE 29

Resistant starch content in food products at varying level of incorporation of high amylose wheat (HAW)

| | Resistant Starch (g/100 g product) Incorporation level | | | | | | | | | | |
|---|---|---|---|---|---|---|---|---|---|---|---|
| | 0% | | 20% | | 40% | | 60% | | 80% | | 100% | |
| Type of product | control | HAW | Control | HAW | Control | HAW | Control | HAW | Control | HAW | Control | HAW |
| S & D bread | NT | NT | 0.45 | 1.33 | 0.40 | 2.1 | 0.30 | 2.9 | NT | NT | NT | NT |
| YAN | 0.4 | 0 | 0.2 | 0.7 | 0 | 1.1 | 0.2 | 1.2 | | | | |
| Spaghetti | | | 0.3 | 1.3 | 0.1 | 2 | 0 | 2.9 | 0.1 | 4 | 0 | 6 |
| Instant noodle | 0.4 | 0.4 | 0.3 | 0.8 | 0.2 | 1.4 | 0.2 | 1.6 | NT | NT | NT | NT |
| Loaf bread | NT | NT | 0.6 | 1.7 | NT | NT | 0.6 | 3.7 | NT | NT | 1 | 5.2 |
| Flakes | NT | NT | NT | NT | NT | NT | NT | NT | NT | NT | 0.2 | 16.1 |

NT: Not tested

TABLE 30

Genome-specific primers

| SbeIIa SeqId | Primer pair | Covered exons |
|---|---|---|
| IIaA2_3 | SbeIIa_A_deb2F/SbeIIa_A_deb5R | 2, 3 |
| IIaA6_7_8 | SbeIIa_A_deb4F/AR2aE8R07 | 6, 7, 8 |
| IIaA12_14 | Del5rev/Afor4 | 12, 14 |
| IIaB2_3 | SbeIIa_Bdeb7F/BeIIaE3r | 2, 3 |
| IIaB12_14 | BSNP17rev/Afor4 | 12, 14 |
| IIaB21_22 | Sbe2a_Bfin-F2/BeIIaE22r | 21, 22 |
| IIaD2_3 | SbeIIa_D_deb1F/SbeIIa_D_deb4R | 2, 3 |
| IIaD6_7_8 | SbeIIa_D_deb4F/AR2aE8R07 | 6, 7, 8 |
| IIaD12_14 | DSNP7rev/Afor4 | 12, 14 |
| IIaD18_20 | Sbe2a_Dfin-F1/Sbe2a_Dfin-R3 | 18, 20 |

TABLE 31

Selected point mutants from Arche and Apache populations

| Wheat variety | Mutant code | Number of homozygous plants | Total number of plants | Genome | Blosum 62 | Pam 250 | Exons |
|---|---|---|---|---|---|---|---|
| Arche | Arb_177-M2 | 1 | 2 | A | −3 | −3 | E12-14 |
| Apache | ApA_2442 | 2 | 5 | B | 0 | 1 | E12-14 |
| Apache | ApA_1092 | 1 | 10 | B | SM | SM | E12-14 |
| Apache | ApA_2071 | 1 | 5 | B | −2 | −3 | E2-3 |
| Apache | ApA_0613 | 1 | 5 | B | −2 | −3 | E2-3 |
| Apache | ApA_1512 | 3 | 10 | B | SM | SM | E21-22 |
| Apache | ApC_4527 | 1 | 5 | B | −1 | 1 | E21-22 |
| Apache | ApA-1000 | 3 | 12 | B | STOP | STOP | E12-14 |
| Arche | Arb_344-M2 | 1 | 3 | B | 1 | 1 | E21-22 |
| Apache | ApC_5372 | 2 | 5 | D | −1 | 1 | E12-14 |
| Apache | ApA_1205 | 2 | 5 | D | −2 | −3 | E12-14 |
| Apache | ApA_1482 | 3 | 10 | D | SM | SM | E12-14 |
| Apache | ApC_4483 | 1 | 4 | D | −2 | 0 | E18-20 |
| Apache | ApB_2719 | 2 | 10 | D | SM | SM | E2-3 |
| Apache | ApC_4058 | 2 | 9 | D | SM | SM | E2-3 |
| Apache | ApA_0958 | 2 | 3 | D | −2 | 0 | E2-3 |
| Apache | ApA-1878 | 16 | 44 | D | STOP | STOP | E12-14 |
| Arche | Ara-0255-M2 | 2 | 3 | D | 1 | 2 | E2-3 |
| Arche | Arb_147-M2 | 3 | 3 | D | −1 | 1 | E6-7-8 |

TABLE 32

Selected point mutant plants for crosses with double null (HIB deletions) mutants

| Original point mutant | Genome | Point mutant type | Exons | Selected homozygous mutant plant for crosses with double HIB mutants |
|---|---|---|---|---|
| Arb_177 | A | Altered protein sequence | E12-14 | Point 224 |
| ApA_1092 | B | Splice mutation | E12-14 | Point 78 |
| ApA_1512 | B | Splice mutation | E21-22 | Point 123, 125, 125 |
| ApA-1000 | B | Stop codon | E12-14 | Point 5, 7, 10 |
| ApA-1878 | D | Stop codon | E12-14 | Point 15, 17, 18, 19, 21, 22, 24, 33, 36, 37, 41, 42, 46, 50, 52, 65 |
| ApA_1482 | D | Splice mutation | E12-14 | Point 112, Point 115, Point 117 |
| ApB_2719 | D | Splice mutation | E2-3 | Point 173, Point 174 |
| ApC_4058 | D | Splice mutation | E2-3 | Point 177, Point 178 |

TABLE 33

F1 seed production from crosses between single SBEIIa point mutants and double null (deletion) mutants

| HIB mutant ID code | HIB SBEIIa double mutant status | Point mutant ID code | Point mutant type | Cultivar | F1 seeds |
|---|---|---|---|---|---|
| 430 | A1 | D2 | Point 5 | Stop codon - B genome | Apache | 25 |
| 431 | A1 | D2 | Point 5 |  |  | 22 |
| 445 | A1 | D2 | Point 5 |  |  | 24 |
| 422 | A1 | D2 | Point 7 |  |  | 29 |
| 73 | A1 | D2 | Point 10 |  |  | 23 |
| 420 | A1 | D2 | Point 10 |  |  | 26 |
| 443 | A1 | D2 | Point 10 |  |  | 28 |
| 420 | A1 | D2 | Point 123 | Splice site mutation - B genome | Apache | 33 |
| 435 | A1 | D2 | Point 123 |  |  | 11 |
| 438 | A1 | D2 | Point 123 |  |  | 29 |
| 73 | A1 | D2 | Point 123 |  |  | 18 |
| 38 | A2 | D2 | Point 5 | Stop codon - B genome | Apache | 13 |
| 448 | A2 | D2 | Point 5 |  |  | 11 |
| 39 | A2 | D2 | Point 7 |  |  | 29 |
| 413 | A1 | B2 | Point 15 | Stop codon - D genome | Apache | 30 |
| 412 | A1 | B2 | Point 19 |  |  | 22 |
| 380 | A1 | B2 | Point 21 |  |  | 24 |
| 368 | A1 | B2 | Point 22 |  |  | 28 |
| 405 | A1 | B2 | Point 22 |  |  | 18 |
| 412 | A1 | B2 | Point 22 |  |  | 13 |
| 374 | A1 | B2 | Point 33 |  |  | 30 |
| 368 | A1 | B2 | Point 36 |  |  | 18 |
| 410 | A1 | B2 | Point 36 |  |  | 12 |

TABLE 33-continued

F1 seed production from crosses between single SBEIIa point mutants and double null (deletion) mutants

| HIB mutant ID code | HIB SBEIIa double mutant status | | Point mutant ID code | Point mutant type | Cultivar | F1 seeds |
|---|---|---|---|---|---|---|
| 409 | A1 | B2 | Point 37 | | | 7 |
| 380 | A1 | B2 | Point 37 | | | 13 |
| 154 | A1 | B1 | Point 41 | | | 24 |
| 367 | A1 | B2 | Point 41 | | | 19 |
| 367 | A1 | B2 | Point 42 | | | 33 |
| 397 | A1 | B2 | Point 42 | | | 19 |
| 405 | A1 | B2 | Point 56 | | | 21 |
| 396 | A1 | B2 | Point 112 | Splice site mutation - D genome | Apache | 24 |
| 405 | A1 | B2 | Point 112 | | | 24 |
| 412 | A1 | B2 | Point 115 | | | 25 |
| 459 | B2 | D2 | Point 224 | Altered protein sequence - A genome | Arche | 2 |
| 790 | A1 | D2 | 797 | Altered protein - B genome | Sunstate | 39 |
| 38 | A2 | D2 | 797 | | | 25 |
| 422 | A1 | D2 | 797 | | | 4 |
| 412 | A1 | B2 | 798 | Altered protein - D genome | | 15 |
| 791 | A1 | B2 | 798 | | | 26 |
| 792 | A1 | B2 | 798 | | | 11 |
| 793 | A1 | B2 | 798 | | | 64 |

TABLE 34

NIRS screening of F2 seeds from crosses between single SBEIIa point mutants and double null (HIB deletions) mutants

| Cross code | Original Point mutant code | Point mutant type | Point mutant Code | HIB mutant code | HIB mutant status | | Weight (g) | Number of seeds | No of HAW seeds |
|---|---|---|---|---|---|---|---|---|---|
| BD70 | MC6-60 | Altered protein B genome | 797 | 38 | A1 | D2 | 31 | 712 | 28 |
| BD71 | | | | 422 | A1 | D2 | 17 | 337 | 14 |
| BD73 | | | | 790 | A1 | D2 | 42 | 1104 | 83 |
| BD72 | MC7-25 | Altered protein D genome | 798 | 412 | A1 | B2 | 45 | 1016 | 44 |
| BD74 | | | | 791 | A1 | B2 | 39 | 2204 | 34 |
| BD75 | | | | 792 | A1 | B2 | 41 | 1023 | 13 |
| BD76 | | | | 793 | A1 | B2 | 35 | 859 | 36 |
| BD77 | APA-1000 | Stop codon B genome | TIL 5 | 38 | A2 | D2 | 47 | 1348 | 89 |
| BD78 | | | | 430 | A1 | D2 | 51 | 1543 | 79 |
| BD80 | | | | 445 | A1 | D2 | 38 | 1052 | 54 |
| BD81 | | | | 448 | A2 | D2 | 40 | 1194 | 67 |
| BD82 | | | TIL 7 | 39 | A2 | D2 | 53 | 1684 | 105 |
| BD83 | | | | 422 | A1 | D2 | 52 | 1689 | 69 |
| BD84 | | | TIL 10 | 73 | A1 | D2 | 56 | 1681 | 60 |
| BD85 | | | | 420 | A1 | D2 | 58 | 1947 | 140 |
| BD86 | | | | 443 | A1 | D2 | 59 | 1936 | 161 |
| BD87 | APA_1512 | Splice site mutation - B genome | TIL 123 | 420 | A1 | D2 | 62 | 1993 | 136 |
| BD88 | | | | 435 | A1 | D2 | 37 | 1142 | 62 |
| BD89 | | | | 438 | A1 | D2 | 67 | 2125 | 114 |
| BD90 | | | | 73 | A1 | D2 | 52 | 1727 | 97 |
| BD91 | APA-1878 | Stop codon - D genome | TIL 15 | 413 | A1 | B2 | 61 | 2092 | 128 |
| BD92 | | | TIL 19 | 412 | A1 | B2 | 30 | 1064 | 47 |
| BD93 | | | TIL 21 | 380 | A1 | B2 | 34 | 1129 | 44 |
| BD94 | | | TIL 22 | 368 | A1 | B2 | 36 | 1241 | 35 |
| BD95 | | | | 405 | A1 | B2 | 40 | 1259 | 50 |
| BD96 | | | | 412 | A1 | B2 | 36 | 1017 | 43 |
| BD97 | | | TIL 33 | 374 | A1 | B2 | 35 | 493 | 31 |
| BD98 | | | TIL 36 | 368 | A1 | B2 | 42 | 1406 | 16 |
| BD99 | | | | 410 | A1 | B2 | 54 | 1662 | 102 |
| BD100 | | | TIL 37 | 409 | A1 | B2 | 16 | 493 | 13 |
| BD101 | | | | 380 | A1 | B2 | 44 | 1434 | 52 |
| BD102 | | | TIL 41 | 154 | A1 | B1 | 33 | 967 | 46 |
| BD104 | | | TIL 42 | 367 | A1 | B2 | 50 | 1577 | 57 |
| BD105 | | | | 397 | A1 | B2 | 29 | 921 | 37 |
| BD106 | | | TIL 56 | 405 | A1 | B2 | 35 | 1120 | 41 |
| BD107 | APA_1482 | Splice site mutation - D genome | TIL 112 | 396 | A1 | B2 | 30 | 946 | 17 |
| BD108 | | | | 405 | A1 | B2 | 39 | 1242 | 29 |
| BD109 | | | TIL 115 | 412 | A1 | B2 | 37 | 865 | 20 |

TABLE 34-continued

NIRS screening of F2 seeds from crosses between single SBEIIa point mutants and double null (HIB deletions) mutants

| Cross code | Original Point mutant code | Point mutant type | Point mutant Code | HIB mutant code | HIB mutant status | Weight (g) | Number of seeds | No of HAW seeds |
|---|---|---|---|---|---|---|---|---|
| BD111 | Arb_177 | Altered protein sequence - A genome | TIL 224 | 459 | B2 D2 | 1 | 30 | 0 |
| TOTAL | | | | | | | 49856 | 2296 |

TABLE 35

Amylose levels and thousand kernel weight (TKW) for HAW SBEIIa triple null grain compared to control grain and RNAi reference line 85.2c

| Lines | TKW | Amylose % increase compared to control line |
|---|---|---|
| Ctrl1 | 55 | |
| Ctrl2 | 52 | |
| GM 85.2c | — | 58 |
| HAW12-090 | 49 | 158 |
| HAW12-057 | 50 | 155 |
| HAW12-081 | 50 | 110 |
| HAW12-034 | 41 | 147 |
| HAW12-050 | 42 | 150 |
| HAW12-044 | 47 | 151 |
| HAW12-046 | 46 | 138 |
| HAW12-014 | 53 | 48 |
| HAW12-003 | 52 | 31 |

BIBLIOGRAPHY

Abel et al., *The Plant Journal* 10: 981-991, 1996
Altschul et al., *Nucl. Acids Res.* 25:3389, 1997
Alvarez et al., *Plant Cell* 18: 1134-1151, 2006
Ausubel et al., "Current Protocols in Molecular Biology", John Wiley & Sons Inc, Chapter 15, 1994-1998
Baga et al., *Plant Mol Biol.* 40(6): 1019-1030, 1999
Batey and Curtin, *Starch* 48: 338-344, 1996
Batey et al., *Cereal Chemistry* 74: 497-501, 1997
Bechtold et al., *C.R. Acad. Sci. Paris*, 316:1194, 1993
Bekes et al., *Crit Care Med.* 30(8): 1906-1907, 2002
Blauth et al., *Plant Physiology* 125: 1396-1405, 2001
Botticella et al., *BMC Plant Biology* 11: 156, 2011
Boyer and Preiss, *Carbohydrate Research*, 61: 321-334, 1978
Boyer and Preiss, *Plant Physiology* 67: 1141-1145, 1981
Boyer et al., *Starch* 32: 217-222, 1980
Cao et al., *Archives of Biochemistry and Biophysics*, 373: 135-146, 2000
Case et al., *Journal of Cereal Science* 27: 301-314, 1998
Cheng et al., *Plant Physiol* 115: 971-980, 1997
Comai et al., *Plant J.* 37: 778-786, 2004
Craig et al., *Plant Cell* 10: 413-426, 1998
Delwiche et al. *Cereal Chem.* 83(3):287-292, 2006
Dowell et al *Cereal Chem.* 86(3):251-255, 2009
Durai et al., *Nuclieic Acids Research* 33(18): 5978-5990, 2005
Eagles et al., *Aust. J. Agric. Res.* 52: 1349-1356, 2001
Fergason, *Speciality Corns eds, CRC Press Inc.* pp 55-77, 1994
Fisher et al., *Plant Physiol* 102: 1045-1046, 1993
Fisher et al., *Journal Plant Physiol.* 108(3): 1313-1314, 1995
Fuwa et al., *Starch-Stärke* 51: 147-151, 1999
Gao et al., *Plant Cell*, 10: 399-412, 1998
Gao et al., *Plant Physiol* 114: 69-78, 1997
Goddard et al., *Am J Clin Nutr* 39: 388-392, 1984
Gras et al., In: *Proc. ICC 11th Int. Cereal and Bread Congress.* RACI: Melbourne, 2001b
Green et al., *Plant Physiol* 114: 203-212, 1997
Harayama, *Trends Biotechnol.* 16: 76-82, 1998
Hartmann and Endres, *Manual of Antisense Methodology*, Kluwer, 1999
Hayashi et al., *Effects of ion beam irradiation on mutation induction in rice. Cyclotrons and Their Applications* 2007, Eighteenth International Conference 237-239, 2007
Hedman and Boyer, *Biochemical Genetics* 20: 483-492, 1982
Henikoff et al., *Plant Physiol.* 135: 630-636, 2004
Hinchee et al., *Biotech.*, 6: 915, 1988
James et al., *Plant Cell*, 7: 417-429, 1995
Jobling et al., *Plant Journal* 18: 163-171, 1999
Kanna and Daggard, *Plant Cell Rep* 21: 429-436, 2003
Kawasaki et al., *Mol Gen Genet.* 237(1-2): 10-6, 1993
Kazama et al., *Plant Biotechnology* 25: 113-117, 2008
Kim et al., *Plant Physiol.* 121(1): 225-236, 1999
Kim et al., *Gene.* 216(2): 233-43, 1998a
Klein et al., *Nature* 327: 70, 1987
Konik-Rose et al., *Starch-Stärke*, 53: 14-20, 2001
Krueger et al., *Cereal Chemistry* 64: 187-190, 1987
Kubo et al., *Plant Physiology*, 121: 399-409, 1999
Langridge et al., *Aust. J. Agric. Res.* 52: 1043-1077, 2001
Lazo et al., *Biotechnology* (N Y). 9(10): 963-967, 1991
Le Provost et al., *Trends in Biotechnology* 28(3): 134-141, 2009
Li et al., *Plant Physiology*, 120: 1147-1155, 1999a
Li et al., *Theoretical and Applied Genetics*, 98: 1208-1216, 1999b
Li et al., *Plant Physiology*, 123: 613-624, 2000
Liu et al., *Biotechnology and Bioengineering*, 106: 97-105, 2010
Mann et al., In 'Workshop on gluten proteins' Eds. Lafiandra et al., The Royal Society of Chemistry: Cambridge, UK, pp. 215-218, 2003
Mann, New crop phenomenon in wheat and the mechanisms involved, PhD thesis, University of Reading, UK, 2002
McCallum et al., *Nat Biotechnol* 18:455-457, 2000
McClure, *J. Near Infrared Spectrosc.* 11, 487-518, 2003
McCreery and Helentjaris, *Methods in Molecular Biology, Vol. 28: Protocols for nucleic acid analysis by non-radioactive probes*, Humana Press Inc., Totawa, N.J., pp 67-71, 1994
Mizuno et al., *Journal of Biological Chemistry* 268: 19084-19091, 1993
Morell et al., *Electrophoresis* 19: 2603-2611, 1998
Morell et al., *Plant J.* 34: 173-185, 2003
Morell et al., *Plant Physiol* 113: 201-208, 1997
Morrison and Laignelet, *J Cereal Sci*, 1: 9-20, 1983
Moullet et al., *Theor Appl Genet* 99: 305-313, 1999

Myers et al., *Plant Physiology*, 122: 989-997, 2000
Nair et al., *Plant Sci* 122: 153-163, 1997
Nakamura, *Plant Cell Physiology* 43: 718-725, 2002
Needleman and Wunsch, *J. Mol. Biol.* 48: 443-453, 1970
Niedz et al., *Plant Cell Reports*, 14: 403, 1995
Nishi et al., *Plant Physiology* 127: 459-472, 2001
Ow et al., *Science*, 234: 856, 1986
Palatnik et al., *Nature* 425: 257-263, 2003
Parizotto et al., *Genes Dev* 18: 2237-2242, 2004
Potrykus et al., *Mol. Gen. Genet.*, 199: 183, 1985
Prasher et al., *Biochem. Biophys. Res. Comm.* 126: 1259-68, 1985
Rahman et al., *Genome* 40: 465-474, 1997
Rahman et al., *Theor. Appl. Genet.* 98: 156-163, 1999
Rahman et al., *Aust. J. Plant Physiol.* 22: 793-803, 1995
Rahman et al., *Plant Physiol* 125: 1314-1324, 2001
Regina et al., *J Exp Bot.* 61(5): 1469-1482, 2010
Regina et al., *Funct Plant Biol*, 31: 591-601, 2004
Regina et al., *Planta* 222: 899-909, 2005
Regina et al., *Proc Natl Acad Sci USA*, 103: 3546-3551, 2006
Repellin et al., *Plant Gene Reg pp.* 97-094, 1997
Safford et al., *Carbohydrate Polymers* 35: 155-168, 1998
Schulman and Kammiovirta, *Starch* 43: 387-389, 1991
Schwab et al., *Plant Cell* 18: 1121-1133, 2006
Schwall et al., *Nature Biotachnology* 18: 551-554, 2000
Sestili et al., *Mol Breeding* 25:145-154, 2010
Sharp et al., *Aust J Agric Res* 52: 1357-1366, 2001
Shure et al., *Cell* 35: 225-233, 1983
Sidebottom et al., *Journal of Cereal Science* 27: 279-287, 1998
Sissons et al., *Journal of the Science of Food and Agriculture* 87: 1874-1885, 2007
Slade and Knauf, *Transgenic Res.* 14: 109-115, 2005
Smewing, The measurement of dough and gluten extensibility using the SMS/Kieffer rig and the TA.TX2 texture analyzer handbook, SMS Ltd: Surrey, UK, 1995
Smith et al., *Nature*, 407: 319-320, 2000
Sparks and Jones in *Transgenic Crops of the World—Essential protocols*, Ed. I P Curtis, Kluwer Academic Publishers, Dordrecht, Netherlands, pp 19-34, 2004
Stacey and Isaac, *Methods in Molecular Biology, Vol. 28: Protocols for nucleic acid analysis by non-radioactive probes*, Humana Press Inc., Totawa, N.J., pp 9-15, 1994
Stalker et al., *Science*, 242: 419, 1988
Sun et al., *Plant Physiol* 118: 37-49, 1998
Takeda et al., *Carbohydrate Research* 240: 253-262, 1993a
Takeda et al., *Carbohydrate Research* 246: 273-281, 1993b
Tanaka et al., *Nucl. Acids Res.* 18: 6767-6770, 1990
Tetlow et al., *Plant Cell* 16: 694-708, 2004
Tetlow et al., *Plant Physiol* 146: 1878-1891, 2008
Thillet et al., *J. Biol. Chem.*, 263: 12500, 1988
Vogel et al., *Fermentation and Biochemical Engineering Handbook: Principles, Process Design, and Equipment*, Noyes Publications, Park Ridge, N.J., USA, 1996
Waterhouse et al., *Proc. Natl. Acad. Sci. U.S.A.* 95: 13959-13964, 1998
Weir et al., *Aust J Plant Physiol* 28: 807-818, 2001
Wu et al., *Plant Cell Rep* 21: 659-668, 2003
Yamamori et al., *Theor Appl Genet*, 101: 21-29, 2000
Nakamura and Yamanouchi, *Plant Physiol.* 99(3): 1265-1266, 1992
Yu et al., *Science* 307: 932-935, 2005
Zwar and Chandler, *Planta* 197: 39-48, 1995

The claims defining the invention are as follows:

1. A process for producing a milled product, comprising the steps of
   (i) obtaining wheat grain (*Triticum aestivum*) comprising an embryo and starch, wherein the embryo comprises two identical null alleles of an SBEIIa-A gene, two identical null alleles of an SBEIIa-B gene and two identical null alleles of an SBEIIa-D gene, wherein either the two identical null alleles of the SBEIIa-A gene, or of the SBEIIa-B gene or of the SBEIIa-D gene are point mutations, wherein SBEIIa protein is undetectable in the wheat grain, and wherein
   (a) the starch comprises amylose such that the grain has an amylase content of between 50% and 90% (w/w) as a proportion of the extractable starch of the grain; and
   (b) the wheat grain has a germination rate of about 70% to about 100% relative to the germination rate of a wild-type wheat grain, and
   (ii) milling the grain, thereby producing the milled product.

2. The process of claim 1, wherein the starch of the wheat grain has an amylose content of at least 67% (w/w) as a proportion of the extractable starch of the grain.

3. The process of claim 1, wherein the wheat grain is free of any exogenous nucleic acid that encodes an RNA which reduces expression of an SBEIIa gene.

* * * * *

SEQUENCE LISTING

```
<160> NUMBER OF SEQ ID NOS: 168

<210> SEQ ID NO 1
<211> LENGTH: 823
<212> TYPE: PRT
<213> ORGANISM: Triticum aestivum

<400> SEQUENCE: 1

Met Ala Thr Phe Ala Val Ser Gly Ala Thr Leu Gly Val Ala Arg Pro
1               5                   10                  15

Ala Gly Ala Gly Gly Leu Leu Pro Arg Ser Gly Ser Glu Arg Arg
            20                  25                  30

Gly Gly Val Asp Leu Pro Ser Leu Leu Arg Lys Lys Asp Ser Ser
        35                  40                  45

Arg Ala Val Leu Ser Arg Ala Ala Ser Pro Gly Lys Val Leu Val Pro
    50                  55                  60

Asp Gly Glu Ser Asp Asp Leu Ala Ser Pro Ala Gln Pro Glu Glu Leu
65                  70                  75                  80

Gln Ile Pro Glu Asp Ile Glu Glu Gln Thr Ala Glu Val Asn Met Thr
                85                  90                  95

Gly Gly Thr Ala Glu Lys Leu Glu Ser Ser Glu Pro Thr Gln Gly Ile
            100                 105                 110

Val Glu Thr Ile Thr Asp Gly Val Thr Lys Gly Val Lys Glu Leu Val
        115                 120                 125

Val Gly Glu Lys Pro Arg Val Val Pro Lys Pro Gly Asp Gly Gln Lys
    130                 135                 140

Ile Tyr Glu Ile Asp Pro Thr Leu Lys Asp Phe Arg Ser His Leu Asp
```

```
            145                 150                 155                 160
Tyr Arg Tyr Ser Glu Tyr Arg Ile Arg Ala Ala Ile Asp Gln His
                165                 170                 175
Glu Gly Gly Leu Glu Ala Phe Ser Arg Gly Tyr Glu Lys Leu Gly Phe
            180                 185                 190
Thr Arg Ser Ala Glu Gly Ile Thr Tyr Arg Glu Trp Ala Pro Gly Ala
                195                 200                 205
His Ser Ala Ala Leu Val Gly Asp Phe Asn Asn Trp Asn Pro Asn Ala
            210                 215                 220
Asp Thr Met Thr Arg Asp Asp Tyr Gly Val Trp Glu Ile Phe Leu Pro
225                 230                 235                 240
Asn Asn Ala Asp Gly Ser Pro Ala Ile Pro His Gly Ser Arg Val Lys
                245                 250                 255
Ile Arg Met Asp Thr Pro Ser Gly Val Lys Asp Ser Ile Ser Ala Trp
                260                 265                 270
Ile Lys Phe Ser Val Gln Ala Pro Gly Glu Ile Pro Phe Asn Gly Ile
            275                 280                 285
Tyr Tyr Asp Pro Pro Glu Glu Glu Lys Tyr Val Phe Gln His Pro Gln
            290                 295                 300
Pro Lys Arg Pro Glu Ser Leu Arg Ile Tyr Glu Ser His Ile Gly Met
305                 310                 315                 320
Ser Ser Pro Glu Pro Lys Ile Asn Ser Tyr Ala Asn Phe Arg Asp Glu
                325                 330                 335
Val Leu Pro Arg Ile Lys Arg Leu Gly Tyr Asn Ala Val Gln Ile Met
                340                 345                 350
Ala Ile Gln Glu His Ser Tyr Tyr Ala Ser Phe Gly Tyr His Val Thr
            355                 360                 365
Asn Phe Phe Ala Pro Ser Ser Arg Phe Gly Thr Pro Glu Asp Leu Lys
            370                 375                 380
Ser Leu Ile Asp Arg Ala His Glu Leu Gly Leu Leu Val Leu Met Asp
385                 390                 395                 400
Ile Val His Ser His Ser Ser Asn Asn Thr Leu Asp Gly Leu Asn Gly
                405                 410                 415
Phe Asp Gly Thr Asp Thr His Tyr Phe His Gly Gly Pro Arg Gly His
            420                 425                 430
His Trp Met Trp Asp Ser Arg Leu Phe Asn Tyr Gly Ser Trp Glu Val
            435                 440                 445
Leu Arg Phe Leu Leu Ser Asn Ala Arg Trp Trp Leu Glu Glu Tyr Lys
            450                 455                 460
Phe Asp Gly Phe Arg Phe Asp Gly Val Thr Ser Met Met Tyr Thr His
465                 470                 475                 480
His Gly Leu Gln Met Thr Phe Thr Gly Asn Tyr Gly Glu Tyr Phe Gly
                485                 490                 495
Phe Ala Thr Asp Val Asp Ala Val Val Tyr Leu Met Leu Val Asn Asp
                500                 505                 510
Leu Ile His Gly Leu His Pro Asp Ala Val Ser Ile Gly Glu Asp Val
            515                 520                 525
Ser Gly Met Pro Thr Phe Cys Ile Pro Val Pro Asp Gly Gly Val Gly
            530                 535                 540
Leu Asp Tyr Arg Leu His Met Ala Val Ala Asp Lys Trp Ile Glu Leu
545                 550                 555                 560
Leu Lys Gln Ser Asp Glu Ser Trp Lys Met Gly Asp Ile Val His Thr
                565                 570                 575
```

Leu Thr Asn Arg Arg Trp Leu Glu Lys Cys Val Thr Tyr Ala Glu Ser
            580                 585                 590

His Asp Gln Ala Leu Val Gly Asp Lys Thr Ile Ala Phe Trp Leu Met
        595                 600                 605

Asp Lys Asp Met Tyr Asp Phe Met Ala Leu Asp Arg Pro Ser Thr Pro
    610                 615                 620

Arg Ile Asp Arg Gly Ile Ala Leu His Lys Met Ile Arg Leu Val Thr
625                 630                 635                 640

Met Gly Leu Gly Gly Glu Gly Tyr Leu Asn Phe Met Gly Asn Glu Phe
                645                 650                 655

Gly His Pro Glu Trp Ile Asp Phe Pro Arg Gly Pro Gln Thr Leu Pro
            660                 665                 670

Thr Gly Lys Val Leu Pro Gly Asn Asn Asn Ser Tyr Asp Lys Cys Arg
        675                 680                 685

Arg Arg Phe Asp Leu Gly Asp Ala Asp Phe Leu Arg Tyr His Gly Met
    690                 695                 700

Gln Glu Phe Asp Gln Ala Met Gln His Leu Glu Glu Lys Tyr Gly Phe
705                 710                 715                 720

Met Thr Ser Glu His Gln Tyr Val Ser Arg Lys His Glu Glu Asp Lys
                725                 730                 735

Val Ile Ile Phe Glu Arg Gly Asp Leu Val Phe Val Phe Asn Phe His
            740                 745                 750

Trp Ser Asn Ser Phe Phe Asp Tyr Arg Val Gly Cys Ser Arg Pro Gly
        755                 760                 765

Lys Tyr Lys Val Ala Leu Asp Ser Asp Ala Leu Phe Gly Gly Phe
    770                 775                 780

Ser Arg Leu Asp His Asp Val Asp Tyr Phe Thr Thr Glu His Pro His
785                 790                 795                 800

Asp Asn Arg Pro Arg Ser Phe Ser Val Tyr Thr Pro Ser Arg Thr Ala
                805                 810                 815

Val Val Tyr Ala Leu Thr Glu
            820

<210> SEQ ID NO 2
<211> LENGTH: 823
<212> TYPE: PRT
<213> ORGANISM: Triticum aestivum

<400> SEQUENCE: 2

Met Ala Thr Phe Ala Val Ser Gly Ala Thr Leu Gly Val Ala Arg Pro
1               5                   10                  15

Ala Ser Ala Gly Gly Gly Leu Leu Arg Ser Gly Ser Glu Arg Arg Gly
            20                  25                  30

Gly Val Asp Leu Pro Ser Leu Leu Arg Lys Lys Asp Ser Ser Arg
        35                  40                  45

Ala Val Leu Ser Arg Ala Ala Ser Pro Gly Lys Val Leu Val Pro Asp
    50                  55                  60

Gly Glu Ser Asp Asp Leu Ala Ala Thr Pro Ala Gln Pro Glu Glu Leu
65                  70                  75                  80

Gln Ile Pro Glu Asp Ile Glu Glu Gln Thr Ala Glu Val Asn Met Thr
                85                  90                  95

Gly Gly Thr Ala Glu Lys Leu Gln Tyr Ser Glu Pro Thr Gln Gly Ile
            100                 105                 110

Val Glu Thr Ile Thr Asp Gly Val Thr Lys Gly Val Lys Glu Leu Val

```
            115                 120                 125
Val Gly Glu Lys Pro Arg Val Pro Lys Pro Gly Asp Gly Gln Lys
    130                 135                 140

Ile Tyr Glu Ile Asp Pro Thr Leu Lys Asp Phe Arg Ser His Leu Asp
145                 150                 155                 160

Tyr Arg Tyr Ser Glu Tyr Lys Arg Ile Arg Ala Ala Ile Asp Gln His
                    165                 170                 175

Glu Gly Gly Leu Glu Ala Phe Ser Arg Gly Tyr Glu Lys Leu Gly Phe
                180                 185                 190

Thr Arg Ser Ala Glu Gly Ile Thr Tyr Arg Glu Trp Ala Pro Gly Ala
            195                 200                 205

His Ser Ala Ala Leu Val Gly Asp Phe Asn Asn Trp Asn Pro Asn Ala
        210                 215                 220

Asp Thr Met Thr Arg Asp Asp Tyr Gly Val Trp Glu Ile Phe Leu Pro
225                 230                 235                 240

Asn Asn Ala Asp Gly Ser Pro Ala Ile Pro His Gly Ser Arg Val Lys
                245                 250                 255

Ile Arg Met Asp Thr Pro Ser Gly Val Lys Asp Ser Ile Ser Ala Trp
                260                 265                 270

Ile Lys Phe Ser Val Gln Ala Pro Gly Glu Ile Pro Phe Asn Gly Ile
            275                 280                 285

Tyr Tyr Asp Pro Pro Glu Glu Glu Lys Tyr Val Phe Gln His Pro Gln
        290                 295                 300

Pro Lys Arg Pro Glu Ser Leu Arg Ile Tyr Glu Ser His Ile Gly Met
305                 310                 315                 320

Ser Ser Pro Glu Pro Lys Ile Asn Ser Tyr Ala Asn Phe Arg Asp Gly
                325                 330                 335

Val Leu Pro Arg Ile Lys Arg Leu Gly Tyr Asn Ala Val Gln Ile Met
                340                 345                 350

Ala Ile Gln Glu His Ser Tyr Tyr Ala Ser Phe Gly Tyr His Val Thr
            355                 360                 365

Asn Phe Phe Ala Pro Ser Ser Arg Phe Gly Thr Pro Glu Asp Leu Lys
        370                 375                 380

Ser Leu Ile Asp Arg Ala His Glu Leu Gly Leu Leu Val Leu Met Asp
385                 390                 395                 400

Ile Val His Ser His Ser Ser Asn Asn Thr Leu Asp Gly Leu Asn Gly
                405                 410                 415

Phe Asp Gly Thr Asp Thr His Tyr Phe His Gly Gly Pro Arg Gly His
                420                 425                 430

His Trp Met Trp Asp Ser Arg Leu Phe Asn Tyr Gly Ser Trp Glu Val
            435                 440                 445

Leu Arg Phe Leu Leu Ser Asn Ala Arg Trp Trp Leu Glu Glu Tyr Lys
        450                 455                 460

Phe Asp Gly Phe Arg Phe Asp Gly Val Thr Ser Met Met Tyr Thr His
465                 470                 475                 480

His Gly Leu Gln Met Thr Phe Thr Gly Asn Tyr Gly Glu Tyr Phe Gly
                485                 490                 495

Phe Ala Thr Asp Val Asp Ala Val Val Tyr Leu Met Leu Val Asn Asp
                500                 505                 510

Leu Ile His Gly Leu Tyr Pro Asp Ala Val Ser Ile Gly Glu Asp Val
            515                 520                 525

Ser Gly Met Pro Thr Phe Cys Ile Pro Val Pro Asp Gly Gly Val Gly
        530                 535                 540
```

Phe Asp Tyr Arg Leu His Met Ala Val Ala Asp Lys Trp Ile Glu Leu
545                 550                 555                 560

Leu Lys Gln Ser Asp Glu Ser Trp Lys Met Gly Asp Ile Val His Thr
            565                 570                 575

Leu Thr Asn Arg Arg Trp Leu Glu Lys Cys Val Thr Tyr Ala Glu Ser
            580                 585                 590

His Asp Gln Ala Leu Val Gly Asp Lys Thr Ile Ala Phe Trp Leu Met
            595                 600                 605

Asp Lys Asp Met Tyr Asp Phe Met Ala Leu Asp Arg Pro Ser Thr Pro
610                 615                 620

Arg Ile Asp Arg Gly Ile Ala Leu His Lys Met Ile Arg Leu Val Thr
625                 630                 635                 640

Met Gly Leu Gly Gly Glu Gly Tyr Leu Asn Phe Met Gly Asn Glu Phe
            645                 650                 655

Gly His Pro Glu Trp Ile Asp Phe Pro Arg Gly Pro Gln Thr Leu Pro
            660                 665                 670

Thr Gly Lys Val Leu Pro Gly Asn Asn Ser Tyr Asp Lys Cys Arg
            675                 680                 685

Arg Arg Phe Asp Leu Gly Asp Ala Asp Phe Leu Arg Tyr Arg Gly Met
            690                 695                 700

Gln Glu Phe Asp Gln Ala Met Gln His Leu Glu Glu Lys Tyr Gly Phe
705                 710                 715                 720

Met Thr Ser Glu His Gln Tyr Val Ser Arg Lys His Glu Glu Asp Lys
                725                 730                 735

Val Ile Ile Phe Glu Arg Gly Asp Leu Val Phe Val Phe Asn Phe His
                740                 745                 750

Trp Ser Asn Ser Phe Phe Asp Tyr Arg Val Gly Cys Ser Lys Pro Gly
            755                 760                 765

Lys Tyr Lys Val Ala Leu Asp Ser Asp Ala Leu Phe Gly Gly Phe
    770                 775                 780

Ser Arg Leu Asp His Asp Val Asp Tyr Phe Thr Thr Glu His Pro His
785                 790                 795                 800

Asp Asn Arg Pro Arg Ser Phe Leu Val Tyr Thr Pro Ser Arg Thr Ala
            805                 810                 815

Val Val Tyr Ala Leu Thr Glu
            820

<210> SEQ ID NO 3
<211> LENGTH: 819
<212> TYPE: PRT
<213> ORGANISM: Triticum aestivum

<400> SEQUENCE: 3

Met Ala Thr Phe Ala Val Ser Gly Ala Thr Leu Gly Val Ala Arg Ala
1               5                   10                  15

Gly Val Gly Val Ala Arg Ala Gly Ser Glu Arg Gly Gly Ala Asp
            20                  25                  30

Leu Pro Ser Leu Leu Arg Lys Lys Asp Ser Ser Arg Ala Val Leu
            35                  40                  45

Ser Arg Ala Ala Ser Pro Gly Lys Val Leu Val Pro Asp Gly Glu Ser
            50                  55                  60

Asp Asp Leu Ala Ser Pro Ala Gln Pro Glu Glu Leu Gln Ile Pro Glu
65                  70                  75                  80

Asp Ile Glu Glu Gln Thr Ala Glu Val Asn Met Thr Gly Gly Thr Ala

```
                    85                  90                  95
Glu Lys Leu Gln Ser Ser Glu Pro Thr Gln Gly Ile Val Glu Thr Ile
                100                 105                 110
Thr Asp Gly Val Thr Lys Gly Val Lys Glu Leu Val Val Gly Glu Lys
                115                 120                 125
Pro Arg Val Val Pro Lys Pro Gly Asp Gly Gln Lys Ile Tyr Glu Ile
                130                 135                 140
Asp Pro Thr Leu Lys Asp Phe Arg Ser His Leu Asp Tyr Arg Tyr Ser
145                 150                 155                 160
Glu Tyr Lys Arg Ile Arg Ala Ala Ile Asp Gln His Glu Gly Gly Leu
                165                 170                 175
Glu Ala Phe Ser Arg Gly Tyr Glu Lys Leu Gly Phe Thr Arg Ser Ala
                180                 185                 190
Glu Gly Ile Thr Tyr Arg Glu Trp Ala Pro Gly Ala His Ser Ala Ala
                195                 200                 205
Leu Val Gly Asp Phe Asn Asn Trp Asn Pro Asn Ala Asp Thr Met Thr
                210                 215                 220
Arg Asp Asp Tyr Gly Val Trp Glu Ile Phe Leu Pro Asn Asn Ala Asp
225                 230                 235                 240
Gly Ser Ser Ala Ile Pro His Gly Ser Arg Val Lys Ile Arg Met Asp
                245                 250                 255
Thr Pro Ser Gly Val Lys Asp Ser Ile Ser Ala Trp Ile Lys Phe Ser
                260                 265                 270
Val Gln Ala Pro Gly Glu Ile Pro Phe Asn Gly Ile Tyr Tyr Asp Pro
                275                 280                 285
Pro Glu Glu Glu Lys Tyr Val Phe Gln His Pro Gln Arg Lys Arg Pro
290                 295                 300
Glu Ser Leu Arg Ile Tyr Glu Ser His Ile Gly Met Ser Ser Pro Glu
305                 310                 315                 320
Pro Lys Ile Asn Ser Tyr Ala Asn Phe Arg Asp Glu Val Leu Pro Arg
                325                 330                 335
Ile Lys Arg Leu Gly Tyr Asn Ala Val Gln Ile Met Ala Ile Gln Glu
                340                 345                 350
His Ser Tyr Tyr Ala Ser Phe Gly Tyr His Val Thr Asn Phe Phe Ala
                355                 360                 365
Pro Ser Ser Arg Phe Gly Thr Pro Glu Asp Leu Lys Ser Leu Ile Asp
                370                 375                 380
Arg Ala His Glu Leu Gly Leu Leu Val Leu Met Asp Ile Val His Ser
385                 390                 395                 400
His Ser Ser Asn Asn Thr Leu Asp Gly Leu Asn Gly Phe Asp Gly Thr
                405                 410                 415
Asp Thr His Tyr Phe His Gly Gly Pro Arg Gly His His Trp Met Trp
                420                 425                 430
Asp Ser Arg Leu Phe Asn Tyr Gly Ser Trp Glu Val Leu Arg Phe Leu
                435                 440                 445
Leu Ser Asn Ala Arg Trp Trp Leu Glu Glu Tyr Lys Phe Asp Gly Phe
                450                 455                 460
Arg Phe Asp Gly Val Thr Ser Met Met Tyr Thr His His Gly Leu Gln
465                 470                 475                 480
Met Thr Phe Thr Gly Asn Tyr Gly Glu Tyr Phe Gly Phe Ala Thr Asp
                485                 490                 495
Val Asp Ala Val Val Tyr Leu Met Leu Val Asn Asp Leu Ile His Gly
                500                 505                 510
```

```
Leu Tyr Pro Asp Ala Val Ser Ile Gly Glu Asp Val Ser Gly Met Pro
            515                 520                 525

Thr Phe Cys Ile Pro Val Pro Asp Gly Gly Val Gly Phe Asp Tyr Arg
    530                 535                 540

Leu His Met Ala Val Ala Asp Lys Trp Ile Glu Leu Leu Lys Gln Ser
545                 550                 555                 560

Asp Glu Ser Trp Lys Met Gly Asp Ile Val His Thr Leu Thr Asn Arg
                565                 570                 575

Arg Trp Leu Glu Lys Cys Val Thr Tyr Ala Glu Ser His Asp Gln Ala
            580                 585                 590

Leu Val Gly Asp Lys Thr Ile Ala Phe Trp Leu Met Asp Lys Asp Met
            595                 600                 605

Tyr Asp Phe Met Ala Leu Asp Arg Pro Ser Thr Leu Arg Ile Asp Arg
            610                 615                 620

Gly Ile Ala Leu His Lys Met Ile Arg Leu Val Thr Met Gly Leu Gly
625                 630                 635                 640

Gly Glu Gly Tyr Leu Asn Phe Met Gly Asn Glu Phe Gly His Pro Glu
                645                 650                 655

Trp Ile Asp Phe Pro Arg Gly Pro Gln Thr Leu Pro Thr Gly Lys Val
                660                 665                 670

Leu Pro Gly Asn Asn Asn Ser Tyr Asp Lys Cys Arg Arg Arg Phe Asp
            675                 680                 685

Leu Gly Asp Ala Asp Phe Leu Arg Tyr Arg Gly Met Gln Glu Phe Asp
            690                 695                 700

Gln Ala Met Gln His Leu Glu Glu Lys Tyr Gly Phe Met Thr Ser Glu
705                 710                 715                 720

His Gln Tyr Val Ser Arg Lys His Glu Glu Asp Lys Val Ile Ile Leu
                725                 730                 735

Lys Arg Gly Asp Leu Val Phe Val Phe Asn Phe His Trp Ser Asn Ser
            740                 745                 750

Phe Phe Asp Tyr Arg Val Gly Cys Ser Lys Pro Gly Lys Tyr Lys Val
            755                 760                 765

Ala Leu Asp Ser Asp Asp Ala Leu Phe Gly Gly Phe Ser Arg Leu Asp
            770                 775                 780

His Asp Val Asp Tyr Phe Thr Thr Glu His Pro His Asp Asn Arg Pro
785                 790                 795                 800

Arg Ser Phe Ser Val Tyr Thr Pro Ser Arg Thr Ala Val Val Tyr Ala
                805                 810                 815

Leu Thr Glu

<210> SEQ ID NO 4
<211> LENGTH: 157
<212> TYPE: PRT
<213> ORGANISM: Triticum aestivum

<400> SEQUENCE: 4

Met Ala Ala Pro Ala Phe Ala Val Ser Ala Ala Gly Leu Ala Arg Pro
1               5                   10                  15

Ser Ala Pro Arg Ser Gly Gly Pro Glu Arg Arg Gly Arg Gly Val Glu
            20                  25                  30

Leu Gln Ser Pro Ser Leu Leu Phe Gly Arg Asn Lys Gly Thr Arg Ser
        35                  40                  45

Pro Arg Ala Val Gly Val Gly Gly Ser Gly Trp Arg Val Val Met Arg
    50                  55                  60
```

```
Ala Gly Gly Pro Ser Gly Glu Val Met Ile Pro Asp Gly Ser Gly
 65                  70                  75                  80

Gly Thr Pro Pro Ser Ile His Gly Pro Val Gln Phe Asp Ser Asp
                 85                  90                  95

Leu Lys Val Pro Phe Ile Asp Asp Glu Thr Ser Leu Gln Asp Gly Gly
            100                 105                 110

Glu Asp Thr Ile Trp Ser Ser Glu Thr Asn Gln Val Thr Glu Glu Ile
            115                 120                 125

Asp Ala Glu Gly Thr Ser Arg Met Asp Lys Glu Ser Ser Thr Gly Glu
130                 135                 140

Lys Leu Arg Ile Leu Pro Pro Gly Asn Gly Gln Gln
145                 150                 155

<210> SEQ ID NO 5
<211> LENGTH: 99
<212> TYPE: PRT
<213> ORGANISM: Triticum aestivum

<400> SEQUENCE: 5

Ala Val Ser Val Gly Gly Ser Gly Trp Arg Val Met Arg Ala Gly
 1               5                  10                  15

Gly Pro Ser Gly Glu Val Met Ile Pro Asp Gly Gly Ser Gly Gly Thr
                20                  25                  30

Ser Pro Ser Ile Asp Gly Pro Val Gln Phe Asp Ser Asp Asp Leu Lys
                35                  40                  45

Val Pro Phe Ile Asp Asp Glu Pro Ser Leu Gln Asp Glu Gly Glu Asp
 50                  55                  60

Ser Ile Trp Ser Ser Glu Thr Asn Gln Val Thr Glu Glu Ile Asp Val
 65                  70                  75                  80

Glu Gly Met Lys Ile Met Asp Lys Glu Ser Ser Thr Gly Glu Lys Leu
                 85                  90                  95

Arg Ile Val

<210> SEQ ID NO 6
<211> LENGTH: 836
<212> TYPE: PRT
<213> ORGANISM: Triticum sp.

<400> SEQUENCE: 6

Met Ala Ala Pro Ala Phe Ala Val Ser Ala Ala Gly Leu Ala Arg Pro
 1               5                  10                  15

Ser Ala Pro Arg Ser Gly Gly Ala Glu Arg Arg Gly Arg Gly Val Glu
                20                  25                  30

Leu Gln Ser Pro Ser Leu Leu Phe Gly Arg Asn Lys Gly Thr Arg Ser
                35                  40                  45

Pro Arg Ala Val Gly Val Gly Gly Ser Gly Trp Arg Val Val Met Arg
 50                  55                  60

Ala Gly Gly Pro Ser Gly Glu Val Met Ile Pro Asp Gly Gly Ser Gly
 65                  70                  75                  80

Gly Thr Pro Pro Ser Ile Asp Gly Pro Val Gln Phe Asp Ser Asp
                 85                  90                  95

Leu Lys Val Pro Phe Ile Asp Asp Glu Thr Ser Leu Gln Asp Gly Gly
            100                 105                 110

Glu Asp Ser Ile Trp Ser Ser Glu Thr Asn Gln Val Ser Glu Glu Ile
            115                 120                 125
```

-continued

Asp Ala Glu Asp Thr Ser Arg Met Asp Lys Glu Ser Ser Thr Arg Glu
    130                 135                 140

Lys Leu Arg Ile Leu Pro Pro Gly Asn Gly Gln Gln Ile Tyr Glu
145                 150                 155                 160

Ile Asp Pro Thr Leu Arg Asp Phe Lys Tyr His Leu Glu Tyr Arg Tyr
                165                 170                 175

Ser Leu Tyr Arg Arg Ile Arg Ser Asp Ile Asp Glu His Glu Gly Gly
            180                 185                 190

Met Asp Val Phe Ser Arg Gly Tyr Glu Lys Phe Gly Phe Met Arg Ser
        195                 200                 205

Ala Glu Gly Ile Thr Tyr Arg Glu Trp Ala Pro Gly Ala Asp Ser Ala
    210                 215                 220

Ala Leu Val Gly Asp Phe Asn Asn Trp Asp Pro Asn Ala Asp His Met
225                 230                 235                 240

Ser Lys Asn Asp Leu Gly Val Trp Glu Ile Phe Leu Pro Asn Asn Ala
                245                 250                 255

Asp Gly Ser Pro Pro Ile Pro His Gly Ser Arg Val Lys Val Arg Met
            260                 265                 270

Gly Thr Pro Ser Gly Thr Lys Asp Ser Ile Pro Ala Trp Ile Lys Tyr
        275                 280                 285

Ser Val Gln Thr Pro Gly Asp Ile Pro Tyr Asn Gly Ile Tyr Tyr Asp
    290                 295                 300

Pro Pro Glu Glu Glu Lys Tyr Val Phe Lys His Pro Gln Pro Lys Arg
305                 310                 315                 320

Pro Lys Ser Leu Arg Ile Tyr Glu Thr His Val Gly Met Ser Ser Pro
                325                 330                 335

Glu Pro Lys Ile Asn Thr Tyr Ala Asn Phe Arg Asp Glu Val Leu Pro
            340                 345                 350

Arg Ile Lys Arg Leu Gly Tyr Asn Ala Val Gln Ile Met Ala Ile Gln
        355                 360                 365

Glu His Ser Tyr Tyr Gly Ser Phe Gly Tyr His Val Thr Asn Phe Phe
    370                 375                 380

Ala Pro Ser Ser Arg Phe Gly Ser Pro Glu Asp Leu Lys Ser Leu Ile
385                 390                 395                 400

Asp Arg Ala His Glu Leu Gly Leu Val Val Leu Met Asp Val Val His
                405                 410                 415

Ser His Ala Ser Asn Asn Thr Leu Asp Gly Leu Asn Gly Phe Asp Gly
            420                 425                 430

Thr Asp Thr His Tyr Phe His Gly Gly Ser Arg Gly His His Trp Met
        435                 440                 445

Trp Asp Ser Arg Val Phe Asn Tyr Gly Asn Lys Glu Val Ile Arg Phe
    450                 455                 460

Leu Leu Ser Asn Ala Arg Trp Trp Leu Glu Glu Tyr Lys Phe Asp Gly
465                 470                 475                 480

Phe Arg Phe Asp Gly Ala Thr Ser Met Met Tyr Thr His His Gly Leu
                485                 490                 495

Gln Val Thr Phe Thr Gly Ser Tyr His Glu Tyr Phe Gly Phe Ala Thr
            500                 505                 510

Asp Val Asp Ala Val Val Tyr Leu Met Leu Met Asn Asp Leu Ile His
        515                 520                 525

Gly Phe Tyr Pro Glu Ala Val Thr Ile Gly Glu Asp Val Ser Gly Met
    530                 535                 540

Pro Thr Phe Ala Leu Pro Val Gln Val Gly Gly Val Gly Phe Asp Tyr

```
                545                 550                 555                 560
        Arg Leu His Met Ala Val Ala Arg Lys Trp Ile Glu Leu Leu Lys Gly
                        565                 570                 575

Asn Asp Glu Ala Trp Glu Met Gly Asn Ile Val His Thr Leu Thr Asn
                        580                 585                 590

Arg Arg Trp Leu Glu Lys Cys Val Thr Tyr Ala Glu Ser His Asp Gln
                        595                 600                 605

Ala Leu Val Gly Asp Lys Thr Ile Ala Phe Trp Leu Met Asp Lys Asp
                        610                 615                 620

Met Tyr Asp Phe Met Ala Leu Asn Gly Pro Ser Thr Pro Asn Ile Asp
        625                 630                 635                 640

Arg Gly Ile Ala Leu His Lys Met Ile Arg Leu Ile Thr Met Gly Leu
                        645                 650                 655

Gly Gly Glu Gly Tyr Leu Asn Phe Met Gly Asn Glu Phe Gly His Pro
                        660                 665                 670

Glu Trp Ile Asp Phe Pro Arg Gly Pro Gln Val Leu Pro Ser Gly Lys
                        675                 680                 685

Phe Ile Pro Gly Asn Asn Asn Ser Tyr Asp Lys Cys Arg Arg Arg Phe
                        690                 695                 700

Asp Leu Gly Asp Ala Glu Phe Leu Arg Tyr His Gly Met Gln Gln Phe
        705                 710                 715                 720

Asp Gln Ala Met Gln His Leu Glu Glu Lys Tyr Gly Phe Met Thr Ser
                        725                 730                 735

Asp His Gln Tyr Val Ser Arg Lys His Glu Glu Asp Lys Val Ile Val
                        740                 745                 750

Phe Glu Lys Gly Asp Leu Val Phe Val Phe Asn Phe His Trp Ser Ser
                        755                 760                 765

Ser Tyr Phe Asp Tyr Arg Val Gly Cys Leu Lys Pro Gly Lys Tyr Lys
                        770                 775                 780

Val Val Leu Asp Ser Asp Ala Gly Leu Phe Gly Gly Phe Gly Arg Ile
        785                 790                 795                 800

His His Thr Ala Glu His Phe Thr Ser Asp Cys Gln His Asp Asn Arg
                        805                 810                 815

Pro His Ser Phe Ser Val Tyr Thr Pro Ser Arg Thr Cys Val Val Tyr
                        820                 825                 830

Ala Pro Met Asn
                        835

<210> SEQ ID NO 7
<211> LENGTH: 2966
<212> TYPE: DNA
<213> ORGANISM: Triticum sp.
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (2937)..(2937)
<223> OTHER INFORMATION: n is a, c, g, or t
<220> FEATURE:
<221> NAME/KEY: misc_feature
<222> LOCATION: (2958)..(2958)
<223> OTHER INFORMATION: n is a, c, g, or t
<220> FEATURE:
<221> NAME/KEY: misc_feature
<222> LOCATION: (2965)..(2965)
<223> OTHER INFORMATION: n is a, c, g, or t

<400> SEQUENCE: 7
```

```
atggtcgacc tgcaggcggc cgcgaatgca ctagngattt tgacaccaga ccaactggta    60
atggtagcga ccggcgctca gctggaattc gcggccgcgt cgaccgtggg tttaagcagg   120
agacgaggcg gggtcagttg ggcagttagg ttggatccga tccggctgcg gcggcggcga   180
cgggatggct cgcgccggca tcgcagtttc cgcggcgggg ctggcccggc cgtcggctcc   240
tcgatccggc ggggcagagc ggaggggggcg cggggtggag ctgcagtcgc catcgctgct   300
cttcggccgc aacaagggca cccgttcacc ccgtgccgtc ggcgtcggag gttctggatg   360
gcgcgtggtc atgcgcgcgg gggggccgtc cggggaggtg atgatccctg acggcggtag   420
tggcggaaca ccgccttcca tcgacggtcc cgttcagttc gattctgatg atctgaaggt   480
tccattcatt gatgatgaaa caagcctaca ggatggaggt gaagatagta tttggtcttc   540
agagacaaat caggttagtg aagaaattga tgctgaagac acgagcagaa tggacaaaga   600
atcatctacg agggagaaat tacgcattct gccaccaccg ggaaatggac agcaaatata   660
cgagattgac ccaacgctcc gagactttaa gtaccatctt gagtatcgat atagcctata   720
caggagaata cgttcagaca ttgatgaaca cgaaggaggc atggatgtat tttcccgcgg   780
ttacgagaag tttggattta tgcgcagcgc tgaaggtatc acttaccgag aatgggctcc   840
tggagcagat tctgcagcat tagttggcga cttcaacaat tgggatccaa atgcagacca   900
tatgagcaaa aatgaccttg gtgtttggga gatttttctg ccaaacaatg cagatggttc   960
gccaccaatt cctcacggct cacgggtgaa ggtgcgaatg ggtactccat ctgggacaaa  1020
ggattcaatt cctgcttgga tcaagtactc cgtgcagact ccaggagata taccatacaa  1080
tggaatatat tatgatcctc ccgaagagga gaagtatgta ttcaagcatc ctcaacctaa  1140
acgaccaaaa tcattgcgga tatatgaaac acatgttggc atgagtagcc cggaaccaaa  1200
gatcaacaca tatgcaaact tcagggatga ggtgcttcca agaattaaaa gacttggata  1260
caatgcagtg caaataatgg caatccaaga gcactcatac tatggaagct ttgggtacca  1320
tgttaccaat ttcttttgcac caagtagccg ttttgggtcc ccagaagatt taaaatcttt  1380
gattgataga gctcacgagc ttggcttggt tgtcctcatg gatgttgttc acagtcacgc  1440
gtcaaataat accttggacg ggttgaatgg ttttgatggc acggatacac attacttcca  1500
tggcggttca cggggccatc actggatgtg ggattcccgt gtgtttaact atgggaataa  1560
ggaagttata aggtttctac tttccaatgc aagatggtgg ctagaggagt ataagtttga  1620
tggtttccga ttcgatggcg cgacctccat gatgtatacc catcatggat tacaagtaac  1680
ctttacagga agctaccatg aatattttgg ctttgccact gatgtagatg cggtcgttta  1740
cttgatgctg atgaatgatc taattcatgg gttttatcct gaagccgtaa ctatcggtga  1800
agatgttagt ggaatgccta catttgccct tcctgttcaa gttggtgggg ttggttttga  1860
ctatcgctta catatggctg ttgcccgcaa atggattgaa cttctcaaag gaaacgatga  1920
agcttgggag atgggtaata ttgtgcacac actaacaaac agaaggtggc tggaaaagtg  1980
tgttacttat gctgaaagtc acgatcaagc acttgttgga gacaagacta ttgcattctg  2040
gttgatggac aaggatatgt atgatttcat ggcgctgaac ggaccttcga cgcctaatat  2100
tgatcgtgga atagcactgc ataaaatgat tagacttatc acaatgggtc taggaggaga  2160
gggttatctt aactttatgg gaaatgagtt cgggcatcct gaatggatag actttccaag  2220
aggcccacaa gtacttccaa gtggtaagtt catcccagga aacaacaaca gttacgacaa  2280
atgccgtcga agatttgacc tgggtgatgc agaatttctt aggtatcatg gtatgcagca  2340
```

```
gtttgatcag gcaatgcagc atcttgagga aaaatatggt tttatgacat cagaccacca    2400
gtacgtatct cggaaacatg aggaagataa ggtgatcgtg tttgaaaaag gggacttggt    2460
atttgtgttc aacttccact ggagtagtag ctatttcgac taccgggtcg gctgtttaaa    2520
gcctgggaag tacaaggtgg tcttagactc ggacgctgga ctctttggtg gatttggtag    2580
gatccatcac actgcagagc acttcacttc tgactgccaa catgacaaca ggccccattc    2640
attctcagtg tacactccta gcagaacctg tgttgtctat gctccaatga actaacagca    2700
aagtgcagca tacgcgtgcg cgctgttgtt gctagtagca agaaaaatcg tatggtcaat    2760
acaaccaggt gcaaggttta ataaggattt tgcttcaac gagtcctgga tagacaagac     2820
aacatgatgt tgtgctgtgt gctcccaatc cccagggcgt tgtgaagaaa acatgctcat    2880
ctgtgttatt ttatggatca gcgacgaaac ctcccccaaa tacccctttt tttttnaaa     2940 ggaggatagg cccccggnct ttgcnt                                         2966

<210> SEQ ID NO 8
<211> LENGTH: 695
<212> TYPE: PRT
<213> ORGANISM: Triticum aestivum

<400> SEQUENCE: 8

Thr Arg Glu Lys Leu Arg Ile Leu Pro Pro Gly Asn Gly Gln Gln
1               5                   10                  15

Ile Tyr Glu Ile Asp Pro Thr Leu Arg Asp Phe Lys Tyr His Leu Glu
                20                  25                  30

Tyr Arg Tyr Ser Leu Tyr Arg Arg Ile Arg Ser Asp Ile Asp Glu His
            35                  40                  45

Glu Gly Gly Met Asp Val Phe Ser Arg Gly Tyr Glu Lys Phe Gly Phe
        50                  55                  60

Met Arg Ser Ala Glu Gly Ile Thr Tyr Arg Glu Trp Ala Pro Gly Ala
65                  70                  75                  80

Asp Ser Ala Ala Leu Val Gly Asp Phe Asn Asn Trp Asp Pro Asn Ala
                85                  90                  95

Asp His Met Ser Lys Asn Asp Leu Gly Val Trp Glu Ile Phe Leu Pro
                100                 105                 110

Asn Asn Ala Asp Gly Ser Pro Pro Ile Pro His Gly Ser Arg Val Lys
            115                 120                 125

Val Arg Met Asp Thr Pro Ser Gly Ile Lys Asp Ser Ile Pro Ala Trp
        130                 135                 140

Ile Lys Tyr Ser Val Gln Thr Pro Gly Asp Ile Pro Tyr Asn Gly Ile
145                 150                 155                 160

Tyr Tyr Asp Pro Pro Glu Glu Glu Lys Tyr Val Phe Lys His Pro Gln
                165                 170                 175

Pro Lys Arg Pro Lys Ser Leu Arg Ile Tyr Glu Thr His Val Gly Met
                180                 185                 190

Ser Ser Pro Glu Pro Lys Ile Asn Thr Tyr Ala Asn Phe Arg Asp Glu
            195                 200                 205

Val Leu Pro Arg Ile Lys Arg Leu Gly Tyr Asn Ala Val Gln Ile Met
        210                 215                 220

Ala Ile Gln Glu His Ser Tyr Tyr Gly Ser Phe Gly Tyr His Val Thr
225                 230                 235                 240

Asn Phe Phe Ala Pro Ser Ser Arg Phe Gly Ser Pro Glu Asp Leu Lys
                245                 250                 255

Ser Leu Ile Asp Arg Ala His Glu Leu Gly Leu Val Val Leu Met Asp
```

```
                260             265             270
Val Val His Ser His Ala Ser Asn Asn Thr Leu Asp Gly Leu Asn Gly
            275             280             285

Phe Asp Gly Thr Asp Thr His Tyr Phe His Gly Gly Ser Arg Gly His
            290             295             300

His Trp Met Trp Asp Ser Arg Val Phe Asn Tyr Gly Asn Lys Glu Val
305             310             315             320

Ile Arg Phe Leu Leu Ser Asn Ala Arg Trp Trp Leu Glu Glu Tyr Lys
            325             330             335

Phe Asp Gly Phe Arg Phe Asp Gly Ala Thr Ser Met Met Tyr Thr His
            340             345             350

His Gly Leu Gln Val Thr Phe Thr Gly Ser Tyr His Glu Tyr Phe Gly
            355             360             365

Phe Ala Thr Asp Val Asp Ala Val Val Tyr Leu Met Leu Met Asn Asp
            370             375             380

Leu Ile His Gly Phe Tyr Pro Glu Ala Val Thr Ile Gly Glu Asp Val
385             390             395             400

Ser Gly Met Pro Thr Phe Ala Leu Pro Val Gln Val Gly Gly Val Gly
            405             410             415

Phe Asp Tyr Arg Leu His Met Ala Val Ala Asp Lys Trp Ile Glu Leu
            420             425             430

Leu Lys Gly Asn Asp Glu Ala Trp Glu Met Gly Asn Ile Val His Thr
            435             440             445

Leu Thr Asn Arg Arg Trp Leu Glu Lys Cys Val Thr Tyr Ala Glu Ser
            450             455             460

His Asp Gln Ala Leu Val Gly Asp Lys Thr Ile Ala Phe Trp Leu Met
465             470             475             480

Asp Lys Asp Met Tyr Asp Phe Met Ala Leu Asn Gly Pro Ser Thr Pro
            485             490             495

Asn Ile Asp Arg Gly Ile Ala Leu His Lys Met Ile Arg Leu Ile Thr
            500             505             510

Met Gly Leu Gly Gly Glu Gly Tyr Leu Asn Phe Met Gly Asn Glu Phe
            515             520             525

Gly His Pro Glu Trp Ile Asp Phe Pro Arg Gly Pro Gln Val Leu Pro
            530             535             540

Ser Gly Lys Phe Ile Pro Gly Asn Asn Asn Ser Tyr Asp Lys Cys Arg
545             550             555             560

Arg Arg Phe Asp Leu Gly Asp Ala Glu Phe Leu Arg Tyr His Gly Met
            565             570             575

Gln Gln Phe Asp Gln Ala Met Gln His Leu Glu Glu Lys Tyr Gly Phe
            580             585             590

Met Thr Ser Asp His Gln Tyr Val Ser Arg Lys His Glu Glu Asp Lys
            595             600             605

Val Ile Val Phe Glu Lys Gly Asp Leu Val Phe Val Phe Asn Phe His
            610             615             620

Trp Ser Ser Tyr Phe Asp Tyr Arg Val Gly Cys Leu Lys Pro Gly
625             630             635             640

Lys Tyr Lys Val Val Leu Asp Ser Asp Ala Gly Leu Phe Gly Gly Phe
            645             650             655

Gly Arg Ile His His Thr Ala Glu His Val Thr Ser Asp Cys Gln His
            660             665             670

Asp Asn Arg Pro His Ser Phe Ser Val Tyr Thr Pro Ser Arg Thr Cys
            675             680             685
```

```
Val Val Tyr Ala Pro Met Asn
    690             695

<210> SEQ ID NO 9
<211> LENGTH: 836
<212> TYPE: PRT
<213> ORGANISM: Triticum aestivum

<400> SEQUENCE: 9

Met Ala Ala Pro Ala Phe Ala Val Ser Ala Ala Gly Leu Ala Arg Pro
1               5                   10                  15

Ser Ala Pro Arg Ser Gly Gly Ala Glu Arg Arg Gly Arg Gly Val Glu
            20                  25                  30

Leu Gln Ser Pro Ser Leu Leu Phe Gly Arg Asn Lys Gly Thr Arg Ser
        35                  40                  45

Pro Arg Ala Val Gly Val Gly Gly Ser Gly Trp Arg Val Val Met Arg
    50                  55                  60

Ala Gly Gly Pro Ser Gly Glu Val Met Ile Pro Asp Gly Gly Ser Gly
65                  70                  75                  80

Gly Thr Pro Pro Ser Ile Asp Gly Pro Val Gln Phe Asp Ser Asp Asp
                85                  90                  95

Leu Lys Val Pro Phe Ile Asp Asp Glu Thr Ser Leu Gln Asp Gly Gly
            100                 105                 110

Glu Asp Ser Ile Trp Ser Ser Glu Thr Asn Gln Val Ser Glu Glu Ile
        115                 120                 125

Asp Ala Glu Asp Thr Ser Arg Met Asp Lys Glu Ser Ser Thr Arg Glu
130                 135                 140

Lys Leu Arg Ile Leu Pro Pro Gly Asn Gly Gln Gln Ile Tyr Glu
145                 150                 155                 160

Ile Asp Pro Thr Leu Arg Asp Phe Lys Tyr His Leu Glu Tyr Arg Tyr
                165                 170                 175

Ser Leu Tyr Arg Arg Ile Arg Ser Asp Ile Asp Glu His Glu Gly Gly
            180                 185                 190

Met Asp Val Phe Ser Arg Gly Tyr Glu Lys Phe Gly Phe Met Arg Ser
        195                 200                 205

Ala Glu Gly Ile Thr Tyr Arg Glu Trp Ala Pro Gly Ala Asp Ser Ala
210                 215                 220

Ala Leu Val Gly Asp Phe Asn Asn Trp Asp Pro Asn Ala Asp His Met
225                 230                 235                 240

Ser Lys Asn Asp Leu Gly Val Trp Glu Ile Phe Leu Pro Asn Asn Ala
                245                 250                 255

Asp Gly Ser Pro Pro Ile Pro His Gly Ser Arg Val Lys Val Arg Met
            260                 265                 270

Asp Thr Pro Ser Gly Ile Lys Asp Ser Ile Pro Ala Trp Ile Lys Tyr
        275                 280                 285

Ser Val Gln Thr Pro Gly Asp Ile Pro Tyr Asn Gly Ile Tyr Tyr Asp
    290                 295                 300

Pro Pro Glu Glu Glu Lys Tyr Val Phe Lys His Pro Gln Pro Lys Arg
305                 310                 315                 320

Pro Lys Ser Leu Arg Ile Tyr Glu Thr His Val Gly Met Ser Ser Pro
                325                 330                 335

Glu Pro Lys Ile Asn Thr Tyr Ala Asn Phe Arg Asp Glu Val Leu Pro
            340                 345                 350

Arg Ile Lys Arg Leu Gly Tyr Asn Ala Val Gln Ile Met Ala Ile Gln
```

```
                355                 360                 365
Glu His Ser Tyr Tyr Gly Ser Phe Gly Tyr His Val Thr Asn Phe Phe
    370                 375                 380
Ala Pro Ser Ser Arg Phe Gly Ser Pro Glu Asp Leu Lys Ser Leu Ile
385                 390                 395                 400
Asp Arg Ala His Glu Leu Gly Leu Val Val Leu Met Asp Val Val His
                405                 410                 415
Ser His Ala Ser Asn Asn Thr Leu Asp Gly Leu Asn Gly Phe Asp Gly
            420                 425                 430
Thr Asp Thr His Tyr Phe His Gly Gly Ser Arg Gly His His Trp Met
            435                 440                 445
Trp Asp Ser Arg Val Phe Asn Tyr Gly Asn Lys Glu Val Ile Arg Phe
            450                 455                 460
Leu Leu Ser Asn Ala Arg Trp Trp Leu Glu Glu Tyr Lys Phe Asp Gly
465                 470                 475                 480
Phe Arg Phe Asp Gly Ala Thr Ser Met Met Tyr Thr His His Gly Leu
                485                 490                 495
Gln Val Thr Phe Thr Gly Ser Tyr His Glu Tyr Phe Gly Phe Ala Thr
            500                 505                 510
Asp Val Asp Ala Val Val Tyr Leu Met Leu Met Asn Asp Leu Ile His
            515                 520                 525
Gly Phe Tyr Pro Glu Ala Val Thr Ile Gly Glu Asp Val Ser Gly Met
            530                 535                 540
Pro Thr Phe Ala Leu Pro Val Gln Val Gly Gly Val Gly Phe Asp Tyr
545                 550                 555                 560
Arg Leu His Met Ala Val Ala Asp Lys Trp Ile Glu Leu Leu Lys Gly
                565                 570                 575
Asn Asp Glu Ala Trp Glu Met Gly Asn Ile Val His Thr Leu Thr Asn
            580                 585                 590
Arg Arg Trp Leu Glu Lys Cys Val Thr Tyr Ala Glu Ser His Asp Gln
            595                 600                 605
Ala Leu Val Gly Asp Lys Thr Ile Ala Phe Trp Leu Met Asp Lys Asp
            610                 615                 620
Met Tyr Asp Phe Met Ala Leu Asn Gly Pro Ser Thr Pro Asn Ile Asp
625                 630                 635                 640
Arg Gly Ile Ala Leu His Lys Met Ile Arg Leu Ile Thr Met Gly Leu
                645                 650                 655
Gly Gly Glu Gly Tyr Leu Asn Phe Met Gly Asn Glu Phe Gly His Pro
            660                 665                 670
Glu Trp Ile Asp Phe Pro Arg Gly Pro Gln Val Leu Pro Ser Gly Lys
            675                 680                 685
Phe Ile Pro Gly Asn Asn Asn Ser Tyr Asp Lys Cys Arg Arg Arg Phe
            690                 695                 700
Asp Leu Gly Asp Ala Glu Phe Leu Arg Tyr His Gly Met Gln Gln Phe
705                 710                 715                 720
Asp Gln Ala Met Gln His Leu Glu Glu Lys Tyr Gly Phe Met Thr Ser
                725                 730                 735
Asp His Gln Tyr Val Ser Arg Lys His Glu Glu Asp Lys Val Ile Val
            740                 745                 750
Phe Glu Lys Gly Asp Leu Val Phe Val Phe Asn Phe His Trp Ser Ser
            755                 760                 765
Ser Tyr Phe Asp Tyr Arg Val Gly Cys Leu Lys Pro Gly Lys Tyr Lys
            770                 775                 780
```

```
Val Val Leu Asp Ser Asp Ala Gly Leu Phe Gly Gly Phe Gly Arg Ile
785                 790                 795                 800

His His Thr Ala Glu His Val Thr Ser Asp Cys Gln His Asp Asn Arg
            805                 810                 815

Pro His Ser Phe Ser Val Tyr Thr Pro Ser Arg Thr Cys Val Val Tyr
            820                 825                 830

Ala Pro Met Asn
        835

<210> SEQ ID NO 10
<211> LENGTH: 829
<212> TYPE: PRT
<213> ORGANISM: Hordeum vulgare

<400> SEQUENCE: 10

Met Ala Ala Pro Ala Phe Ala Val Ser Ala Gly Ile Ala Arg Pro
1               5                   10                  15

Ser Ala Arg Arg Ser Ser Gly Ala Glu Pro Arg Ser Leu Leu Phe Gly
            20                  25                  30

Arg Asn Lys Gly Thr Arg Phe Pro Arg Ala Val Gly Val Gly Gly Ser
            35                  40                  45

Gly Trp Arg Val Val Met Arg Ala Gly Gly Pro Ser Gly Glu Val Met
50                  55                  60

Ile Pro Asp Gly Gly Ser Gly Ser Gly Thr Pro Ser Ile Glu
65                  70                  75                  80

Gly Ser Val Gln Phe Glu Ser Asp Asp Leu Glu Val Pro Phe Ile Asp
                85                  90                  95

Asp Glu Pro Ser Leu His Asp Gly Gly Glu Asp Thr Ile Arg Ser Ser
            100                 105                 110

Glu Thr Tyr Gln Val Thr Glu Glu Ile Asp Ala Glu Gly Val Ser Arg
        115                 120                 125

Met Asp Lys Glu Ser Ser Thr Val Lys Lys Ile Arg Ile Val Pro Gln
    130                 135                 140

Pro Gly Asn Gly Gln Gln Ile Tyr Asp Ile Asp Pro Met Leu Arg Asp
145                 150                 155                 160

Phe Lys Tyr His Leu Glu Tyr Arg Tyr Ser Leu Tyr Arg Arg Ile Arg
                165                 170                 175

Ser Asp Ile Asp Glu Tyr Asp Gly Gly Met Asp Val Phe Ser Arg Gly
            180                 185                 190

Tyr Glu Lys Phe Gly Phe Val Arg Ser Ala Glu Gly Ile Thr Tyr Arg
        195                 200                 205

Glu Trp Ala Pro Gly Ala Asp Ser Ala Ala Leu Val Gly Asp Phe Asn
    210                 215                 220

Asn Trp Asp Pro Thr Ala Asp His Met Ser Lys Asn Asp Leu Gly Ile
225                 230                 235                 240

Trp Glu Ile Phe Leu Pro Asn Asn Ala Asp Gly Ser Pro Pro Ile Pro
                245                 250                 255

His Gly Ser Arg Val Lys Val Arg Met Asp Thr Pro Ser Gly Thr Lys
            260                 265                 270

Asp Ser Ile Pro Ala Trp Ile Lys Tyr Ser Val Gln Thr Pro Gly Asp
        275                 280                 285

Ile Pro Tyr Asn Gly Ile Tyr Tyr Asp Pro Pro Glu Glu Lys Tyr
    290                 295                 300

Val Phe Lys His Pro Gln Pro Lys Arg Pro Lys Ser Leu Arg Ile Tyr
```

```
        305                 310                 315                 320
Glu Thr His Val Gly Met Ser Ser Pro Glu Pro Lys Ile Asn Thr Tyr
                    325                 330                 335
Ala Asn Phe Arg Asp Glu Val Leu Pro Arg Ile Lys Arg Leu Gly Tyr
                    340                 345                 350
Asn Ala Val Gln Ile Met Ala Ile Gln Glu His Ser Tyr Tyr Gly Ser
                    355                 360                 365
Phe Gly Tyr His Val Thr Asn Phe Phe Ala Pro Ser Ser Arg Phe Gly
                    370                 375                 380
Ser Pro Glu Asp Leu Lys Ser Leu Ile Asp Arg Ala His Glu Leu Gly
385                 390                 395                 400
Leu Leu Val Leu Met Asp Val Val His Ser His Ala Ser Ser Asn Thr
                    405                 410                 415
Leu Asp Gly Leu Asn Gly Phe Asp Gly Thr Asp Thr His Tyr Phe His
                    420                 425                 430
Gly Gly Ser Arg Gly His His Trp Met Trp Asp Ser Arg Val Phe Asn
                    435                 440                 445
Tyr Gly Asn Lys Glu Val Ile Arg Phe Leu Leu Ser Asn Ala Arg Trp
                    450                 455                 460
Trp Leu Glu Glu Tyr Lys Phe Asp Gly Phe Arg Phe Asp Gly Ala Thr
465                 470                 475                 480
Ser Met Met Tyr Thr His His Gly Leu Gln Val Thr Phe Thr Gly Ser
                    485                 490                 495
Tyr His Glu Tyr Phe Gly Phe Ala Thr Asp Val Asp Ala Val Val Tyr
                    500                 505                 510
Leu Met Leu Val Asn Asp Leu Ile His Ala Leu Tyr Pro Glu Ala Val
                    515                 520                 525
Thr Ile Gly Glu Asp Val Ser Gly Met Pro Thr Phe Ala Leu Pro Val
                    530                 535                 540
Gln Val Gly Gly Val Gly Phe Asp Tyr Arg Leu His Met Ala Val Ala
545                 550                 555                 560
Asp Lys Trp Ile Glu Leu Leu Lys Gly Ser Asp Glu Gly Trp Glu Met
                    565                 570                 575
Gly Asn Ile Val His Thr Leu Thr Asn Arg Arg Trp Leu Glu Lys Cys
                    580                 585                 590
Val Thr Tyr Ala Glu Ser His Asp Gln Ala Leu Val Gly Asp Lys Thr
                    595                 600                 605
Ile Ala Phe Trp Leu Met Asp Lys Asp Met Tyr Asp Phe Met Ala Leu
                    610                 615                 620
Asn Gly Pro Ser Thr Pro Asn Ile Asp Arg Gly Ile Ala Leu His Lys
625                 630                 635                 640
Met Ile Arg Leu Ile Thr Met Ala Leu Gly Gly Glu Gly Tyr Leu Asn
                    645                 650                 655
Phe Met Gly Asn Glu Phe Gly His Pro Glu Trp Ile Asp Phe Pro Arg
                    660                 665                 670
Gly Pro Gln Val Leu Pro Thr Gly Lys Phe Ile Pro Gly Asn Asn Asn
                    675                 680                 685
Ser Tyr Asp Lys Cys Arg Arg Phe Asp Leu Gly Asp Ala Glu Phe
                    690                 695                 700
Leu Arg Tyr His Gly Met Gln Gln Phe Asp Gln Ala Met Gln His Leu
705                 710                 715                 720
Glu Glu Lys Tyr Gly Phe Met Thr Ser Asp His Gln Tyr Val Ser Arg
                    725                 730                 735
```

```
Lys His Glu Glu Asp Lys Val Ile Val Phe Glu Lys Gly Asp Leu Val
            740                 745                 750

Phe Val Phe Asn Phe His Trp Ser Asn Ser Tyr Phe Asp Tyr Arg Val
            755                 760                 765

Gly Cys Leu Lys Pro Gly Lys Tyr Lys Val Val Leu Asp Ser Asp Ala
770                 775                 780

Gly Leu Phe Gly Gly Phe Gly Arg Ile His His Thr Gly Glu His Phe
785                 790                 795                 800

Thr Asn Gly Cys Gln His Asp Asn Arg Pro His Ser Phe Ser Val Tyr
                805                 810                 815

Thr Pro Ser Arg Thr Cys Val Val Tyr Ala Pro Met Asn
            820                 825
```

<210> SEQ ID NO 11
<211> LENGTH: 1267
<212> TYPE: DNA
<213> ORGANISM: Triticum aestivum

<400> SEQUENCE: 11

```
catatggctg ttgccgacaa atggattgaa cttctcaaag gaaacgatga agcttgggag    60
atgggtaata ttgtgcacac actaacaaac agaaggtggc tggaaaagtg tgttacttat   120
gctgaaagtc acgatcaagc acttgttgga gacaagacta ttgcattctg ttgatggac   180
aaggatatgt atgatttcat ggcgctgaac ggaccttcga ctgacctaat attgatcgtg   240
gaatagcact gcataaaatg attagactta tcacaatggg tctaggagga gagggttatc   300
ttaactttat gggaaatgag ttcgggcatc ctgaatggat agactttcca agaggcccac   360
aagtacttcc aagtggtaag ttcatcccag gaaacaacaa cagttacgac aaatgccgtc   420
gaagatttga cctgggtgat gcagaatttc ttaggtatca tggtatgcag cagtttgatc   480
aggcaatgca gcatcttgag gaaaaatatg gttttatgac atcagaccac cagtacgtat   540
ctcggaaaca tgaggaagat aaggtgatcg tgtttgaaaa agggacttg gtatttgtgt   600
tcaacttcca ctggagtagt agctatttcg actaccgggt cggctgttta aagcctggga   660
agtacaaggt ggtcttagac tcagtacgct ggactctttg gtggatttgg taggatccat   720
cacactgcag agcacttcac ttctgactgc aacatgaca acaggcccca ttcattctca   780
gtgtacactc ctagcagaac ctgtgttgtc tatgctccta tatgaactaa cagcaaagtg   840
cagcatacgc gtgcgcgctg ttgttgctag tagcaagaaa aatcgtatgg tccaatacaa   900
ccaggtgcaa ggtttaataa ggattttttgc ttcaacgagt cctggataga caagacaaca   960
tgatgttgtg ctgtgtgctc cccaatcccc agggcgttgt gaagaaaaca tgctcatctg  1020
tgttatttta tggatcagcg acgaaacctc ccccaaatac cccttttttt tttgaaagga  1080
ggataggccc ccggtctctg catctggatg cctccttaaa tctttgtagc cataaaccat  1140
tgctagtgtc ctctaaattg acagtttaga atagaggttc tactttttgta tcttcttttt  1200
gacagttaga ctgtattcct caaataatcg acatgttgtt tactcgaaga tgagaaataa  1260
aatcaga                                                           1267
```

<210> SEQ ID NO 12
<211> LENGTH: 1267
<212> TYPE: DNA
<213> ORGANISM: Triticum aestivum

<400> SEQUENCE: 12

| | |
|---|---|
| catatggctg ttgccgacaa atggattgaa cttctcaaag gaaacgatga agcttgggag | 60 |
| atgggtaata ttgtgcacac actaacaaac agaaggtggc tggaaaagtg tgttacttat | 120 |
| gctgaaagtc acgatcaagc acttgttgga gacaagacta ttgcattctg gttgatggac | 180 |
| aaggatatgt atgatttcat ggcgctgaac ggaccttcga ctgacctaat attgatcgtg | 240 |
| gaatagcact gcataaaatg attagactta tcacaatggg tctaggagga gagggttatc | 300 |
| ttaactttat gggaaatgag ttcgggcatc ctgaatggat agactttcca agaggcccac | 360 |
| aagtacttcc aagtggtaag ttcatcccag gaaacaacaa cagttacgac aaatgccgtc | 420 |
| gaagatttga cctgggtgat gcagaatttc ttaggtatca tggtatgcag cagtttgatc | 480 |
| aggcaatgca gcatcttgag gaaaaatatg gttttatgac atcagaccac cagtacgtat | 540 |
| ctcggaaaca tgaggaagat aaggtgatcg tgtttgaaaa aggggacttg gtatttgtgt | 600 |
| tcaacttcca ctggagtagt agctatttcg actaccgggt cggctgttta aagcctggga | 660 |
| agtacaaggt ggtcttagac tcagtacgct ggactctttg gtggatttgg taggatccat | 720 |
| cacactgcag agcacttcac ttctgactgc aacatgaca acaggcccca ttcattctca | 780 |
| gtgtacactc ctagcagaac ctgtgttgtc tatgctccta tatgaactaa cagcaaagtg | 840 |
| cagcatacgc gtgcgcgctg ttgttgctag tagcaagaaa aatcgtatgg tccaatacaa | 900 |
| ccaggtgcaa ggtttaataa ggattttgc ttcaacgagt cctggataga caagacaaca | 960 |
| tgatgttgtg ctgtgtgctc cccaatcccc agggcgttgt gaagaaaaca tgctcatctg | 1020 |
| tgttatttta tggatcagcg acgaaacctc ccccaaatac ccctttttt tttgaaagga | 1080 |
| ggataggccc ccggtctctg catctggatg cctccttaaa tctttgtagc cataaaccat | 1140 |
| tgctagtgtc ctctaaattg acagtttaga atagaggttc tacttttgta tcttcttttt | 1200 |
| gacagttaga ctgtattcct caaataatcg acatgttgtt tactcgaaga tgagaaataa | 1260 |
| aatcaga | 1267 |

<210> SEQ ID NO 13
<211> LENGTH: 5832
<212> TYPE: DNA
<213> ORGANISM: T. urartu
<220> FEATURE:
<221> NAME/KEY: misc_feature
<222> LOCATION: (3054)..(3054)
<223> OTHER INFORMATION: n is a, c, g, or t
<220> FEATURE:
<221> NAME/KEY: misc_feature
<222> LOCATION: (3955)..(3955)
<223> OTHER INFORMATION: n is a, c, g, or t

<400> SEQUENCE: 13

| | |
|---|---|
| attttagctg ctttctgttt ttggtattct aaatggcagg gccgtatcga cgagtatttt | 60 |
| tccattctat ataattgtgc tacatgactt ctttttctc agatgtatta aaccagttgg | 120 |
| acatcaaatg tatttggtac atctagtaaa ctgacagttt caagaatat cgttttgtaa | 180 |
| tggcaacatg atttgatgcc atagatgtgg actgagaagt tcagatgcta tcaagaaaat | 240 |
| taatcaactg gccatgtact cgtggcacta catagagttt gcaagttgga aaactgacag | 300 |
| caatacctca ctgataagta gctaggcccc acttgccagc ttcatattag atgttacttc | 360 |
| cctgttgaac tcatttgaac atattactta agttcttca tttgtcctaa gtcaaacttc | 420 |
| tttaagtttg accaagtcta ctgaaaaata tatcaacatc tacaaccacca aattggtttc | 480 |
| attagattca caattttat tttgttatat tagcacacct ttgatgttgt agatatcagc | 540 |
| acatttttct acagacttgg tcaaatatag agaagtttga cttaggacaa atctagaact | 600 |

-continued

```
tcaatcaatt tggatcagag gggatagtcc atactggttg attatattcg gtaacatcaa    660
ataatataga tagatgtcaa cactttaaca aaaaatcaga ccttgtcacc aaatatgtat    720
cagaccatct gtttgcttta gccacttgtt ttcatattta tgtgtttgta cctaatctat    780
ttttacttct acttggtttg gttgattttt tttcagttgc attgcttcat caatgatttt    840
gtgtacccct tgacggtttga atggtttcga tggcactgat acacattact tccacggtgg    900
tccacgcggc cacattggat gtgggattct cgtctattca ctatgggagt tgggaagtat    960
gtagctctga cttctgtcac catatttggc taactgttcc tgttaaatct gttcttacac   1020
atgtcgatat tctattctta tgtaggtatt gagattctta ctgtcaaacg cgagatggtg   1080
gcttgaagaa tataagtttg atggatttcg atttgatggg gtgacctcca tgatgtatac   1140
tcaccatgga ttacaagtaa gtcatcaagt ggtttcagta actttttttag ggcactgaaa   1200 taattgctat gcatcataac atgtatcatg atcaggactt gtgctacgga gtcttagata   1260
gttccctagt acgcttgtac aattttacct gatgagatca tggacgattc gaagtgatta   1320
ttatttattt ttcttctaag tttgcttctt gttctagatg acatttactg ggaactatgg   1380
cgagtatttt ggatttgcta ctgatgttga tgcggtagtt tacttgatgc tggtcaacga   1440
tctaattcat ggactttatc ctgatgctgt atccattggt gaagatgtaa gtgcttacag   1500
tatttatgat ttttaaccag ttaagtagtt ttatttggg atcaggctgt tactctttttt   1560 gttaggggta agatctctct tttcataaca atgctaattt ataccttgta tgataatgca   1620
tcacttaggt aatttgaaaa gtgctaggcc attcaagctt acgagcatat ttttttgatgg   1680 ctgtaattta tttgatagta tgcttgtttg ggttttttcag taaatgggag tgtgtgacgg   1740
acatgaaatt atacttcagt gtgttctgta catgtatttg taagagcaag agcaacatgg   1800
tttaacttaa attcctgcac tgctatggaa tctcactgta tgttgttagt gtacacatcc   1860
gcaaacaagt aatcctgagc tttcaactca tgagaaaata tgaggttcca cttctgccag   1920
cattaactgt tcacagttct aatttgtgta actgtgaaat tgttcaggtc agtggaatgc   1980
ccacattttg catccctgtt ccagatggtg gtgttggttt tgactatcgc ctgcatatgg   2040
ctgtagcaga taaatggatt gaactcctca gtaagtgca ggaatattgg tgattacatg   2100
cgcacaatga tctagattac awttttctaaa tggtaaaaag gaaaatatgt atgtgaatat   2160
ctagacattt tcctgttatc agcttgtata cgagaagtca tacatggttt aaatagcaaa   2220
tctcagaaat gtaatggcta gtgtcttttat gctggacatt gtacattgcg ctgtagcagc   2280
cagtcaacac agttagcaat attttcagaa acaataatta tttatatccg tatatgggga   2340
aagtaggtat ataaactgtg gtcattaatt gtgttcacct tttgtcctgt ataagcatgg   2400
gcagtaggta ataaatttag ccagataaaa taaatcgtta ttaggtttac aaaaggaata   2460
tacagggtca tgtagcatat ctagttgtaa ttattgaaaa ggctgacaaa aggctcggta   2520
aaaaaaatcc agatacgcag gaacgcgact aaagctcaaa tatttatagt ggtctctgtt   2580
gcttgctgta tatttgtatc tgcacatata tgaaattact actacacagc tgccaatctg   2640
tcatgatctg tgttctgctt tgtgctattt aaattttaat tcgatacatt ggcaataata   2700
aacttaacta ttcaaccaat ttggtggata ccagagattt ctgccctctt ttcgtaatgt   2760
tgtgctcctg ctgctgttct ctgctgttac aaaagctgtt ctcagttttt ttacatcatt   2820
atttttgtgt gtgagtactt ttagcatgtt tttcgaagct gtgagttgtt ggtacttaat   2880
acattcttgg tagtgtccaa atatgctgca gtctaattta gcatttcttt aacacaggca   2940
```

```
aagtgacgaa tcttggaaaa tgggygatat tgtgcacacc ctaacaaata gaaggtggct   3000
tgagaagtgt gtaaacttat gcagaaagtc atgatcaagc actagttggt gacncgacta   3060
ttgcattctg gttgatggat aaggtactag ctgttacttt tggaccaaaa gaattacaca   3120
attgatttgt ctcatcagat tgctagtgtt ttcttgtgat aaagattggc tgcgtcaccc   3180
atcaccagct atttcccaac tgttacttga gcaaaatttg ctgaaaacgt accatgtggt   3240
actgtggcgg cttgtgaact ttgactgtta tggtgcaaat ttctgttctt attttttga   3300 ttgcttatgt taccgttcat ttgctcatcc ctttcagaga ccagccaaag tcacgtgtag   3360
ctgtgtgatc tattatctga atcttgagca aattttatta atagggtaaa acccaacgaa   3420
ttatttgctt gaattttaat atacagacgt atagtcacct ggtgctttct taaatgatta   3480
ccatagtgcc tgaaggctga aatagttttg gcgtttcttg gacgccgcct aaaggagtga   3540
ttttgggtag attcctggtc gagccctcgt tacaacatac attttggaga tatgcttagt   3600
aactgctctg ggaagtttgg tcacaagtct gcatctacac gctccttgag gttttattat   3660
gacgccatct ttgtaactag tggcagctgt aaggaaaaca attcaaaagg aaacggtcac   3720
attattctag tcaggaccac cacactaaga ggaatattct gttccaattt tatgagtttt   3780
tgggactcca aagggaacaa aagtgtctca tattgtgctt ataactacag ttgttttat   3840 accagtgtag ttccattcca ggacagttga tacttggtac tgtgctgtaa attattgatc   3900
tggcatagaa cagcatgaac atatcaagct ctctttgtgc aggatatgta tgatngcatg   3960
gctctggata ggccttcaac tcccagctct cttgggcagg atatgtagga ttcaggcwyg   4020
ggataggcct tcaactcctc gcattgatcg tggcatagca ttacataaaa tgatcaggct   4080
tgtcaccatg ggtttaggtg gtgaaggcta tcttaacttc atgggaaatg agtttgggca   4140
tcctggtcag tctttacaac ttaattgcat tctgcatagt tgtgatttac tgtaatttga   4200
accatgcttt gttttcacat tgtatgatta tgtaatctgt tgcttccaag gaggaagtta   4260
acttctattt acttggcaga atggatagat tttccaagag gtccgcaaac tcttccaacc   4320
ggcaaagttc tccctggaaa taacaatagt tatgataaat gccgccgtag atttgatctt   4380
gtaagtttta gcttagctat tacatttcct cactagatct ttatcggcca tttatttctt   4440
gatgaaatca taatgtttgt taggaaagat caacattgct tttgtagttt tgtagacgtt   4500
aacataaatt gtgttaagag ttgttgatca ttaagaatat catgattttt tgtagggaga   4560
tgcagatttt cttagatatc gtggtatgca agagttcgat caggcaatgc agcatcttga   4620
ggaaaaatat ggggtatgtc actggttgt ctttgttgca taacaagtca cagtttaaca   4680
ttagtctctt caaatggtca aaaaagtgta gaattaattt ctgtaatgag atgaaaactg   4740
tgcaaaggcg ggagctggaa ttgcttttca ccaattaaaa ctattttctk gagatagtgt   4800
atkgawacct ataccaacac tgacaatgta actgcagttt atgacatctg agcaccagta   4860
tgtttcacgg aaacatgagg aagataaggt gatcatcttc gaaagaggag atttggtatt   4920
tgttttcaac ttccactgga gcaatagctt ttttgactac cgtgttgggt gttccaggcc   4980
tgggaagtac aaggtatgct ttgcttttgc attgtccacc cttcaccagt agggttagtg   5040
ggggcttcta caacttttaa gtccacatgt atagagtttg ttggtcgtgc agctatcaat   5100
ataaagaata ggataatttg taaagaaaag aatttgttgc tcgagctgtt gtagtcatat   5160
aacatccccg aagcacatct actattcatt catattatct acttaagggt tgttacaat   5220 cttgtactc agttggactc actctaatac tggaactatt taccgaatct accctaatca   5280
tcctagcagt tttagagcag ccccatttgg acagtccact gggtttagtt ggtttgtgac   5340
```

-continued

```
agtttctgct atttcttatc aggtggcctt agactccgac gatgcactct ttggtggatt    5400
cagcaggctt gatcatgatg tcgactactt cacaaccgta agtctgggcc caagcgttac    5460
ttgactcgtc ttgactcaac tgcttacaaa tctgaatcaa cttctcattt gctgatgccc    5520
ttgcaggaac atccgcatga acaggccg cgctctttct cggtgtacac tccgagcaga     5580
actgcggtcg tgtatgccct tacagagtaa gaaccagcag ctgcttgtta caaggcaaag    5640
agagaactcc agagagctcg tggatcgtga gcgaagcgac gggcaacggc gcgaggctgc    5700
tctaagcgcc atgactggga ggggatcgtg cctcttcccc agatgccagg aggagcagat    5760
ggataggtag cttgttggtg agcgctcgaa agaaaatgga cgggcctggg tgtttgtcgt    5820
gctgcactac cc                                                        5832
```

<210> SEQ ID NO 14
<211> LENGTH: 739
<212> TYPE: PRT
<213> ORGANISM: T. urartu

<400> SEQUENCE: 14

```
Cys Thr Cys Thr Gly Cys Gly Cys Gly Cys Gly Cys Ala Thr Gly Gly
1               5                   10                  15

Cys Cys Thr Gly Thr Thr Cys Gly Ala Thr Gly Cys Thr Gly Thr Thr
            20                  25                  30

Cys Cys Cys Cys Ala Gly Thr Thr Gly Ala Thr Cys Thr Cys Cys Ala
        35                  40                  45

Thr Cys Ala Ala Cys Gly Ala Gly Ala Gly Ala Thr Ala Gly
    50                  55                  60

Cys Thr Gly Gly Ala Thr Thr Ala Gly Cys Gly Ala Thr Cys Gly
65                  70                  75                  80

Cys Cys Thr Gly Cys Gly Thr Cys Ala Gly Thr Gly Cys Ala Cys
            85                  90                  95

Cys Cys Ala Gly Gly Cys Cys Cys Thr Gly Gly Thr Gly Thr Thr Ala
        100                 105                 110

Thr Cys Ala Cys Gly Gly Cys Thr Thr Thr Gly Ala Thr Cys Ala Thr
    115                 120                 125

Cys Thr Cys Cys Thr Cys Cys Thr Cys Cys Ala Thr Thr Cys Thr
130                 135                 140

Gly Ala Thr Ala Thr Thr Thr Cys Thr Ala Cys Thr Cys Thr
145                 150                 155                 160

Thr Thr Cys Thr Thr Cys Thr Gly Thr Thr Cys Thr Thr Gly Cys Thr
            165                 170                 175

Gly Thr Ala Ala Cys Thr Gly Cys Ala Ala Gly Thr Thr Gly Thr Ala
        180                 185                 190

Gly Cys Ala Thr Thr Gly Thr Cys Thr Cys Ala Cys Thr Ala Thr Thr
    195                 200                 205

Gly Thr Ala Gly Thr Cys Ala Thr Cys Cys Thr Thr Gly Cys Ala Thr
210                 215                 220

Thr Thr Gly Cys Ala Gly Gly Cys Gly Cys Gly Thr Cys Thr
225                 230                 235                 240

Gly Ala Gly Cys Cys Gly Cys Gly Cys Gly Gly Cys Cys Thr Cys Thr
            245                 250                 255

Cys Cys Ala Gly Gly Gly Ala Ala Gly Gly Thr Cys Cys Thr Gly Gly
        260                 265                 270

Thr Gly Cys Cys Thr Gly Ala Cys Gly Gly Thr Gly Ala Gly Ala Gly
```

```
        275                 280                 285

Cys Gly Ala Cys Gly Ala Cys Thr Thr Gly Gly Cys Ala Ala Gly Thr
    290                 295                 300

Cys Cys Gly Gly Cys Gly Cys Ala Ala Cys Cys Thr Gly Ala Ala Gly
305                 310                 315                 320
Ala Ala Thr Thr Ala Cys Ala Gly Gly Thr Ala Cys Ala Cys Ala Cys
                325                 330                 335

Cys Ala Thr Cys Gly Thr Gly Cys Cys Gly Gly Gly Ala Ala Ala Thr
            340                 345                 350
Cys Thr Thr Cys Ala Thr Ala Cys Ala Ala Thr Cys Gly Thr Thr Ala
        355                 360                 365

Thr Thr Cys Ala Cys Thr Thr Ala Cys Cys Ala Ala Ala Thr Gly Cys
    370                 375                 380
Cys Gly Gly Ala Thr Gly Ala Ala Ala Cys Cys Ala Ala Gly Cys Cys
385                 390                 395                 400
Gly Cys Gly Gly Ala Gly Gly Cys Gly Thr Cys Ala Gly Gly Thr Thr
                405                 410                 415

Thr Thr Gly Ala Gly Cys Thr Thr Cys Thr Thr Cys Thr Ala Thr Cys
            420                 425                 430
Ala Gly Cys Ala Thr Thr Gly Thr Gly Cys Ala Gly Thr Ala Cys Thr
        435                 440                 445

Gly Cys Ala Cys Thr Gly Cys Cys Thr Thr Gly Thr Gly Cys Ala Thr
    450                 455                 460
Thr Thr Thr Gly Thr Thr Ala Gly Cys Cys Gly Thr Gly Gly Cys Cys
465                 470                 475                 480
Cys Cys Gly Thr Gly Cys Thr Gly Gly Cys Thr Cys Thr Thr Gly Gly
                485                 490                 495

Gly Cys Cys Ala Cys Thr Gly Ala Ala Ala Ala Cys Thr Cys Ala Gly
            500                 505                 510
Ala Thr Gly Gly Ala Thr Gly Thr Gly Cys Ala Thr Thr Cys Thr Ala
        515                 520                 525

Gly Cys Ala Ala Gly Ala Ala Cys Thr Thr Cys Ala Cys Gly Ala Ala
    530                 535                 540
Ala Thr Ala Ala Thr Gly Cys Ala Cys Thr Gly Thr Thr Thr Gly Thr
545                 550                 555                 560
Gly Gly Thr Thr Thr Cys Gly Thr Thr Ala Gly Thr Cys Thr Gly Cys
                565                 570                 575

Thr Cys Thr Ala Cys Ala Ala Thr Thr Gly Cys Thr Ala Thr Thr Thr
            580                 585                 590

Thr Thr Cys Gly Thr Gly Cys Thr Gly Thr Ala Gly Ala Thr Ala Cys
        595                 600                 605

Cys Thr Gly Ala Ala Gly Ala Cys Ala Thr Cys Gly Ala Gly Gly Ala
    610                 615                 620

Gly Cys Ala Ala Ala Cys Gly Gly Cys Thr Gly Ala Ala Gly Thr Ala
625                 630                 635                 640

Ala Ala Cys Ala Thr Gly Ala Cys Ala Gly Gly Gly Gly Gly Gly Ala
                645                 650                 655

Cys Thr Gly Cys Ala Gly Ala Ala Ala Ala Ala Cys Thr Thr Gly Ala
            660                 665                 670

Ala Thr Cys Thr Thr Cys Ala Gly Ala Ala Cys Cys Gly Ala Cys Thr
        675                 680                 685

Cys Ala Ala Gly Gly Cys Ala Thr Thr Gly Thr Gly Gly Ala Ala Ala
    690                 695                 700
```

```
Cys Ala Ala Thr Cys Ala Cys Thr Gly Ala Thr Gly Thr Gly Thr
705                 710                 715                 720

Ala Ala Cys Cys Ala Ala Gly Gly Ala Gly Thr Thr Ala Ala Gly
                725                 730                 735

Gly Ala Ala

<210> SEQ ID NO 15
<211> LENGTH: 1517
<212> TYPE: PRT
<213> ORGANISM: T. urartu

<400> SEQUENCE: 15

Thr Thr Gly Ala Cys Thr Ala Cys Cys Gly Gly Thr Ala Ala Thr Gly
1               5                   10                  15

Cys Cys Thr Ala Cys Cys Cys Gly Cys Thr Ala Cys Thr Thr Cys
                20                  25                  30

Gly Cys Thr Cys Ala Thr Thr Thr Gly Ala Ala Thr Thr Ala Ala
            35                  40                  45

Gly Gly Thr Cys Cys Thr Thr Thr Cys Gly Thr Cys Ala Thr Gly Cys
        50                  55                  60

Ala Ala Ala Thr Thr Thr Gly Gly Gly Ala Ala Cys Ala Thr Cys
65                  70                  75                  80

Ala Ala Ala Gly Ala Gly Ala Cys Ala Ala Gly Ala Cys Thr Ala
                85                  90                  95

Gly Gly Gly Ala Cys Cys Ala Cys Thr Ala Thr Thr Cys Thr Thr
            100                 105                 110

Ala Cys Ala Gly Thr Thr Cys Cys Cys Thr Cys Ala Thr Gly Gly
        115                 120                 125

Thr Cys Thr Gly Ala Gly Ala Ala Thr Ala Thr Gly Cys Thr Gly Gly
    130                 135                 140

Gly Ala Cys Gly Thr Ala Gly Ala Thr Gly Thr Ala Thr Ala Ala Thr
145                 150                 155                 160

Thr Gly Ala Thr Gly Gly Cys Thr Ala Cys Ala Ala Thr Thr Thr Gly
                165                 170                 175

Cys Thr Cys Ala Thr Ala Ala Thr Thr Ala Cys Gly Ala Thr Ala Cys
                180                 185                 190

Ala Ala Ala Thr Ala Ala Cys Thr Gly Thr Cys Thr Cys Thr Gly Ala
            195                 200                 205

Thr Cys Ala Thr Gly Cys Ala Ala Thr Thr Ala Cys Ala Gly Ala
        210                 215                 220

Gly Thr Gly Gly Cys Ala Ala Ala Cys Thr Gly Ala Thr Thr Ala Ala
225                 230                 235                 240

Ala Ala Thr Gly Thr Gly Ala Thr Ala Gly Ala Thr Gly Gly Thr
                245                 250                 255

Thr Ala Thr Ala Gly Ala Thr Thr Thr Thr Ala Cys Thr Thr Thr Gly
        260                 265                 270

Cys Thr Ala Ala Thr Thr Cys Cys Thr Cys Thr Ala Cys Cys Ala Ala
    275                 280                 285

Ala Thr Thr Cys Cys Thr Gly Gly Gly Ala Ala Ala Ala Ala
        290                 295                 300

Ala Thr Cys Thr Ala Cys Cys Ala Gly Thr Gly Gly Gly Cys Ala
305                 310                 315                 320

Ala Cys Thr Thr Ala Gly Thr Thr Thr Cys Thr Ala Thr Cys Thr
                325                 330                 335
```

-continued

```
Thr Thr Gly Thr Thr Gly Cys Thr Cys Thr Thr Gly Thr Thr
            340                 345                 350
Thr Thr Gly Gly Gly Ala Ala Ala Cys Ala Cys Ala Cys Thr
            355                 360                 365
Gly Cys Thr Ala Ala Ala Thr Thr Thr Gly Ala Ala Thr Gly Ala Thr
370                 375                 380
Thr Thr Thr Gly Gly Thr Ala Thr Gly Cys Cys Thr Cys Gly
385                 390                 395                 400
Thr Gly Gly Ala Thr Thr Cys Ala Ala Cys Ala Gly Ala Thr Ala Cys
                405                 410                 415
Ala Gly Cys Gly Ala Ala Thr Ala Cys Ala Gly Gly Ala Gly Ala Ala
            420                 425                 430
Thr Thr Cys Gly Thr Gly Cys Thr Gly Cys Thr Ala Thr Thr Gly Ala
            435                 440                 445
Cys Cys Ala Ala Cys Ala Thr Gly Ala Ala Gly Gly Thr Gly Gly Ala
            450                 455                 460
Thr Thr Gly Gly Ala Ala Gly Cys Ala Thr Thr Thr Cys Thr Cys
465                 470                 475                 480
Gly Thr Gly Gly Thr Thr Ala Thr Gly Ala Ala Ala Gly Cys Thr
                485                 490                 495
Thr Gly Gly Ala Thr Thr Thr Ala Cys Cys Cys Gly Cys Ala Gly Gly
            500                 505                 510
Thr Ala Ala Ala Thr Thr Ala Ala Ala Gly Cys Thr Cys Ala
            515                 520                 525
Gly Thr Ala Thr Ala Thr Gly Ala Ala Gly Cys Gly Cys Cys Thr
            530                 535                 540
Cys Cys Ala Cys Thr Ala Gly Thr Cys Thr Ala Cys Thr Gly Cys
545                 550                 555                 560
Ala Thr Ala Thr Cys Thr Thr Ala Cys Ala Ala Gly Ala Ala Ala Ala
                565                 570                 575
Thr Thr Thr Ala Thr Ala Ala Thr Thr Cys Cys Thr Gly Thr Thr Thr
            580                 585                 590
Thr Cys Gly Cys Cys Thr Cys Thr Cys Thr Thr Thr Thr Thr Cys
            595                 600                 605
Cys Ala Gly Thr Gly Cys Thr Gly Ala Ala Gly Gly Thr Ala Thr Thr
            610                 615                 620
Gly Thr Cys Thr Ala Gly Thr Thr Gly Cys Ala Thr Ala Thr Cys Thr
625                 630                 635                 640
Thr Ala Thr Ala Ala Gly Ala Ala Ala Thr Thr Ala Thr Gly
                645                 650                 655
Thr Thr Cys Cys Thr Gly Thr Thr Thr Cys Cys Cys Thr Ala
            660                 665                 670
Thr Thr Thr Thr Cys Cys Ala Gly Thr Gly Cys Thr Gly Ala Ala Gly
            675                 680                 685
Gly Thr Ala Thr Cys Ala Cys Thr Ala Cys Cys Gly Ala Gly Ala
            690                 695                 700
Ala Thr Gly Gly Gly Cys Thr Cys Cys Thr Gly Gly Ala Gly Cys Gly
705                 710                 715                 720
Cys Ala Thr Gly Thr Ala Cys Gly Thr Cys Thr Thr Thr Ala Ala
                725                 730                 735
Gly Thr Cys Thr Thr Ala Ala Cys Ala Gly Ala Cys Ala Cys Cys Thr
            740                 745                 750
```

```
Thr Cys Cys Ala Ala Thr Thr Cys Ala Thr Thr Gly Thr Ala Ala
        755                 760                 765
Thr Gly Gly Thr Cys Ala Cys Ala Cys Thr Thr Ala Thr Thr Cys Ala
        770                 775                 780
Cys Cys Ala Ala Cys Thr Ala Gly Cys Thr Thr Ala Cys Thr Gly Gly
785                 790                 795                 800
Ala Cys Thr Thr Ala Cys Ala Ala Cys Thr Thr Ala Gly Cys Thr Thr
                    805                 810                 815
Ala Cys Thr Gly Ala Ala Thr Ala Cys Thr Gly Ala Cys Cys Ala Gly
                820                 825                 830
Thr Thr Gly Cys Thr Cys Thr Ala Ala Ala Thr Thr Thr Ala Thr Gly
            835                 840                 845
Ala Thr Cys Thr Gly Gly Cys Thr Thr Thr Gly Cys Ala Thr Cys
    850                 855                 860
Cys Thr Ala Thr Thr Ala Cys Ala Gly Thr Cys Thr Gly Cys Ala Gly
865                 870                 875                 880
Cys Ala Thr Thr Ala Gly Thr Ala Gly Gly Thr Gly Ala Cys Thr Thr
                    885                 890                 895
Cys Ala Ala Cys Ala Ala Thr Thr Gly Gly Ala Ala Thr Cys Cys Gly
                900                 905                 910
Ala Ala Thr Gly Cys Ala Gly Ala Thr Ala Cys Thr Ala Thr Gly Ala
            915                 920                 925
Cys Cys Ala Gly Ala Gly Thr Ala Thr Gly Thr Cys Thr Ala Cys Ala
    930                 935                 940
Gly Cys Thr Thr Gly Gly Cys Ala Ala Thr Cys Thr Thr Cys Cys Ala
945                 950                 955                 960
Cys Cys Thr Thr Thr Gly Cys Thr Thr Cys Ala Thr Ala Ala Cys Thr
                    965                 970                 975
Ala Cys Thr Gly Ala Thr Ala Cys Ala Thr Cys Thr Ala Thr Thr Thr
                980                 985                 990
Gly Thr Ala Thr Thr Thr Ala Thr Thr Thr Thr Gly Cys Thr Gly Thr
            995                 1000                1005
Thr Thr Gly Cys Ala Cys Ala Thr Thr Cys Cys Thr Thr Ala Ala
    1010                1015                1020
Ala Gly Thr Thr Gly Ala Gly Cys Cys Thr Cys Ala Ala Cys Thr
    1025                1030                1035
Ala Thr Ala Thr Cys Ala Thr Ala Cys Ala Ala Ala Ala Ala Thr
    1040                1045                1050
Gly Gly Thr Ala Thr Ala Ala Thr Thr Thr Gly Thr Cys Ala Gly
    1055                1060                1065
Thr Gly Thr Cys Thr Thr Ala Ala Gly Cys Thr Thr Cys Ala Gly
    1070                1075                1080
Cys Cys Thr Ala Ala Ala Gly Ala Thr Cys Thr Ala Cys Thr
    1085                1090                1095
Gly Ala Ala Ala Thr Thr Gly Gly Thr Cys Cys Ala Thr Cys Thr
    1100                1105                1110
Thr Thr Thr Thr Gly Ala Gly Ala Thr Thr Gly Ala Ala Ala Ala
    1115                1120                1125
Thr Gly Ala Gly Thr Ala Thr Ala Thr Ala Ala Gly Gly Ala
    1130                1135                1140
Thr Gly Ala Ala Thr Gly Ala Ala Thr Ala Gly Gly Thr Gly Cys
    1145                1150                1155
Ala Ala Cys Ala Cys Thr Cys Cys Cys Ala Thr Thr Cys Thr Thr
```

```
                        1160                1165                1170

Thr Gly Gly Thr Ala Gly Ala Ala Cys Cys Thr Thr Cys Thr Ala
        1175                1180                1185

Cys Ala Thr Thr Ala Thr Gly Thr Gly Thr Gly Thr Thr Thr Thr
        1190                1195                1200

Thr Tyr Cys Ala Thr Cys Thr Ala Cys Ala Ala Thr Gly Ala Gly
        1205                1210                1215

Cys Ala Thr Ala Thr Thr Thr Cys Cys Ala Thr Gly Cys Thr Ala
        1220                1225                1230

Thr Cys Ala Gly Thr Gly Ala Ala Gly Gly Thr Thr Gly Cys
        1235                1240                1245

Thr Cys Cys Thr Ala Thr Thr Gly Ala Thr Gly Cys Cys Gly Ala
        1250                1255                1260

Thr Ala Thr Thr Thr Gly Ala Thr Ala Thr Gly Ala Thr Cys Thr
        1265                1270                1275

Thr Thr Thr Cys Ala Gly Gly Ala Thr Gly Ala Thr Thr Ala Thr
        1280                1285                1290

Gly Gly Thr Gly Thr Thr Thr Gly Gly Gly Ala Gly Ala Thr Thr
        1295                1300                1305

Thr Thr Cys Cys Thr Cys Cys Cys Thr Ala Ala Cys Ala Ala Thr
        1310                1315                1320

Gly Cys Thr Gly Ala Thr Gly Gly Ala Thr Cys Cys Cys Cys Ala
        1325                1330                1335

Gly Cys Thr Ala Thr Thr Cys Cys Thr Cys Ala Thr Gly Gly Cys
        1340                1345                1350

Thr Cys Ala Cys Gly Thr Gly Thr Ala Ala Ala Gly Gly Thr Ala
        1355                1360                1365

Ala Gly Cys Thr Gly Gly Cys Cys Ala Ala Thr Thr Ala Thr Thr
        1370                1375                1380

Thr Ala Gly Thr Thr Gly Ala Gly Gly Ala Thr Gly Thr Ala Gly
        1385                1390                1395

Cys Ala Thr Thr Thr Cys Gly Ala Ala Cys Thr Cys Thr Gly
        1400                1405                1410

Cys Cys Cys Ala Cys Thr Ala Ala Gly Gly Thr Cys Cys Cys
        1415                1420                1425

Thr Thr Thr Gly Cys Cys Thr Thr Cys Thr Gly Thr Thr Thr
        1430                1435                1440

Thr Cys Thr Ala Gly Ala Thr Ala Cys Gly Gly Ala Thr Gly Gly
        1445                1450                1455

Ala Thr Ala Cys Thr Cys Cys Ala Thr Cys Thr Gly Gly Thr Gly
        1460                1465                1470

Thr Gly Ala Ala Gly Gly Ala Thr Thr Cys Ala Ala Thr Thr Thr
        1475                1480                1485

Cys Thr Gly Cys Thr Thr Gly Gly Ala Thr Cys Ala Ala Gly Thr
        1490                1495                1500

Thr Cys Thr Cys Thr Gly Thr Gly Cys Ala Gly Gly Cys Thr
        1505                1510                1515
```

<210> SEQ ID NO 16
<211> LENGTH: 17
<212> TYPE: PRT
<213> ORGANISM: Triticum aestivum

<400> SEQUENCE: 16

```
Ala Ala Ser Pro Gly Lys Val Leu Val Pro Asp Gly Glu Ser Asp Asp
1               5                   10                  15

Leu

<210> SEQ ID NO 17
<211> LENGTH: 10
<212> TYPE: PRT
<213> ORGANISM: Triticum aestivum

<400> SEQUENCE: 17

Ala Gly Gly Pro Ser Gly Glu Val Met Ile
1               5                   10

<210> SEQ ID NO 18
<211> LENGTH: 16
<212> TYPE: PRT
<213> ORGANISM: Triticum aestivum

<400> SEQUENCE: 18

Val Ser Ala Pro Arg Asp Tyr Thr Met Ala Thr Ala Glu Asp Gly Val
1               5                   10                  15

<210> SEQ ID NO 19
<211> LENGTH: 22
<212> TYPE: DNA
<213> ORGANISM: Triticum aestivum

<400> SEQUENCE: 19
cccgctgctt tcgctcattt tg                                          22

<210> SEQ ID NO 20
<211> LENGTH: 22
<212> TYPE: DNA
<213> ORGANISM: Triticum aestivum

<400> SEQUENCE: 20
gactaccgga gctcccacct tc                                          22

<210> SEQ ID NO 21
<211> LENGTH: 26
<212> TYPE: DNA
<213> ORGANISM: Triticum aestivum

<400> SEQUENCE: 21
cattcgtcaa ataataccct tgacgg                                      26

<210> SEQ ID NO 22
<211> LENGTH: 24
<212> TYPE: DNA
<213> ORGANISM: Triticum aestivum

<400> SEQUENCE: 22
cttcaccaat ggatacagca tcag                                        24

<210> SEQ ID NO 23
<211> LENGTH: 29
<212> TYPE: DNA
<213> ORGANISM: Triticum aestivum

<400> SEQUENCE: 23
ggtaccggca aatatacgag attgacccg                                   29

<210> SEQ ID NO 24
```

-continued

```
<211> LENGTH: 29
<212> TYPE: DNA
<213> ORGANISM: Triticum aestivum

<400> SEQUENCE: 24
gagctcccac cttcatgttg gtcaatagc                                            29

<210> SEQ ID NO 25
<211> LENGTH: 23
<212> TYPE: DNA
<213> ORGANISM: Triticum aestivum

<400> SEQUENCE: 25
gatacctgaa gatatcgagg agc                                                  23

<210> SEQ ID NO 26
<211> LENGTH: 20
<212> TYPE: DNA
<213> ORGANISM: Triticum aestivum

<400> SEQUENCE: 26
cggtagtcaa gatggctccg                                                      20

<210> SEQ ID NO 27
<211> LENGTH: 21
<212> TYPE: DNA
<213> ORGANISM: Triticum aestivum

<400> SEQUENCE: 27
cacacgttgc tcccccttct c                                                    21

<210> SEQ ID NO 28
<211> LENGTH: 23
<212> TYPE: DNA
<213> ORGANISM: Triticum aestivum

<400> SEQUENCE: 28
gagaggagtc cttcttcctg agg                                                  23

<210> SEQ ID NO 29
<211> LENGTH: 27
<212> TYPE: DNA
<213> ORGANISM: Triticum aestivum

<400> SEQUENCE: 29
gtacaatttt acctgatgag atcatgg                                              27

<210> SEQ ID NO 30
<211> LENGTH: 24
<212> TYPE: DNA
<213> ORGANISM: Triticum aestivum

<400> SEQUENCE: 30
cttcaggaat ggatacagca tcag                                                 24

<210> SEQ ID NO 31
<211> LENGTH: 21
<212> TYPE: DNA
<213> ORGANISM: Triticum aestivum

<400> SEQUENCE: 31
acgatgcact ctttggtgga t                                                    21
```

```
<210> SEQ ID NO 32
<211> LENGTH: 26
<212> TYPE: DNA
<213> ORGANISM: Triticum aestivum

<400> SEQUENCE: 32
acttacggtt gtgaagtagt cgacat                                          26

<210> SEQ ID NO 33
<211> LENGTH: 16
<212> TYPE: DNA
<213> ORGANISM: Triticum aestivum

<400> SEQUENCE: 33
cagcaggctt gatcat                                                     16

<210> SEQ ID NO 34
<211> LENGTH: 24
<212> TYPE: DNA
<213> ORGANISM: Triticum aestivum

<400> SEQUENCE: 34
gatccgaata gctggctcaa gtat                                            24

<210> SEQ ID NO 35
<211> LENGTH: 23
<212> TYPE: DNA
<213> ORGANISM: Triticum aestivum

<400> SEQUENCE: 35
ggagactgca ggtagggatc aac                                             23

<210> SEQ ID NO 36
<211> LENGTH: 19
<212> TYPE: DNA
<213> ORGANISM: Triticum aestivum

<400> SEQUENCE: 36
gttcgatgct gttccccag                                                  19

<210> SEQ ID NO 37
<211> LENGTH: 19
<212> TYPE: DNA
<213> ORGANISM: Triticum aestivum

<400> SEQUENCE: 37
agccgtttgc tcctcgatg                                                  19

<210> SEQ ID NO 38
<211> LENGTH: 20
<212> TYPE: DNA
<213> ORGANISM: Triticum aestivum

<400> SEQUENCE: 38
ttccccagtt gatctccatc                                                 20

<210> SEQ ID NO 39
<211> LENGTH: 22
<212> TYPE: DNA
<213> ORGANISM: Triticum aestivum

<400> SEQUENCE: 39
cttactgaat actgaccagt tg                                              22
```

```
<210> SEQ ID NO 40
<211> LENGTH: 25
<212> TYPE: DNA
<213> ORGANISM: Triticum aestivum

<400> SEQUENCE: 40
tttatgatct ggcttttgca tccta                                           25

<210> SEQ ID NO 41
<211> LENGTH: 23
<212> TYPE: DNA
<213> ORGANISM: Triticum aestivum

<400> SEQUENCE: 41
gatgttcccc aaatttgcat gac                                             23

<210> SEQ ID NO 42
<211> LENGTH: 22
<212> TYPE: DNA
<213> ORGANISM: Triticum aestivum

<400> SEQUENCE: 42
aatgcacaag gcagtgaagt ag                                              22

<210> SEQ ID NO 43
<211> LENGTH: 20
<212> TYPE: DNA
<213> ORGANISM: Triticum aestivum

<400> SEQUENCE: 43
cccaattgat ctccatgagt                                                 20

<210> SEQ ID NO 44
<211> LENGTH: 21
<212> TYPE: DNA
<213> ORGANISM: Triticum aestivum

<400> SEQUENCE: 44
aaccccaaac ggtgcattat g                                               21

<210> SEQ ID NO 45
<211> LENGTH: 19
<212> TYPE: DNA
<213> ORGANISM: Triticum aestivum

<400> SEQUENCE: 45
cggctttgat cattcctcg                                                  19

<210> SEQ ID NO 46
<211> LENGTH: 23
<212> TYPE: DNA
<213> ORGANISM: Triticum aestivum

<400> SEQUENCE: 46
gctagaatgc acatccatct gat                                             23

<210> SEQ ID NO 47
<211> LENGTH: 19
<212> TYPE: DNA
<213> ORGANISM: Triticum aestivum

<400> SEQUENCE: 47
gtaactgcaa gttgtggcg                                                  19
```

<210> SEQ ID NO 48
<211> LENGTH: 26
<212> TYPE: DNA
<213> ORGANISM: Triticum aestivum

<400> SEQUENCE: 48
gcttactgaa tactgaccag ttacta                                  26

<210> SEQ ID NO 49
<211> LENGTH: 24
<212> TYPE: DNA
<213> ORGANISM: Triticum aestivum

<400> SEQUENCE: 49
ccttaattca aaatgagcga aagc                                    24

<210> SEQ ID NO 50
<211> LENGTH: 20
<212> TYPE: DNA
<213> ORGANISM: Triticum aestivum

<400> SEQUENCE: 50
ggctaactgt tcctgttaaa                                         20

<210> SEQ ID NO 51
<211> LENGTH: 20
<212> TYPE: DNA
<213> ORGANISM: Triticum aestivum

<400> SEQUENCE: 51
gatgagatca tggacgattc                                         20

<210> SEQ ID NO 52
<211> LENGTH: 20
<212> TYPE: PRT
<213> ORGANISM: Triticum aestivum

<400> SEQUENCE: 52

Ala Ala Thr Ala Ala Ala Thr Ala Ala Thr Ala Ala Thr Cys Ala Cys
 1               5                  10                  15

Thr Thr Cys Gly
         20

<210> SEQ ID NO 53
<211> LENGTH: 20
<212> TYPE: DNA
<213> ORGANISM: Triticum aestivum

<400> SEQUENCE: 53
gagtaacagc ctgatcccaa                                         20

<210> SEQ ID NO 54
<211> LENGTH: 20
<212> TYPE: DNA
<213> ORGANISM: Triticum aestivum

<400> SEQUENCE: 54
taacaaaaag agtaacagcc                                         20

<210> SEQ ID NO 55
<211> LENGTH: 19
<212> TYPE: DNA

```
<213> ORGANISM: Triticum aestivum

<400> SEQUENCE: 55
gtcaatctgt tcttacacg                                              19

<210> SEQ ID NO 56
<211> LENGTH: 20
<212> TYPE: DNA
<213> ORGANISM: Triticum aestivum

<400> SEQUENCE: 56
caaaaagagt agtaacagct                                             20

<210> SEQ ID NO 57
<211> LENGTH: 20
<212> TYPE: DNA
<213> ORGANISM: Triticum aestivum

<400> SEQUENCE: 57
caaggtataa attagcattc                                             20

<210> SEQ ID NO 58
<211> LENGTH: 20
<212> TYPE: DNA
<213> ORGANISM: Triticum aestivum

<400> SEQUENCE: 58
gttttatttt ggggatcagt                                             20

<210> SEQ ID NO 59
<211> LENGTH: 22
<212> TYPE: DNA
<213> ORGANISM: Triticum aestivum

<400> SEQUENCE: 59
ccctaacaaa aagtgtaaca ga                                          22

<210> SEQ ID NO 60
<211> LENGTH: 20
<212> TYPE: DNA
<213> ORGANISM: Triticum aestivum

<400> SEQUENCE: 60
atcagacctt gtcaccaaat                                             20

<210> SEQ ID NO 61
<211> LENGTH: 21
<212> TYPE: DNA
<213> ORGANISM: Triticum aestivum

<400> SEQUENCE: 61
gcacttacat cttcaccaat g                                           21

<210> SEQ ID NO 62
<211> LENGTH: 22
<212> TYPE: DNA
<213> ORGANISM: Triticum aestivum

<400> SEQUENCE: 62
gccttctgaa gcaattgaca ag                                          22

<210> SEQ ID NO 63
<211> LENGTH: 20
```

```
<212> TYPE: DNA
<213> ORGANISM: Triticum aestivum

<400> SEQUENCE: 63
ggctaactgt tcctgttaaa                                              20

<210> SEQ ID NO 64
<211> LENGTH: 20
<212> TYPE: DNA
<213> ORGANISM: Triticum aestivum

<400> SEQUENCE: 64
cgacatgtgt aagaacagat                                              20

<210> SEQ ID NO 65
<211> LENGTH: 21
<212> TYPE: DNA
<213> ORGANISM: Triticum aestivum

<400> SEQUENCE: 65
gtcgatattc tattcttatg t                                            21

<210> SEQ ID NO 66
<211> LENGTH: 20
<212> TYPE: DNA
<213> ORGANISM: Triticum aestivum

<400> SEQUENCE: 66
cttttttagg gcactgaaat                                              20

<210> SEQ ID NO 67
<211> LENGTH: 20
<212> TYPE: DNA
<213> ORGANISM: Triticum aestivum

<400> SEQUENCE: 67
gttatgatgc atagcaatta                                              20

<210> SEQ ID NO 68
<211> LENGTH: 21
<212> TYPE: DNA
<213> ORGANISM: Triticum aestivum

<400> SEQUENCE: 68
tcttagatag ttccctagta c                                            21

<210> SEQ ID NO 69
<211> LENGTH: 20
<212> TYPE: DNA
<213> ORGANISM: Triticum aestivum

<400> SEQUENCE: 69
caggtaaaat tgtacaagcg                                              20

<210> SEQ ID NO 70
<211> LENGTH: 19
<212> TYPE: DNA
<213> ORGANISM: Triticum aestivum

<400> SEQUENCE: 70
acctgatgag atcatggac                                               19

<210> SEQ ID NO 71
```

```
<211> LENGTH: 20
<212> TYPE: DNA
<213> ORGANISM: Triticum aestivum

<400> SEQUENCE: 71
tacctgatga gatcatggac                                                    20

<210> SEQ ID NO 72
<211> LENGTH: 20
<212> TYPE: DNA
<213> ORGANISM: Triticum aestivum

<400> SEQUENCE: 72
gatgagatca tggacgattc                                                    20

<210> SEQ ID NO 73
<211> LENGTH: 20
<212> TYPE: DNA
<213> ORGANISM: Triticum aestivum

<400> SEQUENCE: 73
aataaataat aatcacttcg                                                    20

<210> SEQ ID NO 74
<211> LENGTH: 19
<212> TYPE: DNA
<213> ORGANISM: Triticum aestivum

<400> SEQUENCE: 74 tcttttgtt aggggtaag                                                      19

<210> SEQ ID NO 75
<211> LENGTH: 19
<212> TYPE: DNA
<213> ORGANISM: Triticum aestivum

<400> SEQUENCE: 75
agtttgacca agtctactg                                                     19

<210> SEQ ID NO 76
<211> LENGTH: 20
<212> TYPE: DNA
<213> ORGANISM: Triticum aestivum

<400> SEQUENCE: 76
atcagacctt gtcaccaaat                                                    20

<210> SEQ ID NO 77
<211> LENGTH: 21
<212> TYPE: DNA
<213> ORGANISM: Triticum aestivum

<400> SEQUENCE: 77
gcacttacat cttcaccaat g                                                  21

<210> SEQ ID NO 78
<211> LENGTH: 18
<212> TYPE: DNA
<213> ORGANISM: Triticum aestivum

<400> SEQUENCE: 78
gtagttataa gcaatatg                                                      18
```

```
<210> SEQ ID NO 79
<211> LENGTH: 20
<212> TYPE: DNA
<213> ORGANISM: Triticum aestivum

<400> SEQUENCE: 79
catcaagtgg tttcagtaac                                               20

<210> SEQ ID NO 80
<211> LENGTH: 20
<212> TYPE: DNA
<213> ORGANISM: Triticum aestivum

<400> SEQUENCE: 80
gttactgaaa ccacttgatg                                               20

<210> SEQ ID NO 81
<211> LENGTH: 20
<212> TYPE: DNA
<213> ORGANISM: Triticum aestivum

<400> SEQUENCE: 81
ttgggatcag gctgttactc                                               20

<210> SEQ ID NO 82
<211> LENGTH: 20
<212> TYPE: DNA
<213> ORGANISM: Triticum aestivum

<400> SEQUENCE: 82
gagtaacagc ctgatcccaa                                               20

<210> SEQ ID NO 83
<211> LENGTH: 20
<212> TYPE: DNA
<213> ORGANISM: Triticum aestivum

<400> SEQUENCE: 83
ggctgttact cttttttgtta                                              20

<210> SEQ ID NO 84
<211> LENGTH: 20
<212> TYPE: DNA
<213> ORGANISM: Triticum aestivum

<400> SEQUENCE: 84
taacaaaaag agtaacagcc                                               20

<210> SEQ ID NO 85
<211> LENGTH: 18
<212> TYPE: DNA
<213> ORGANISM: Triticum aestivum

<400> SEQUENCE: 85
ttaaccagtt aagtagtt                                                 18

<210> SEQ ID NO 86
<211> LENGTH: 18
<212> TYPE: DNA
<213> ORGANISM: Triticum aestivum

<400> SEQUENCE: 86
aactacttaa ctggttaa                                                 18
```

<210> SEQ ID NO 87
<211> LENGTH: 21
<212> TYPE: DNA
<213> ORGANISM: Triticum aestivum

<400> SEQUENCE: 87
gatcccaaaa taaaactact t                                              21

<210> SEQ ID NO 88
<211> LENGTH: 18
<212> TYPE: DNA
<213> ORGANISM: Triticum aestivum

<400> SEQUENCE: 88
cccaaaataa aactactt                                                  18

<210> SEQ ID NO 89
<211> LENGTH: 16
<212> TYPE: DNA
<213> ORGANISM: Triticum aestivum

<400> SEQUENCE: 89
gtgggattct cgtctg                                                    16

<210> SEQ ID NO 90
<211> LENGTH: 19
<212> TYPE: DNA
<213> ORGANISM: Triticum aestivum

<400> SEQUENCE: 90
ttgggaagta tgtagctgc                                                 19

<210> SEQ ID NO 91
<211> LENGTH: 19
<212> TYPE: DNA
<213> ORGANISM: Triticum aestivum

<400> SEQUENCE: 91
ttggctaact gttcctgtc                                                 19

<210> SEQ ID NO 92
<211> LENGTH: 19
<212> TYPE: DNA
<213> ORGANISM: Triticum aestivum

<400> SEQUENCE: 92
gtcaatctgt tcttacacg                                                 19

<210> SEQ ID NO 93
<211> LENGTH: 20
<212> TYPE: DNA
<213> ORGANISM: Triticum aestivum

<400> SEQUENCE: 93
atctgttctt acacgtgtca                                                20

<210> SEQ ID NO 94
<211> LENGTH: 20
<212> TYPE: DNA
<213> ORGANISM: Triticum aestivum

<400> SEQUENCE: 94
gtcaatattc tattcttata                                                20

<210> SEQ ID NO 95
<211> LENGTH: 20
<212> TYPE: DNA
<213> ORGANISM: Triticum aestivum

<400> SEQUENCE: 95
ctattcttat acaggtatta                                              20

<210> SEQ ID NO 96
<211> LENGTH: 21
<212> TYPE: DNA
<213> ORGANISM: Triticum aestivum

<400> SEQUENCE: 96
aacgcgagat ggtggcttga t                                            21

<210> SEQ ID NO 97
<211> LENGTH: 20
<212> TYPE: DNA
<213> ORGANISM: Triticum aestivum

<400> SEQUENCE: 97
caagtggttt cagtaacttc                                              20

<210> SEQ ID NO 98
<211> LENGTH: 19
<212> TYPE: DNA
<213> ORGANISM: Triticum aestivum

<400> SEQUENCE: 98
tggtttcagt aacttcttc                                               19

<210> SEQ ID NO 99
<211> LENGTH: 19
<212> TYPE: DNA
<213> ORGANISM: Triticum aestivum

<400> SEQUENCE: 99
ggaagattgg aagtgattg                                               19

<210> SEQ ID NO 100
<211> LENGTH: 19
<212> TYPE: DNA
<213> ORGANISM: Triticum aestivum

<400> SEQUENCE: 100
tggaagtgat tgttattat                                               19

<210> SEQ ID NO 101
<211> LENGTH: 20
<212> TYPE: DNA
<213> ORGANISM: Triticum aestivum

<400> SEQUENCE: 101
ttgcttcttg ttctagatgg                                              20

<210> SEQ ID NO 102
<211> LENGTH: 21
<212> TYPE: DNA
<213> ORGANISM: Triticum aestivum

<400> SEQUENCE: 102

```
ttcccaactc ccatagtgaa c                                              21

<210> SEQ ID NO 103
<211> LENGTH: 21
<212> TYPE: DNA
<213> ORGANISM: Triticum aestivum

<400> SEQUENCE: 103
caaatatggt gacagaagtc g                                              21

<210> SEQ ID NO 104
<211> LENGTH: 19
<212> TYPE: DNA
<213> ORGANISM: Triticum aestivum

<400> SEQUENCE: 104
cacgtgtaag aacagattg                                                 19

<210> SEQ ID NO 105
<211> LENGTH: 18
<212> TYPE: DNA
<213> ORGANISM: Triticum aestivum

<400> SEQUENCE: 105
agaatagaat attgacac                                                  18

<210> SEQ ID NO 106
<211> LENGTH: 20
<212> TYPE: DNA
<213> ORGANISM: Triticum aestivum

<400> SEQUENCE: 106
gtaagaatct taatacctgt                                                20

<210> SEQ ID NO 107
<211> LENGTH: 22
<212> TYPE: DNA
<213> ORGANISM: Triticum aestivum

<400> SEQUENCE: 107
cgcgtttgac agtaagaatc tt                                             22

<210> SEQ ID NO 108
<211> LENGTH: 18
<212> TYPE: DNA
<213> ORGANISM: Triticum aestivum

<400> SEQUENCE: 108
ccatcaaact tatattca                                                  18

<210> SEQ ID NO 109
<211> LENGTH: 22
<212> TYPE: DNA
<213> ORGANISM: Triticum aestivum

<400> SEQUENCE: 109
caattgtttc agtgccctga ag                                             22

<210> SEQ ID NO 110
<211> LENGTH: 20
<212> TYPE: DNA
<213> ORGANISM: Triticum aestivum

<400> SEQUENCE: 110
```

```
gcaattgttt cagtgccctg                                                    20

<210> SEQ ID NO 111
<211> LENGTH: 21
<212> TYPE: DNA
<213> ORGANISM: Triticum aestivum

<400> SEQUENCE: 111
cttagaagaa aaataataa c                                                   21

<210> SEQ ID NO 112
<211> LENGTH: 19
<212> TYPE: DNA
<213> ORGANISM: Triticum aestivum

<400> SEQUENCE: 112
gcaaacttag aagaaaaaa                                                     19

<210> SEQ ID NO 113
<211> LENGTH: 20
<212> TYPE: DNA
<213> ORGANISM: Triticum aestivum

<400> SEQUENCE: 113
ccatagttcc cagtaaatgc                                                    20

<210> SEQ ID NO 114
<211> LENGTH: 18
<212> TYPE: DNA
<213> ORGANISM: Triticum aestivum

<400> SEQUENCE: 114
ctactattaa attaactg                                                      18

<210> SEQ ID NO 115
<211> LENGTH: 22
<212> TYPE: DNA
<213> ORGANISM: Triticum aestivum

<400> SEQUENCE: 115
atccccaaaa taaaactact at                                                 22

<210> SEQ ID NO 116
<211> LENGTH: 20
<212> TYPE: DNA
<213> ORGANISM: Triticum aestivum

<400> SEQUENCE: 116
caaaaagagt agtaacagct                                                    20

<210> SEQ ID NO 117
<211> LENGTH: 20
<212> TYPE: DNA
<213> ORGANISM: Triticum aestivum

<400> SEQUENCE: 117
caaggtataa attagcattc                                                    20

<210> SEQ ID NO 118
<211> LENGTH: 18
<212> TYPE: DNA
<213> ORGANISM: Triticum aestivum
```

<400> SEQUENCE: 118
gcattcttat gaaaagac                                         18

<210> SEQ ID NO 119
<211> LENGTH: 18
<212> TYPE: DNA
<213> ORGANISM: Triticum aestivum

<400> SEQUENCE: 119
tctgttctta cacatgtt                                         18

<210> SEQ ID NO 120
<211> LENGTH: 20
<212> TYPE: DNA
<213> ORGANISM: Triticum aestivum

<400> SEQUENCE: 120
cttttttagg gcactgaaac                                       20

<210> SEQ ID NO 121
<211> LENGTH: 30
<212> TYPE: DNA
<213> ORGANISM: Triticum aestivum

<400> SEQUENCE: 121
gattattatt tattttcctt ctaagtttgt                            30

<210> SEQ ID NO 122
<211> LENGTH: 24
<212> TYPE: DNA
<213> ORGANISM: Triticum aestivum

<400> SEQUENCE: 122
acctgatgag atcatggaag attg                                  24

<210> SEQ ID NO 123
<211> LENGTH: 19
<212> TYPE: DNA
<213> ORGANISM: Triticum aestivum

<400> SEQUENCE: 123
gtgattatta tttattttc                                        19

<210> SEQ ID NO 124
<211> LENGTH: 21
<212> TYPE: DNA
<213> ORGANISM: Triticum aestivum

<400> SEQUENCE: 124
ttattttcct tctaagtttg t                                     21

<210> SEQ ID NO 125
<211> LENGTH: 19
<212> TYPE: DNA
<213> ORGANISM: Triticum aestivum

<400> SEQUENCE: 125
gtgattatta tttattttc                                        19

<210> SEQ ID NO 126
<211> LENGTH: 23
<212> TYPE: DNA
<213> ORGANISM: Triticum aestivum

```
<400> SEQUENCE: 126
tgatgcggta gtttacttga tgt                                              23

<210> SEQ ID NO 127
<211> LENGTH: 23
<212> TYPE: DNA
<213> ORGANISM: Triticum aestivum

<400> SEQUENCE: 127
gatttttaac tagttaagta gtt                                              23

<210> SEQ ID NO 128
<211> LENGTH: 20
<212> TYPE: DNA
<213> ORGANISM: Triticum aestivum

<400> SEQUENCE: 128
gttttatttt ggggatcagt                                                  20

<210> SEQ ID NO 129
<211> LENGTH: 22
<212> TYPE: DNA
<213> ORGANISM: Triticum aestivum

<400> SEQUENCE: 129
cctgcataag aatagaatat ca                                               22

<210> SEQ ID NO 130
<211> LENGTH: 23
<212> TYPE: DNA
<213> ORGANISM: Triticum aestivum

<400> SEQUENCE: 130
catgttatga tgcatagcaa ttg                                              23

<210> SEQ ID NO 131
<211> LENGTH: 24
<212> TYPE: DNA
<213> ORGANISM: Triticum aestivum

<400> SEQUENCE: 131
gtaaatgtca tctagaacaa gaaa                                             24

<210> SEQ ID NO 132
<211> LENGTH: 20
<212> TYPE: DNA
<213> ORGANISM: Triticum aestivum

<400> SEQUENCE: 132
caagaaacaa acttagaagg                                                  20

<210> SEQ ID NO 133
<211> LENGTH: 21
<212> TYPE: DNA
<213> ORGANISM: Triticum aestivum

<400> SEQUENCE: 133
acaaacttag aaggaaaata a                                                21

<210> SEQ ID NO 134
<211> LENGTH: 23
<212> TYPE: DNA
```

```
<213> ORGANISM: Triticum aestivum

<400> SEQUENCE: 134
catcagtagc aaatccaaaa tat                                          23

<210> SEQ ID NO 135
<211> LENGTH: 20
<212> TYPE: DNA
<213> ORGANISM: Triticum aestivum

<400> SEQUENCE: 135
accccgtaat tattggcgct                                              20

<210> SEQ ID NO 136
<211> LENGTH: 21
<212> TYPE: DNA
<213> ORGANISM: Triticum aestivum

<400> SEQUENCE: 136
actctgatga tctgaaggta g                                            21

<210> SEQ ID NO 137
<211> LENGTH: 19
<212> TYPE: DNA
<213> ORGANISM: Triticum aestivum

<400> SEQUENCE: 137
tcatgcaggc aggtactag                                               19

<210> SEQ ID NO 138
<211> LENGTH: 23
<212> TYPE: DNA
<213> ORGANISM: Triticum aestivum

<400> SEQUENCE: 138
gtggcagaat gcgtaatttc tct                                          23

<210> SEQ ID NO 139
<211> LENGTH: 20
<212> TYPE: DNA
<213> ORGANISM: Triticum aestivum

<400> SEQUENCE: 139
cagcgatctt acgttcccta                                              20

<210> SEQ ID NO 140
<211> LENGTH: 19
<212> TYPE: DNA
<213> ORGANISM: Triticum aestivum

<400> SEQUENCE: 140
atgtctgtag gtgccgtca                                               19

<210> SEQ ID NO 141
<211> LENGTH: 25
<212> TYPE: DNA
<213> ORGANISM: Triticum aestivum

<400> SEQUENCE: 141
caacaaatta gaaagaggat attcc                                        25

<210> SEQ ID NO 142
<211> LENGTH: 24
```

<212> TYPE: DNA
<213> ORGANISM: Triticum aestivum

<400> SEQUENCE: 142
ccgtagatga ttctttgtcc atta                                    24

<210> SEQ ID NO 143
<211> LENGTH: 21
<212> TYPE: DNA
<213> ORGANISM: Triticum aestivum

<400> SEQUENCE: 143
atggaaccta acacaatgtg c                                       21

<210> SEQ ID NO 144
<211> LENGTH: 19
<212> TYPE: DNA
<213> ORGANISM: Triticum aestivum

<400> SEQUENCE: 144
gcgccacctt tctcactca                                          19

<210> SEQ ID NO 145
<211> LENGTH: 19
<212> TYPE: DNA
<213> ORGANISM: Triticum aestivum

<400> SEQUENCE: 145
cggtcccgtt cagttcgat                                          19

<210> SEQ ID NO 146
<211> LENGTH: 21
<212> TYPE: DNA
<213> ORGANISM: Triticum aestivum

<400> SEQUENCE: 146
cctgagtaaa tactgccacc a                                       21

<210> SEQ ID NO 147
<211> LENGTH: 22
<212> TYPE: DNA
<213> ORGANISM: Triticum aestivum

<400> SEQUENCE: 147
agaatgcgta atttctccct cg                                      22

<210> SEQ ID NO 148
<211> LENGTH: 24
<212> TYPE: DNA
<213> ORGANISM: Triticum aestivum

<400> SEQUENCE: 148
tgtcttcagc atcaatttct tcac                                    24

<210> SEQ ID NO 149
<211> LENGTH: 22
<212> TYPE: DNA
<213> ORGANISM: Triticum aestivum

<400> SEQUENCE: 149
ctgtaggctt gtttcatcat ca                                      22

<210> SEQ ID NO 150

<211> LENGTH: 2970
<212> TYPE: DNA
<213> ORGANISM: Triticum aestivum

<400> SEQUENCE: 150

```
cgccagcttc acccccgcc gcacacgttg ctcccccttc tcatcgcttc tcaattaata      60
tctccatcac tcgggttccg cgctgcattt cggccggcgg gttgagtgag atctgggcca     120
ctgaccgact cactcgctcg ctgcgcgggg atggcgacgt tcgcggtgtc cggcgcgacc     180
ctcggtgtgg cgcggcccgc cggcgccggc ggcggactgc tgccgcgatc cggctcggag     240
cggaggggcg gggtggacct gccgtcgctg ctcctcagga agaaggactc ctctcgcgcc     300
gtcctgagcc gcgcggcctc tccagggaag gtcctggtgc ctgacggtga gagcgacgac     360
ttggcaagtc cggcgcaacc tgaagaatta cagatacctg aagacatcga ggagcaaacg     420
gctgaagtaa acatgacagg ggggactgca gaaaaacttg aatcttcaga accgactcaa     480
ggcattgtgg aaacaatcac tgatggtgta accaaaggag ttaaggaact agtcgtgggg     540
gagaaaccgc gagttgtccc aaaaccagga gatgggcaga aaatatacga gattgaccca     600
acgctgaaag attttcggag ccatcttgac taccgataca gcgaatacag gagaattcgt     660
gctgctattg accaacatga aggtggattg aagcattttt ctcgtggtta tgaaaagctt     720
ggatttaccc gcagtgctga aggtatcact taccgagaat gggctcctgg agcgcattct     780
gcagcattag taggtgactt caacaattgg aatccgaatg cagatactat gaccagagat     840
gattatggtg tttgggagat ttcctcccct aacaatgctg atggatcccc agctattcct     900
catggctcac gtgtaaagat acggatggat actccatctg gtgtgaagga ttcaatttct     960
gcttggatca agttctctgt gcaggctcca ggtgaaatac cattcaatgg catatattat    1020
gatccacctg aagaggagaa gtatgtcttc caacatcctc aacctaaacg accagagtca    1080
ctgaggattt atgaatcaca cattggaatg agcagcccag aaccgaagat aaattcatat    1140
gctaattttta gggatgaggt gctgccaaga attaaaaggc ttggatacaa tgcagtgcag    1200
ataatggcaa tccaggagca ttcatactat gcgagctttg ggtaccatgt tactaatttt    1260
tttgcaccaa gtagccgttt tggaactcca gaggacttaa atccctgat cgatagagca    1320
catgagcttg gtttgcttgt tcttatggat attgttcata gtcattcatc aaataatacc    1380
cttgacggct tgaatggttt cgatggcact gatacacatt acttccacgg tggtccacgt    1440
ggccatcatt ggatgtggga ttctcgtcta ttcaactatg ggagttggga agtattgaga    1500
ttcttactgt caaacgcgag atggtggctt gaagaatata agtttgatgg atttcgatt     1560
gatggggtga cctccatgat gtatactcac catggattac aaatgacatt tactgggaac    1620
tatgcgagt atttttggatt tgctactgat gttgatgcgg tagtttactt gatgctggtc    1680
aacgatctaa ttcatggact tcatcctgat gctgtatcca ttggtgaaga tgtcagtgga    1740
atgcccacat tttgcatccc tgttccagat ggtggtgttg gtttggacta tcgcttgcat    1800
atggctgtag cagataaatg gattgaactc ctcaagcaaa gtgacgaatc ttggaaaatg    1860
ggtgatattg tgcacaccct aacaaataga aggtggcttg agaagtgtgt aacttatgca    1920
gaaagtcatg atcaagcact agttggtgac aagactattg cattctggtt gatggataag    1980
gatatgtatg atttcatggc tctggatagg ccttcaactc ctcgcattga tcgtggcata    2040
gcattacata aaatgatcag gcttgtcacc atgggtttag gtggtgaagg ctatcttaac    2100
ttcatgggaa atgagtttgg gcatcctgaa tggatagatt ttccaagagg tccgcaaact    2160
cttccaaccg gcaaagttct ccctggaaat aacaatagtt atgataaatg ccgccgtaga    2220
```

```
tttgatcttg gagatgcaga ttttcttaga tatcatggta tgcaagagtt cgatcaggca      2280
atgcagcatc ttgaggaaaa atatgggttt atgacatctg agcaccagta tgtttcacgg      2340
aaacatgagg aagataaggt gatcatcttc gaaagaggag atttggtatt tgttttcaac      2400
ttccactgga gcaatagctt ttttgactac cgtgttgggt gttccaggcc tgggaagtac      2460
aaggtggcct tagactccga cgatgcactc tttggtggat tcagcaggct tgatcatgat      2520
gtcgactact tcacaaccga acatccgcat gacaacaggc cgcgctcttt ctcggtgtac      2580
actccgagca gaactgcggt cgtgtatgcc cttacagagt aagaaccagc agctgcttgt      2640
tacaaggcaa agagagaact ccagagagct cgtggatcgt gagcgaagcg acgggcaacg      2700
gcgcgaggct gctctaagcg ccatgactgg gaggggatcg tgcctcttcc ccagatgcca      2760
ggaggagcag atggataggt agcttgttgg tgagcgctcg aaagaaaatg acgggcctg      2820 ggtgtttgtc gtgctgcact accctcctcc tatcttgcac attcccggtt gttttgtac      2880 atataactaa taattgcccg tgcgctccac gtgaacatat aaatattcta ataataggtt      2940
atcccgtgaa aaaaaaaaa aaaaaaaaa                                          2970

<210> SEQ ID NO 151
<211> LENGTH: 2760
<212> TYPE: DNA
<213> ORGANISM: Aegilops tauschii

<400> SEQUENCE: 151
atggcgacgt tcgcggtgtc cggcgcgact ctcggtgtgg cgcgggccgg cgtcggagtg        60
gcgcgggccg gctcggagcg gaggggcggg gcggacttgc cgtcgctgct cctcaggaag       120
aaggactcct ctcgcgccgt cctgagccgc gcggcctctc cagggaaggt cctggtgcct       180
gacggcgaga gcgacgactt ggcaagtccg gcgcaacctg aagaattaca gatacctgaa       240
gatatcgagg agcaaacggc ggaagtgaac atgacagggg ggactgcaga gaaacttcaa       300
tcttcagaac cgactcaggg cattgtggaa acaatcactg atggtgtaac caaaggagtt       360
aaggaactag tcgtggggga gaaaccgcga gttgtcccaa accaggaga tgggcagaaa        420 atatacgaga ttgacccaac actgaaagat tttcggagcc atcttgacta ccgatacagc       480
gaatacaaga gaattcgtgc tgctattgac caacatgaag gtggattgga agcattttct       540
cgtggttatg aaaagcttgg atttacccgc agtgctgaag gtatcactta ccgagaatgg       600
gctcctggag cgcattctgc agcattagta ggtgacttca caattggaa tccaaatgca       660 gatactatga ccagagatga ttatggtgtt tgggagattt tcctccctaa caacgctgat       720
ggatcctcag ctattcctca tggctcacgt gtaaagatac ggatggatac tccatccggt       780
gtgaaggatt caatttctgc ttggatcaag ttctctgtgc aggctccagg tgaaatacct       840
ttcaatggca tatattatga tccacctgaa gaggagaagt atgtcttcca acatcctcaa       900
cgtaaacgac cagagtcact aaggatttat gaatcacaca ttggaatgag cagcccggaa       960
ccgaagataa attcatatgc taattttagg gatgaggtgt tgccaagaat taaaaggctt      1020
ggatacaatg cagtgcagat aatggcaatc caggagcatt catactatgc aagctttggg      1080
taccatgtta ctaattttt tgcaccaagt agccgttttg gaactccaga ggacttaaaa      1140
tccttgatcg atagagcaca tgagcttggt ttgcttgttc ttatggatat tgttcatagt      1200
cattcgtcaa ataataccct tgacggtttg aatggtttcg atggcactga tacacattac      1260
ttccacggtg gtccacgcgg ccatcattgg atgtgggatt ctcgtctatt caactatggg      1320
```

-continued

| | |
|---|---|
| agttgggaag tattgagatt cttactgtca aacgcgagat ggtggcttga agaatataag | 1380 |
| tttgatggat ttcgatttga tggggtgacc tccatgatgt atactcacca tggattacaa | 1440 |
| atgacattta ctgggaacta tggcgaatat tttggatttg ctactgatgt tgatgcggta | 1500 |
| gtttacttga tgctggtcaa cgatctaatt catggacttt atcctgatgc tgtatccatt | 1560 |
| ggtgaagatg tcagtggaat gcctacattt tgcatccctg ttccagatgg tggtgttggt | 1620 |
| tttgactacc gcctgcatat ggctgtagca gataaatgga ttgaactcct caagcaaagt | 1680 |
| gacgaatctt ggaaaatggg cgatattgtg cacaccctaa caaatagaag gtggcttgag | 1740 |
| aagtgtgtaa cttatgcaga aagtcatgat caagcactag ttggtgacaa gactattgca | 1800 |
| ttctggttga tggataagga tatgtatgat ttcatggctc tggataggcc ttcaactctt | 1860 |
| cgcattgatc gtggcatagc attacataaa atgatcaggc ttgtcaccat ggGtttaggt | 1920 |
| ggtgaaggct atcttaactt catgggaaat gagtttgggc atcctgaatg gatagatttt | 1980 |
| ccaagaggcc cacaaactct tccaaccggc aaagttctcc ctggaaataa caatagttat | 2040 |
| gataaatgcc gccgtagatt tgatcttgga gatgcagatt ttcttagata tcgtggtatg | 2100 |
| caagagttcg atcaggcaat gcagcatctt gaggaaaaat atgggtttat gacatctgag | 2160 |
| caccagtatg tttcacggaa acatgaggaa gataaggtga tcatcctcaa aagaggagat | 2220 |
| ttggtatttg ttttcaactt ccactggagc aatagctttt ttgactaccg tgttgggtgt | 2280 |
| tccaagcctg ggaagtacaa ggtggccttg gactctgacg atgcactctt tggtggattc | 2340 |
| agcaggcttg atcatgatgt cgactacttc acaaccgaac atccgcatga caacaggccg | 2400 |
| cgctcttcct cggtgtacac tccgagcaga actgcggtcg tgtatgccct tacagagtaa | 2460 |
| gaaccagcag cggcttgtta caaggcaaag agaaactcc agagagctcg tggatcgtga | 2520 |
| gcgaagcgac gggcaacggc gcgaggctgc tccaagcgcc atgactggga ggggatcgtg | 2580 |
| cctcttcccc agatgccagg aggagcagat ggataggtag cttgttggtg agcgctcgaa | 2640 |
| agaaaatgga cgggcctggg tgtttgttgt gctgcactga accctcctcc tatcttgcac | 2700 |
| attcccggtt gttttttgtac atataactaa taattgcccg tgcgctcaac gtgaaaatcc | 2760 |

<210> SEQ ID NO 152
<211> LENGTH: 21
<212> TYPE: DNA
<213> ORGANISM: Triticum aestivum

<400> SEQUENCE: 152

| cattttttgg tagaaccttt g | 21 |
|---|---|

<210> SEQ ID NO 153
<211> LENGTH: 21
<212> TYPE: DNA
<213> ORGANISM: Triticum aestivum

<400> SEQUENCE: 153

| atccatccgt atctagaaaa t | 21 |
|---|---|

<210> SEQ ID NO 154
<211> LENGTH: 20
<212> TYPE: DNA
<213> ORGANISM: Triticum aestivum

<400> SEQUENCE: 154

| ctgttgtagc cataggaagg | 20 |
|---|---|

-continued

```
<210> SEQ ID NO 155
<211> LENGTH: 22
<212> TYPE: DNA
<213> ORGANISM: Triticum aestivum

<400> SEQUENCE: 155
gagcgctcac caacaagcta cc                                              22

<210> SEQ ID NO 156
<211> LENGTH: 24
<212> TYPE: DNA
<213> ORGANISM: Triticum aestivum

<400> SEQUENCE: 156
gtcagtggaa tgcctacatt ttgc                                            24

<210> SEQ ID NO 157
<211> LENGTH: 24
<212> TYPE: DNA
<213> ORGANISM: Triticum aestivum

<400> SEQUENCE: 157
gtcagtggaa tgcctacatt ttgc                                            24

<210> SEQ ID NO 158
<211> LENGTH: 20
<212> TYPE: DNA
<213> ORGANISM: Triticum aestivum

<400> SEQUENCE: 158
ggagatatgc ttagtaacag                                                 20

<210> SEQ ID NO 159
<211> LENGTH: 20
<212> TYPE: DNA
<213> ORGANISM: Triticum aestivum

<400> SEQUENCE: 159
gctgttaaga acaaccttcc                                                 20

<210> SEQ ID NO 160
<211> LENGTH: 193
<212> TYPE: PRT
<213> ORGANISM: Unknown
<220> FEATURE:
<223> OTHER INFORMATION: Partial amino acid sequence of SBE IIb turgidum
      A/B genome (in Figure 3)

<400> SEQUENCE: 160

Arg Ile Leu Pro Pro Gly Asn Gly Gln Gln Ile Tyr Glu Ile Asp
1               5                   10                  15

Pro Thr Leu Arg Asp Phe Lys Tyr His Leu Glu Tyr Arg Tyr Ser Leu
                20                  25                  30

Tyr Arg Arg Ile Arg Ser Asp Ile Asp Glu His Lys Gly Gly Met Asp
            35                  40                  45

Val Phe Ser Arg Gly Tyr Glu Lys Phe Gly Phe Val Arg Ser Ala Glu
        50                  55                  60

Gly Ile Thr Tyr Arg Glu Trp Ala Pro Gly Ala Asp Ser Ala Ala Leu
65                  70                  75                  80

Val Gly Asp Phe Asn Asn Trp Asp Pro Asn Ala Asp His Met Ser Lys
                85                  90                  95

Asn Asp Leu Gly Ile Trp Glu Ile Phe Leu Pro Asn Asn Ala Asp Gly
```

```
            100                 105                 110
Ser Pro Pro Ile Pro His Gly Ser Arg Val Lys Val Arg Met Gly Thr
        115                 120                 125

Pro Ser Gly Thr Lys Asp Ser Ile Pro Ala Trp Ile Lys Tyr Ser Val
        130                 135                 140

Gln Thr Pro Gly Asp Ile Pro Tyr Asn Gly Ile Tyr Tyr Asp Pro Pro
145                 150                 155                 160

Glu Glu Glu Lys Tyr Val Phe Lys His Pro Gln Pro Lys Arg Pro Lys
            165                 170                 175

Ser Leu Arg Ile Tyr Glu Thr His Val Gly Met Ser Ser Pro Glu Pro
        180                 185                 190

Lys

<210> SEQ ID NO 161
<211> LENGTH: 658
<212> TYPE: DNA
<213> ORGANISM: Unknown
<220> FEATURE:
<223> OTHER INFORMATION: Chara IIa B genome F1-13 0686 (in Figure 7)

<400> SEQUENCE: 161
cattcgtcaa ataataccct tgacggtttg aatggttttg atggcactga tacacattac      60
ttccacggtg gtccacgtgg ccatcattgg atgtgggatt ctcgtctgtt ccactatggg     120
agttgggaag tatgtagctg cgacttctgt caccatattt ggctaactgt tcctgtcaat     180
ctgttcttac acgtgtcaat attctattct tatacaggta ttaagattct tactgtcaaa     240
cgcgagatgg tggcttgatg aatataagtt tgatggattt cgatttgatg gggtgacctc     300
catgatgtat actcaccatg gattacaagt aagtcatcaa gtggtttcag taacttcttc     360
agggcactga aacaattgct atgcatcata acatgtatca tgatcagtac ttatgctacg     420
gagtctcaga tagttcccta gtatgcttgt acaattttac ctgacgagat catggaagat     480
tggaagtgat tgttattatt ttttcttcta agtttgcttc ttgttctaga tgacatttac     540
tgggaactat ggcgagtatt ttggatttgc cactgatgtt gatgcggtgg tatacttaat     600
gctggtcaac gatctaattc atggacttta tcctgatgct gtatccattg gtgaagaa       658

<210> SEQ ID NO 162
<211> LENGTH: 511
<212> TYPE: DNA
<213> ORGANISM: Unknown
<220> FEATURE:
<223> OTHER INFORMATION: Tasman0257 D genome (in Figure 8)

<400> SEQUENCE: 162
gcagaaaata tacgagattg acccaacact gaaagatttt cggagccatc ttgactaccg      60
gtaatgccta cccgctgctt tcgctcattt tgaattaagg tcctttcatc atgcaaattt     120
ggggaacatc aaagagacaa agactaggga ccaccatttc atacagatcc cctcgtggtc     180
tgagaatatg ctgggaagta aatgtataat tgatggctac aatttgctca aaattgcaat     240
acgaataact gtctccgatc attacaatta aagagtggca aactgatgaa atgtggtgga     300
tgggttatag attttacttt gctaattcct ctaccaaatt cctagggggg aaatctacca     360
gttgggaaac ttagtttctt atctttgtgg ccttttttgtt ttggggaaaa cacattgcta     420
aattcgaatg atttttgggta tacctcggtg gattcaacag atacagcgaa tacaagagaa     480
ttcgtgctgc tattgaccaa catgaaggtg g                                    511
```

<210> SEQ ID NO 163
<211> LENGTH: 243
<212> TYPE: DNA
<213> ORGANISM: Unknown
<220> FEATURE:
<223> OTHER INFORMATION: CS_exon_3a D genome (in Figure 9)

<400> SEQUENCE: 163

```
gatacctgaa gatatcgagg agcaaacggc ggaagtgaac atgacagggg ggactgcaga      60
gaaacttcaa tcttcagaac cgactcaggg cattgtggaa acaatcactg atggtgtaac     120
caaaggagtt aaggaactag tcgtggggga gaaaccgcga gttgtcccaa aaccaggaga     180
tgggcagaaa atatacgaga ttgacccaac actgaaagat tttcggagcc atcttgacta     240
ccg                                                                   243
```

<210> SEQ ID NO 164
<211> LENGTH: 267
<212> TYPE: DNA
<213> ORGANISM: Unknown
<220> FEATURE:
<223> OTHER INFORMATION: CS_exon 1a B genome (in Figure 10)

<400> SEQUENCE: 164

```
cacacgttgc tcccccttct catcgcttct caattaatat ctccatcact cgggttccgc      60
gctgcatttc ggccggcggg ttgagtgaga tctgggccac tgaccgactc actcgctgcg     120
cggggatggc gacgttcgcg gtgtccggcg cgaccctcgg tgtggcgcgg cccgccagcg     180
ccggcggcgg actgctgcga tccggctcgg agcggagggg cggggtggac ttgccgtcgc     240
tgctcctcag gaagaaggac tcctctc                                         267
```

<210> SEQ ID NO 165
<211> LENGTH: 2760
<212> TYPE: DNA
<213> ORGANISM: Aegilops tauschii

<400> SEQUENCE: 165

```
atggcgacgt tcgcggtgtc cggcgcgact ctcggtgtgg cgcgggccgg cgtcggagtg      60
gcgcgggccg gctcggagcg gaggggcggg gcggacttgc cgtcgctgct cctcaggaag     120
aaggactcct ctcgcgccgt cctgagccgc gcggcctctc cagggaaggt cctggtgcct     180
gacggcgaga gcgacgactt ggcaagtccg gcgcaacctg aagaattaca gatacctgaa     240
gatatcgagg agcaaacggc ggaagtgaac atgacagggg ggactgcaga gaaacttcaa     300
tcttcagaac cgactcaggg cattgtggaa acaatcactg atggtgtaac caaaggagtt     360
aaggaactag tcgtggggga gaaaccgcga gttgtcccaa aaccaggaga tgggcagaaa     420
atatacgaga ttgacccaac actgaaagat tttcggagcc atcttgacta ccgatacagc     480
gaatacaaga gaattcgtgc tgctattgac caacatgaag gtggattgga agcattttct     540
cgtggttatg aaaagcttgg attttacccgc agtgctgaag gtatcactta ccgagaatgg     600
gctcctggag cgcattctgc agcattagta ggtgacttca acaattggaa tccaaatgca     660
gatactatga ccagagatga ttatggtgtt tgggagattt tcctccctaa caacgctgat     720
ggatcctcag ctattcctca tggctcacgt gtaaagatac ggatggatac tccatccggt     780
gtgaaggatt caatttctgc ttggatcaag ttctctgtgc aggctccagg tgaaatacct     840
ttcaatggca tatattatga tccacctgaa gaggagaagt atgtcttcca acatcctcaa     900
cgtaaacgac cagagtcact aaggatttat gaatcacaca ttggaatgag cagcccggaa     960
```

```
ccgaagataa attcatatgc taattttagg gatgaggtgt tgccaagaat taaaaggctt    1020
ggatacaatg cagtgcagat aatggcaatc caggagcatt catactatgc aagctttggg    1080
taccatgtta ctaattttt tgcaccaagt agccgttttg gaactccaga ggacttaaaa    1140
tccttgatcg atagagcaca tgagcttggt ttgcttgttc ttatggatat tgttcatagt    1200
cattcgtcaa ataataccct tgacggtttg aatggtttcg atggcactga tacacattac    1260
ttccacggtg gtccacgcgg ccatcattgg atgtgggatt ctcgtctatt caactatggg    1320
agttgggaag tattgagatt cttactgtca aacgcgagat ggtggcttga agaatataag    1380
tttgatggat ttcgatttga tggggtgacc tccatgatgt atactcacca tggattacaa    1440
atgacattta ctgggaacta tggcgaatat tttggatttg ctactgatgt tgatgcggta    1500
gtttacttga tgctggtcaa cgatctaatt catggacttt atcctgatgc tgtatccatt    1560
ggtgaagatg tcagtggaat gcctacattt tgcatccctg ttccagatgg tggtgttggt    1620
tttgactacc gcctgcatat ggctgtagca gataaatgga ttgaactcct caagcaaagt    1680
gacgaatctt ggaaaatggg cgatattgtg cacaccctaa caaatagaag gtggcttgag    1740
aagtgtgtaa cttatgcaga aagtcatgat caagcactag ttggtgacaa gactattgca    1800
ttctggttga tggataagga tatgtatgat ttcatggctc tggataggcc ttcaactctt    1860
cgcattgatc gtggcatagc attacataaa atgatcaggc ttgtcaccat gggtttaggt    1920
ggtgaaggct atcttaactt catgggaaat gagtttgggc atcctgaatg gatagatttt    1980
ccaagaggcc cacaaactct tccaaccggc aaagttctcc ctggaaataa caatagttat    2040
gataaatgcc gccgtagatt tgatcttgga gatgcagatt ttcttagata tcgtggtatg    2100
caagagttcg atcaggcaat gcagcatctt gaggaaaaat atgggtttat gacatctgag    2160
caccagtatg tttcacggaa acatgaggaa gataaggtga tcatcctcaa aagaggagat    2220
ttggtatttg ttttcaactt ccactggagc aatagctttt ttgactaccg tgttgggtgt    2280
tccaagcctg gaagtacaa ggtggccttg gactctgacg atgcactctt tggtggattc    2340
agcaggcttg atcatgatgt cgactacttc acaaccgaac atccgcatga caacaggccg    2400
cgctctttct cggtgtacac tccgagcaga actgcgtcg tgtatgccct tacagagtaa    2460
gaaccagcag cggcttgtta caaggcaaag agagaactcc agagagctcg tggatcgtga    2520
gcgaagcgac gggcaacggc gcgaggctgc tccaagcgcc atgactggga ggggatcgtg    2580
cctcttcccc agatgccagg aggagcagat ggataggtag cttgttggtg agcgctcgaa    2640
agaaaatgga cgggcctggg tgtttgttgt gctgcactga accctcctcc tatcttgcac    2700
attcccggtt gttttttgtac atataactaa taattgcccg tgcgctcaac gtgaaaatcc    2760
```

<210> SEQ ID NO 166
<211> LENGTH: 2472
<212> TYPE: DNA
<213> ORGANISM: Unknown
<220> FEATURE:
<223> OTHER INFORMATION: SBE IIa B cDNA Botticella FM86, 2472nt

<400> SEQUENCE: 166

```
atggcgacgt tcgcggtgtc cggcgcgacc ctcggtgtgg cgcggcccgc cagcgccggc      60
ggcggactgc tgcgatccgg ctcggagcgg aggggcgggg tggacttgcc gtcgctgctc     120
ctcaggaaga aggactcctc tcgcgccgtc ctgagccgcg cggcctctcc agggaaggtc     180
ctggtgcctg acggtgagag cgacgacttg gcggccactc cagcgcaacc cgaagaatta     240
```

```
cagatacctg aagacatcga ggagcaaacg gctgaagtaa acatgacagg ggggactgca        300
gaaaaacttc aatattcaga accgactcaa ggcattgtgg aaacaatcac tgatggtgta        360
accaaaggag ttaaggaact agtcgtgggg gagaaaccgc gagttgtccc aaaaccagga        420
gatgggcaga aaatatacga gattgaccca acgctgaaag attttcggag ccatcttgac        480
taccgataca gcgaatacaa gagaattcgt gctgctattg accaacatga aggtggattg        540
gaagcatttt ctcgtggtta tgaaaagctt ggatttaccc gcagtgctga aggtatcact        600
taccgagaat gggctcctgg agcgcattct gcagcattag taggtgactt caacaattgg        660
aatccaaatg cagatactat gaccagagat gattatggtg tttgggagat cttcctccct        720
aacaatgctg atggatcccc agctattcct catggctcac gtgtaaagat acggatggat        780
actccatctg gtgtgaagga ttcgatttct gcttggatca agttctctgt gcaggctcca        840
ggtgaaatac cattcaatgg catatattat gatccacctg aagaggagaa gtatgtcttc        900
caacatcctc aacctaaacg accagagtca ctaaggattt atgaatcaca cattggaatg        960
agcagcccag aaccgaagat aaattcatat gctaatttta gggatggggt gctgccaaga       1020
attaaaaggc ttggatacaa tgcagtgcag ataatggcaa tccaggagca ttcatactat       1080
gcaagctttg ggtaccatgt tactaatttt tttgcaccaa gtagccgttt tggaactcca       1140
gaggacttaa aatccttgat cgatagagca catgagcttg gtttgcttgt tcttatggat       1200
attgttcata gtcattcgtc aaataatacc cttgacggtt tgaatggttt cgatggcact       1260
gatacacatt acttccacgg tggtccacgt ggccatcatt ggatgtggga ttctcgtctg       1320
ttcaactatg gagttgggga agtattaaga ttccttactgt caaacgcgag atggtggctt       1380
gaagaatata agtttgatgg atttcgattt gatgggtga cctccatgat gtatactcac       1440 catgattac aaatgacatt tactgggaac tatggcgagt attttggatt tgccactgat       1500
gttgatgcgg tggtatactt aatgctggtc aacgatctaa ttcatggact ttatcctgat       1560
gctgtatcca ttggtgaaga tgtcagtgga atgcctacat tttgcatccc tgttccagat       1620
ggtggtgttg gttttgacta tcgcctgcat atggctgtag cagataaatg gatcgaactc       1680
ctcaagcaaa gtgacgaatc ttggaaaatg ggtgatattg tgcacaccct aacaaataga       1740
aggtggcttg agaagtgcgt cacttatgca gaaagtcatg atcaagcact agttggtgac       1800
aagactattg cattctggtt gatggataag gatatgtatg atttcatggc tctggataga       1860
ccttcaactc ctcgcattga tcgtggcata gcattacata aaatgatcag gcttgtcacc       1920
atgggtttag gtgcgaaagg ctatcttaac ttcatgggaa atgagtttgg gcatcctgaa       1980
tggatagatt ttccaagagg tccgcaaact cttccaaccg gcaaagttct ccctggaaat       2040
aacaatagtt atgataaatg ccgccgtaga tttgatcttg gagatgcaga ttttcttaga       2100
tatcgtggta tgcaagagtt cgaccaggca atgcagcatc ttgaggaaaa atatgggttt       2160
atgacatctg agcaccagta tgtttcacgg aaacatgagg aagataaggt gatcatcttc       2220
gaaagaggag atttggtatt tgttttcaac ttccactgga gcaatagctt ttttgactac       2280
cgtgttgggt gttccaagcc tgggaagtac aaggtggcct tagactccga cgatgcactc       2340
tttggtggat tcagcaggct tgatcatgat gtcgactact tcacaaccga acatccgcat       2400
gacaataggc cgcgctcttt cttggtgtac actcctagca gaactgcggt cgtgtatgcc       2460
cttacagagt aa                                                           2472

<210> SEQ ID NO 167
<211> LENGTH: 2978
```

<212> TYPE: DNA
<213> ORGANISM: Triticum aestivum

<400> SEQUENCE: 167

```
ggcaccgtcc ccgccagctt ccaccccgc cgcacacgtt gctccccctt ctcatcgctt      60
ctcaattaat atctccatca ctcgggttcc gcgctgcatt tcggccggcg ggttgagtga     120
gatctgggcc actgaccgac tcactcgctc gctgcgcggg gatggcgacg tttgcggtgt     180
ccggcgcgac cctcggtgtg gcgcggcccg ccggcgccgg cggcggactg ctgccgcgat     240
ccggctcgga gcggaggggc ggggtggacc tgccgtcgct gctcctcagg aagaaggact     300
cctctcgcgc cgtcctgagc cgcgcggcct tcccagggaa ggtcctggtg cctgacggtg     360
agagcgacga cttggcaagt ccggcgcaac ctgaagaatt acagatacct gaagacatcg     420
aggagcaaac ggctgaagta acatgacag ggggactgc agaaaaactt gaatcttcag      480
aaccgactca aggcattgtg gaaacaatca ctgatggtgt aaccaaagga gttaaggaac     540
tagtcgtggg ggagaaaccg cgagttgtcc caaaaccagg agatgggcag aaaatatacg     600
agattgaccc aacgctgaaa gattttcgga gccatcttga ctaccgatac agcgaataca     660
ggagaattcg tgctgctatt gaccaacatg aaggtggatt ggaagcattt tctcgtggtt     720
atgaaaagct tggatttacc cgcagtgctg aaggtatcac ttaccgagaa tgggctcctg     780
gagcgcattc tgcagcatta gtaggtgact caacaattg gaatccgaat gcagatacta      840
tgaccagaga tgattatggt gtttgggaga ttttcctccc taacaatgct gatggatccc     900
cagctattcc tcatggctca cgtgtaaaga tacggatgga tactccatct ggtgtgaagg     960
attcaatttc tgcttggatc aagttctctg tgcaggctcc aggtgaaata ccattcaatg    1020
gcatatatta tgatccacct gaagaggaga agtatgtctt ccaacatcct caacctaaac    1080
gaccagagtc actgaggatt tatgaatcac acattggaat gagcagccca gaaccgaaga    1140
taaattcata tgctaatttt agggatgagg tgctgccaag aattaaaagg cttggataca    1200
atgcagtgca gataatggca atccaggagc attcatacta tgcgagcttt gggtaccatg    1260
ttactaattt ttttgcacca agtagccgtt ttggaactcc agaggactta aaatccctga    1320
tcgatagagc acatgagctt ggtttgcttg ttcttatgga tattgttcat agtcattcat    1380
caaataatac ccttgacggc ttgaatggtt tcgatggcac tgatacacat tacttccacg    1440
gtggtccacg tggccatcat tggatgtggg attctcgtct attcaactat gggagttggg    1500
aagtattgag attcttactg tcaaacgcga gatggtggct tgaagaatat aagtttgatg    1560
gatttcgatt tgatggggtg acctccatga tgtatactca ccatggatta caaatgacat    1620
ttactgggaa ctatggcgag tattttggat ttgctactga tgttgacgcg gtagtttact    1680
tgatgctggt caacgatcta attcatggac tttatcctga tgctgtatcc attggtgaag    1740
atgtcagtgg aatgcccaca ttttgcatcc ctgttccaga tggtggtgtt ggttttgact    1800
atcgcttgca tatggctgta gcagataaat ggattgaact cctcaagcaa agtgacgaat    1860
cttggaaaat gggtgatatt gtgcacaccc taacaaatag aaggtggctt gagaagtgtg    1920
taacttatgc agaaagtcat gatcaagcac tagttggtga caagactatt gcattctggt    1980
tgatggataa ggatatgtat gatttcatgg ctctggatag gccttcaact cctcgcattg    2040
atcgtggcat agcattacat aaaatgatca ggcttgtcac catgggttta ggtggtgaag    2100
gctatcttaa cttcatggga aatgagtttg gcatcctga atggatagat tttccaagag    2160
gtccgcaaac tcttccaacc ggcaaagttc tccctggaaa taacaatagt tatgataaat    2220
```

```
gccgccgtag atttgatctt ggagatgcag attttcttag atatcgtggt atgcaagagt   2280
tcgatcaggc aatgcagcat cttgaggaaa aatatgggtt tatgacatct gagcaccagt   2340
atgtttcacg gaaacacgag gaagataagg tgatcatctt cgaaagagga gatttggtat   2400
ttgttttcaa cttccactgg agcaatagct ttttgactac cgtgttggg tgttccaggc    2460 ctgggaagta caaggtggcc ttagactccg acgatgcact ctttggtgga ttcagcaggc   2520
ttgatcatga tgtcgactac ttcacaaccg aacatccgca tgacaacagg ccgcgctctt   2580
tctcggtgta cactccgagc agaactgcgg tcgtgtatgc ccttacagag taagaaccag   2640
cagctgcttg ttacaaggca agagagaac tccagagagc tcgtggatcg tgagcgaagc    2700
gacgggcaac ggcgcgaggc tgctctaagc gccatgactg ggaggggatc gtgcctcttc   2760
cccagatgcc aggaggagca gatggatagg tagcttgttg gtgagcgctc gaaagaaaat   2820
ggacgggcct gggtgtttgt cgtgctgcac taccctcctc atatcttgca cattcccggt   2880
tgtttttgta catataacta ataattgccc gtgcgctcaa catgaacata taaatattct    2940
aataataggt tatcccgtga aaaaaaaaaa aaaaacga                           2978

<210> SEQ ID NO 168
<211> LENGTH: 2970
<212> TYPE: DNA
<213> ORGANISM: Triticum aestivum

<400> SEQUENCE: 168
ccagcttcca cccccgccgc acacgttgct cccccttctc atcgcttctc aattaatatc    60
tccatcactc gggttccgcg ctgcatttcg gccggcgggt tgagtgagat ctgggccact   120
gaccgactca ctcgctcgct gcgcggggat ggcgacgttc gcggtgtccg gcgcgaccct   180
cggtgtggcg cggcccgccg gcgccggcgg cggactgctg ccgcgatccg gctcggagcg   240
gaggggcggg gtggacctgc cgtcgctgct cctcaggaag aaggactcct ctcgcgccgt   300
cctgagccgc gcggcctctc cagggaaggt cctggtgcct gacggtgaga gcgacgactt   360
ggcaagtccg gcgcaacctg aagaattaca gataccgtgaa gacatcgagg agcaaacggc   420
tgaagtaaac atgacagggg ggactgcaga aaaacttgaa tcctcagaac cgactcaagg   480
cattgtggaa acaatcactg atggtgtaac caaaggagtt aaggaactag tcgtggggga   540
gaaaccgcga gttgtcccaa aaccaggaga tgggcagaaa atatacgaga ttgacccaac   600
gctgaaagat tttcggagcc atcttgacta ccgatacagc gaatacagga gaattcgtgc   660
tgctattgac caacatgaag gtggattgga agcattttct cgtggttatg aaaagcttgg   720
atttacccgc agtgctgaag gtatcactta ccgagaatgg gctcctggag cgcattctgc   780
agcattagta ggtgacttca acaattggaa tccgaatgca gatactatga ccagagatga   840
ttatggtgtt tgggagattt tcctccctaa caatgctgat ggatcccag ctattcctca    900 tggctcacgt gtaaagatac ggatggatac tccatctggt gtgaaggatt caatttctgc   960
ttggatcaag ttctctgtgc aggctccagg tgaaatacca ttcaatggca tatattatga   1020
tccacctgaa gaggagaagt atgtcttcca acatcctcaa cctaaacgac cagagtcact   1080
gaggatttat gaatcacaca ttggaatgag cagcccagaa ccgaagataa attcatatgc   1140 taatttagg gatgaggtgc tgccaagaat taaaaggctt ggatacaatg cagtgcagat    1200
aatggcaatc caggagcatt catactatgc gagcttggg taccatgtta ctaattttttt   1260 tgcaccaagt agccgttttg gaactccaga ggacttaaaa tccctgatcg atagagcaca   1320
tgagcttggt ttgcttgttc ttatggatat tgttcatagt cattcatcaa ataatacccct   1380
```

```
tgacggcttg aatggtttcg atggcactga tacacattac ttccacggtg gtccacgtgg    1440
ccatcattgg atgtgggatt ctcgtctatt caactatggg agttgggaag tattgagatt    1500
cttactgtca aacgcgagat ggtggcttga agaatataag tttgatggat ttcgatttga    1560
tggggtgacc tccatgatgt atactcacca tggattacaa atgacattta ctgggaacta    1620
tggcgagtat tttggatttg ctactgatgt tgatgcggta gtttacttga tgctggtcaa    1680
cgatctaatt catggacttc atcctgatgc tgtatccatt ggtgaagatg tcagtggaat    1740
gcccacattt tgcatccctg ttccagatgg tggtgttggt tttgactatc gcttgcatat    1800
ggctgtagca gataaatgga ttgaactcct caagcaaagt gacgaatctt ggaaaatggg    1860
tgatattgtg cacaccctaa caaatagaag gtggcttgag aagtgtgtaa cttatgcaga    1920
aagtcatgat caagcactag ttggtgacaa gactattgca ttctggttga tggataagga    1980
tatgtatgat ttcatggctc tggataggcc ttcaactcct cgcattgatc gtggcatagc    2040
attacataaa atgatcaggc ttgtcaccat gggtttaggt ggtgaaggct atcttaactt    2100
catgggaaat gagtttgggc atcctgaatg gatagatttt ccaagaggtc cgcaaactct    2160
tccaaccggc aaagttctcc ctggaaataa caatagttat gataaatgcc gccgtagatt    2220
tgatcttgga gatgcagatt ttcttagata tcatggtatg caagagttcg atcaggcaat    2280
gcagcatctt gaggaaaaat atgggtttat gacatctgag caccagtatg tttcacggaa    2340
acatgaggaa gataaggtga tcatcttcga aagaggagat ttggtatttg ttttcaactt    2400
ccactggagc aatagctttt ttgactaccg tgttgggtgt tccaggcctg ggaagtacaa    2460
ggtggcctta gactccgacg atgcactctt tggtggattc agcaggcttg atcatgatgt    2520
cgactacttc acaaccgaac atccgcatga caacaggccg cgctctttct cggtgtacac    2580
tccgagcaga actgcggtcg tgtatgccct tacagagtaa gaaccagcag ctgcttgtta    2640
caaggcaaag agagaactcc agagagctcg tggatcgtga gcgaagcgac gggcaacggc    2700
gcgaggctgc tctaagcgcc atgactggga ggggatcgtg cctcttcccc agatgccagg    2760
aggagcagat ggataggtag cttgttggtg agcgctcgaa agaaaatgga cgggcctggg    2820
tgtttgtcgt gctgcactac cctcctccta tcttgcacat tcccggttgt ttttgtacat    2880
ataactaata attgcccgtg cgctcaacgt gaacatataa atattctaat aataggttat    2940
cccgtgattt acctgcctaa aaaaaaaaaa                                     2970
```